(12) United States Patent
Vicker et al.

(10) Patent No.: US 8,119,627 B2
(45) Date of Patent: Feb. 21, 2012

(54) HETEROCYCLIC COMPOUNDS AS INHIBITORS OF 17BETA-HSD3

(75) Inventors: Nigel Vicker, Slough (GB); Joanna Mary Day, Slough (GB); Helen Victoria Bailey, Slough (GB); Wesley Heaton, Slough (GB); Ana Maria Ramos Gonzalez, Slough (GB); Christopher Mark Sharland, Slough (GB); Michael John Reed, Slough (GB); Atul Purohit, Slough (GB); Barry Victor Lloyd Potter, Slough (GB)

(73) Assignee: Sterix Limited, Berkshire (GB)

( * ) Notice: Subject to any disclaimer, the term of this patent is extended or adjusted under 35 U.S.C. 154(b) by 577 days.

(21) Appl. No.: 11/968,436

(22) Filed: Jan. 2, 2008

(65) Prior Publication Data

US 2009/0023710 A1    Jan. 22, 2009

Related U.S. Application Data

(63) Continuation-in-part of application No. PCT/GB2006/002465, filed on Jul. 3, 2006.

(30) Foreign Application Priority Data

Jul. 4, 2005   (GB) .................................. 0513702.1

(51) Int. Cl.
*A61K 31/55* (2006.01)
(52) U.S. Cl. ................... 514/213.01; 540/593
(58) Field of Classification Search .................. 540/593
See application file for complete search history.

(56) References Cited

U.S. PATENT DOCUMENTS

| 2,543,266 | A | 2/1951 | Bambas |
| 6,541,463 | B1 | 4/2003 | Labrie et al. |
| 2003/0232837 | A1 | 12/2003 | Guzi et al. |
| 2004/0138226 | A1 | 7/2004 | Guzi et al. |

FOREIGN PATENT DOCUMENTS

| WO | WO 86/01105 | 2/1986 |
| WO | WO 90/10462 | 9/1990 |
| WO | WO 91/00731 | 1/1991 |
| WO | WO 91/00733 | 1/1991 |
| WO | WO 94/26767 | 11/1994 |
| WO | WO 96/26201 | 8/1996 |
| WO | WO 97/11162 | 3/1997 |
| WO | WO 98/00556 | 1/1998 |
| WO | WO 98/05635 A | 2/1998 |
| WO | WO 98/07859 A | 2/1998 |
| WO | WO 98/08870 A | 3/1998 |
| WO | WO 98/09985 A | 3/1998 |
| WO | WO 98/13348 A | 4/1998 |
| WO | WO 98/32724 | 7/1998 |
| WO | WO 99/12540 | 3/1999 |
| WO | WO 99/46279 | 9/1999 |
| WO | WO 99/52890 A | 10/1999 |
| WO | WO 01/42181 | 6/2001 |
| WO | WO 01/92227 | 12/2001 |
| WO | WO 03/022835 | 3/2003 |
| WO | WO 03/033487 | 4/2003 |
| WO | WO 2004/033427 | 4/2004 |
| WO | WO 2004/046111 | 6/2004 |
| WO | WO 2004/047755 | 6/2004 |
| WO | WO 2004/083167 | 9/2004 |
| WO | WO 2004/089896 | 10/2004 |
| WO | WO 2004/110459 | 12/2004 |
| WO | WO 2005/037809 | 4/2005 |

OTHER PUBLICATIONS

Labrie, et al., Trends Endocrinol. Metab., 2000, vol. 11, p. 421-7.
Labrie, F. et al., Steroids, 1997, vol. 62, p. 148-158.
Geissler W.M., et al., Nat. Genet., 1994, vol. 7, p. 34-39.
Oefelein M.G. & Cornum R., J. Urol., 2000, vol. 164, p. 726-9.
Poirer D., Curr. Med. Chem., 2003, vol. 10, p. 453-477.
Gennaro A.R. (ed.), Remington's Pharmaceutical Sciences, Mack Publishing Co., 1985.
Lodish, et al., Molecular Cell Biology, 3rd ed., 1995, p. 177-181.
Burmistov S.I., et al., Chemical Abstracts: Noncondensed Aromatics: 84:163313q: Synthesis and reactions of 2,2-chloronitrodiaryl ethers, 1976, 19 (1) p. 39-41.
Wardrop, et al., Inch T.D., J. Chem. Soc. Perkin I, 1976, p. 1279-1285.
Miriyala B., et al., J. Tetrahedron, 2004, vol. 60, p. 1463-1471.
Atkinson, D.C., et al., J., Med. Chem., 1983, vol. 26, p. 1353-1360.
F. N. Hayes, et al., New Compounds, J. Am. Chem. Soc. (1952) vol. 74, p. 1106-1107.
R. Henning, et al., Synthesis and Neuroleptic Activity of a Series of 1-[1-(Benzo-1, 4-Dioxan-2-ylmethyl)-4-Piperidinyl]Benzimidazolone Derivatives, Journal of Medicinal Chemistry (1987) vol. 30, No. 5, p. 814-819.
Sugasawa et al., 1-Azacycloalkyl-1, 4-Benzodiazepin-2-ones With Antianxiety-Antidepressant Actions, Journal of Medical Chemistry (1985) vol. 28, No. 6, p. 699-707.

*Primary Examiner* — James O Wilson
*Assistant Examiner* — Brian McDowell
(74) *Attorney, Agent, or Firm* — Frommer Lawrence & Haug LLP; Sandra Kuzmich, Esq.

(57) ABSTRACT

There is provided a compound having Formula (I)

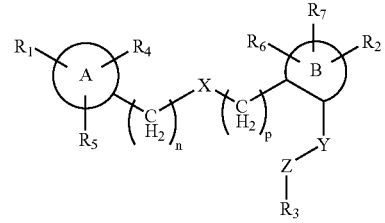

Formula I wherein each of rings A and B is selected from five or six membered carbon rings optionally containing one or more hetero atoms selected from N, S, and O and optionally having fused thereto a further ring; X is an optional group selected from O, S, —S=O, —S(=O)$_2$, —C=O, —S(=O)$_2$NR$_8$, —C=ONR$_9$, and —NR$_{10}$, wherein n and p are independently selected from 0 and 1; Y is (R$_{11}$)$_{1-3}$ wherein each R$_{11}$ is independently selected from —NR$_{12}$, —CR$_{13}$R$_{14}$, —S(=O)$_2$ and —C=O; Z is selected from (i) six or seven membered ring containing carbon and at least one nitrogen, which may be optionally substituted wherein the substituents may together form further ring fused thereto; and (ii) a —R$_{15}$—NR$_{16}$— group.

26 Claims, No Drawings

HETEROCYCLIC COMPOUNDS AS INHIBITORS OF 17BETA-HSD3

REFERENCE TO RELATED APPLICATIONS

This application is a continuation-in-part of International Patent Application PCT/GB20067002465 filed Jul. 3, 2006 and published as WO 2007/003934 on Jan. 11, 2007, which claims priority from GB Application No. 0513702.1 filed Jul. 4,2005.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g.. they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

FIELD OF INVENTION

The present invention relates to a compound. In particular the present invention provides compounds capable of inhibiting 17β-hydroxysteroid dehydrogenase Type 3 (17β-HSD3).

INTRODUCTION

As discussed in WO03/03347, WO04/110459 and WO99/46279 androgen-dependent diseases, i.e. diseases whose onset or progress is aided by androgenic activity, are well known. These diseases include, but are not limited to, prostate cancer, other androgen-dependent neoplasms such as prostatic intraepithelial neoplasia, benign prostatic hyperplasia, acne, seborrhea, hirsutism, androgenic alopecia, precocious puberty, adrenal hyperplasia and polycystic ovarian syndrome. Estrogen-dependent diseases, i.e. diseases whose onset or progress is aided by estrogenic activity, are also well known. These include but are not limited to breast cancer, endometriosis, leiomyoma and precocious puberty. Androgenic and estrogenic activity may be suppressed by administering androgen receptor antagonists or estrogen receptor antagonists respectively, see for example WO 94/26767 and WO 96/26201. Androgenic and estrogenic activity may also be reduced by suppressing ovarian or testicular secretions by known methods, see for example WO 90/10462, WO 91/00731, WO 91/00733, and WO86/01105. Examples of such anti-androgenic agents include LHRH agonists (e.g. leuprolide and zoladex) and LHRH antagonists (e.g. abarelix and cetrorelix).

Androgenic and estrogenic activity may also be reduced by suppressing androgen or estrogen biosynthesis using inhibitors of enzymes that catalyze one or more steps of such biosynthesis. These include inhibitors of 5alpha-reductase Type 1 and/or Type 2 (for example. finasteride, SKF105,657, LY191,704, LY320,236, dutasteride, Flutamide, nicalutamide, bicalutamide); inhibitors of 17alpha-hydroxylase/C17-20 lyase (for example YM116, CB7630 and liarozole); and inhibitors of 17beta-HSD Types 3 and 5. Inhibitors of 17beta-hydroxysteroid dehydrogenase Type 5 are described in WO 97/11162. Novel inhibitors of both Type 3 and Type 5 17beta-hydroxysteroid dehydrogenase are described in WO 99/46279.

Mammalian 17beta-hydroxysteroid dehydrogenases (17beta-HSDs) are NAD(H) or NADP(H)-dependent enzymes which catalyse, besides other reactions, the final steps in male and female sex hormone biosynthesis. These enzymes convert inactive 17-ketosteroids into their active 17beta-hydroxy forms or catalyze the oxidation of the 17beta-hydroxysteroids into the inactive 17beta-keto forms. Because both estrogens and androgens have the highest affinity for their receptors in the 17beta-hydroxy form, 17beta-HSD enzymes play an essential role in the tissue-selective regulation of the activity of sex steroid hormones.

At present, 11 human members of the 17beta-HSD enzyme family have been described (Types 1-5, 7, 8, and 10-13). The human 17beta-HSD family members share less than 30% similarity in their primary structure. The 17beta-HSDs are expressed in distinct, though in some cases, overlapping patterns. The different types of 17beta-HSDs also differ in their substrate and cofactor specificities. In intact cells in culture, the 17beta-HSDs catalyze the reaction in a unidirectional way: e.g. Types 1, 3, 5 and 7 use NADP (H) as a cofactor and catalyze the reductive reaction (activation), while Types 2, 4, and 8 catalyze the oxidative reaction (inactivation) using NAD (H) as a cofactor (see e.g. Labrie et al. (2000) Trends Endocrinol Metab., 11, 421-7).

Due to their essential role in the tissue-selective regulation of the activity of sex steroid hormones, 17beta-HSDs can be involved in the occurrence and development of both estrogen-sensitive pathologies (e.g. breast, ovarian, uterine and endometrium cancers) and androgen-sensitive pathologies (e.g. prostate cancer, benign prostatic hyperplasia, acne, hirsutism). Furthermore, many types of 17beta-HSD have been shown to be involved in the pathogenesis of particular human disorders. For example, 17beta-HSD3 is known to be involved in the development of pseudohermaphroditism, 17beta-HSD8 plays a role in polycystic kidney disease, and 17beta-HSD4 is implicated in bifunctional enzyme deficiency. Therefore treatment of sex steroid-sensitive disease by administration of specific inhibitors of the 17beta-HSD enzymes has been suggested, optionally in combination with potent and specific anti-estrogens and anti-androgens (Labrie F et al. (1997) Steroids, 62, 148-58).

As each type of 17beta-HSD has a selective substrate affinity, directional (reductive or oxidative) activity in intact cells, and a particular tissue distribution, selectivity of drug action should be achieved by targeting a particular 17beta-HSD enzyme. By individual modulation of the particular 17beta-HSDs it is possible to influence or even control the local and paracrine concentration of estrogens and androgens in different target tissues.

The 17beta-HSD Type 3 enzyme (17beta-HSD3) is a well-characterized member of the 17beta-HSD family. Most of the 17beta-HSDs are expressed in a wide variety of tissues, however the 17beta-HSD3 enzyme is found to be expressed almost exclusively in the testis. 17beta-HSD3 has a crucial role in androgen biosynthesis. It converts 4-androstene-3,17-one (A) to testosterone (T). The physiological significance of 17beta-HSD3 is undeniable. Mutations in the 17beta-HSD3 gene have been found to lead to decreased testosterone formation in the foetal testis, and consequently to a human inter-sex disorder termed male pseudohermaphroditism (Geissler, W. M. et al. (1994) Nat. Genet. 7, 34-9).

Prostate tumours remain androgen-responsive for some time; the presence of active androgens regulates the proliferation and differentiation of the tumour cells. At present, androgen deprivation is the only effective systemic hormonal therapy available for prostate cancer. The development of selective inhibitors of 17beta-HSD3 is a therapeutic approach for the treatment of androgen-dependent disease (Labrie et al. (2000) Trends Endocrinol. Metab. 11, 421-7). Furthermore, Oefelein et al. reported that a GnRH analogue fails, in nearly 20% of cases, to achieve castrated levels of testosterone in men (Oefelein, M. G. & Cornum, R. (2000) J. Urol. 164, 726-9). In order to improve the response rate to endocrine therapy for men with prostate cancer it may be important to selectively inhibit testicular 17beta-HSD3 activity. Besides prostate cancer, many other androgen-sensitive diseases, i.e. diseases whose onset or progress is aided by androgenic activity, may be treated by selectively inhibiting 17beta-HSD3 activity. These diseases include, but are not limited to, benign prostatic hyperplasia, prostatitis, acne, seborrhea, hirsutism, androgenic alopecia, precocious puberty (usually associated with an excess of androgen secretion, often of adrenal origin), adrenal hyperplasia, and polycystic ovarian syndrome (associated with an excess of androgen secretion by the ovaries). Furthermore, considering the fact that 17beta-HSD3 is found mainly in the testis, the development of potent inhibitors could be of interest for blocking spermatogenesis as an anti-fertility agent for males.

Current therapies for the treatment of androgenic and estrogenic-dependent diseases include the use of glucocorticoids to block adrenal secretions, and luteinizing hormone releasing hormone (LHRH) agonists to cause medical castration. Both therapies are associated with undesirable side effects. An improved therapy would include compounds that specifically inhibit Type 3 17beta-hydroxysteroid dehydrogenase, while avoiding inhibition of other 17beta-hydroxysteroid dehydrogenases.

Several reversible or irreversible inhibitors of the 17beta-HSD3 enzymes of steroidal and even non-steroidal origin are already known in the literature. The characteristics of these inhibitory molecules are reviewed in Poirier, D. (2003) Curr. Med. Chem. 10, 453-77. For example, U.S. Pat. No. 6,541,463 discloses androsterone-derived inhibitors for 17beta-HSD3. These derivatives have been synthesised by parallel solid and liquid-phase chemistry, and some of these compounds showed 2 to 18-fold higher inhibitory activity than that of the natural substrate of the enzyme, A-dione, used itself as a inhibitor. Furthermore, WO01/42181 discloses benzyl-tetralins, the chemical structure of which is related to that of the phytoestrogen biochanin, as 17beta-HSD3 inhibitors. Furthermore, WO 98/32724, WO 98/30556 and WO99/12540 disclose tetralone, benzopyrane and benzofuranone derivatives, which have 17beta-HSD inhibitory activity, for the treatment of hormone-sensitive diseases.

There is a need for the development of compounds that selectively inhibit the 17beta-HSD3 enzyme, while desirably failing to substantially inhibit other members of the 17beta-HSD protein family, or other catalysts of sex steroid degradation or activation. In particular, it is an aim of the present invention to develop selective inhibitors of the 17beta-HSD3 enzyme, whereby in addition the compounds have no or only pure antagonistic binding affinities to the androgen receptor.

Aspects of the invention are defined in the appended claims.

SUMMARY ASPECTS OF THE PRESENT INVENTION

In one aspect the present invention provides a compound having Formula I

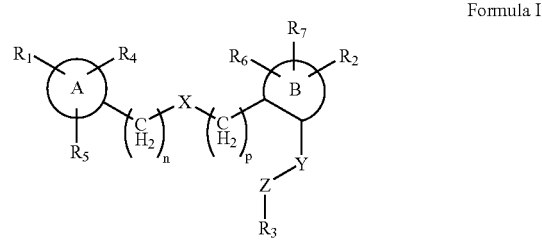

Formula I wherein
each of $R_1$, $R_2$, $R_4$, $R_5$, $R_6$ and $R_7$ are independently selected from (a) H, (b) $R_{17}$, —OC($R_{17}$)$_3$, —OCH($R_{17}$)$_2$, —OCH$_2$$R_{17}$, —C($R_{17}$)$_3$, —CH($R_{17}$)$_2$, or —CH$_2$$R_{17}$ wherein $R_{17}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —SO$_2$-alkyl; and (n) —N($R_{11}$)C(O)$R_{13}$,
wherein the optional substituents of (d) (e) (f) (h) and (i) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl;
each of rings A and B are selected from five or six membered carbon rings optionally containing one or more hetero atoms selected from N, S, and O and optionally having fused thereto a further ring,
X is an optional group selected from O, S, S=O, S(=O)$_2$, C=O, S(=O)$_2$NR$_8$, C=ONR$_9$, NR$_{10}$, wherein R$_8$, R$_9$ and R$_{10}$ are independently selected from H and hydrocarbyl,
wherein n and p are independently selected from 0 and 1
Y is (R$_{11}$)$_{1-3}$ wherein each R$_{11}$ is independently selected from NR$_{12}$, CR$_{13}$R$_{14}$, S(=O)$_2$ and C=O, wherein R$_{12}$, R$_{13}$ and R$_{14}$ are independently selected from H and hydrocarbyl
Z is selected from (i) six or seven membered ring containing carbon and at least one nitrogen, which may be optionally substituted wherein the substituents may together form further ring fused thereto; and (ii) a —R$_{15}$—NR$_{16}$— group wherein R$_{15}$ is an optionally substituted $C_{1-6}$ alkyl chain and R$_{16}$ is selected from H and hydrocarbyl R$_3$ is selected from

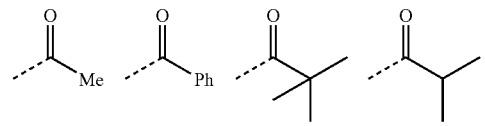

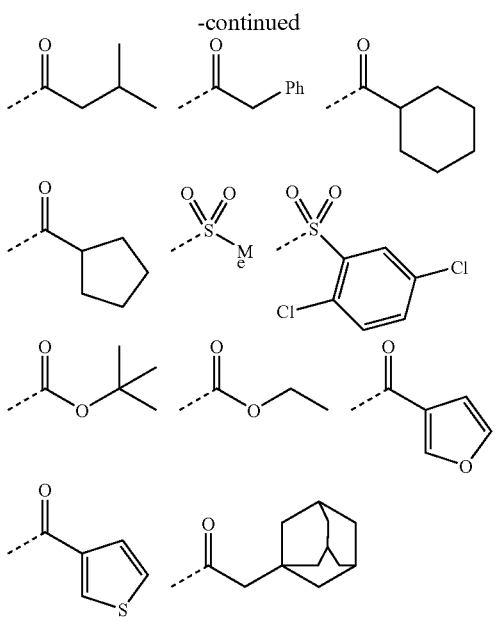

In one aspect the present invention provides a pharmaceutical composition comprising
(i) a compound having Formula I

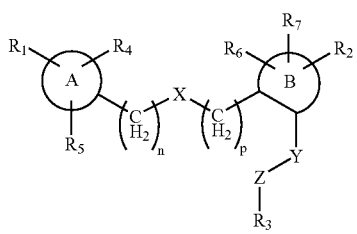

Formula I wherein
each of $R_1$, $R_2$, $R_4$, $R_5$, $R_6$ and $R_7$ are independently selected from (a) H, (b) $R_{17}$, —$OC(R_{17})_3$, —$OCH(R_{17})_2$, —$OCH_2R_{17}$, —$C(R_{17})_3$, —$CH(R_{17})_2$, or —$CH_2R_{17}$ wherein $R_{17}$ is a halogen; (c) —CN; (d) optionally substituted alkyl; (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —$SO_2$-alkyl; and (n) —$N(R_{11})C(O)R_{13}$,
wherein the optional substituents of (d) (e) (f) (h) and (i) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl;
each of rings A and B are selected from five or six membered carbon rings optionally containing one or more hetero atoms selected from N, S, and O and optionally having fused thereto a further ring,
X is an optional group selected from O, S, S=O, S(=O)$_2$, C=O, S(=O)$_2$NR$_8$, C=ONR$_9$, NR$_{10}$, wherein R$_8$, R$_9$ and R$_{10}$ are independently selected from H and hydrocarbyl,
wherein n and p are independently selected from 0 and 1
Y is (R$_{11}$)$_{1-3}$ wherein each R$_{11}$ is independently selected from NR$_{12}$, CR$_{13}$R$_{14}$, S(=O)$_2$ and C=O, wherein R$_{12}$, R$_{13}$ and R$_{14}$ are independently selected from H and hydrocarbyl Z is selected from (i) six or seven membered ring containing carbon and at least one nitrogen, which may be optionally substituted wherein the substituents may together form further ring fused thereto; and (ii) a —R$_{15}$—NR$_{16}$— group wherein R$_{15}$ is an optionally substituted C$_{1-6}$ alkyl chain and R$_{16}$ is selected from H and hydrocarbyl R$_3$ is selected from

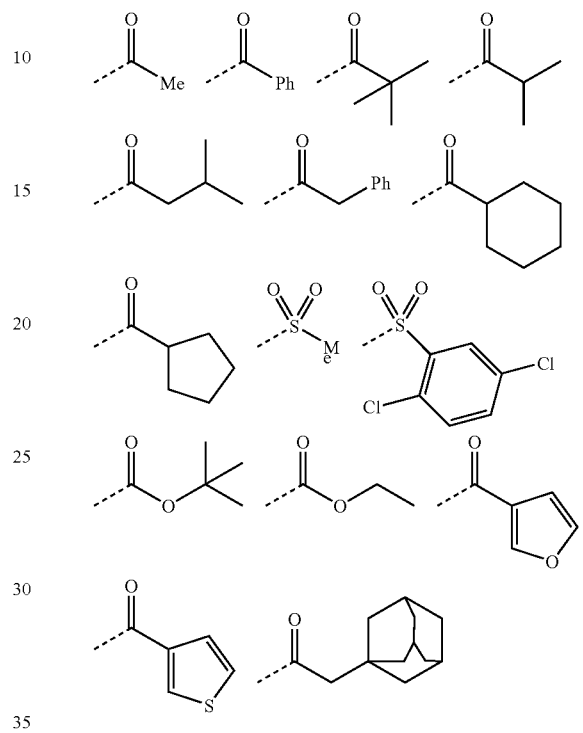

(ii) optionally admixed with a pharmaceutically acceptable carrier, diluent, excipient or adjuvant.
In one aspect the present invention provides a compound for use in medicine wherein the compound is of Formula I

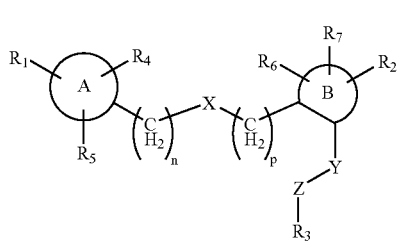

Formula I wherein
each of $R_1$, $R_2$, $R_4$, $R_5$, $R_6$ and $R_7$ are independently selected from (a) H, (b) $R_{17}$, —$OC(R_{17})_3$, —$OCH(R_{17})_2$, —$OCH_2R_{17}$, —$C(R_{17})_3$, —$CH(R_{17})_2$, or —$CH_2R_{17}$ wherein $R_{17}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —$SO_2$-alkyl; and (n) —$N(R_{11})C(O)R_{13}$,
wherein the optional substituents of (d) (e) (f) (h) and (i) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl;

each of rings A and B are selected from five or six membered carbon rings optionally containing one or more hetero atoms selected from N, S, and O and optionally having fused thereto a further ring, X is an optional group selected from O, S, S=O, S(=O)$_2$, C=O, S(=O)$_2$NR$_8$, C=ONR$_9$, NR$_{10}$, wherein R$_8$, R$_9$ and R$_{10}$ are independently selected from H and hydrocarbyl, wherein n and p are independently selected from 0 and 1

Y is (R$_{11}$)$_{1-3}$ wherein each R$_{11}$ is independently selected from NR$_{12}$, CR$_{13}$R$_{14}$, S(=O)$_2$ and C=O, wherein R$_{12}$, R$_{13}$ and R$_{14}$ are independently selected from H and hydrocarbyl Z is selected from (i) six or seven membered ring containing carbon and at least one nitrogen, which may be optionally substituted wherein the substituents may together form further ring fused thereto; and (ii) a —R$_{15}$—NR$_{16}$— group wherein R$_{15}$ is an optionally substituted C$_{1-6}$ alkyl chain and R$_{16}$ is selected from H and hydrocarbyl R$_3$ is selected from

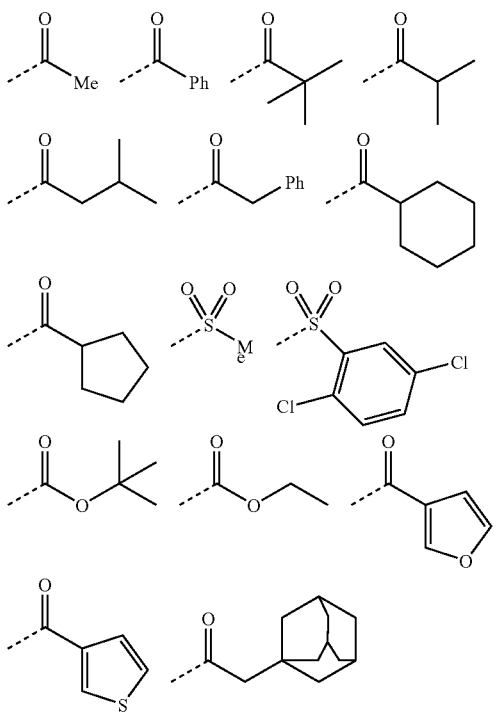

In one aspect the present invention provides a use of a compound in the manufacture of a medicament (i) for use in the therapy of an androgen dependent disease or estrogen dependent disease, or (ii) for use in the therapy of a condition or disease selected from the group consisting of prostate cancer, androgen dependent neoplasms, benign prostatic hyperplasia, prostatic intraepithelial neoplasia, androgenic alopecia, hirsutism, polycystic ovary syndrome and acne; or (iii) for use in the therapy of a condition or disease associated with 17β-HSD (preferably 17β-HSD Type 3); or (iv) for use in the therapy of a condition or disease associated with adverse 17β-HSD (preferably 17β-HSD Type 3) levels; or (v) for modulating 17β-HSD (preferably 17β-HSD Type 3) activity; or (vi) for inhibiting 17β-HSD (preferably 17β-HSD Type 3) activity;

wherein the compound has Formula I

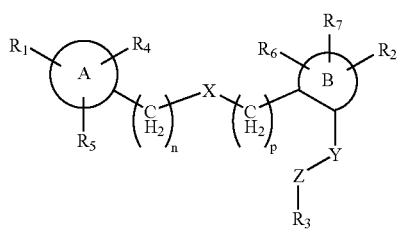

Formula I wherein each of R$_1$, R$_2$, R$_4$, R$_5$, R$_6$ and R$_7$ are independently selected from (a) H, (b) R$_{17}$, —OC(R$_{17}$)$_3$, —OCH(R$_{17}$)$_2$, —OCH$_2$R$_{17}$, —C(R$_{17}$)$_3$, —CH(R$_{17}$)$_2$, or —CH$_2$R$_{17}$ wherein R$_{17}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —SO$_2$-alkyl; and (n) —N(R$_{11}$)C(O)R$_{13}$, wherein the optional substituents of (d) (e) (f) (h) and (i) are selected from the group consisting of: C$_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl;

each of rings A and B are selected from five or six membered carbon rings optionally containing one or more hetero atoms selected from N, S, and O and optionally having fused thereto a further ring, X is an optional group selected from O, S, S=O, S(=O)$_2$, C=O, S(=O)$_2$NR$_8$, C=ONR$_9$, NR$_{10}$, wherein R$_8$, R$_9$ and R$_{10}$ are independently selected from H and hydrocarbyl, wherein n and p are independently selected from 0 and 1

Y is (R$_{11}$)$_{1-3}$ wherein each R$_{11}$ is independently selected from NR$_{12}$, CR$_{13}$R$_{14}$, S(=O)$_2$ and C=O, wherein R$_{12}$, R$_{13}$ and R$_{14}$ are independently selected from H and hydrocarbyl Z is selected from (i) six or seven membered ring containing carbon and at least one nitrogen, which may be optionally substituted wherein the substituents may together form further ring fused thereto; and (ii) a —R$_{15}$—NR$_{16}$— group wherein R$_{15}$ is an optionally substituted C$_{1-6}$ alkyl chain and R$_{16}$ is selected from H and hydrocarbyl R$_3$ is selected from

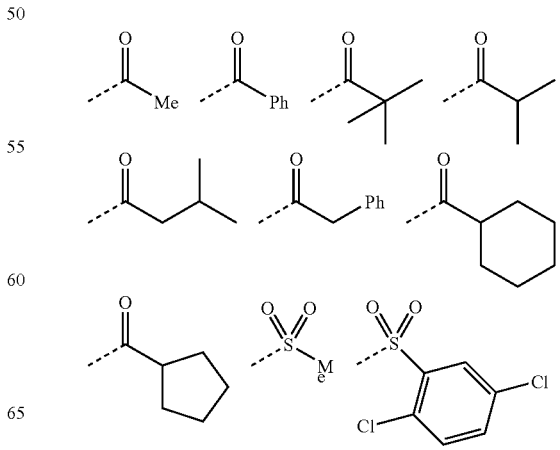

-continued

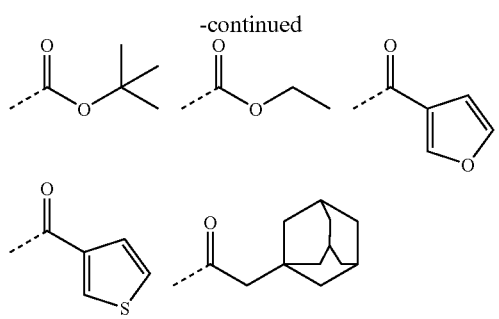

SOME ADVANTAGES

The present invention relates to novel inhibitory compounds of an enzyme involved in the biosynthesis of sex steroids from natural precursors, the 17beta-hydroxysteroid dehydrogenase Type 3 enzyme (17beta-HSD3), to their salts, to pharmaceutical preparations containing these compounds and to processes for the preparation of these compounds. Furthermore, the invention concerns the therapeutic use of said inhibitors, particularly their use in the treatment or prevention of androgen-dependent diseases or disorders, such as diseases or disorders requiring the inhibition of 17beta-HSD Type 3 enzyme, and/or requiring the modulation of the endogenous testosterone concentration. Pharmaceutical use of the inhibitors may reduce the natural production of androgens such as testosterone and dihydrotestosterone, and thereby beneficially treat diseases whose onset or progress is aided by androgenic activity. Because androgens formed by reactions catalyzed by Type 3 enzyme are precursors to estrogens, the invention also has applicability to diseases whose onset or progress is aided by estrogenic activity.

Another advantage of the compounds of the present invention is that they may be potent 17β-HSD inhibitors in vivo.

Some of the compounds of the present invention are also advantageous in that they may be orally active.

DETAILED ASPECTS OF THE PRESENT INVENTION

As previously mentioned, in one aspect the present invention provides a compound having Formula I defined above.

As previously mentioned, in one aspect the present invention provides a pharmaceutical composition comprising
(i) a compound having Formula I defined above
(ii) optionally admixed with a pharmaceutically acceptable carrier, diluent, excipient or adjuvant.

As previously mentioned, in one aspect the present invention provides a compound having Formula I defined above, for use in medicine.

As previously mentioned, in one aspect the present invention provides a use of a compound having Formula I defined above in the manufacture of a medicament for use in the therapy of a condition or disease associated with 17β-HSD.

In one aspect the present invention provides a use of a compound having Formula I defined above in the manufacture of a medicament for use in the therapy of a condition or disease associated with adverse 17β-HSD levels.

In one aspect the present invention provides a use of a compound having Formula I defined above in the manufacture of a pharmaceutical for modulating 17β-HSD activity.

In one aspect the present invention provides a use of a compound having Formula I defined above in the manufacture of a pharmaceutical for inhibiting 17β-HSD activity.

In one aspect the present invention provides a method comprising (a) performing a 17β-HSD assay with one or more candidate compounds having Formula I defined above; (b) determining whether one or more of said candidate compounds is/are capable of modulating 17β-HSD activity; and (c) selecting one or more of said candidate compounds that is/are capable of modulating 17β-HSD activity.

In one aspect the present invention provides a method comprising (a) performing a 17β-HSD assay with one or more candidate compounds having Formula I defined above; (b) determining whether one or more of said candidate compounds is/are capable of inhibiting 17β-HSD activity; and (c) selecting one or more of said candidate compounds that is/are capable of inhibiting 17β-HSD activity.

In one aspect the present invention provides
a compound identified by the above method,
the use of the said compound in medicine,
a pharmaceutical composition comprising the said compound, optionally admixed with a pharmaceutically acceptable carrier, diluent, excipient or adjuvant,
use of the said compound in the manufacture of a medicament for use in the therapy of a condition or disease associated with 17β-HSD, and
use of the said compound in the manufacture of a medicament for use in the therapy of a condition or disease associated with adverse 17β-HSD levels.

For ease of reference, these and further aspects of the present invention are now discussed under appropriate section headings. However, the teachings under each section are not necessarily limited to each particular section.

Preferable Aspects

As previously mentioned, in one aspect the present invention provides a compound In one aspect the present invention provides a compound having Formula I Formula I

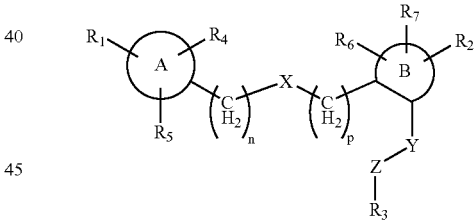

wherein
each of $R_1$, $R_2$, $R_4$, $R_5$, $R_6$ and $R_7$ are independently selected from (a) H, (b) $R_{17}$, —$OC(R_{17})_3$, —$OCH(R_{17})_2$, —$OCH_2R_{17}$, —$C(R_{17})_3$, —$CH(R_{17})_2$, or —$CH_2R_{17}$ wherein $R_{17}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —$SO_2$-alkyl; and (n) —$N(R_{11})C(O)R_{13}$,
wherein the optional substituents of (d) (e) (f) (h) and (i) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl;
each of rings A and B are selected from five or six membered carbon rings optionally containing one or more hetero atoms selected from N, S, and O and optionally having fused thereto a further ring, X is an optional group selected from O, S, S=O, S(=O)$_2$, C=O, S(=O)$_2$NR$_8$, C=ONR$_9$, NR$_{10}$, wherein R$_8$, R$_9$ and R$_{10}$ are independently selected from H and hydrocarbyl, wherein n and p are independently selected from 0 and 1

Y is (R$_{11}$)$_{1-3}$ wherein each R$_{11}$ is independently selected from NR$_{12}$, CR$_{13}$R$_{14}$, S(=O)$_2$ and C=O, wherein R$_{12}$, R$_{13}$ and R$_{14}$ are independently selected from H and hydrocarbyl Z is selected from (i) six or seven membered ring containing carbon and at least one nitrogen, which may be optionally substituted wherein the substituents may together form further ring fused thereto; and (ii) a —R$_{15}$—NR$_{16}$— group wherein R$_{15}$ is an optionally substituted C$_{1-6}$ alkyl chain and R$_{16}$ is selected from H and hydrocarbyl R$_3$ is selected from

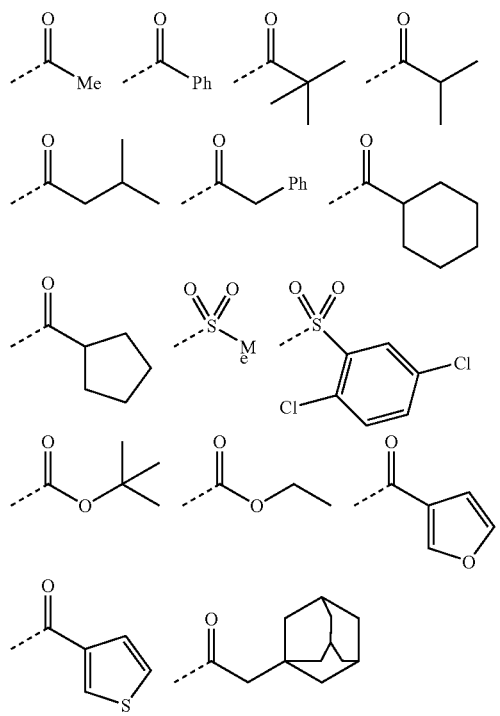

It will be appreciated that the dashed bond of the R3 groups shown herein represent the point of attachment to group Z.

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In some aspects of the present invention, one or more hydrocarbyl groups is independently selected from optionally substituted alkyl group, optionally substituted haloalkyl group, aryl group, alkylaryl group, alkylarylakyl group, and an alkene group.

In some aspects of the present invention, one or more hydrocarbyl groups is independently selected from C$_1$-C$_{10}$ alkyl group, such as C$_1$-C$_6$ alkyl group, and C$_1$-C$_3$ alkyl group. Typical alkyl groups include C$_1$ alkyl, C$_2$ alkyl, C$_3$ alkyl, C$_4$ alkyl, C$_5$ alkyl, C$_7$ alkyl, and C$_8$ alkyl.

In some aspects of the present invention, one or more hydrocarbyl groups is independently selected from aryl groups, alkylaryl groups, alkylarylakyl groups, —(CH$_2$)$_{1-10}$-aryl, —(CH$_2$)$_{1-10}$-Ph, (CH$_2$)$_{1-10}$-Ph-C$_{1-10}$ alkyl, —(CH$_2$)$_{1-5}$-Ph, (CH$_2$)$_{1-5}$-Ph-C$_{1-5}$ alkyl, —(CH$_2$)$_{1-3}$-Ph, (CH$_2$)$_{1-3}$-Ph-C$_{1-3}$ alkyl, —CH$_2$-Ph, and —CH$_2$-Ph-C(CH$_3$)$_3$. The aryl groups may contain a hetero atom. Thus the aryl group or one or more of the aryl groups may be carbocyclic or more may heterocyclic. Typical hetero atoms include O, N and S, in particular N.

In some aspects of the present invention, one or more hydrocarbyl groups is independently selected from —(CH$_2$)$_{1-10}$-cycloalkyl, —(CH$_2$)$_{1-10}$—C$_{3-10}$cycloalkyl, —(CH$_2$)$_{1-7}$—C$_{3-7}$cycloalkyl, —(CH$_2$)$_{1-5}$—C$_{3-5}$cycloalkyl, —(CH$_2$)$_{1-3}$—C$_{3-5}$cycloalkyl, and —CH$_2$—C$_3$cycloalkyl.

In some aspects of the present invention, one or more hydrocarbyl groups is independently selected from alkene groups. Typical alkene groups include C$_1$-C$_{10}$ alkene group, C$_1$-C$_6$ alkene group, C$_1$-C$_3$ alkene group, such as C$_1$, C$_2$, C$_3$, C$_4$, C$_5$, C$_6$, or C$_7$ alkene group. In a preferred aspect the alkene group contains 1, 2 or 3 C=C bonds. In a preferred aspect the alkene group contains 1 C=C bond. In some preferred aspect at least one C=C bond or the only C=C bond is to the terminal C of the alkene chain, that is the bond is at the distal end of the chain to the ring system.

In some aspects of the present invention, one or more hydrocarbyl groups is independently selected from oxyhydrocarbyl groups.

One particular hydrocarbyl group is an oxyhydrocarbyl group. The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula $C_{1-6}O$ (such as a $C_{1-3}O$).

$R_1$-$R_7$

As discussed herein each of $R_1$, $R_2$, $R_4$, $R_5$, $R_6$ and $R_7$ are independently selected from (a) H, (b) $R_{17}$, —$OC(R_{17})_3$, —$OCH(R_{17})_2$, —$OCH_2R_{17}$, —$C(R_{17})_3$, —$CH(R_{17})_2$, or —$CH_2R_{17}$ wherein $R_{17}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —$SO_2$-alkyl; and (n) —$N(R_{11})C(O)R_{13}$, wherein the optional substituents of (d) (e) (f) (h) and (i) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl;

In one preferred aspect each of $R_1$, $R_2$, $R_4$, $R_5$, $R_6$ and $R_7$ is independently selected from (b) $R_{17}$, —$OC(R_{17})_3$, —$OCH(R_{17})_2$, —$OCH_2R_{17}$, —$C(R_{17})_3$, —$CH(R_{17})_2$, or —$CH_2R_{17}$ wherein $R_{17}$ is a halogen; (d) optionally substituted alkyl, (j) hydroxy; (k) alkoxy; (l) aryloxy; and (m) —$SO_2$-alkyl; wherein the optional substituents of (d) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl.

In one preferred aspect each of $R_1$, $R_2$, $R_4$, $R_5$, $R_6$ and $R_7$ is independently selected from (b) $R_{17}$, —$OC(R_{17})_3$, —$OCH(R_{17})_2$, —$OCH_2R_{17}$, —$C(R_{17})_3$, —$CH(R_{17})_2$, or —$CH_2R_{17}$ wherein $R_{17}$ is a halogen; (d) optionally substituted alkyl, (k) alkoxy; and (m) —$SO_2$-alkyl; wherein the optional substituents of (d) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl.

In one preferred aspect each of $R_1$, $R_2$, $R_4$, $R_5$, $R_6$ and $R_7$ is independently selected from (b) $R_{17}$, —$OC(R_{17})_3$, —$OCH(R_{17})_2$, —$OCH_2R_{17}$, —$C(R_{17})_3$, —$CH(R_{17})_2$, or —$CH_2R_{17}$.

In one preferred aspect each of $R_1$, $R_2$, $R_4$, $R_5$, $R_6$ and $R_7$ is independently selected from (d) optionally substituted alkyl, (j) hydroxy; (k) alkoxy; (l) aryloxy; and (m) —$SO_2$-alkyl; wherein the optional substituents of (d) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl.

In one preferred aspect each of $R_1$, $R_2$, $R_4$, $R_5$, $R_6$ and $R_7$ is independently selected from (d) optionally substituted alkyl, (k) alkoxy; and (m) —$SO_2$-alkyl; wherein the optional substituents of (d) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl.

Preferably $R_{17}$ is Cl or F.

In one preferred aspect (b) is Cl, —$OCF_3$, —$OCHF_2$, —$OCH_2F$, —$CF_3$, —$CHF_2$, or —$CH_2F$.

In one preferred aspect each of $R_1$, $R_2$, $R_4$, $R_5$, $R_6$ and $R_7$ is independently selected from Cl, —$OCF_3$, —$OCHF_2$, —$OCH_2F$, —$CF_3$, —$CHF_2$, or —$CH_2F$.

In one preferred aspect (b) is Cl, $CF_3$, $OCF_3$, or —$OCHF_2$.

In one preferred aspect each of $R_1$, $R_2$, $R_4$, $R_5$, $R_6$ and $R_7$ is independently selected from Cl, $CF_3$, $OCF_3$, or —$OCHF_2$.

$R_1$

In one preferred aspect $R_1$ is selected from (b) $R_{17}$, —$OC(R_{17})_3$, —$OCH(R_{17})_2$, —$OCH_2R_{17}$, —$C(R_{17})_3$, —$CH(R_{17})_2$, or —$CH_2R_{17}$ wherein $R_{17}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —$SO_2$-alkyl; and (n) —$N(R_{11})C(O)R_{13}$, wherein the optional substituents of (d) (e) (f) (h) and (i) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl.

In a highly preferred aspect $R_1$ is Cl, $CF_3$, $OCF_3$, or —$OCHF_2$.

$R_2$

In a preferred aspect $R_2$ is selected from (a) H, (b) $R_{17}$, —$OC(R_{17})_3$, —$OCH(R_{17})_2$, —$OCH_2R_{17}$, —$C(R_{17})_3$, —$CH(R_{17})_2$, or —$CH_2R_{17}$ wherein $R_{17}$ is a halogen; (c) —CN; (d) optionally substituted alkyl, (e) optionally substituted heteroalkyl; and (k) alkoxy;

wherein the optional substituents of (d) and (e) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl.

In a preferred aspect $R_2$ is selected from (a) H, (b) $R_{17}$, —$OC(R_{17})_3$, —$OCH(R_{17})_2$, —$OCH_2R_{17}$, —$C(R_{17})_3$, —$CH(R_{17})_2$, or —$CH_2R_{17}$ wherein $R_{17}$ is a halogen; and (d) optionally substituted alkyl, wherein the optional substituents are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl.

In a highly preferred aspect $R_2$ is H, F or Me. In a highly preferred aspect $R_2$ is H or Me. Thus in one highly preferred aspect $R_2$ is Me. In one highly preferred aspect $R_2$ is H. In one highly preferred aspect $R_2$ is F.

$R_3$

As discussed herein group $R_3$ is selected from groups of the formulae

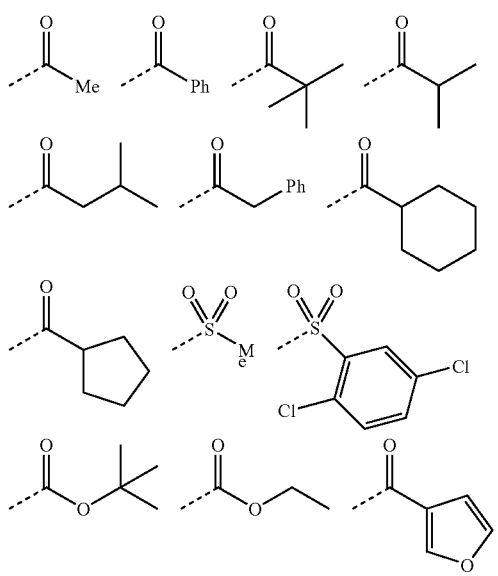

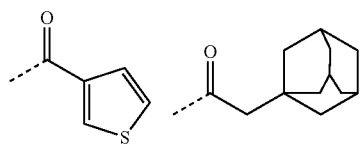
In one aspect $R_3$ is selected from groups of the formulae
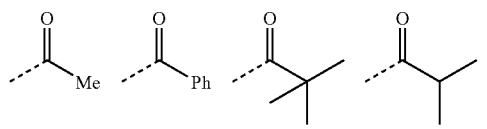
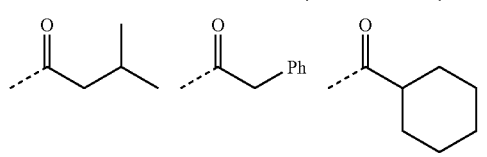
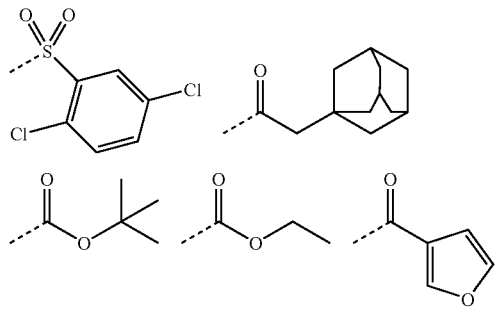
In one aspect $R_3$ is selected from groups of the formulae
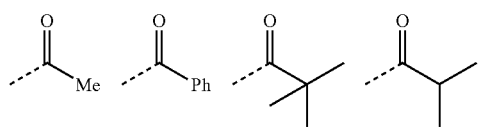
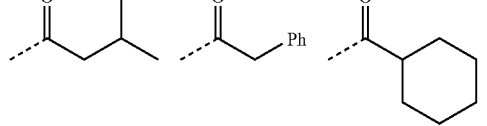
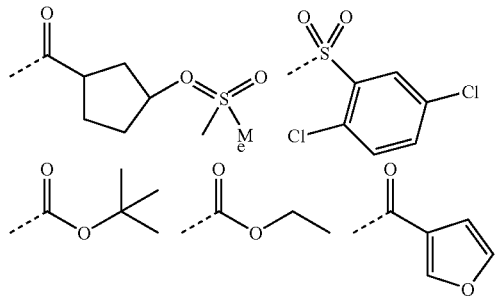
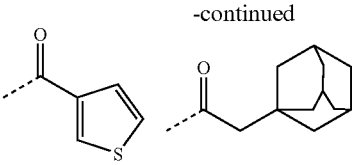
In one aspect $R_3$ is
In one aspect $R_3$ is
In one aspect $R_3$ is
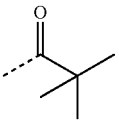
In one aspect $R_3$ is
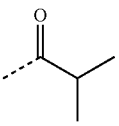
In one aspect $R_3$ is
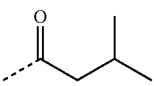
In one aspect $R_3$ is
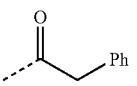
In one aspect $R_3$ is
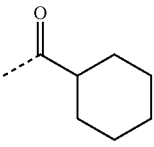

In one aspect $R_3$ is

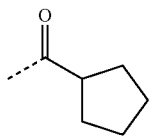

In one aspect $R_3$ is

In one aspect $R_3$ is

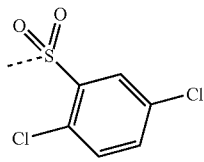

In one aspect $R_3$ is

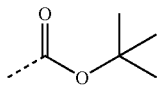

In one aspect $R_3$ is

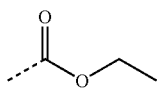

In one aspect $R_3$ is

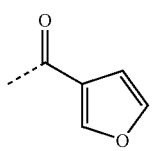

In one aspect $R_3$ is

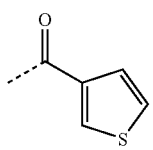

In one aspect $R_3$ is

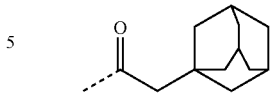

$R_4$-$R_7$

In one preferred aspect $R_4$ is H.
In one preferred aspect $R_5$ is H.
In one preferred aspect $R_6$ is H.
In one preferred aspect $R_7$ is H.
In one preferred highly preferred aspect each of $R_4$, $R_5$, $R_6$ and $R_7$ is H.
Preferably when A is a single ring each of $R_4$ and $R_5$ is H.
In one aspect each of $R_4$ and $R_5$ is H.
In one preferred aspect at least one of $R_4$ and $R_5$, is $R_{17}$, —OC($R_{17}$)$_3$, —OCH($R_{17}$)$_2$, —OCH$_2$$R_{17}$, —C($R_{17}$)$_3$, —CH($R_{17}$)$_2$, or —CH$_2$$R_{17}$ wherein $R_{17}$ is a halogen. In another preferred aspect $R_4$ is $R_{17}$, —OC($R_{17}$)$_3$, —OCH($R_{17}$)$_2$, —OCH$_2$$R_{17}$, —C($R_{17}$)$_3$, —CH($R_{17}$)$_2$, or —CH$_2$$R_{17}$ wherein $R_{17}$ is a halogen, and $R_5$ is H. In these aspects, preferably $R_{17}$ is Cl.
In one preferred highly preferred aspect each of $R_1$ is $C_1$, $R_4$ is $C_1$ and $R_5$ is H.
Preferably when B is a single ring each of $R_6$ and $R_7$ is H.
In one aspect each of $R_6$ and $R_7$ is H.
Preferably when B is a single ring each of $R_2$, $R_6$ and $R_7$ is H.
In one aspect each of $R_2$, $R_6$ and $R_7$ is H.

Rings A and B

It will be appreciated by one skilled in the art that the structures denoted A and B in Formula I and other formulae described herein denote ring systems As discussed herein each of rings A and B are selected from five or six membered carbon rings optionally containing one or more hetero atoms selected from N, S, and O and optionally having fused thereto a further ring. It will be understood that by "five or six membered carbon rings optionally containing one or more hetero atoms selected from N, S, and O" it is meant a ring containing carbon and optionally N, S, and O and wherein the total number of members (both carbon and optional N, S, and O) is five or six.

In one preferred aspect the optional further ring fused to ring A and/or ring B is independently selected from five or six membered carbon rings optionally containing one or more hetero atoms selected from N, S, and O.

Preferably when ring A has fused thereto a further ring (ring A'), ring A together ring A' contains six or more members, preferably from six to ten members.

In one aspect ring A has fused thereto a further ring (ring A') and ring A together with ring A' contains six or more members, preferably from six to ten members.

In one aspect ring A is selected from phenyl, furan, pyrimidine, pyridine, and thiophene. In one aspect ring A is selected from phenyl, pyrimidine, pyridine, and thiophene. Preferably ring A is phenyl.

In one preferred aspect ring A is pyrimidine. In this aspect it is further preferred that the pyrimidine is substituted. In this aspect it is further preferred that the pyrimidine is substituted with group (b) as discussed herein (that is a group selected from $R_{17}$, —OC($R_{17}$)$_3$, —OCH($R_{17}$)$_2$, —OCH$_2$$R_{17}$, —C($R_{17}$)$_3$, —CH($R_{17}$)$_2$, or —CH$_2$$R_{17}$ wherein $R_{17}$ is a halogen).

In one preferred aspect ring A is pyridine. In this aspect it is further preferred that the pyrimidine is substituted. In this aspect it is further preferred that the pyrimidine is unsubstituted.

In one preferred aspect ring A is pyridine. In this aspect it is further preferred that the pyrimidine is substituted. In this aspect it is further preferred that the pyrimidine is unsubstituted.

In one preferred aspect ring A is thiophene. In this aspect it is further preferred that the pyrimidine is substituted. In this aspect it is further preferred that the pyrimidine is unsubstituted.

Preferably when ring B has fused thereto a further ring (ring B'), ring B together ring B' contains six or more members, preferably from six to ten members.

In one aspect ring B has fused thereto a further ring (ring B') and ring B together ring B' contains six or more members, preferably from six to ten members.

In one aspect ring B is selected from phenyl, furan, pyridine, and thiophene. In one aspect ring B is selected from phenyl and pyridines. Preferably ring B is phenyl.

In one preferred aspect ring B is pyrimidine. In this aspect it is further preferred that the pyrimidine is substituted. In this aspect it is further preferred that the pyrimidine is substituted with group (b) as discussed herein (that is a group selected from $R_{17}$, $-OC(R_{17})_3$, $-OCH(R_{17})_2$, $-OCH_2R_{17}$, $-C(R_{17})_3$, $-CH(R_{17})_2$, or $-CH_2R_{17}$ wherein $R_{17}$ is a halogen).

In one preferred aspect ring B is pyridine. In this aspect it is further preferred that the pyrimidine is substituted. In this aspect it is further preferred that the pyrimidine is unsubstituted.

In one preferred aspect ring A and ring B are both pyrimidine. In this aspect it is further preferred that one or each pyrimidine is substituted. In this aspect it is further preferred that one or each pyrimidine is substituted with group (b) as discussed herein (that is a group selected from $R_{17}$, $-OC(R_{17})_3$, $-OCH(R_{17})_2$, $-OCH_2R_{17}$, $-C(R_{17})_3$, $-CH(R_{17})_2$, or $-CH_2R_{17}$ wherein $R_{17}$ is a halogen)

In one preferred aspect ring A and ring B are both phenyl.

X

As discussed herein X is an optional group selected from O, S, S=O, S(=O)$_2$, C=O, S(=O)$_2$NR$_8$, C=ONR$_9$, NR$_{10}$, wherein $R_8$, $R_9$ and $R_{10}$ are independently selected from H and hydrocarbyl.

It will be understood by one skilled in the art that by the term "optional group" it is meant that X represents a bond.

In one aspect X is an optional group selected from O, S, S=O, S(=O)$_2$, S(=O)$_2$NR$_8$, C=ONR$_9$, NR$_{10}$, wherein $R_8$, $R_9$ and $R_{10}$ are independently selected from H and hydrocarbyl.

It will be understood by one skilled in the art that groups S(=O)$_2$NR$_8$ and C=ONR$_9$ may run either way between rings A and B. Thus the groups may be

[Ring A]-(CH$_2$)n-S(=O)$_2$—NR$_8$—(CH$_2$)p-[Ring B]
[Ring A]-(CH$_2$)n-NR$_8$—S(=O)$_2$—(CH$_2$)p-[Ring B]
[Ring A]-(CH$_2$)n—C(=O)—NR$_9$—(CH$_2$)p-[Ring B] or
[Ring A]-(CH$_2$)n—NR$_9$—C(=O)—(CH$_2$)p-[Ring B]

In one aspect X is present and accordingly X is a group selected from O, S, S=O, S(=O)$_2$, C=O, S(=O)$_2$NR$_8$, C=ONR$_9$, NR$_{10}$, wherein $R_8$, $R_9$ and $R_{10}$ are independently selected from H and hydrocarbyl.

In one aspect X is present and accordingly X is a group selected from O, S, S=O, S(=O)$_2$, S(=O)$_2$NR$_8$, C=ONR$_9$, NR$_{10}$, wherein $R_8$, $R_9$ and $R_{10}$ are independently selected from H and hydrocarbyl.

In one aspect X is not present. In this aspect the present invention provides a compound having of the formula

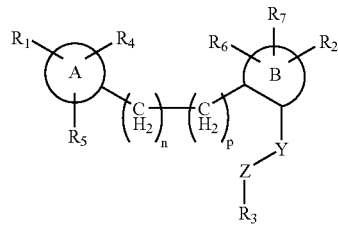

$R_8$, $R_9$ and $R_{10}$

As discussed herein $R_8$, $R_9$ and $R_{10}$ are independently selected from H and hydrocarbyl.

In one preferred aspect $R_8$, $R_9$ and $R_{10}$ are independently selected from H, alkyl and acyl groups.

In one preferred aspect $R_8$, $R_9$ and $R_{10}$ are independently selected from H, $C_1$-$C_{10}$ alkyl (such as $C_1$-$C_6$ alkyl group, and $C_1$-$C_3$ alkyl group, including $C_1$ alkyl, $C_2$ alkyl, $C_3$ alkyl, $C_4$ alkyl, $C_5$ alkyl, $C_7$ alkyl, and $C_8$ alkyl), and $C_1$-$C_{10}$ acyl (such as $C_1$-$C_6$ acyl group, and $C_1$-$C_3$ acyl group, including $C_1$ acyl, $C_2$ acyl, $C_3$ acyl, $C_4$ acyl, $C_5$ acyl, $C_7$ acyl, and $C_8$ acyl).

In one preferred aspect $R_8$, $R_9$ and $R_{10}$ are independently selected from H and Me.

n and p n and p being 1 provide for methylene links between X and ring A or ring B, respectively.

Preferably n and/or p is 0.

Thus in one preferred aspect n is 0. In one preferred aspect p is 0. In one preferred aspect n is 0 and p is 0

Y

Group Y consists of one, two or three $R_{11}$ groups. Each $R_{11}$ group may be the same or different, that is each $R_{11}$ group is independently selected from NR$_{12}$, CR$_{13}$R$_{14}$, S(=O)$_2$ and C=O, wherein $R_{12}$, $R_{13}$ and $R_{14}$ are independently selected from H and hydrocarbyl.

In one aspect Y consists of one $R_{11}$ group. In this aspect Y is $R_{11}$

In one aspect Y consists of two $R_{11}$ groups. In this aspect Y is $(R_{11})_2$ In one aspect Y consists of three $R_{11}$ groups. In this aspect Y is $(R_{11})_3$ In a preferred aspect Y is selected from NR$_{12}$, NR$_{12}$—CR$_{13}$R$_{14}$, NR$_{12}$C=O, CR$_{13}$R$_{14}$—CR$_{13}$R$_{14}$, CR$_{13}$R$_{14}$—NR$_{12}$—CR$_{13}$R$_{14}$, and NR$_{12}$—S(=O)$_2$.

In a highly preferred aspect Y is selected from NR$_{12}$, NR$_{12}$—CR$_{13}$R$_{14}$, and NR$_{12}$C=O.

In one preferred aspect $R_{12}$, $R_{13}$ and $R_{14}$ are independently selected from H, —C(=O)$C_1$-$C_{10}$ alkyl (such as —C(=O)$C_1$-$C_6$ alkyl group, and —C(=O)$C_1$-$C_3$ alkyl group, including —C(=O)$C_1$ alkyl, —C(=O)$C_2$ alkyl, —C(=O)$C_3$ alkyl, —C(=O)$C_4$ alkyl, —C(=O)$C_5$ alkyl, —C(=O)$C_7$ alkyl, and —C(=O)$C_8$ alkyl), and $C_1$-$C_{10}$ alkyl (such as $C_1$-$C_6$ alkyl group, and $C_1$-$C_3$ alkyl group, including $C_1$ alkyl, $C_2$ alkyl, $C_3$ alkyl, $C_4$ alkyl, $C_5$ alkyl, $C_7$ alkyl, and $C_8$ alkyl).

In one preferred aspect $R_{12}$, $R_{13}$ and $R_{14}$ are independently selected from H and $C_1$-$C_{10}$ alkyl (such as $C_1$-$C_6$ alkyl group, and $C_1$-$C_3$ alkyl group, including $C_1$ alkyl, $C_2$ alkyl, $C_3$ alkyl, $C_4$ alkyl, $C_5$ alkyl, $C_7$ alkyl, and $C_8$ alkyl).

Preferably $R_{12}$, $R_{13}$ and $R_{14}$ are independently selected from H, —C(=O)$C_1$-$C_6$ alkyl and $C_{1-6}$ alkyl Preferably $R_{12}$, $R_{13}$ and $R_{14}$ are independently selected from H and $C_{1-6}$ alkyl Preferably $R_{12}$, $R_{13}$ and $R_{14}$ are independently selected from H, —C(=O)Me and Me.

Preferably $R_{12}$, $R_{13}$ and $R_{14}$ are independently selected from H and Me Preferably R$_{12}$ is selected from H, —C(═O)Me and Me.
Preferably R$_{12}$ is selected from H and Me. Preferably R$_{12}$ is H.

As discussed herein the compounds of the present may in the form of a salt. When group Y contains at least one NR$_{12}$, that group may in the form of a salt, for example a chloride salt.

Z

Z is selected from
(i) six or seven membered ring containing carbon and at least one nitrogen, which may be optionally substituted wherein the substituents may together form further ring fused thereto; and
(ii) a —R$_{15}$—NR$_{16}$— group wherein R$_{15}$ is an optionally substituted C$_{1-6}$ alkyl chain and R$_{16}$ is selected from H and hydrocarbyl.

In one aspect Z is a six or seven membered ring containing carbon and at least one nitrogen, which may be optionally substituted wherein the substituents may together form further ring fused thereto; and Preferably the six or seven membered ring containing carbon and at least one nitrogen of Z is selected from groups of the formula

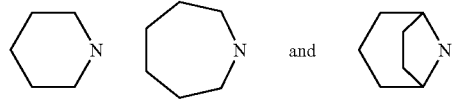

In one preferred aspect Z is selected from groups of the formula

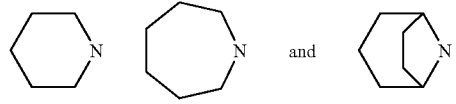

Preferably the six or seven membered ring containing carbon and at least one nitrogen of Z is selected from groups of the formula

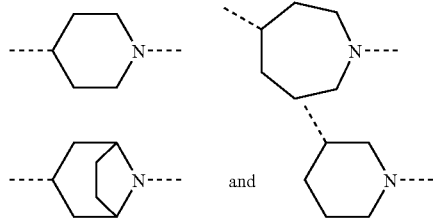

It will be appreciated that the dashed bonds represent the points of attachment.

Preferably the six or seven membered ring containing carbon and at least one nitrogen of Z is selected from groups of the formula

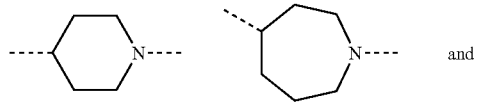

In one preferred aspect Z is selected from groups of the formula

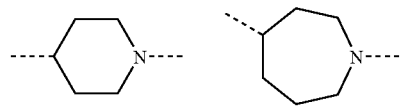

In one preferred aspect Z is selected from groups of the formula

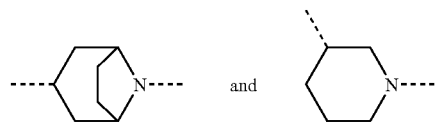

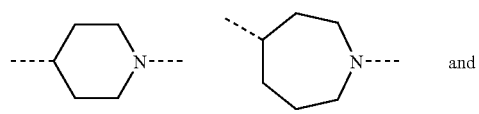

As discussed herein the six or seven membered ring containing carbon and at least one nitrogen may be optionally substituted. Suitable optional substituents may be selected from the group consisting of: C$_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl.

When the substituents are not fused to form a further ring preferred substituents are C$_{1-6}$ alkyl and aryl. Particularly preferred are -Phenyl, —CH$_2$CH$_2$CH$_3$, —CH(CH$_3$)$_2$ and —CH$_3$.

As discussed herein the optional substituents may together form further ring fused thereto. In this aspect Z may be selected from groups of the formula

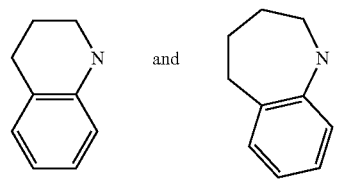

In one preferred aspect Z is selected from groups of the formula

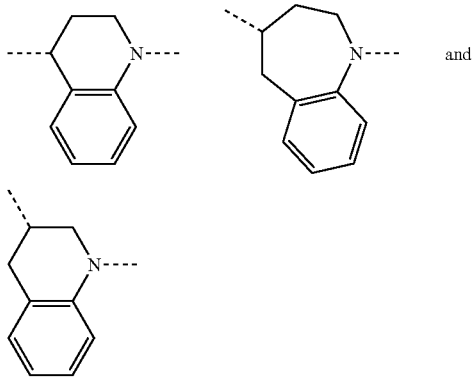

It will be appreciated that the dashed bonds represent the points of attachment.

In one aspect Z is a —$R_{15}$—$NR_{16}$— group wherein $R_{15}$ is an optionally substituted $C_{1-6}$ alkyl chain and $R_{16}$ is selected from H and hydrocarbyl.

The optionally substituted $C_{1-6}$ alkyl chain may be substituted with any suitable substituents. Typically if substituted it will be substituted with halogen or alkyl, such as $C_1$-$C_{10}$ alkyl, $C_1$-$C_6$ alkyl group, and $C_1$-$C_3$ alkyl group, including $C_1$ alkyl, $C_2$ alkyl, $C_3$ alkyl, $C_4$ alkyl, $C_5$ alkyl, $C_7$ alkyl, and $C_8$ alkyl.

Preferably $R_{15}$ is a $C_{1-6}$ alkyl chain optionally substituted with halogen or $C_{1-3}$ alkyl and $R_{16}$ is selected from H and hydrocarbyl.

In one preferred aspect Z is a —$R_{15}$—$NR_{16}$— group wherein $R_{15}$ is a $C_{1-6}$ alkyl chain optionally substituted with halogen or $C_{1-3}$ alkyl and $R_{16}$ is selected from H and hydrocarbyl.

$R_{16}$ may be selected from H and hydrocarbyl. The hydrocarbyl group is as defined herein such as an alkyl group, and more preferably $C_1$-$C_{10}$ alkyl such as $C_1$-$C_6$ alkyl group, and $C_1$-$C_3$ alkyl group, including $C_1$ alkyl, $C_2$ alkyl, $C_3$ alkyl, $C_4$ alkyl, $C_5$ alkyl, $C_7$ alkyl, and $C_8$ alkyl.

Preferred Aspects

In a preferred aspect the compound of the present invention is a compound having Formula II

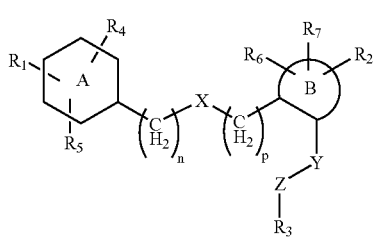
Formula II wherein each of ring A, ring B, $R_1$ to $R_7$, X, Y, Z, n and p are as defined herein.

In a preferred aspect the compound of the present invention is a compound having Formula III

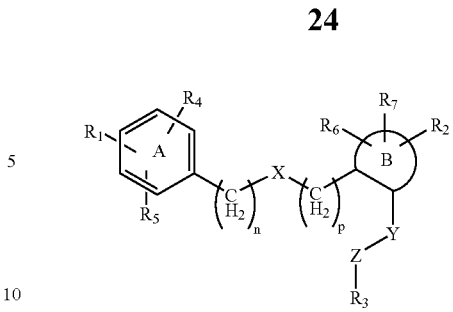
Formula III wherein each of ring A, ring B, $R_1$ to $R_7$, X, Y, Z, n and p are as defined herein.

In a preferred aspect the compound of the present invention is a compound having Formula IV

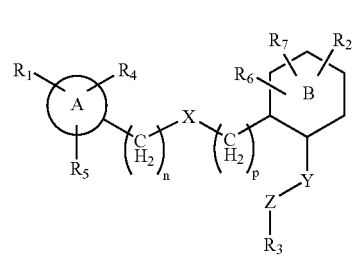
Formula IV wherein each of ring A, ring B, $R_1$ to $R_7$, X, Y, Z, n and p are as defined herein.

In a preferred aspect the compound of the present invention is a compound having Formula IVa

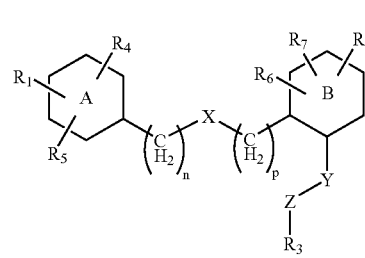
Formula IVa wherein each of ring A, ring B, $R_1$ to $R_7$, X, Y, Z, n and p are as defined herein.

In a preferred aspect the compound of the present invention is a compound having Formula IVb

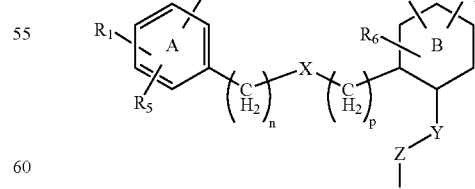
Formula IVb wherein each of ring A, ring B, $R_1$ to $R_7$, X, Y, Z, n and p are as defined herein.

In a preferred aspect the compound of the present invention is a compound having Formula V

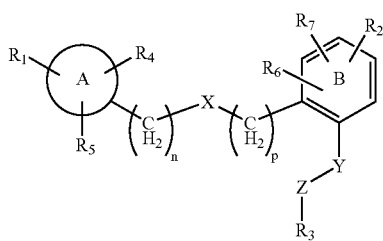

Formula V wherein each of ring A, ring B, $R_1$ to $R_7$, X, Y, Z, n and p are as defined herein.

In a preferred aspect the compound of the present invention is a compound having Formula Va

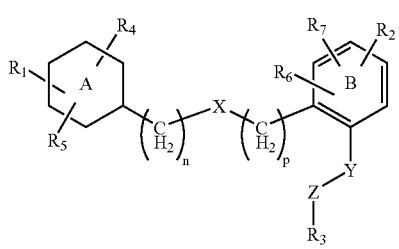

Formula Va wherein each of ring A, ring B, $R_1$ to $R_7$, X, Y, Z, n and p are as defined herein.

In a preferred aspect the compound of the present invention is a compound having Formula VI

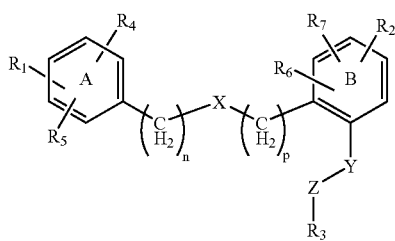

Formula VI wherein each of ring A, ring B, $R_1$ to $R_7$, X, Y, Z, n and p are as defined herein.

In a preferred aspect the compound of the present invention is a compound having Formula VII

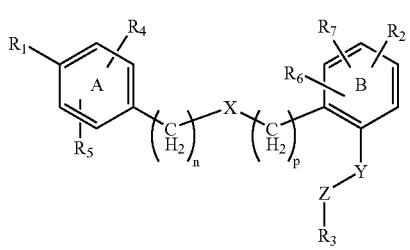

Formula VII wherein each of ring A, ring B, $R_1$ to $R_7$, X, Y, Z, n and p are as defined herein.

In a preferred aspect the compound of the present invention is a compound having Formula VII

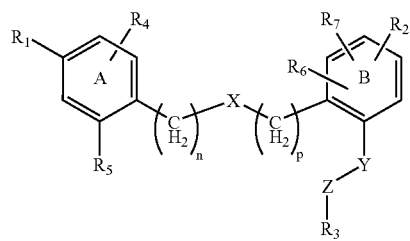

Formula VII wherein each of ring A, ring B, $R_1$ to $R_7$, X, Y, Z, n and p are as defined herein.

In a preferred aspect the compound of the present invention is a compound having Formula VIII

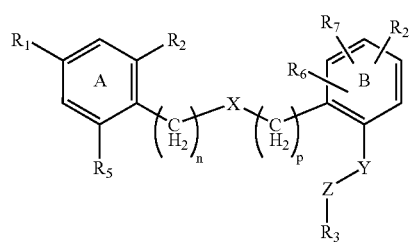

Formula VIII wherein each of ring A, ring B, $R_1$ to $R_7$, X, Y, Z, n and p are as defined herein.

In a preferred aspect the compound of the present invention is a compound having Formula IX

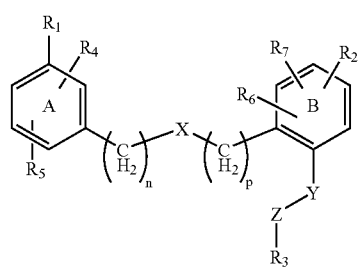

Formula IX wherein each of ring A, ring B, $R_1$ to $R_7$, X, Y, Z, n and p are as defined herein.

In a preferred aspect the compound of the present invention is a compound having Formula X

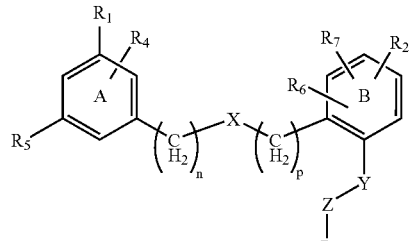

Formula X wherein each of ring A, ring B, $R_1$ to $R_7$, X, Y, Z, n and p are as defined herein.

In a preferred aspect the compound of the present invention is a compound having Formula XI

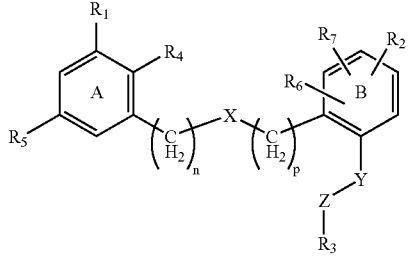

Formula XI wherein each of ring A, ring B, $R_1$ to $R_7$, X, Y, Z, n and p are as defined herein.

In a preferred aspect the compound of the present invention is a compound having Formula VIII or Formula XI.

In a preferred aspect the compound of the present invention is a compound having Formula XII

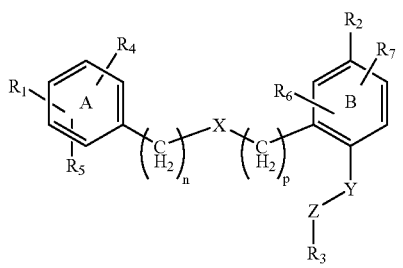

Formula XII wherein each of ring A, ring B, $R_1$ to $R_7$, X, Y, Z, n and p are as defined herein.

In a preferred aspect the compound of the present invention is a compound having Formula XIII

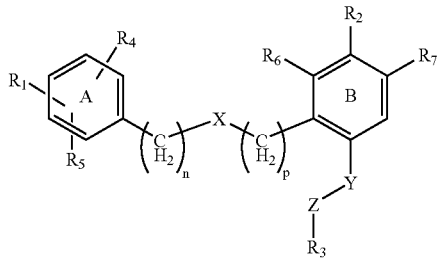

Formula XIII wherein each of ring A, ring B, $R_1$ to $R_7$, X, Y, Z, n and p are as defined herein.

In a preferred aspect the compound of the present invention is a compound having Formula XIV

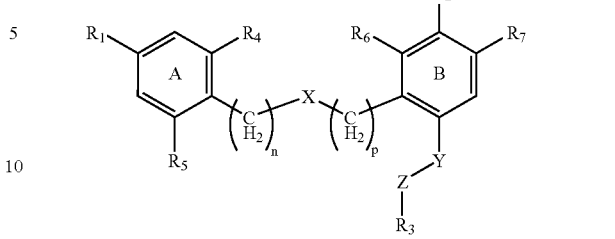

Formula XIV wherein each of ring A, ring B, $R_1$ to $R_7$, X, Y, Z, n and p are as defined herein.

In a preferred aspect the compound of the present invention is a compound having Formula XV

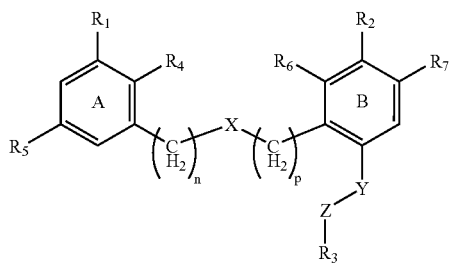

Formula XV wherein each of ring A, ring B, $R_1$ to $R_7$, X, Y, Z, n and p are as defined herein.

In a preferred aspect the compound of the present invention is a compound having Formula XVI

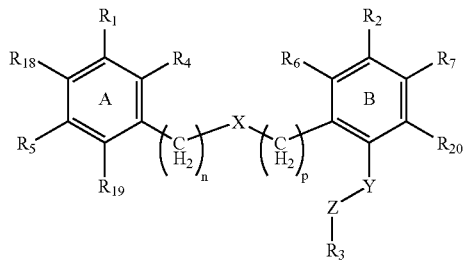

Formula XVI wherein each of ring A, ring B, $R_1$ to $R_7$, X, Y, Z, n and p are as defined herein and $R_{18}$, $R_{19}$ and $R_{20}$ are independently selected from (a) H, (b) $R_{17}$, —OC($R_{17}$)$_3$, —OCH($R_{17}$)$_2$, —OCH$_2$$R_{17}$, —C($R_{17}$)$_3$, —CH($R_{17}$)$_2$, or —CH$_2$$R_{17}$ wherein $R_{17}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —SO$_2$-alkyl; and (n) —N($R_{11}$)C(O)$R_{13}$, wherein the optional substituents of (d) (e) (f) (h) and (i) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl;

Preferably $R_{18}$ and/or $R_{19}$ and/or $R_{20}$ are H. Preferably $R_{18}$, $R_{19}$ and $R_{20}$ are H.

In a preferred aspect the compound of the present invention is a compound having Formula XIV or Formula XV.

It will be understood by one skilled in the art that requirement that each of rings A and B are carbon rings optionally containing one or more hetero atoms selected from N, S, and O and optionally having fused thereto a further ring applies to each of Formulae II to XV. In one preferred aspect in each of Formulae II to XV rings A and B contain only carbon atoms. In one preferred aspect in each of Formulae II to XV rings A and B do not have fused thereto a further ring. In one preferred aspect in each of Formulae II to XV rings A and B contain only carbon atoms and do not have fused thereto a further ring.

In a highly preferred aspect the compound is selected from the following compounds

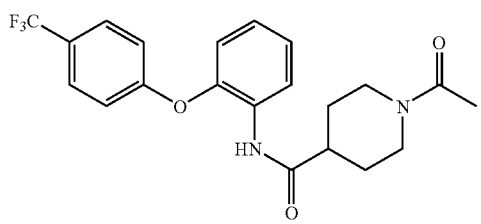
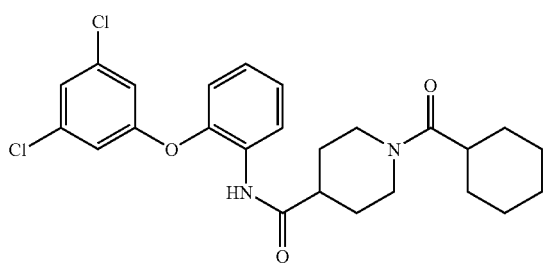
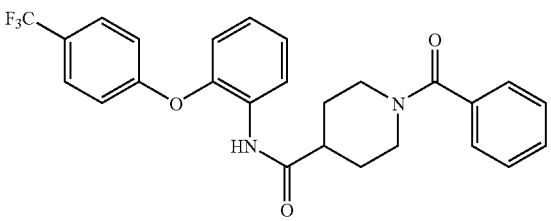
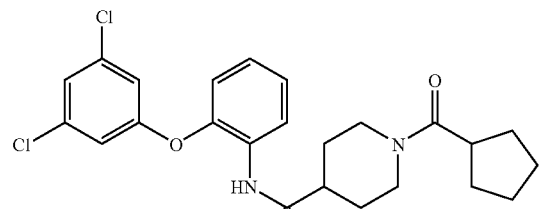
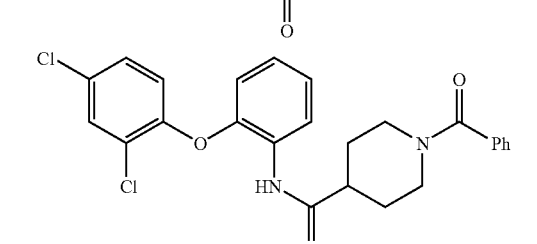

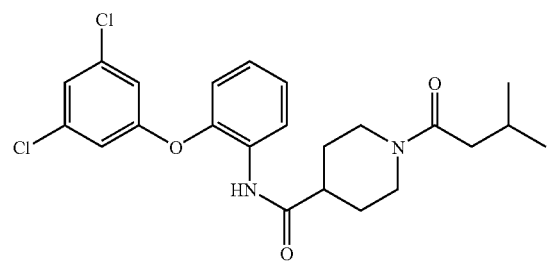
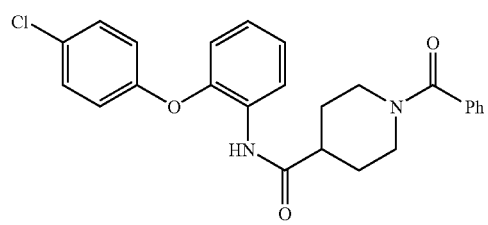
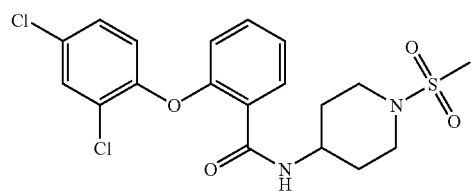
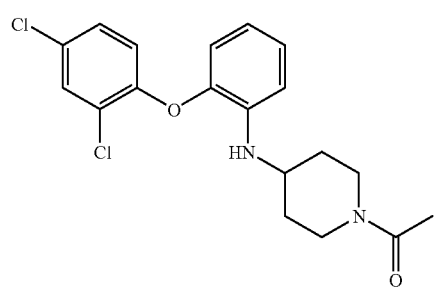
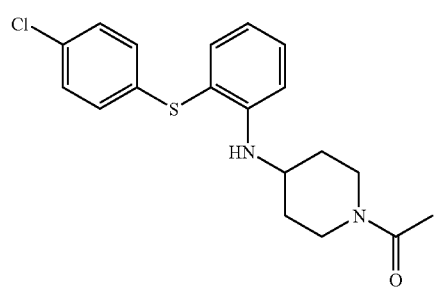
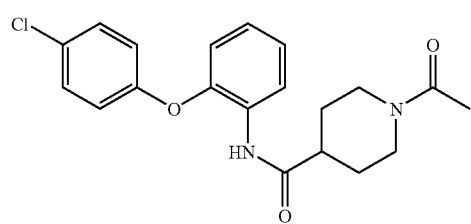
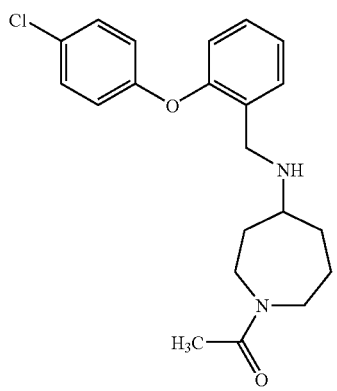
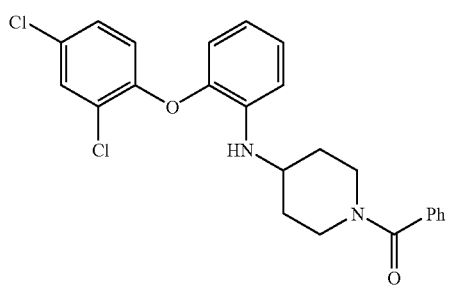
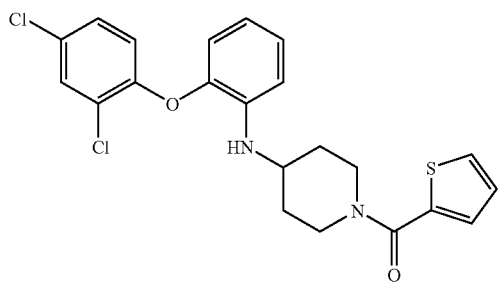
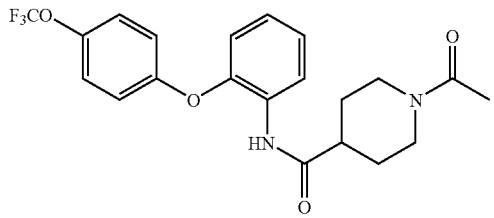
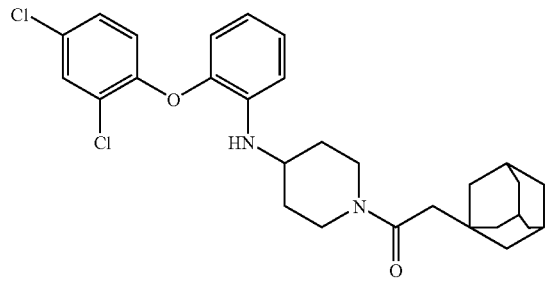
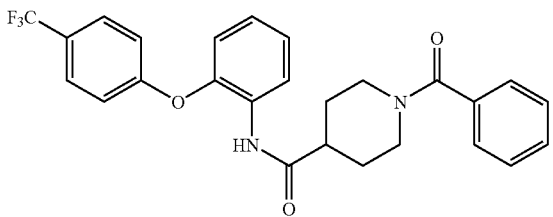

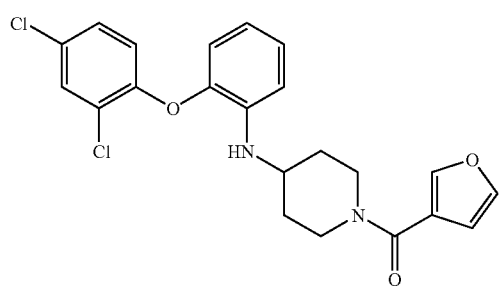
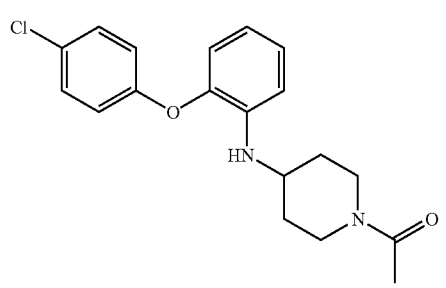
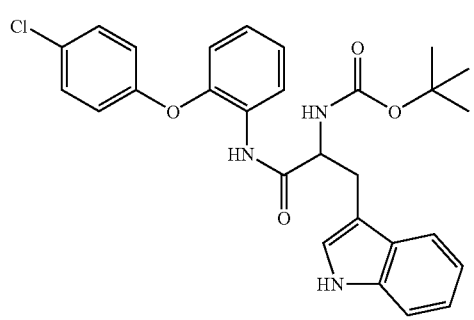
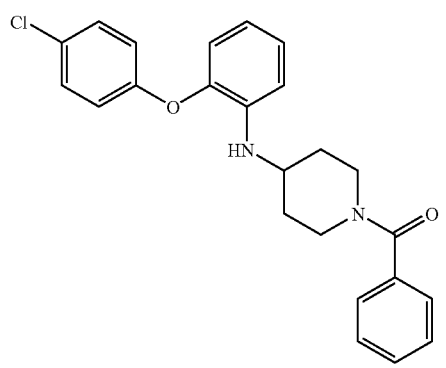
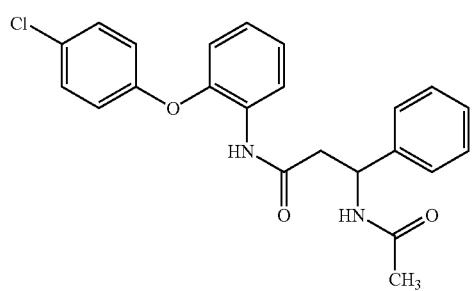
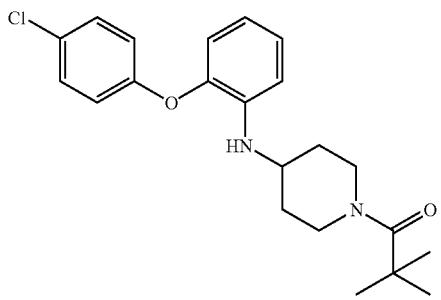
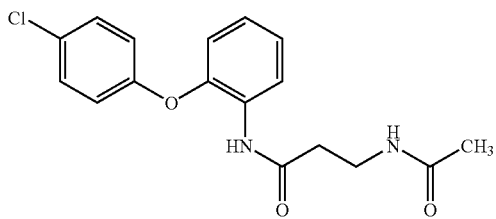
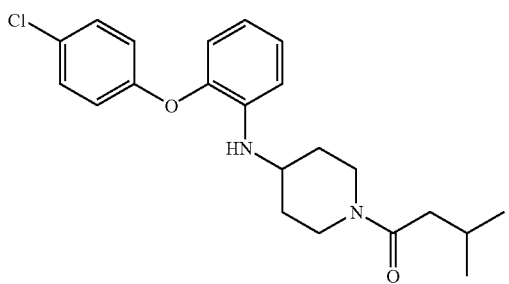
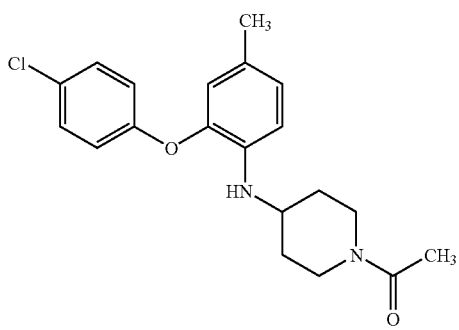
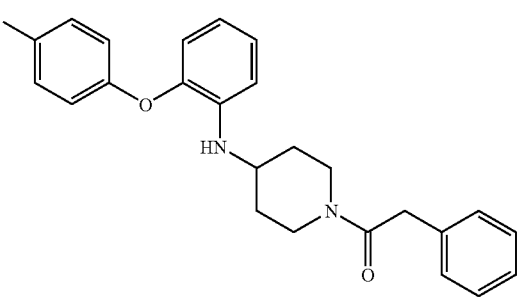
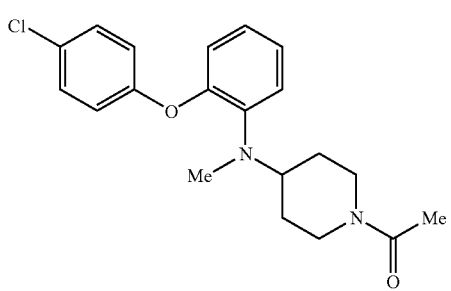

35
-continued
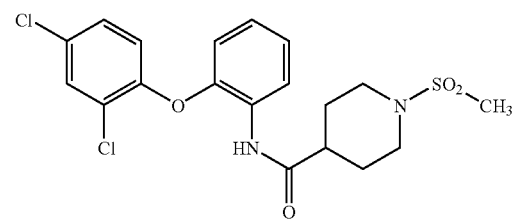
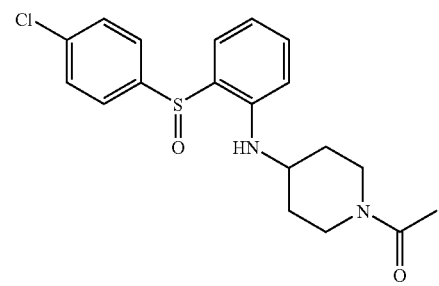
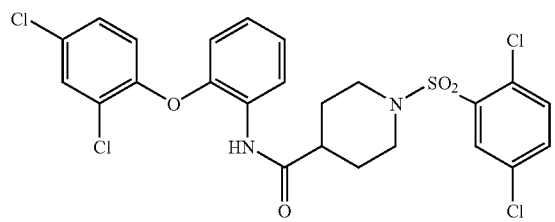
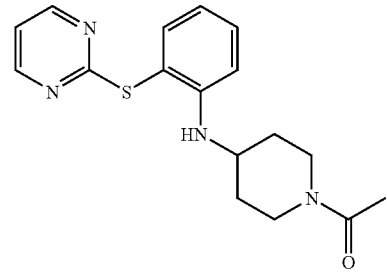
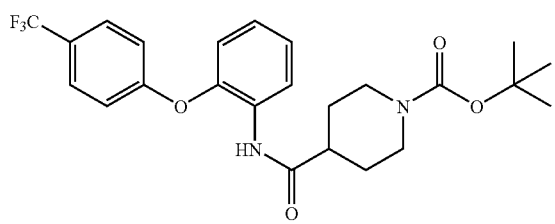
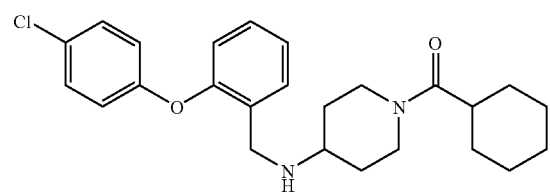
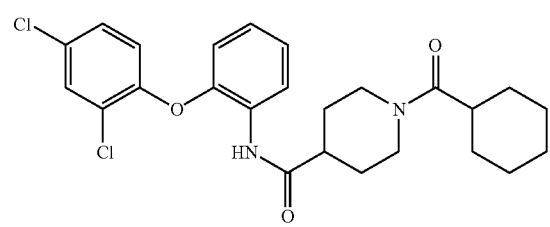
36
-continued
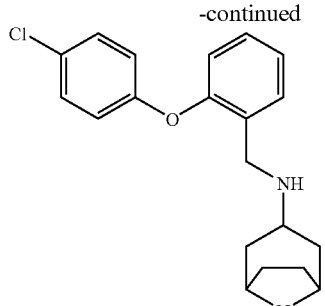
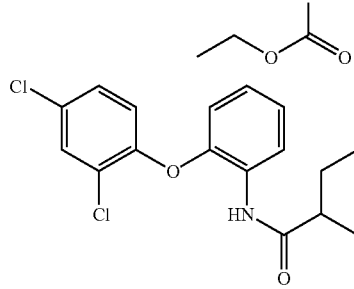
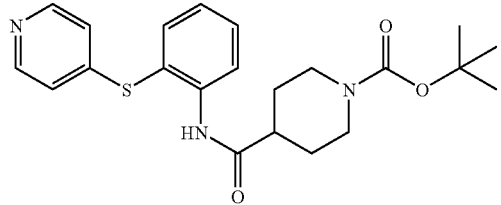
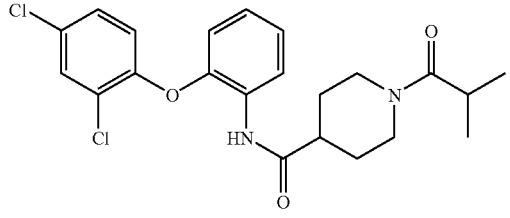
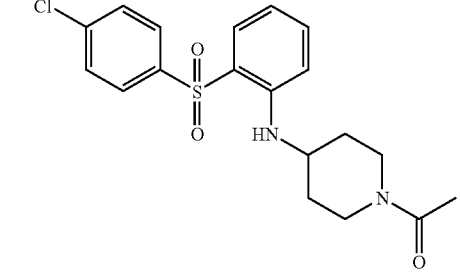
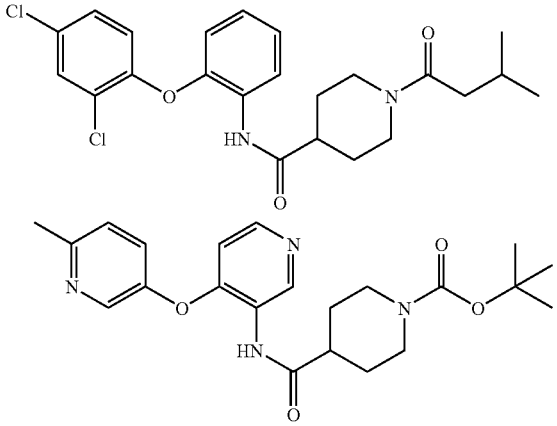

37
-continued
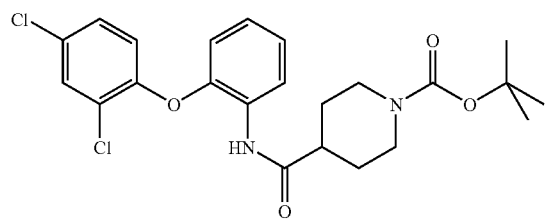
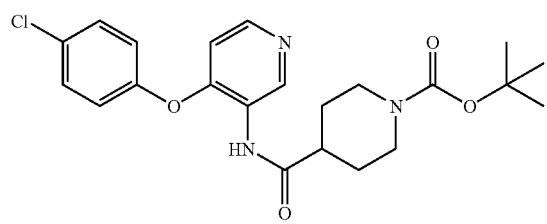
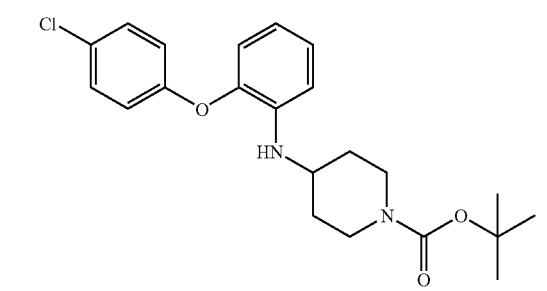
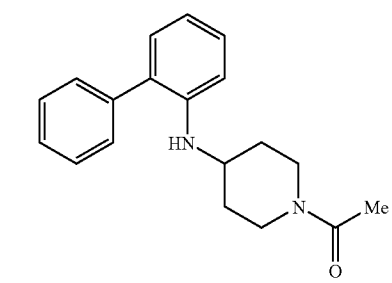
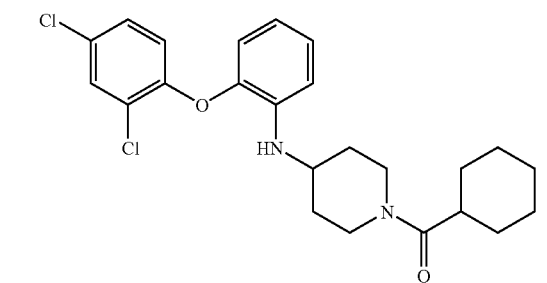
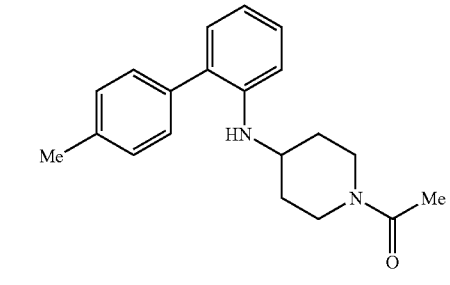
38
-continued
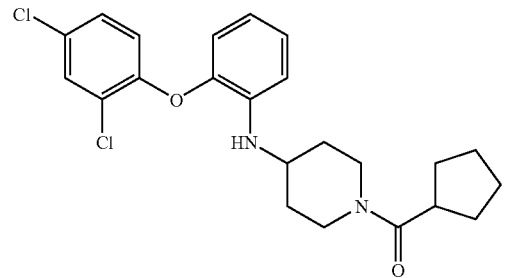
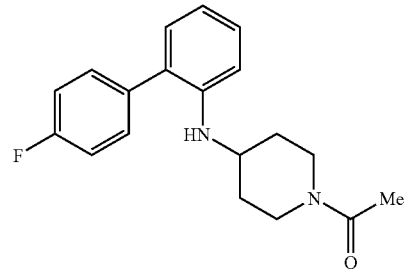
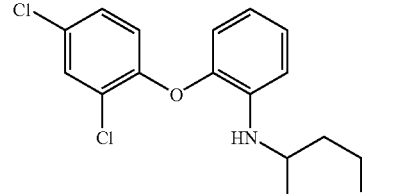
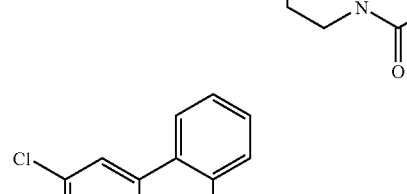
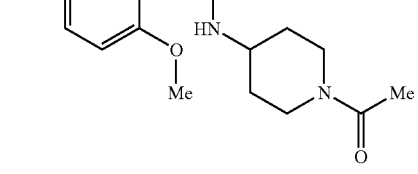
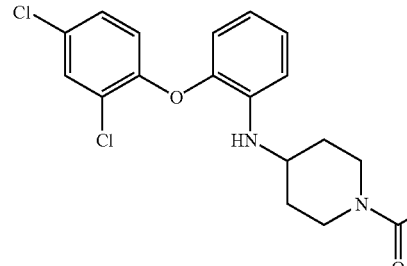
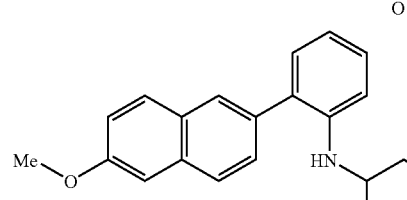

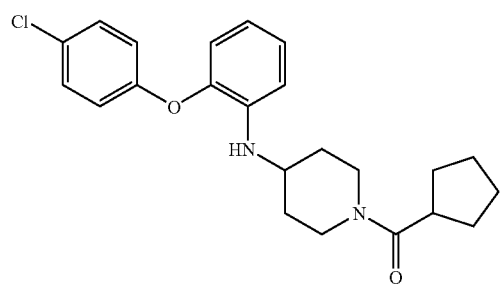
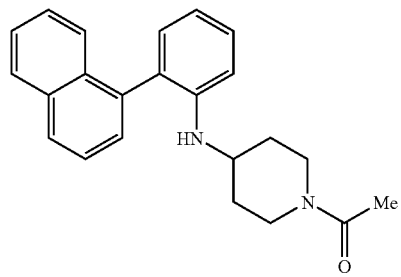
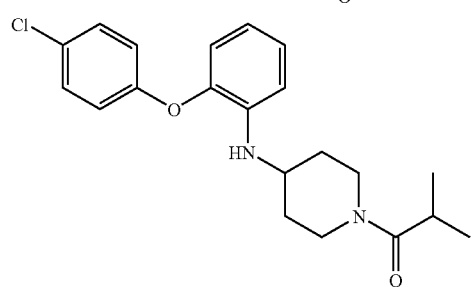
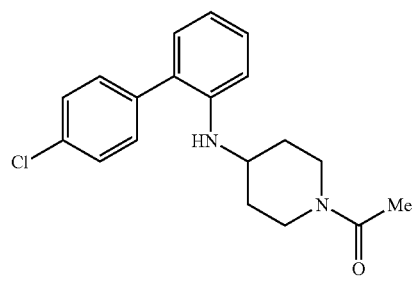
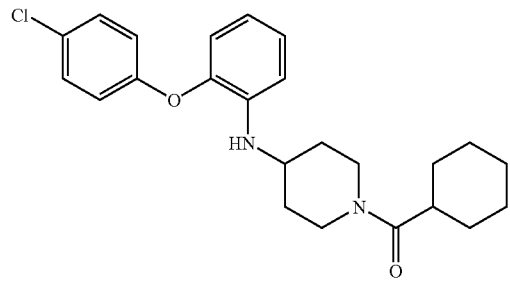
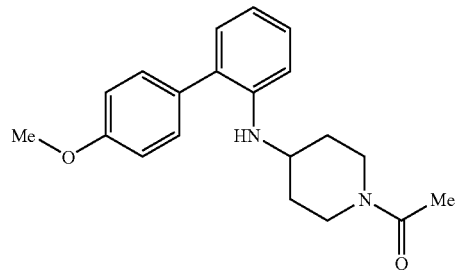
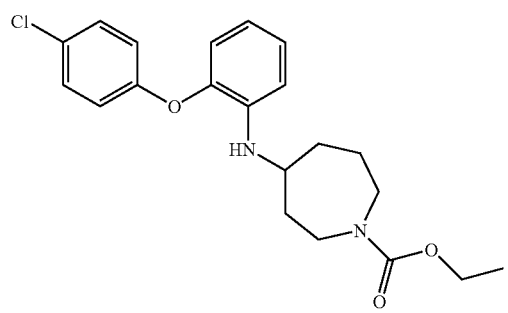
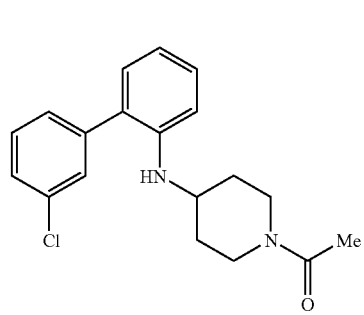
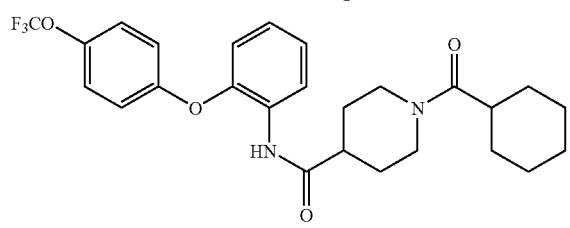
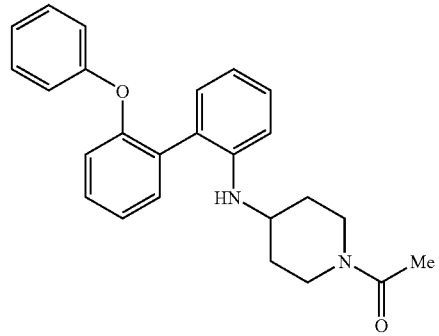
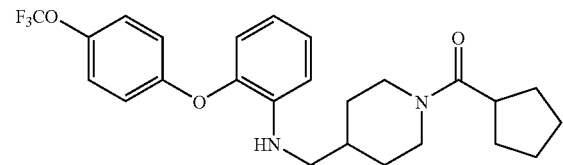
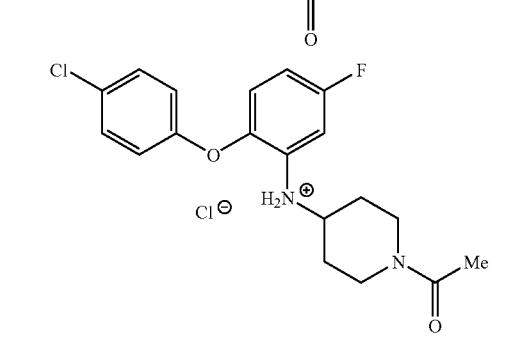
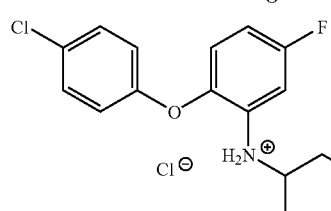
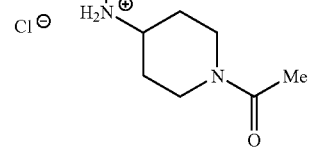

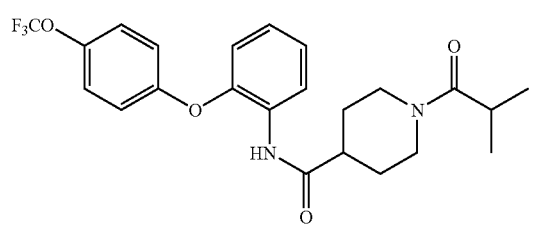
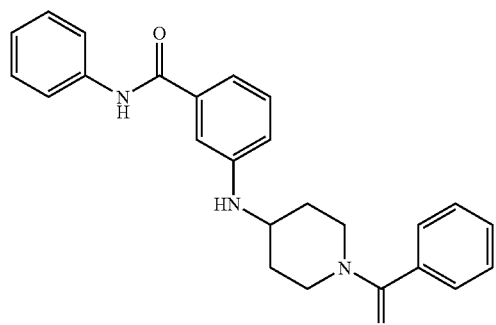
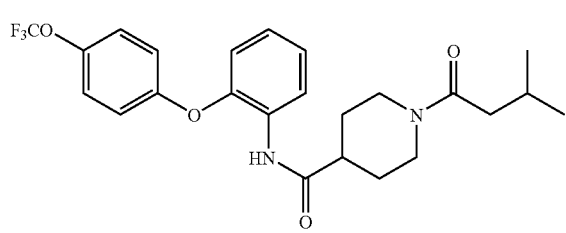
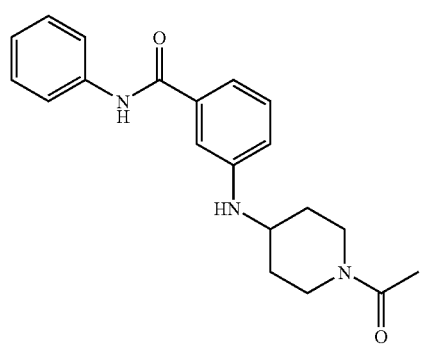
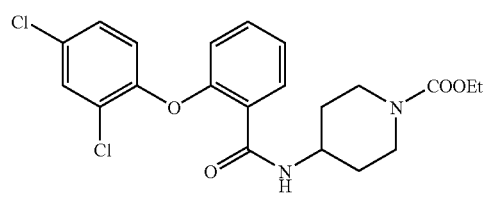
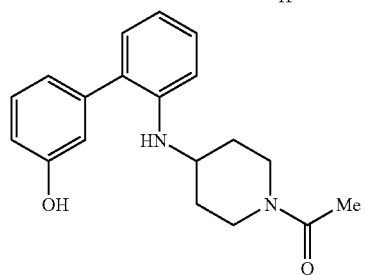
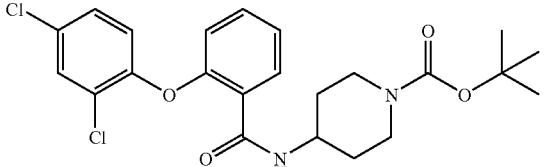
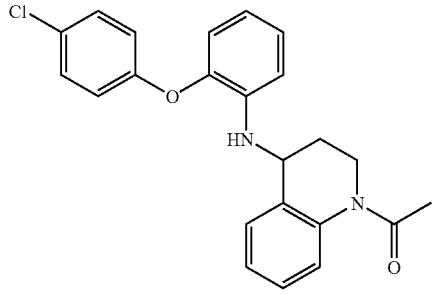
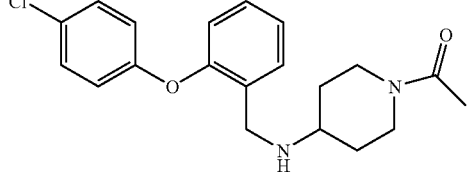
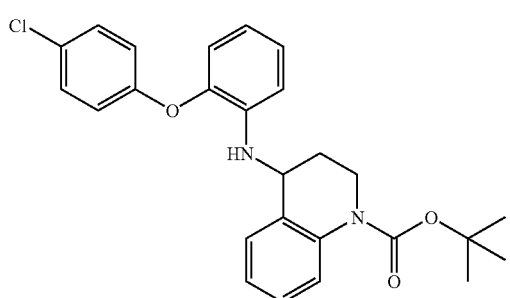
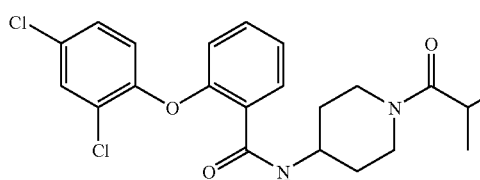
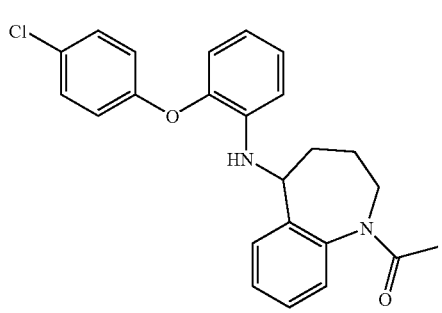
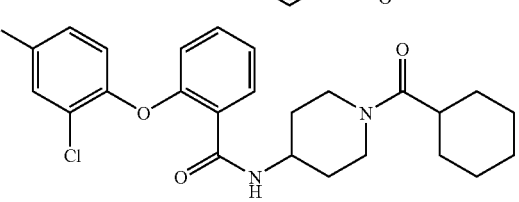

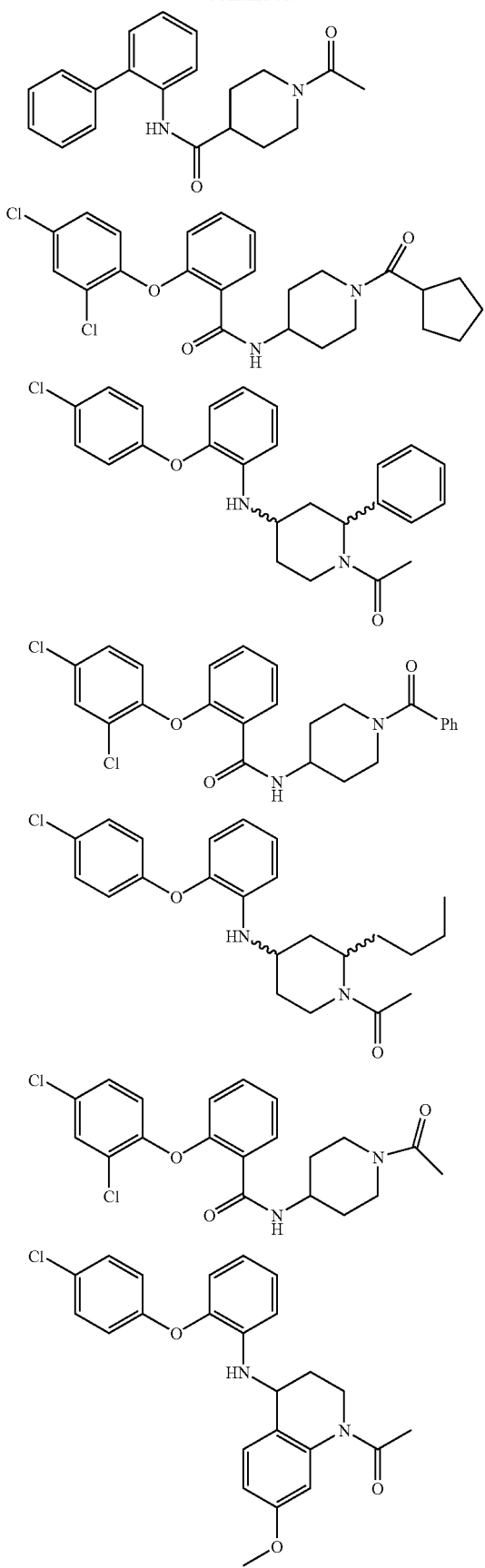
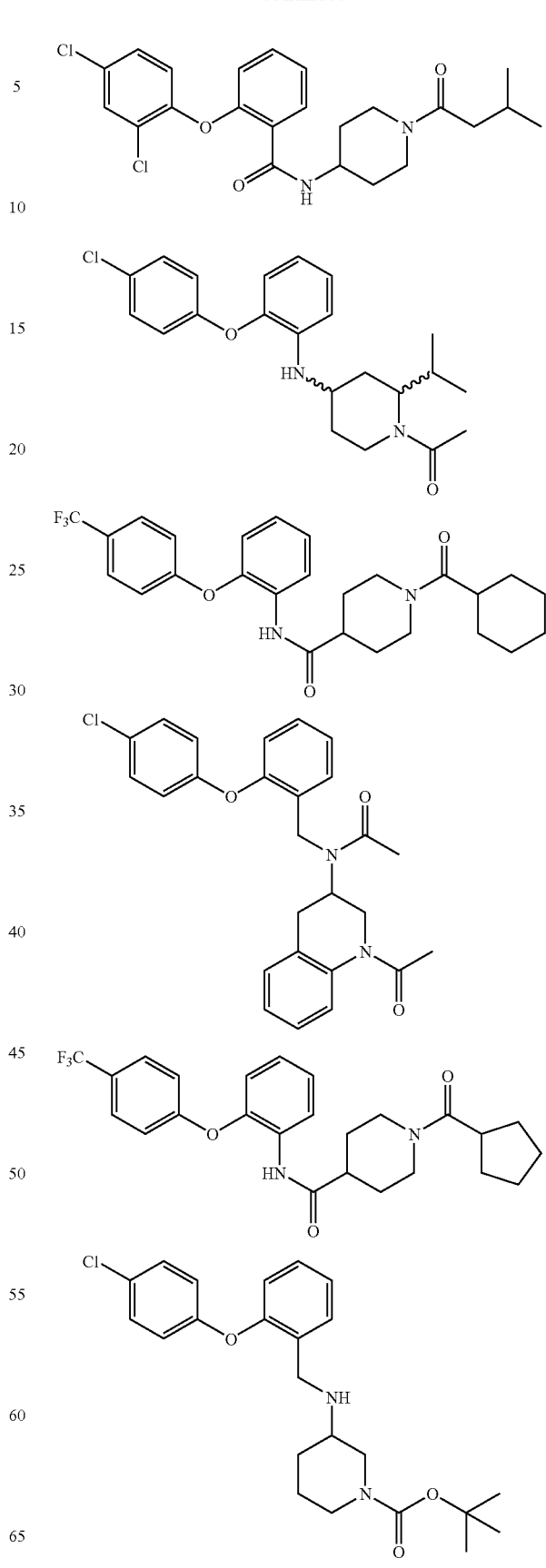

-continued
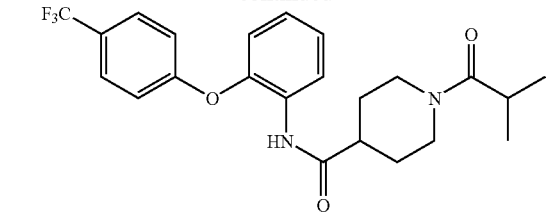
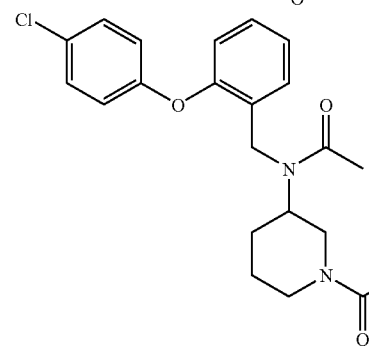
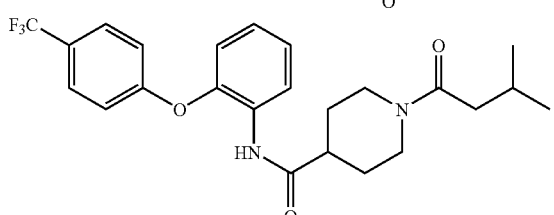
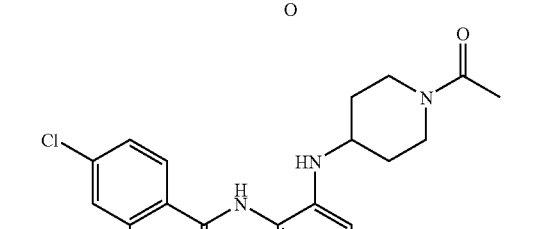
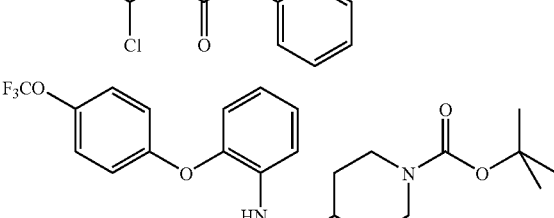
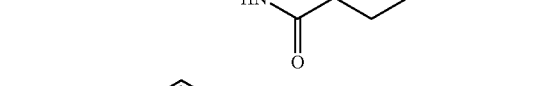
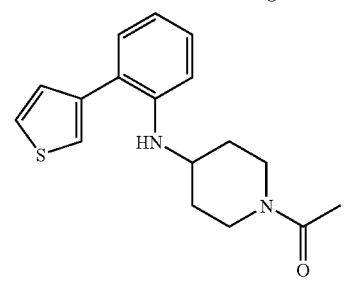
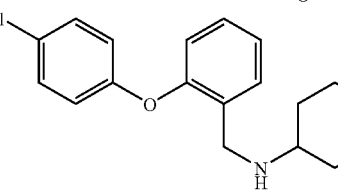
-continued
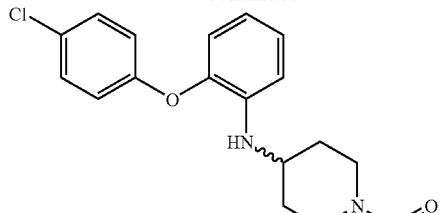
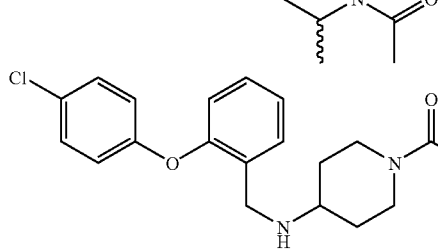
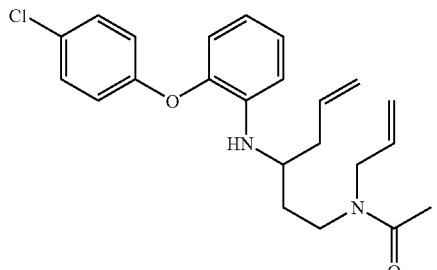
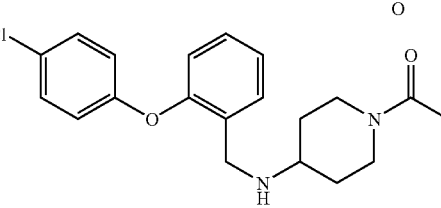
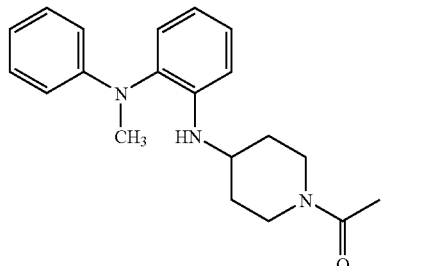
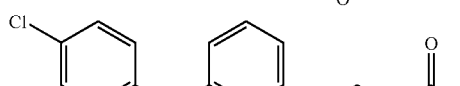
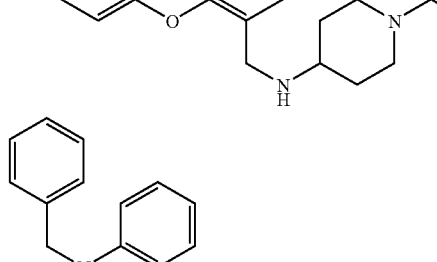
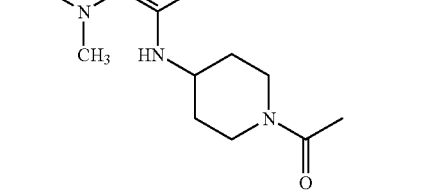

-continued

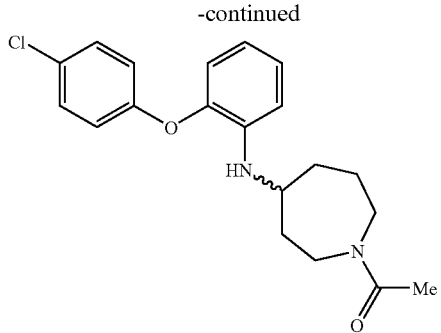

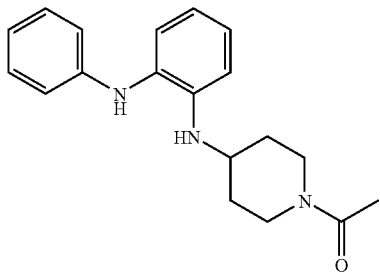

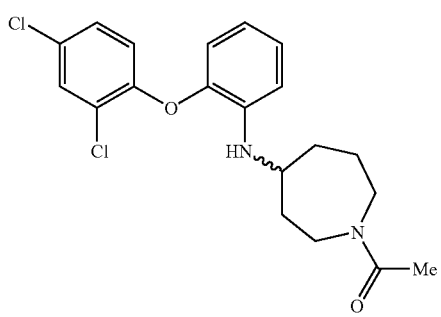

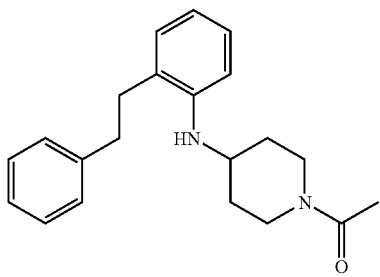

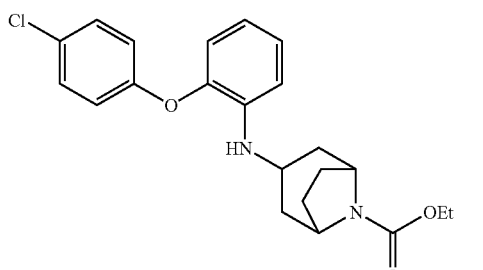

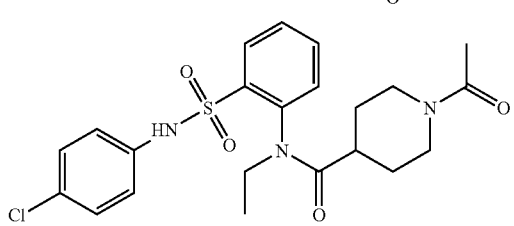

-continued

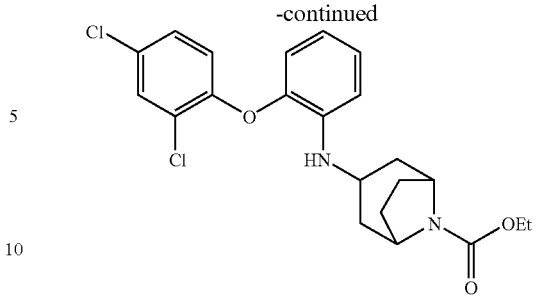

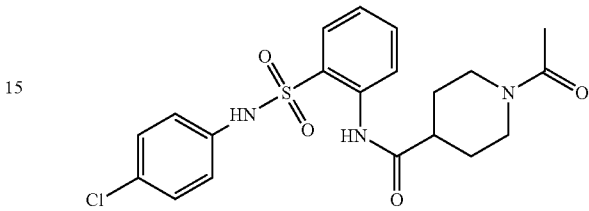

Further Aspects

For some applications, preferably the compounds have a reversible action.

For some applications, preferably the compounds have an irreversible action.

The compounds of the present invention may be in the form of a salt.

The present invention also covers novel intermediates that are useful to prepare the compounds of the present invention. For example, the present invention covers novel alcohol precursors for the compounds. The present invention also encompasses a process comprising precursors for the synthesis of the compounds of the present invention.

The compound of the present invention may have substituents other than those of the ring systems show herein. Furthermore the ring systems herein are given as general formulae and should be interpreted as such. The absence of any specifically shown substituents on a given ring member indicates that the ring member may substituted with any moiety of which H is only one example. Each ring system may contain one or more degrees of unsaturation, for example is some aspects one or more rings of a ring system is aromatic. Each ring system may be carbocyclic or may contain one or more hetero atoms.

The compound of the invention, in particular the ring systems of the compound of the invention may contain substituents other than those show herein. By way of example, these other substituents may be one or more of: one or more halo groups, one or more groups, one or more hydroxy groups, one or more amino groups, one or more sulphur containing group(s), one or more hydrocarbyl group(s)—such as an oxyhydrocarbyl group.

In general terms the ring systems of the present compounds may contain a variety of non-interfering substituents. In particular, the ring systems may contain one or more hydroxy, alkyl especially lower ($C_1$-$C_6$)alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$)alkoxy, e.g. methoxy, ethoxy, propoxy etc., alkinyl, e.g. ethinyl, or halogen, e.g. fluoro substituents.

Hydroxysteroid Dehydrogenase

17β Hydroxysteroid dehydrogenase may be referred to as "17β-HSD" for short.

In some aspects of the invention 17β-HSD is preferably 17β-HSD Type 3.

Hydroxysteroid Dehydrogenase Inhibition

It is believed that some disease conditions associated with 17β-HSD activity are due to conversion of 4-androstene-3,17-one (A) to testosterone (T). In disease conditions associated with 17β-HSD activity, it would be desirable to inhibit 17β-HSD activity and in particular 17β-HSD3 activity.

Here, the term "inhibit" includes reduce and/or eliminate and/or mask and/or prevent the detrimental action of 17β-HSD.

HSD Inhibitor

In accordance with the present invention, the compound of the present invention is capable of acting as an 17β-HSD inhibitor.

Here, the term "inhibitor" as used herein with respect to the compound of the present invention means a compound that can inhibit 17β-HSD activity—such as reduce and/or eliminate and/or mask and/or prevent the detrimental action of 17β-HSD. The 17β-HSD inhibitor may act as an antagonist.

The ability of compounds to inhibit 17β hydroxysteroid dehydrogenase activity can be assessed using the suitable biological assay presented in the Examples section.

It is to be noted that the compound of the present invention may have other beneficial properties in addition to or in the alternative to its ability to inhibit HSD activity.

Therapy

In one aspect the present invention provides use of a compound as described herein in the manufacture of a medicament for use in the therapy of an androgen dependent disease or estrogen dependent disease.

Types of androgen or estrogen dependent diseases include, but are not limited to prostate cancer, benign prostatic hyperplasia, prostatic intraepithelial neoplasia, acne, seborrheas, hirsutism, androgenic alopecia, precocious puberty, adrenal hyperplasia, and polycystic ovarian syndrome, breast cancer, endometriosis and leiomyoma.

In one aspect the present invention provides use of a compound as described herein in the manufacture of a medicament for use in the therapy of a condition or disease selected from the group consisting of prostate cancer, androgen dependent neoplasms, benign prostatic hyperplasia, prostatic intraepithelial neoplasia, androgenic alopecia (i.e. pattern baldness in both male and female patients), hirsutism, polycystic ovary syndrome and acne.

In one aspect the present invention provides use of a compound as described herein in the manufacture of a medicament for use in the therapy of a condition or disease associated with 17β-HSD.

In one aspect the present invention provides use of a compound as described herein in the manufacture of a medicament for use in the therapy of a condition or disease associated with adverse 17β-HSD levels.

In one aspect the present invention provides use of a compound as described herein in the manufacture of a pharmaceutical for modulating 17β-HSD activity.

In one aspect the present invention provides use of a compound as described herein in the manufacture of a pharmaceutical for inhibiting 17β-HSD activity.

Preferably the 17β-HSD is 17β-HSD Type 3.

The compounds of the present invention may be used as therapeutic agents—i.e. in therapy applications.

The term "therapy" includes curative effects, alleviation effects, and prophylactic effects.

The therapy may be on humans or animals, preferably male animals or humans, such as male humans.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other 17β-HSD inhibitors and/or other inhibitors such as an aromatase inhibitor (such as for example, 4hydroxyandrostenedione (4-OHA)), and/or a steroid sulphatase inhibitors such as EMATE and/or steroids and/or Coumate 667—such as the naturally occurring sterneurosteroids dehydroepiandrosterone sulfate (DHEAS) and pregnenolone sulfate (PS) and/or other structurally similar organic compounds.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)— such as TNF-α; Interferon alpha, beta and gamma; TGF-β. For some applications, preferably the cytokine is tumour necrosis factor (TNF). For some applications, the TNF may be any type of TNF—such as TNF-α, TNF-β, including derivatives or mixtures thereof. More preferably the cytokine is TNF-α. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of every second or third day, or 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the compounds of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

(b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell.

Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, testicular cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2$/M phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of androgen receptor positive (AR+) and AR negative (AR−) prostate or testes cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 2

Procedure

Stage 1

MCF-7 breast cancer cells are seeded into multi-well culture plates at a density of $10^5$ cells/well. Cells were allowed to attach and grown until about 30% confluent when they are treated as follows:

Control—no treatment

Compound of Interest (COI) 20 μM

Cells are grown for 6 days in growth medium containing the COI with changes of medium/COI every 3 days. At the end of this period cell numbers were counted using a Coulter cell counter.

Stage 2

After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Cancer

As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Other Therapies

As previously mentioned, in one aspect the present invention provides use of a compound as described herein in the manufacture of a medicament for use in the therapy of a condition or disease associated with 11β-HSD.

It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: diabetes including Type II diabetes, obesity, cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; antiimmune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

SUMMARY

In summation, the present invention provides compounds for use as hydroxysteroid dehydrogenase inhibitors, and pharmaceutical compositions for the same.

The present invention will now be described in further detail in the following examples.

EXAMPLES

The present invention will now be described only by way of example.

Synthetic Routes

The following compounds were synthesised.

| Code | Structure |
|---|---|
| STX 1604 | *(3,5-dichlorophenoxy)phenyl N-acetylpiperidine-4-carboxamide)* |
| STX 1605 | *(3,5-dichlorophenoxy)phenyl N-benzoylpiperidine-4-carboxamide)* |
| STX 1606 | *(4-trifluoromethylphenoxy)phenyl N-acetylpiperidine-4-carboxamide)* |
| STX 1607 | *(4-trifluoromethylphenoxy)phenyl N-benzoylpiperidine-4-carboxamide)* |
| STX 1613 | *(2,4-dichlorophenoxy)phenyl N-benzoylpiperidine-4-carboxamide)* |
| STX 1614 | *(2,4-dichlorophenoxy)phenyl N-acetylpiperidine-4-carboxamide)* |
| STX 1615 | *(4-chlorophenoxy)phenyl N-benzoylpiperidine-4-carboxamide)* |
| STX 1616 | *(2,4-dichlorophenoxy)phenyl 4-aminopiperidine N-acetyl)* |
| STX 1617 | *(4-chlorophenoxy)phenyl N-acetylpiperidine-4-carboxamide)* |
| STX 1623 | *(2,4-dichlorophenoxy)phenyl 4-aminopiperidine N-benzoyl)* |
| STX 1624 | *(4-trifluoromethoxyphenoxy)phenyl N-acetylpiperidine-4-carboxamide)* |

| Code | Structure |
|---|---|
| STX 1625 | 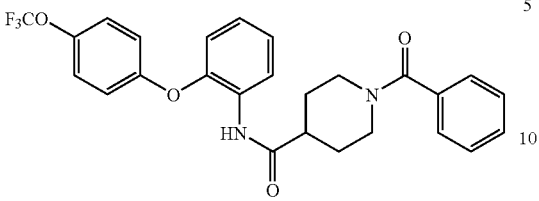 |
| STX 1629 | 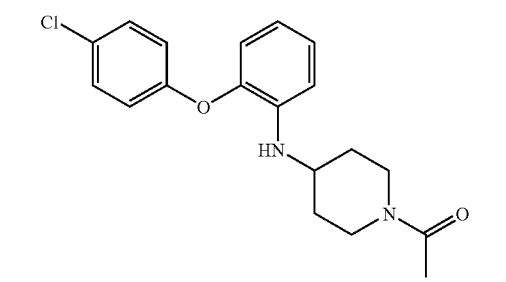 |
| STX 1630 | 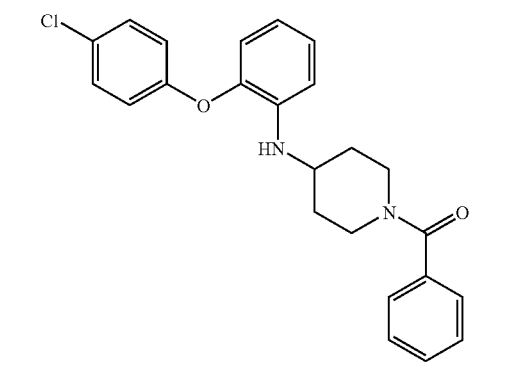 |
| STX 1631 | 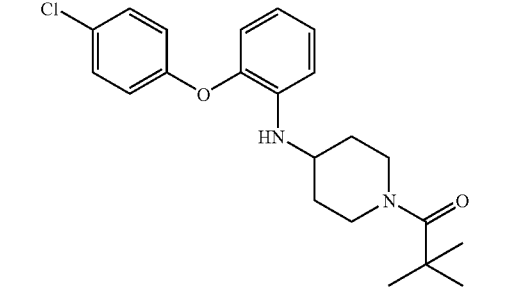 |
| STX 1646 | 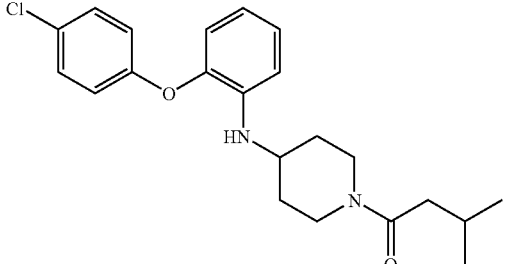 |
| Code | Structure |
|---|---|
| STX 1647 | 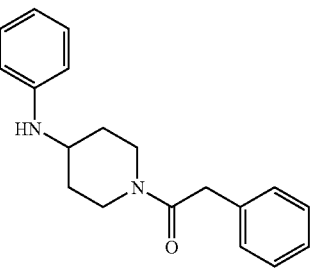 |
| STX 1657 | 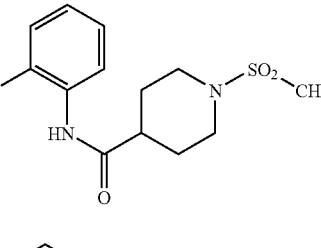 |
| STX 1658 | 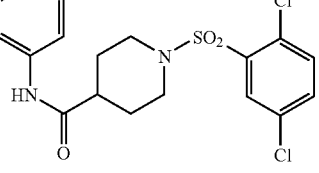 |
| STX 1665 | 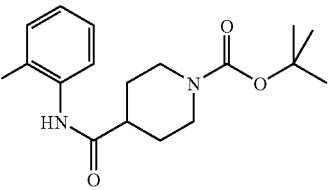 |
| STX 1666 | 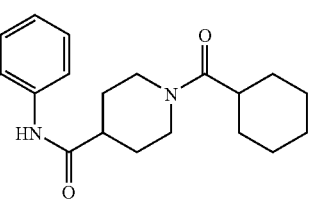 |
| STX 1667 | 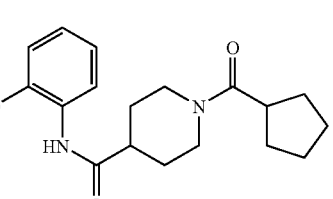 |
| STX 1668 | 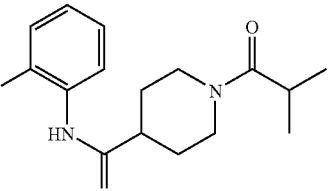 |

-continued
| Code | Structure |
|---|---|
| STX 1669 | 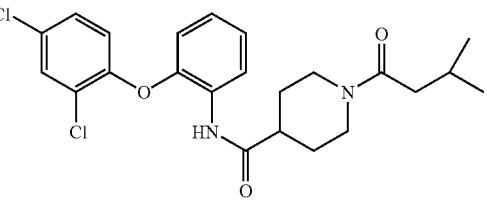 |
| STX 1670 | 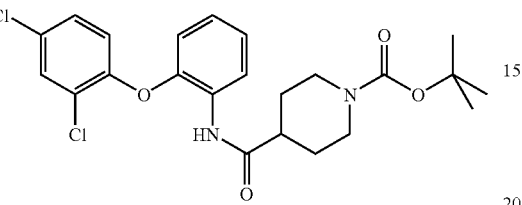 |
| STX 1680 | 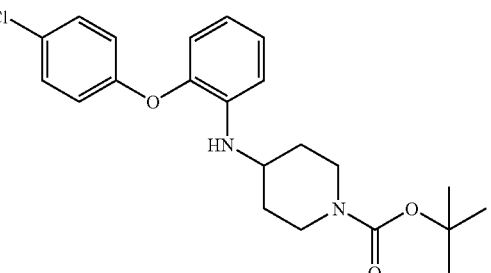 |
| STX 1681 | 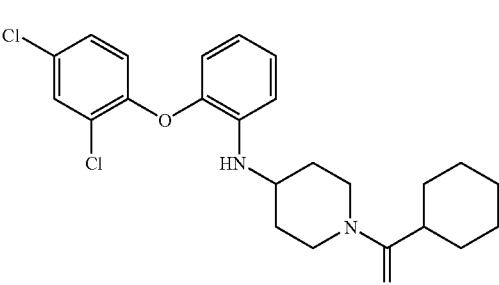 |
| STX 1682 | 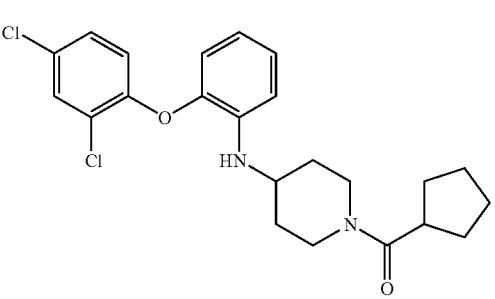 |
| STX 1683 | 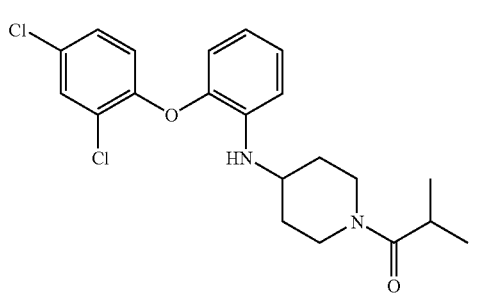 |
-continued
| Code | Structure |
|---|---|
| STX 1684 | 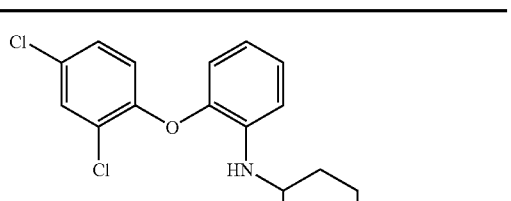 |
| STX 1685 | 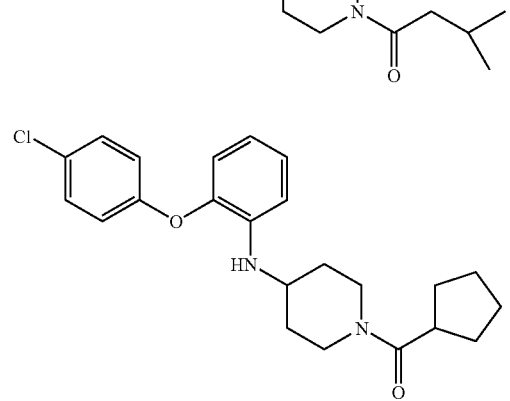 |
| STX 1701 | 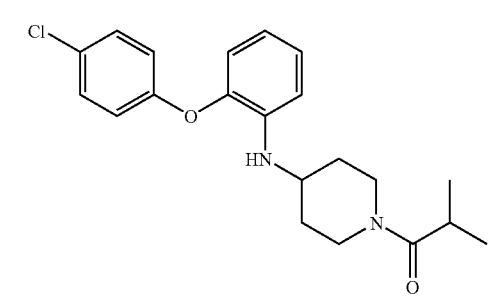 |
| STX 1702 | 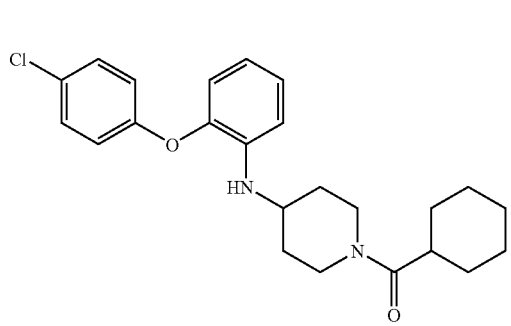 |
| STX 1703 | 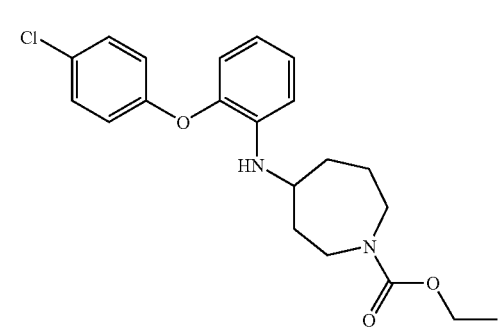 |

| Code | Structure |
|---|---|
| STX 1715 | 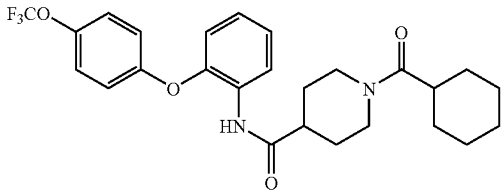 |
| STX 1716 | 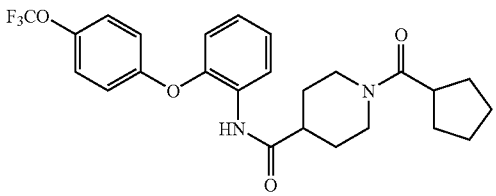 |
| STX 1717 | 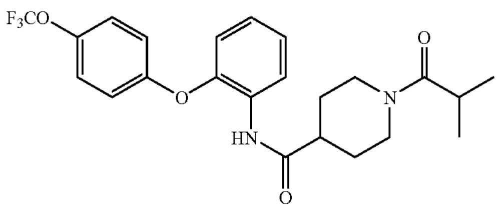 |
| STX 1718 | 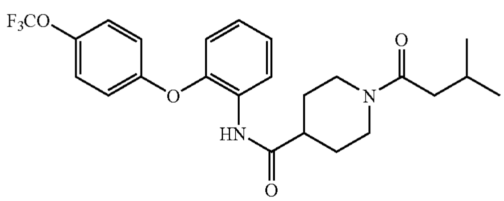 |
| STX 1719 | 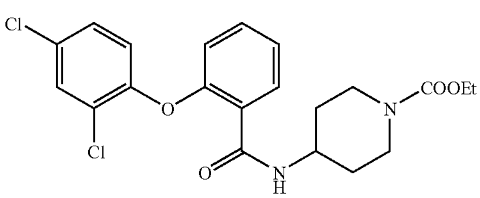 |
| STX 1723 | 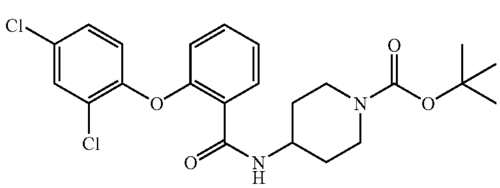 |
| STX 1724 | 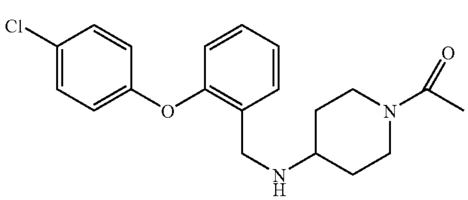 |
| STX 1725 | 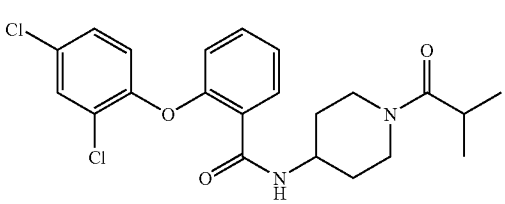 |

| Code | Structure |
|---|---|
| STX 1726 | 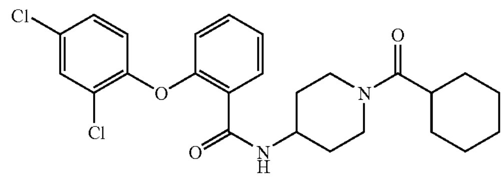 |
| STX 1727 | 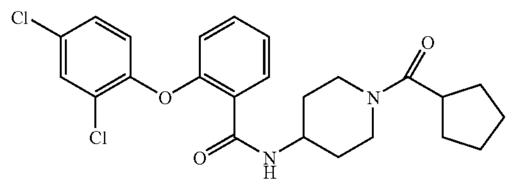 |
| STX 1728 | 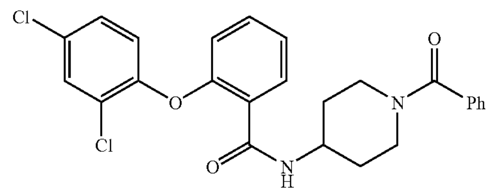 |
| STX 1733 | 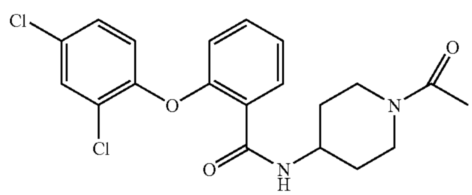 |
| STX 1734 | 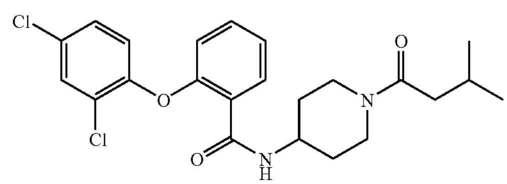 |
| STX 1735 | 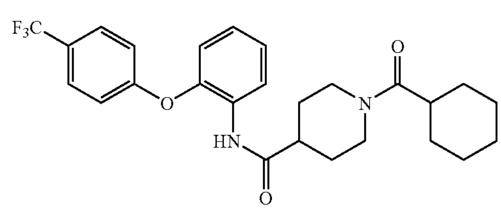 |
| STX 1736 | 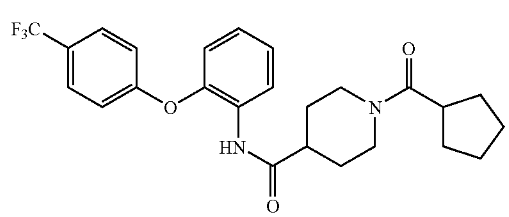 |

| Code | Structure |
|---|---|
| STX 1747 | 4-(trifluoromethyl)phenoxy-phenyl-NH-C(O)-piperidine-N-C(O)-iPr |
| STX 1748 | 4-(trifluoromethyl)phenoxy-phenyl-NH-C(O)-piperidine-N-C(O)-CH2CH(CH3)2 |
| STX 1749 | 4-(trifluoromethoxy)phenoxy-phenyl-NH-C(O)-piperidine-N-C(O)O-tBu |
| STX 1755 | 4-chlorophenoxy-phenyl-CH2-NH-piperidine-N-C(O)-CH2CH(CH3)2 |
| STX 1756 | 4-chlorophenoxy-phenyl-CH2-NH-piperidine-N-C(O)-iPr |
| STX 1757 | 4-chlorophenoxy-phenyl-CH2-NH-piperidine-N-C(O)-cyclopentyl |
| STX 1758 | 4-chlorophenoxy-phenyl-CH2-NH-piperidine-N-C(O)-Ph |

| Code | Structure |
|---|---|
| STX 1762 | 4-chlorophenoxy-phenyl-NH-azepane-N-C(O)Me |
| STX 1763 | 2,4-dichlorophenoxy-phenyl-NH-azepane-N-C(O)Me |
| STX 1764 | 4-chlorophenoxy-phenyl-NH-azabicyclic-N-C(O)OEt |
| STX 1765 | 2,4-dichlorophenoxy-phenyl-NH-azabicyclic-N-C(O)OEt |
| STX 1779 | 2,4-dichlorophenoxy-phenyl-NH-piperidine-N-C(O)-2-furyl |

| Code | Structure |
|---|---|
| STX 1785 | 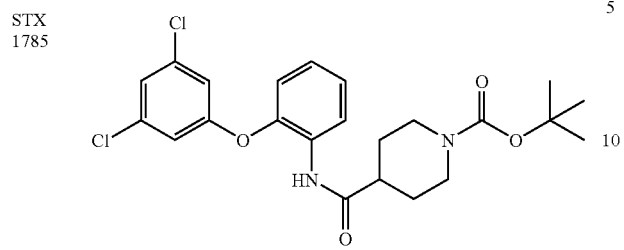 |
| STX 1790 | 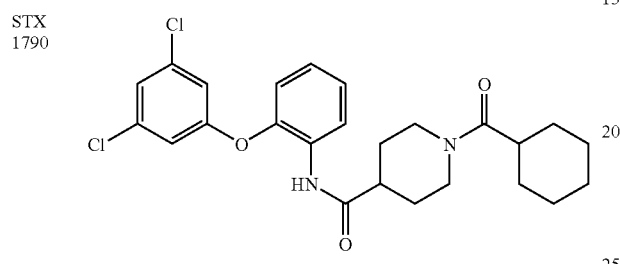 |
| STX 1791 | 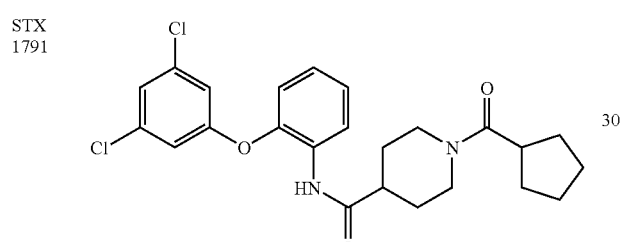 |
| STX 1792 | 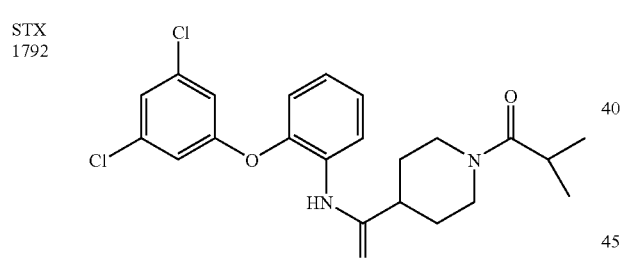 |
| STX 1793 | 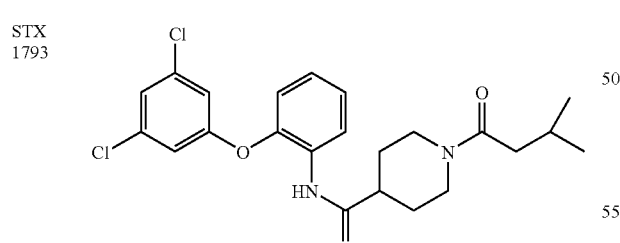 |
| STX 1831 | 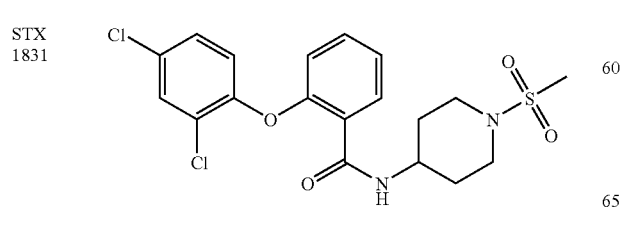 |
| STX 1832 | 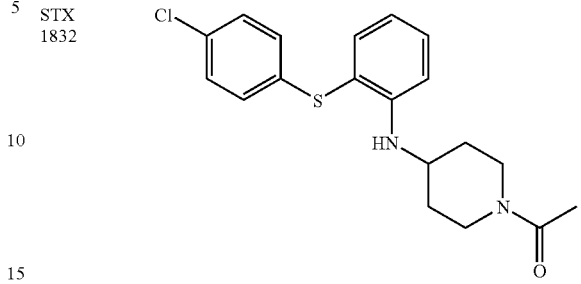 |
| WBH 01098 | 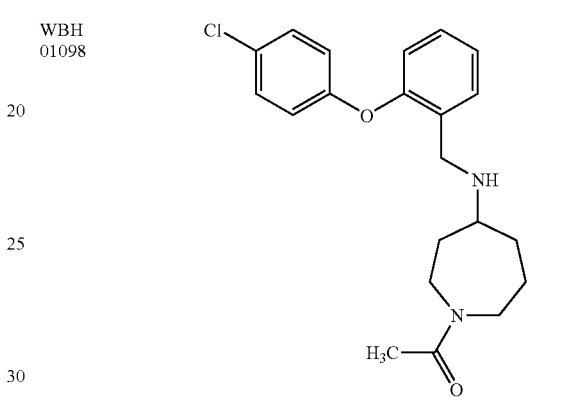 |
| STX 1849 | 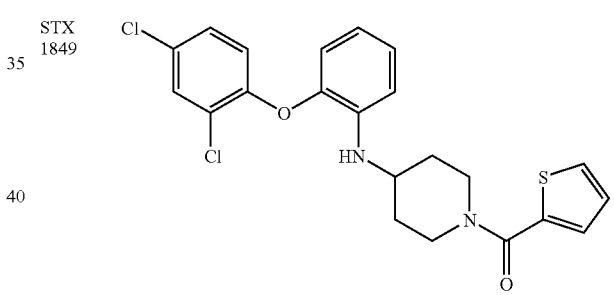 |
| STX 1850 | 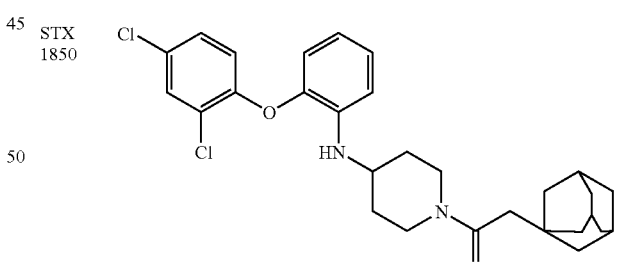 |
| STX 1851 | 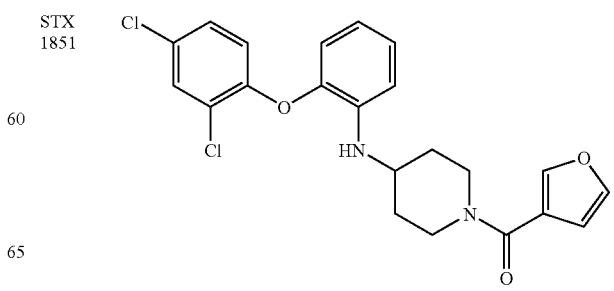 |

| Code | Structure |
|------|-----------|
| STX 1857 | 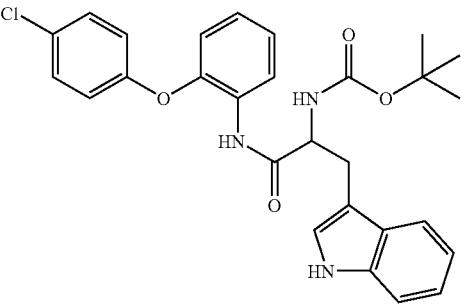 |
| STX 1858 | 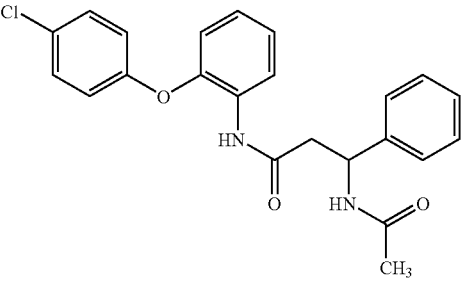 |
| STX 1859 | 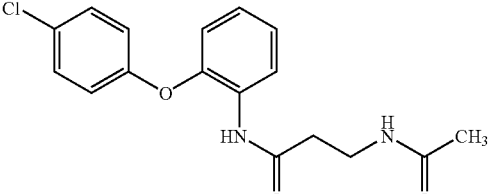 |
| STX 1860 | 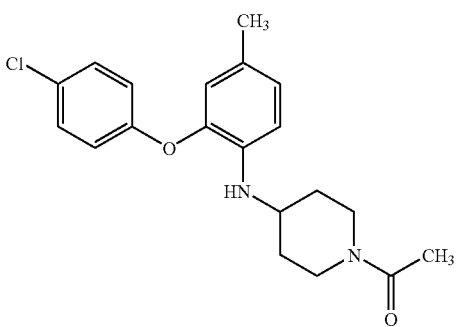 |
| STX 1861 | 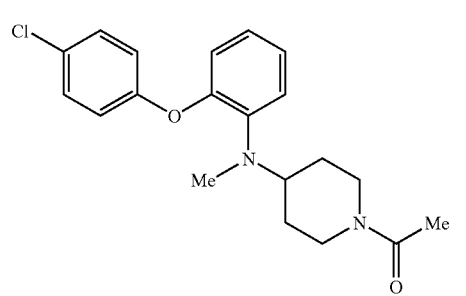 |
| STX 1871 | 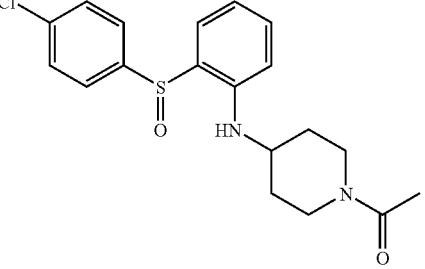 |
| STX 1872 | 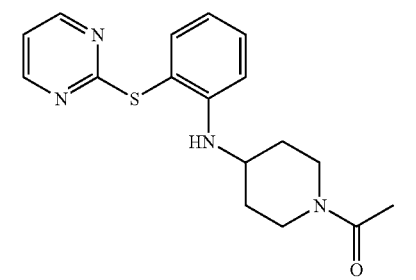 |
| STX 1873 | 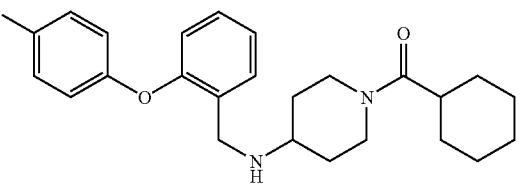 |
| STX 2278 | 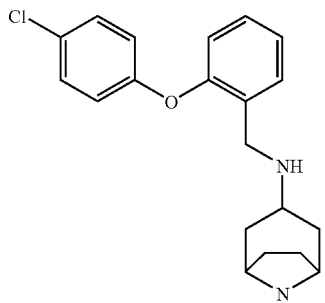 |
| STX 1970 | 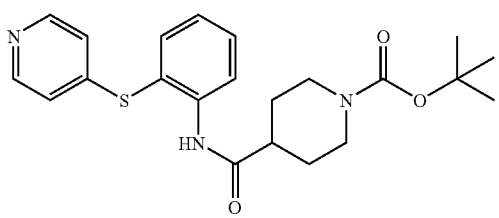 |

-continued
| Code | Structure |
|---|---|
| STX 1961 | 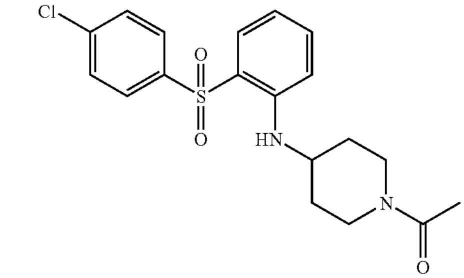 |
| STX 1963 | 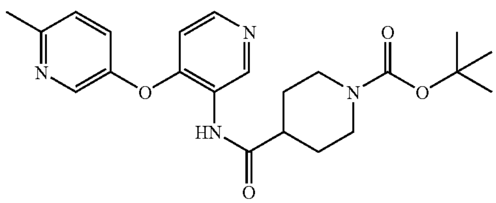 |
| STX 1984 | 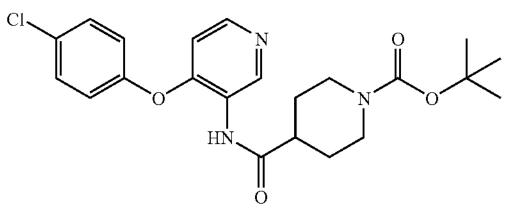 |
| STX 2038 | 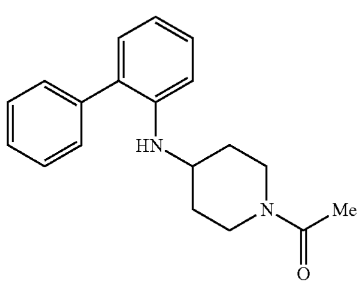 |
| STX 2039 | 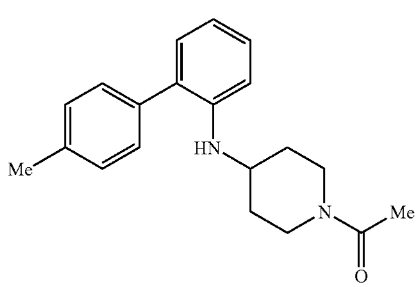 |
| STX 2040 | 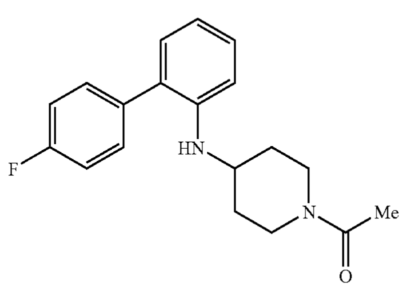 |
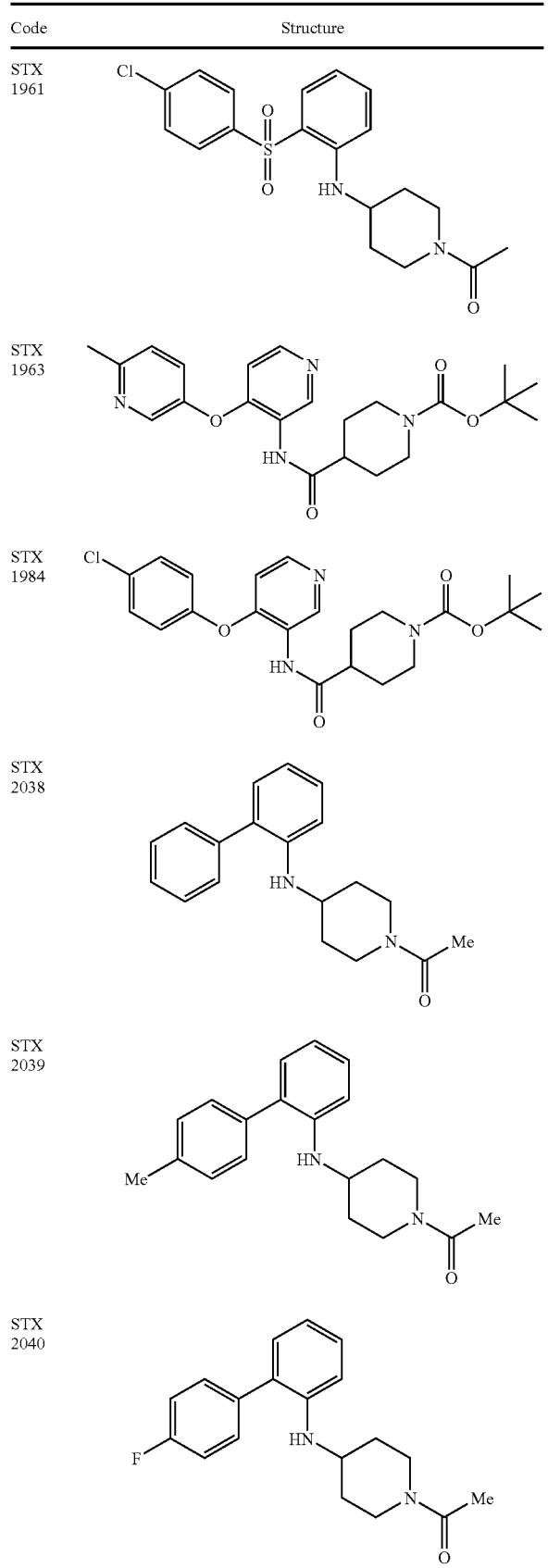
-continued
| Code | Structure |
|---|---|
| STX 2041 | 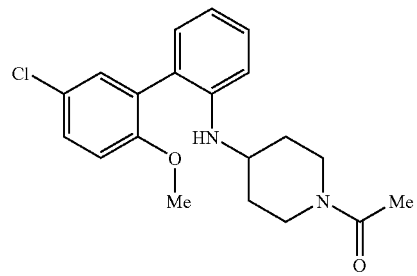 |
| STX 2042 | 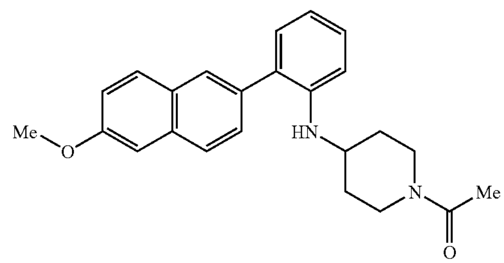 |
| STX 2043 | 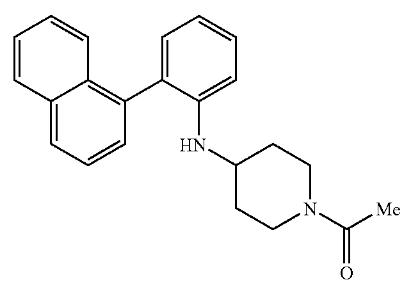 |
| STX 2044 | 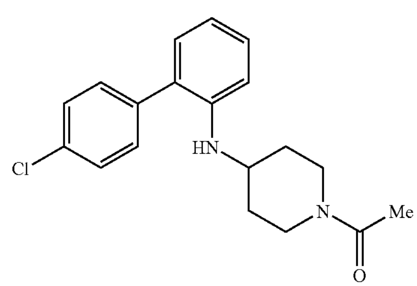 |
| STX 2045 | 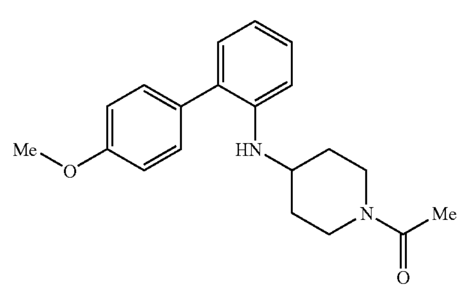 |
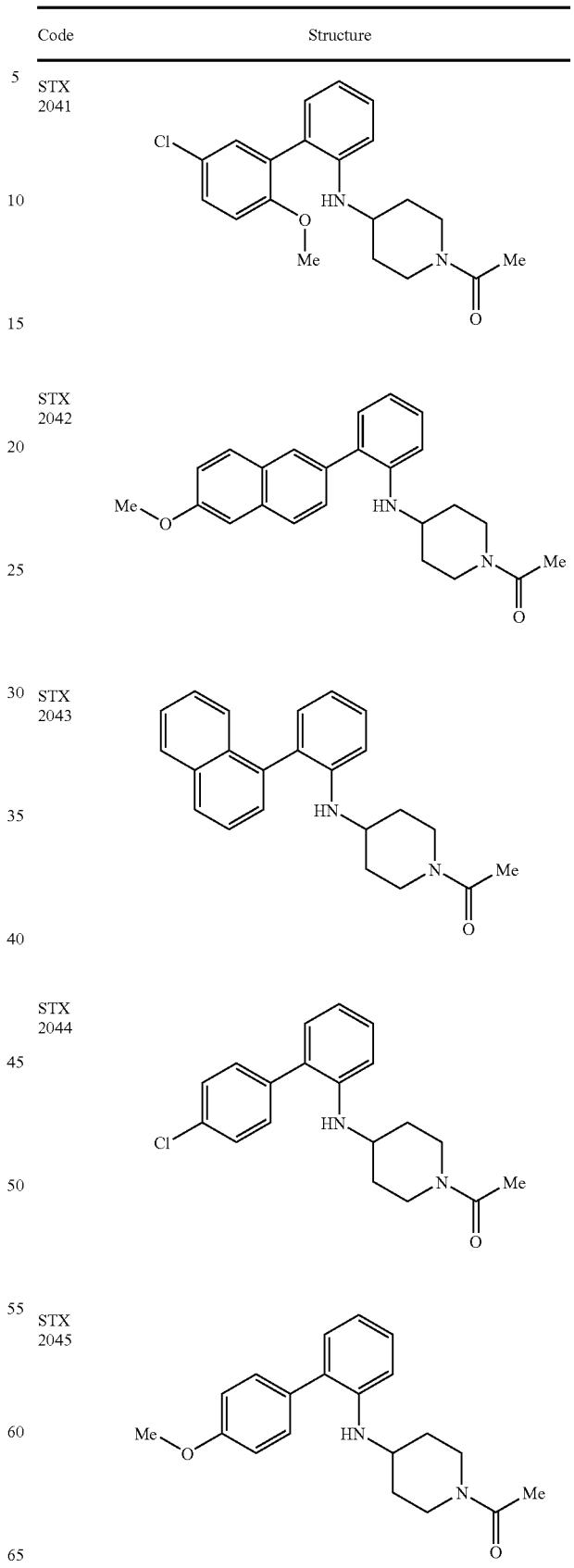

| Code | Structure |
|---|---|
| STX 2046 | 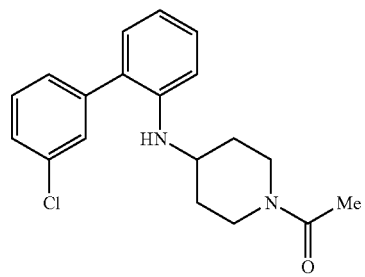 |
| STX 2048 | 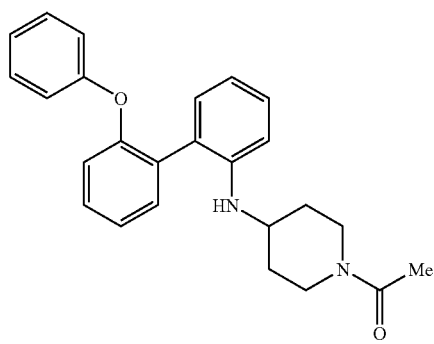 |
| STX 2049 | 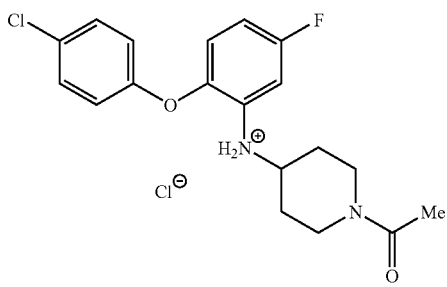 |
| STX 2050 | 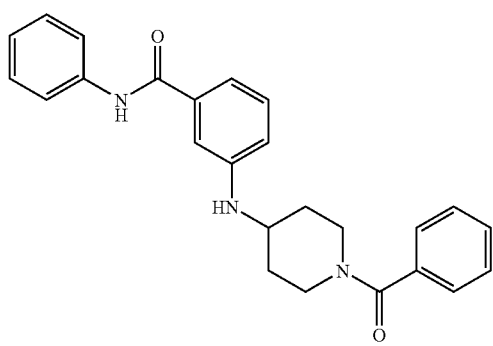 |
| STX 2051 | 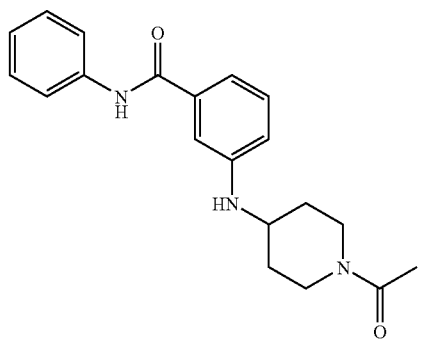 |
| Code | Structure |
|---|---|
| STX 2059 | 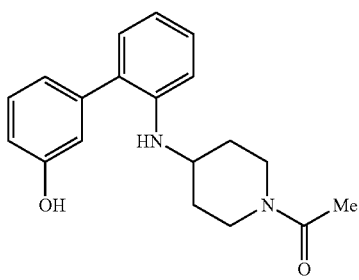 |
| STX 2138 | 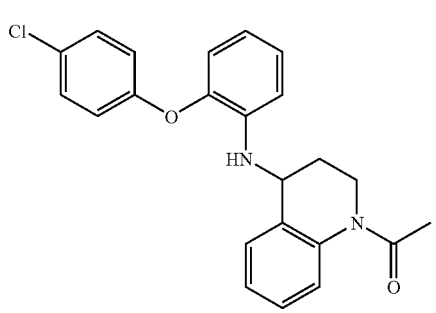 |
| STX 2168 | 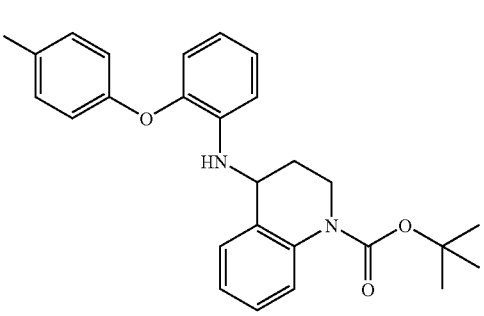 |
| STX 2171 | 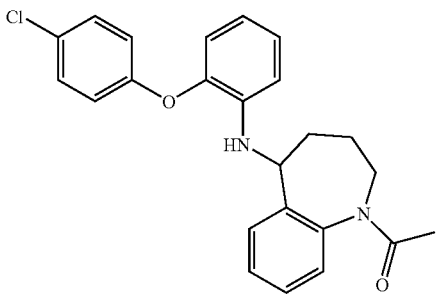 |
| STX 2279 | 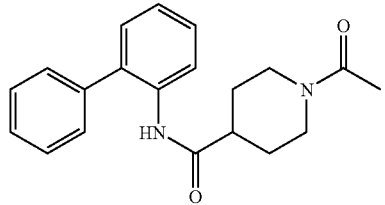 |

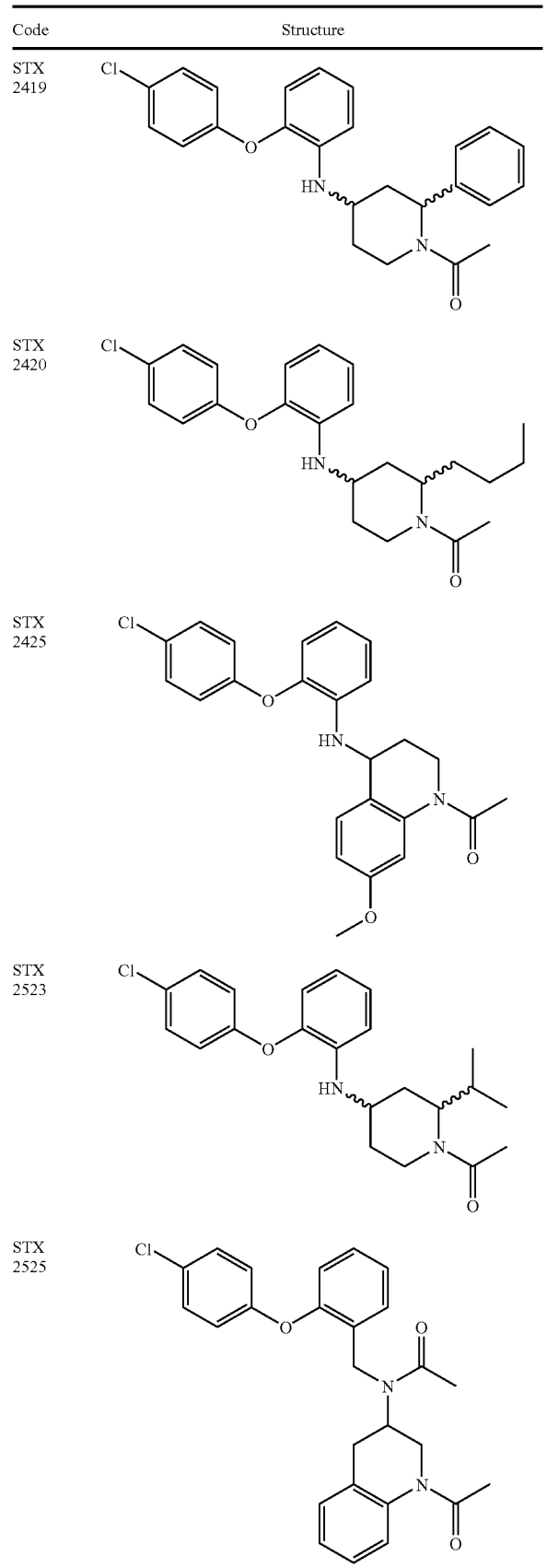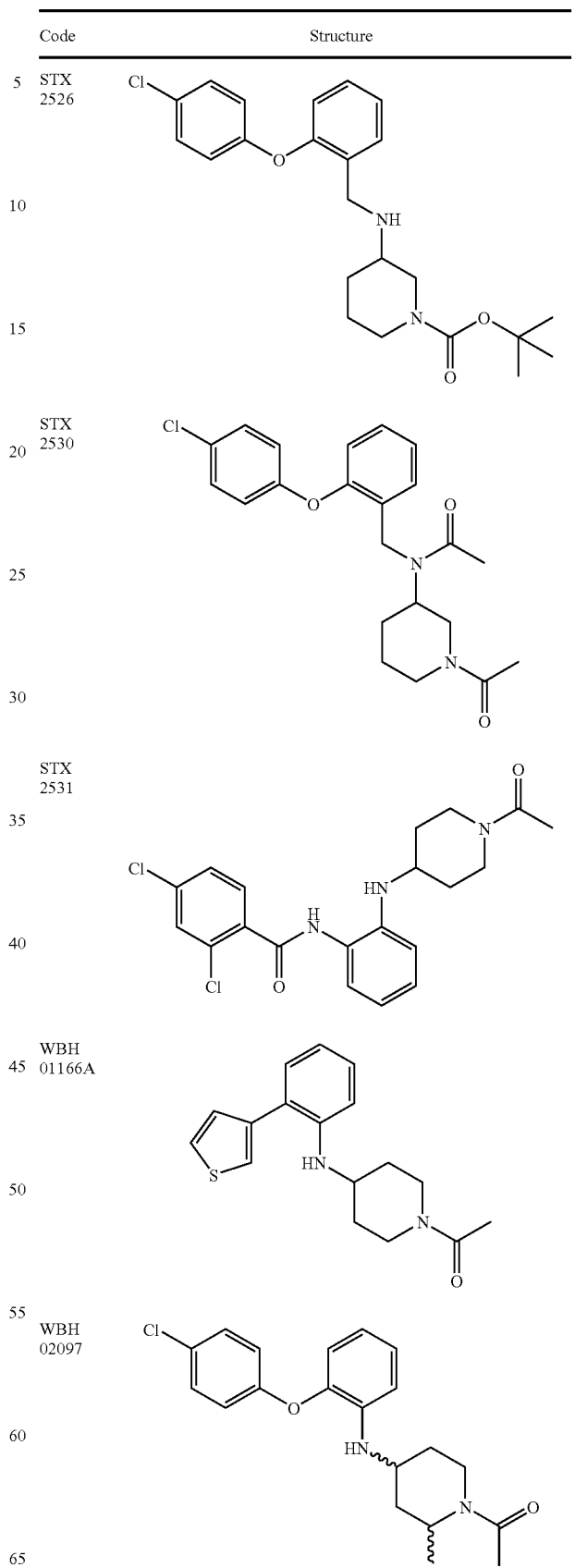

| Code | Structure |
|---|---|
| WBH 02142 | 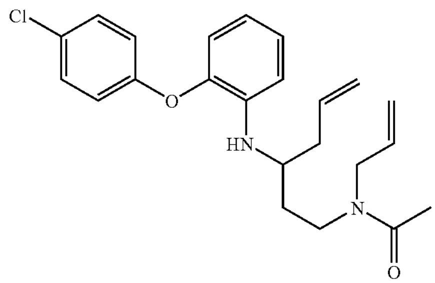 |
| WBH 02154 | 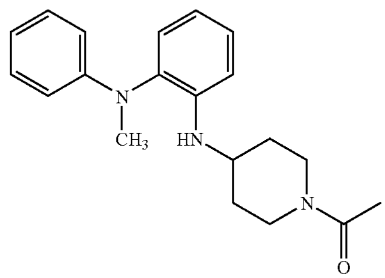 |
| WBH 02155 | 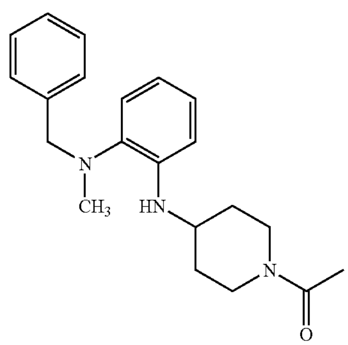 |
| WBH 02156 | 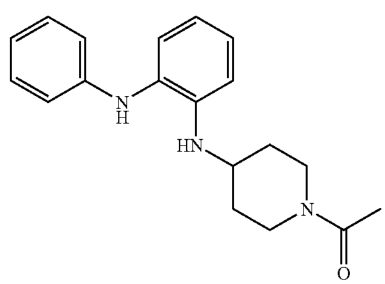 |
| WBH 02153 | 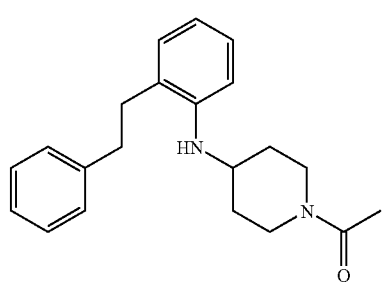 |

| Code | Structure |
|---|---|
| CMS 02110 | 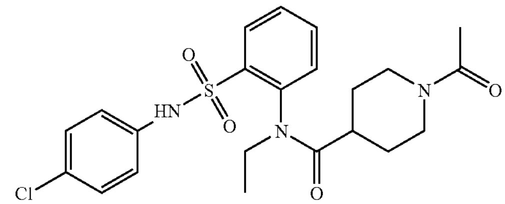 |
| CMS 02111 | 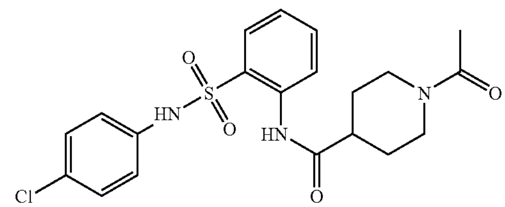 |

Synthetic Route to STX1604 and 1605

1,3-Dichloro-5-(2-nitro-phenoxy)-benzene HVB01025 $C_{12}H_7Cl_2NO_3$, MW 284.1

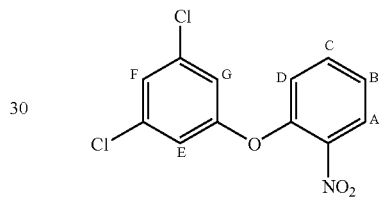

A mixture of 2-fluoro-1-nitrobenzene (0.7 ml, 6.47 mmol), 3,5-dichloro-phenol (1.56 g, 9.8 mmol) and potassium carbonate (1.35 g, 9.78 mmol) in dimethylformamide (4 ml) was refluxed with stirring for 3 h. After removal of dimethylformamide, the residue was dissolved in ether (20 ml), and washed with sodium hydroxide (5%, 3×20 ml). The organic layers were combined, dried (MgSO$_4$), filtered and evaporated in-vacuo. The product was obtained as a light yellow solid, 0.57 g, 33%. m.p. 78-80° C.; $^1$H NMR (270 MHz, CDCl$_3$) δ 6.88 (2H, d, J=1.7 Hz, ArH$_E$, ArH$_G$), 7.12 (1H, t, J=1.7 Hz, ArH$_F$), 7.12 (1H, dd, J=1.2, 8.2 Hz, ArH$_D$), 7.32 (1H, td, J=7.4, 1.2 Hz, ArH$_B$), 7.6 (1H, td, J=7.4, 1.7 Hz, ArH$_C$), 8.0 (1H, dd, J=8.2, 1.7 Hz, ArH$_A$).

2-(3,5-Dichloro-phenoxy)-phenylamine. HVB01030 $Cl_2H_9Cl_2NO$, MW 254.11

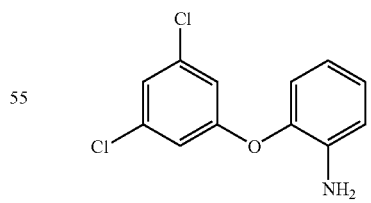

1,3-Dichloro-5-(2-nitro-phenoxy)-benzene (HVB01025, 1.81 g, 6.4 mmol) was added to a solution of iron (1.96 g, 35.2 mmol) and ammonium chloride (0.24 g, 4.5 mmol) in ethanol (30 ml), and water (3 ml) at reflux, and stirred at reflux for 5 h. Ethanol removed in-vacuo and the residue extracted with sodium sodium bicarbonateonate (20 ml) and DCM (3×20 ml). Organic layers combined and dried over anhydrous magnesium sulphate and evaporated to dryness, to afford a brown oil, 1.45 g, 89%. $R_f$ 0.6 (DCM); $^1$H NMR (270 MHz, CDCl$_3$) δ 3.67 (2H, s, NH$_2$), 6.68 (1H, td, J=7.4, 1.5 Hz, ArH$_C$), 6.77 (1H, dd, J=7.9, 1.5 Hz, ArH$_A$), 6.77 (2H, d, J=2.0 Hz, ArH$_E$, ArH$_G$), 6.84 (1H, dd, J=7.9, 1.5 Hz, ArH$_D$), 6.97 (1H, t, J=2.0 Hz, ArH$_F$), 6.98 (1H, td, J=7.4, 1.5 Hz, ArH$_B$).

4-[2-(3,5-Dichloro-phenoxy)-phenylcarbamoyl]-piperidine-1-carboxylic acid tert-butyl ester HVB01039, STX1785 C$_{23}$H$_{26}$Cl$_2$N$_2$O$_4$, MW 465.38

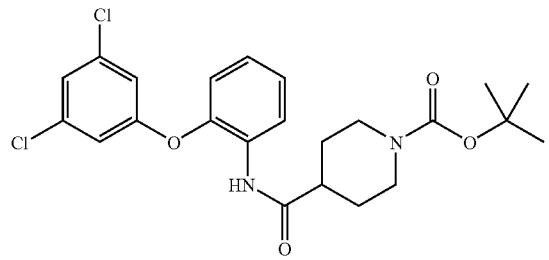

Piperidine-1,4-dicarboxylic acid mono-tert-butyl ester (HVB01031 0.267 g, 1.17 mmol) was dissolved in anhydrous DCM (7 ml), and stirred under nitrogen. To this was added N N-4-dimethylaminopyridine (cat.), 1-(3-dimethylaminopropyl)-3-ethylcarbodiimide hydrochloride (0.81 g, 4.2 mmol) and TEA (0.23 ml). Stirred for 30 min. 2-(3,5-dichloro-phenoxy)-phenylamine (HVB01030 0.36 g, 1.4 mmol) was added and stirred under nitrogen for 40 h. Diluted with DCM, washed with HCl (1M, 20 ml), Sodium hydrogen carbonate (sat. 20 ml), and brine (20 ml). Organic layers combined and dried over anhydrous magnesium sulphate, and evaporated in-vacuo. The crude mixture was purified using flash chromatography (DCM/hexane, 0 to 100%), to afford a white solid, 0.32 g, 60%. m.p. 116-117° C., $^1$HNMR: (CDCl$_3$, 270 MHz) δ 1.43 (9H, s, CH$_3$), 1.66 (2H, td, J=1.2, 4.2 Hz, CH$_2$), 1.80 (2H, dd, J=2.5, 12.8 Hz, CH$_2$), 2.35 (1H, m, CH), 2.74 (2H, t, J=11.8 Hz, CH$_2$N), 4.15 (2H, m, CH$_2$N), 6.87 (2H, d, J=1.7 Hz, ArH$_E$, ArH$_G$), 6.9 (1H, m, ArH$_D$), 7.05 (1H, td, J=5.0, 6.4 Hz, ArH$_B$), 7.11 (1H, t, J=2.0 Hz, ArH$_F$), 7.17 (1H, td, J=1.5, 8.1 Hz, ArH$_C$), 8.40 (1H, dd, J=1.2, 8.1 Hz, ArH$_A$).

Piperidine-4-carboxylic acid [2-(3,5-dichloro-phenoxy)-phenyl]-amide HVB01044 C$_{19}$H$_{19}$F$_3$N$_2$O$_2$, MW 364.37

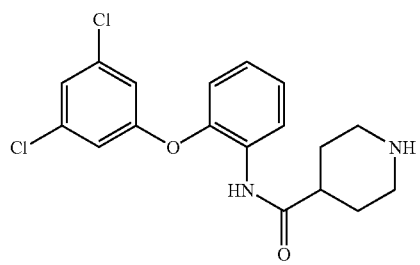

4-[2-(3,5-Dichloro-phenoxy)-phenylcarbamoyl]-piperidine-1-carboxylic acid tert-butyl ester (HVB01036, HVB01039 HVB01042, 1.09 g, 2.3 mmol) was dissolved in HCl/dioxane (4M, 18 ml), and stirred at room temperature for 1 h. The reaction mixture was evaporated to dryness, diluted with DCM (20 ml) and neutralised with sodium hydroxide (1M). Extracted with DCM, organic layers dried over anhydrous magnesium sulphate, and evaporated in-vacuo, 183 mg, 21%. m.p. 138-139° C., Rf. 0.3 (10% Methanol/DCM), $^1$HNMR (CDCl$_3$, 270 MHz) δ 1.65 (3H, m, CH$_2$ and NH), 1.86 (2H, m, CH$_2$), 2.36 (1H, m, CH), 2.65 (2H, td, J=2.7, 9.6 Hz, NCH$_2$), 3.16 (2H, m, NCH$_2$), 6.89 (2H, d, J=1.7 Hz, ArH$_E$, ArH$_G$), 6.90 (1H, m, ArH$_D$), 7.06 (1H, td, J=1.5, 7.4 Hz, ArH$_B$), 7.12 (1H, t, J=1.7 Hz, ArH$_F$), 7.18 (1H, td, J=8.2, 1.46 Hz, ArH$_C$), 7.55 (1H, s, NH), 8.43 (1H, dd, J=8.2 Hz, ArH$_A$).

1-Acetyl-piperidine-4-carboxylic acid [2-(3,5-dichloro-phenoxy)-phenyl]-amide. HVB01047, STX1604 C$_{20}$H$_{20}$Cl$_2$N$_2$O$_3$, MW 407.3

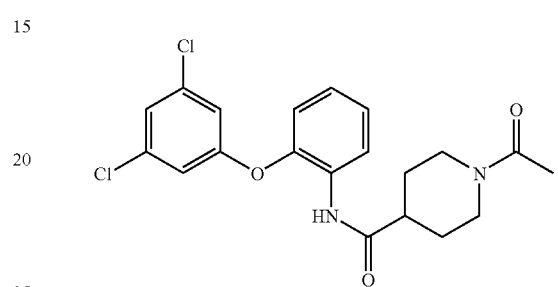

Piperidine-4-carboxylic acid [2-(4-trifluoromethyl-phenoxy)-phenyl]-amide (HVB01044, 60 mg, 0.16 mmol) was dissolved in DCM (5 ml) and cooled to 0° C. To this was added acetyl chloride (0.02 ml, 0.32 mmol) and TEA (0.1 ml, 0.8 mmol). The reaction mixture was allowed to warm to room temperature and stirred for 1 h. The reaction was quenched with sodium hydrogen carbonate (15 ml), extracted with DCM and washed with hydrochloric acid (1M) and brine. The organic layers were dried over anhydrous magnesium sulphate and evaporated in-vacuo. The crude mixture was purified using flash chromatography (0-5% methanol in ethyl acetate), to afford a white solid, 65 mg, 95%. m.p. 112-114° C., Rf: 0.25 (DCM), LC/MS $t_r$=1.04 min (95% MeOH and 5% Water at 1.0 ml/min), m/z M+H 407.30, HPLC $t_r$=2.146 min (Isocratic 90% acetonitrile and 10% water at 1.0 ml/min), 94.94%, $^1$HNMR (CDCl$_3$, 270 MHz) δ 2.06 (3H, s, CH$_3$), 2.46 (1H, m, CH), 2.64 (1H, td, J=3.0, 13.8 Hz, NCH$_2$), 3.07 (1H, td, J=2.7, 11.9 Hz, NCH$_2$), 3.85 (1H, d, J=13.6 Hz, NCH$_2$), 4.56 (1H, d, J=13.5 Hz, NCH$_2$), 6.87 (2H, d, J=1.7 Hz, ArH$_E$, ArH$_G$), 6.90 (1H, dd, J=1.2, 8.2 Hz, ArH$_D$), 7.06 (1H, td, J=1.5, 7.7 Hz, ArH$_C$), 7.11 (1H, t, J=2.0 Hz, ArH$_F$), 7.18 (td, J=1.2, 7.9 Hz, ArH$_B$), 7.64 (1H, s, NH), 8.36 (1H, dd, J=1.0, 8.2 Hz, ArH$_A$). Anal. Calcd for C$_{20}$H$_{20}$Cl$_2$N$_2$O$_3$: C, 58.98; H, 4.95; N, 6.88%. Found: C, 58.6; H, 4.91; N, 6.61%.

1-Benzoyl-piperidine-4-carboxylic acid [2-(3,5-dichloro-phenoxy)-phenyl]-amide HVB01049, STX1605 C$_{25}$H$_{22}$Cl$_2$N$_2$O$_3$, MW 469.37

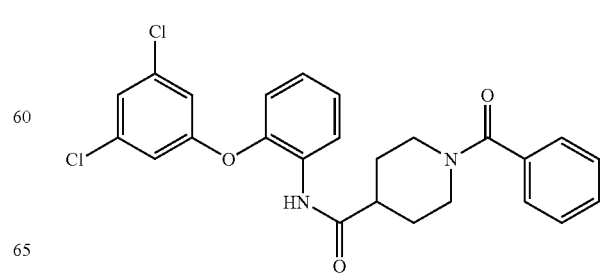

Piperidine-4-carboxylic acid [2-(3,5-dichloro-phenoxy)-phenyl]-amide (HVB01044, 60 mg, 0.16 mmol) was dissolved in DCM (5 ml) and cooled to 0° C. To this was added benzoyl chloride (0.02 ml, 0.16 mmol) and TEA (0.1 ml, 0.8 mmol). The reaction mixture was allowed to warm to room temperature and stirred for 1 h. The reaction was quenched with sodium hydrogen carbonate (15 ml), extracted with DCM and washed with hydrochloric acid (1M) and brine. The organic layers were dried over anhydrous magnesium sulphate and evaporated in-vacuo. The crude mixture was purified using flash chromatography (0-5% methanol in ethyl acetate), to afford a white solid, 50 mg, 64%, m.p. 61-63° C., Rf. 0.3 (DCM), LC/MS $t_r$=1.31 min (95% MeOH and 5% Water at 1.0 ml/min), m/z M+H 469.37, HPLC $t_r$=3.62 min (Isocratic 90% acetonitrile and 10% water at 1.0 ml/min), 97.56%, $^1$HNMR (CDCl$_3$, 400 MHz) δ 1.54 (2H, s, CH$_2$), 2.44 (1H, m, CH), 2.86 (1H, s, CH$_2$), 2.97 (1H, s, CH$_2$), 3.77 (1H, s, NCH$_2$), 4.65 (1H, s, NCH$_2$), 6.83 (2H, m, ArH$_E$, ArH$_G$), 6.83 (1H, m, ArH$_D$), 7.03 (1H, td, J=7.2, 0.8 Hz, ArH$_B$), 7.07 (1H, m, ArH$_F$), 7.14 (1H, t, J=7.6 Hz, ArH$_C$), 7.34 (5H, m, ArH), 7.53 (1H, s, NH), 8.35 (1H, d, J=8.0 Hz, ArH$_A$). Anal. Calcd for C$_{25}$H$_{22}$Cl$_2$N$_2$O$_3$: C, 63.97; H, 4.72; N, 5.97%. Found: C, 63.4; H, 4.7; N, 5.95%.

Synthetic Route to STX1606 and 1607

4-Trifluoromethyl-5-(2-nitro-phenoxy)-benzene
HVB01021 C$_{13}$H$_8$F$_3$NO$_3$, MW 283.21

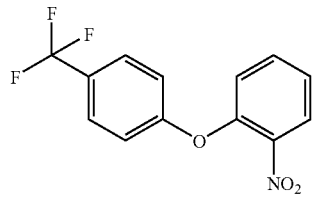

α,α,α-Trifluoro-p-cresol (1.6 g, 9.87 mmol), 2-fluoro-1-nitrobenzene (0.7 ml, 6.51 mmol), potassium carbonate (1.32 g, 9.56 mmol) were mixed in dimethylformamide (5 ml), and stirred at reflux for 6 h. After removal of dimethylformamide the residue was dissolved in ether (20 ml), and washed with sodium hydroxide (5%, 3×20 ml). The organic layers were combined, dried over MgSO$_4$, filtered and evaporated in-vacuo to afford a brown oil, 1.24 g, 68%. R.f. 0.6 (1:1 DCM-Petrol), $^1$H NMR (CDCl$_3$, 400 MHz) δ 7.11 (2H, d, J=8.4 Hz, ArH$_F$), 7.17 (1H, dd, J=8.4, 0.8 Hz, Ar H$_D$), 7.36 (1H, td, J=7.2, 1.2 Hz, Ar H$_B$), 7.64 (1H, m, Ar H$_C$), 7.65 (2H, d, J=9.6 Hz, Ar H$_E$), 8.04 (1H, dd, J=1.6, 8.0 Hz, Ar H$_A$).

2-(4-Trifluoromethyl-phenoxy)-phenylamine.
HVB01029 C$_{13}$H$_{10}$F$_3$NO, MW 253.23

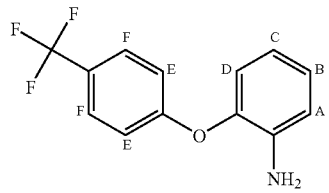

2-(4-Trifluoromethyl-phenoxy)-nitrobenzene (HVB01021, 1.24 g, 4.4 mmol) was added to a solution of iron (1.35 g, 24.2 mmol) and ammonium chloride (0.16 g, 3.08 mmol) in ethanol (23 ml), and water (2.2 ml) at reflux, and stirred at reflux for 1.5 h. Ethanol removed in-vacuo and the residue extracted with sodium sodium bicarbonateonate (20 ml) and DCM (3×20 ml). Organic layers combined and dried over anhydrous magnesium sulphate and evaporated to dryness, to afford a light yellow oil, 0.97 g, 82%. R$_f$ 0.45 (DCM, hexane, 1:1); $^1$H NMR (400 MHz, CDCl$_3$) δ 3.84 (2H, s, NH$_2$), 6.84 (1H, td, J=7.2, 1.2 Hz, Ar H$_B$), 6.91 (1H, dd, J=1.6, 8.0 Hz, Ar H$_D$), 7.01 (1H, dd, J=0.8, 7.6 Hz, Ar H$_A$), 7.10 (2H, d, J=9.2 Hz, Ar H$_F$), 7.13 (1H, td, J=4.0, 7.2 Hz, Ar H$_C$), 7.63 (2H, d, J=8.4 Hz, Ar H$_E$).

4-[2-(4-Trifluoromethyl-phenoxy)-phenylcarbamoyl]-piperidine-1-carboxylic acid tert-butyl ester.
HVB01043 C$_{24}$H$_{27}$F$_3$N$_2$O$_4$, MW 464.49

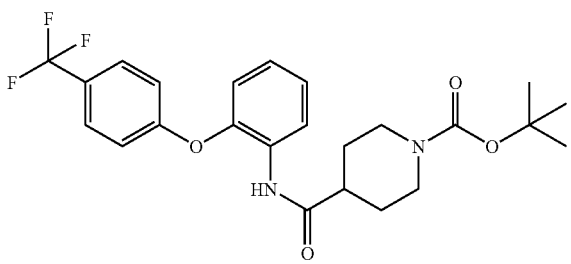

Piperidine-1,4-dicarboxylic acid mono-tert-butyl ester (HVB01045, 0.88 g, 3.85 mmol) was dissolved in anhydrous DCM (20 ml) and stirred under nitrogen. To this was added N N-4-dimethylaminopyridine (cat.), 1-(3-dimethylaminopropyl)-3-ethylcarbodiimide hydrochloride (2.2 g, 11.55 mmol) and TEA (0.62 ml). Stirred at room temperature for 30 min. To this was added 2-(4-trifluoromethyl-phenoxy)-phenylamine (HVB01029, 0.97 g, 3.85 mmol) and stirred for 18 h. The reaction mixture was diluted with DCM, washed with HCl (1M, 20 ml), Sodium hydrogen carbonate (sat. 20 ml), and brine (20 ml). Organic layers combined and dried over anhydrous magnesium sulphate, and evaporated in-vacuo to afford a white solid, 1.28 g, 72%. m.p. 48-50° C., Rf: 0.44 (DCM: Hexane, 1:1) $^1$HNMR (CDCl$_3$, 270 MHz) δ 1.44 (9H, s, CH$_3$), 1.65 (2H, m, CH$_2$), 1.75 (2H, m, CH$_2$), 2.33 (1H, m, CH), 2.73 (2H, m, NCH$_2$), 4.13 (2H, m, NCH$_2$), 6.91 (1H, dd, J=1.5, 8.2 Hz, Ar H$_D$), 7.06 (1H, td, J=1.8, 8.2 Hz, Ar H$_B$), 7.06 (2H, d, J=8.4 Hz, Ar H$_F$), 7.18 (1H, td, J=1.8, 9.2 Hz, Ar H$_C$), 7.56 (1H, s, NH), 7.60 (2H, d, J=8.4 Hz, Ar H$_E$), 8.4 (1H, dd, J=8.2 Hz, Ar H$_A$).

Piperidine-4-carboxylic acid [2-(4-trifluoromethyl-phenoxy)-phenyl]-amide HVB01054 C$_{19}$H$_{19}$F$_3$N$_2$O$_2$
MW 364.37

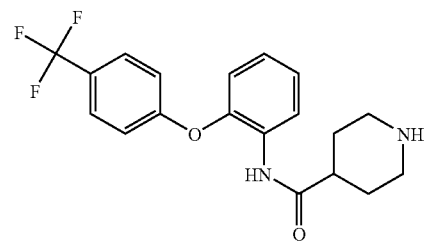

4-[2-(4-Trifluoromethyl-phenoxy)-phenylcarbamoyl]-piperidine-1-carboxylic acid tert-butyl ester (HVB01043, 0.2 g, 0.43 mmol) was dissolved in anhydrous DCM (5 ml), cooled to 0° C. and to this was added TFA (2.3 ml), and the reaction mixture was stirred under nitrogen for 1 h. The reaction mixture was poured onto solid potassium carbonate (6 g), and water (25 ml) added. Extracted with DCM and the organic layers dried over anhydrous magnesium sulphate, and evaporated in-vacuo, to afford an off white oil, 0.14 g, 89%. Rf: 0.47 (DCM), $^1$HNMR: (CDCl$_3$, 270 MHz) δ 1.65 (2H, m, CHCH$_2$), 1.79 (2H, m, CHCH$_2$), 2.30 (1H, m, CH), 2.64 (2H, td, J=12.4, 2.7 Hz, NCH$_2$), 3.10 (2H, m, NCH$_2$), 6.97 (1H, dd, J=6.4, 30.5 Hz, Ar H$_D$), 7.05 (2H, m, Ar H$_F$), 7.06 (1H, m, Ar H$_B$), 7.17 (1 h, t, J=7.2 Hz, Ar H$_C$), 7.58, d, J=8.6 Hz, Ar H$_E$), 8.39 (1H, d, J=7.9 Hz, Ar H$_A$).

1-Acetyl-piperidine-4-carboxylic acid [2-(4-trifluoromethyl-phenoxy)-phenyl]-amide HVB01055, STX1606 C$_{21}$H$_{21}$F$_3$N$_2$O$_3$ MW 406.40

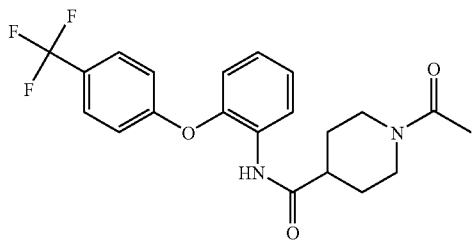

Piperidine-4-carboxylic acid [2-(4-trifluoromethyl-phenoxy)-phenyl]-amide (HVB01054, 70 mg, 0.19 mmol) was dissolved in DCM (5 ml) and cooled to 0° C. To this was added acetyl chloride (0.027 ml, 0.38 mmol) and TEA (0.12 ml). Stirred at r.t. for 1 h. Quenched with NAHCO$_3$, and extracted with DCM. Organic layer was washed with HCl (1M, 10 ml), and then brine, dried over anhydrous MgSO$_4$, and evaporated in-vacuo. The crude mixture was purified using flash chromatography (0-10% methanol/ethyl acetate), to afford a white solid, 38 mg, 49%. m.p. 164-165° C., r.f. 0.4 (5% methanol/ethyl acetate), LCMS t$_r$=1.00 min (95% MeOH and 5% water at 1.0 ml/min), m/z M$^+$H 405.22, HPLC t$_r$=2.17 min (isocratic 90% acetonitrile and 10% water at 1.0 ml/min), 94.56%, $^1$HNMR: (CDCl$_3$, 270 MHz) δ 1.65 (2H, m, CH$_2$), 1.83 (2H, m, CH$_2$), 2.09 (3H, s, CH$_3$), 2.44 (1H, m, CH), 2.64 (1H, td, J=14.1, 2.7 Hz, NCH$_2$), 3.07 (1H, td, J=14.6, 2.9 Hz, NCH$_2$), 3.83 (1H, d, J=13.9 Hz, NCH$_2$), 4.57 (1H, d, J=13.4 Hz, NCH$_2$), 6.90 (1H, dd, J=8.2, 1.2 Hz, Ar H$_B$), 7.06 (2H, d, Ar H$_F$), 7.08 (1H, m, Ar H$_C$), 7.19 (1H, td, J=1.5, 9.2 Hz, Ar H$_B$), 7.60 (2H, d, J=8.9 Hz, Ar H$_E$), 7.60 (1H, s, NH), 8.39 (1H, d, J=7.9 Hz, Ar H$_A$). Anal. Calcd for C$_{21}$H$_{21}$F$_3$N$_2$O$_3$: C, 62.06; H, 5.21; N, 6.89%. Found: C, 61.3; H, 5.22; N, 6.65%.

1-Benzoyl-piperidine-4-carboxylic acid [2-(4-trifluoromethyl-phenoxy)-phenyl]-amide HVB01057, STX1607 C$_{26}$H$_{23}$F$_3$N$_2$O$_3$, MW 468.47

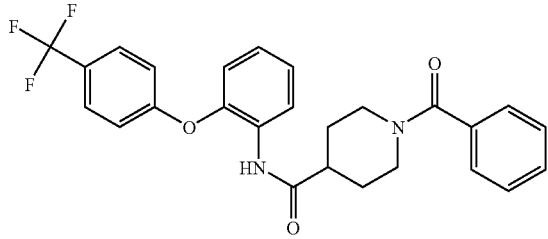

Piperidine-4-carboxylic acid [2-(4-trifluoromethyl-phenoxy)-phenyl]-amide (HVB01054, 70 mg, 0.19 mmol) was dissolved in DCM (5 ml) and cooled to 0° C. To this was added benzoyl chloride (0.05 ml, 0.38 mmol) and TEA (0.1 ml). Stirred at r.t. for 1 h. Quenched with NaHCO$_3$, and extracted with DCM. Organic layer was washed with HCl (1M, 10 ml), and then brine, dried over anhydrous MgSO$_4$, and evaporated in-vacuo. The crude mixture was purified using flash chromatography (0-5% methanol in ethyl acetate), to afford a white solid, 57 mg, 63%, m.p. 69-72° C., Rf. 0.45 (5% methanol/ethyl acetate), LC/MS t$_r$=1.15 min (95% MeOH and 5% water at 1.0 ml/min), M+H 469.44, HPLC t$_r$=2.127 min (isocratic 90% acetonitrile and 10% water at 1.0 ml/min), 95.07%. $^1$HNMR: (CDCl$_3$, 270 MHz) δ 1.83 (2H, m, CH$_2$), 2.47 (1H, m, CH), 3.03 (2H, m, CH$_2$), 3.81 (1H, m, CH$_2$), 4.73 (1H, m, CH$_2$), 6.88 (1H, m, Ar H$_D$), 7.04 (2H, m, Ar H$_F$), 7.18 (1H, m, Ar H$_B$), 7.26 (1H, m, Ar H$_C$), 7.37 (5H, m, ArH), 7.61 (1H, m, NH), 8.40 (1H, d, J=7.9 Hz, Ar H$_A$). Anal. Calcd for C$_{26}$H$_{23}$F$_3$N$_2$O$_3$: C, 66.66; H, 4.95; N, 5.98%. Found: C, 66.4; H, 5.03; N, 5.72%.

Synthetic Route to STX1624, 1625

1-Trifluoromethoxy-4-(2-nitro-phenoxy)-benzene HVB01037 C$_{13}$H$_8$F$_3$NO$_4$, MW 299.21

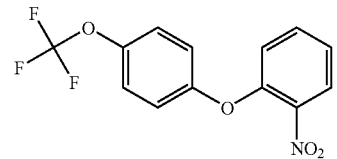

4-(trifluoromethoxy)phenol (1.36 ml, 10.6 mmol), 2-fluoro-1-nitrobenzene (0.74 ml, 7 mmol), potassium carbonate (1.46 g, 10.5 mmol) were mixed together in DMF (4 ml) and heated at reflux for 5 h. Allowed to cool and evaporated in-vacuo. Residue partitioned between diethyl ether and sodium hydroxide (1 M). Organic layers combined and dried over anhydrous magnesium sulphate and evaporated in-vacuo, 2.34 g, >100%. Rf: 0.72 (DCM), $^1$HNMR (CDCl$_3$, 270 MHz) δ 7.03 (3H, m, Ar H$_D$, Ar H$_F$), 7.20 (2H, dd, J=0.9, 10.1 Hz, Ar H$_E$), 7.23 (1H, m, Ar H$_B$), 7.53 (1H, m, Ar H$_C$), 7.97 (1H, dd, J=1.5, 8.2 Hz, Ar H$_A$).

2-(4-Trifluoromethoxy-phenoxy)-phenylamine HVB01062 C$_{13}$H$_{10}$F$_3$NO$_2$, MW 269.22

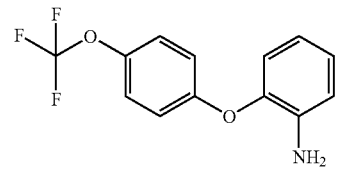

1-Trifluoromethoxy-4-(2-nitro-phenoxy)-benzene (HVB01037, 2.1 g, 7.02 mmol) was added to a solution of iron powder (2.15 g, 38.61 mmol) and ammonium chloride (0.27 g, 4.9 mmol) in ethanol (40 ml) and water (4 ml) at reflux. Stirred at reflux for 3 h. Ethanol removed in-vacuo and the residue was extracted with sodium hydrogen carbonate. Organic layers dried over anhydrous magnesium sulphate and evaporated to dryness, to afford a brown oil, 1.57 g, 95%. Rf: 0.6 (DCM) $^1$HNMR (CDCl$_3$, 270 MHz) δ 3.81 (2H, s, NH$_2$), 6.76 (1H, m, ArH$_B$), 6.84 (1H, dd, J=1.2, 7.9 Hz, ArH$_A$), 6.91 (1H, dd, J=1.0, 7.9 Hz, ArH$_D$), 6.98 (2H, d, J=9.1 Hz, ArH$_F$), 7.04 (1H, m, Ar H$_C$), 7.18 (2H, d, J=8.7 Hz, Ar H$_E$).

4-[2-(4-Trifluoromethoxy-phenoxy)-phenylcarbamoyl]-piperidine-1-carboxylic acid tert-butyl ester HVB01064 C$_{24}$H$_{27}$F$_3$N$_2$O$_5$ MW 480.49

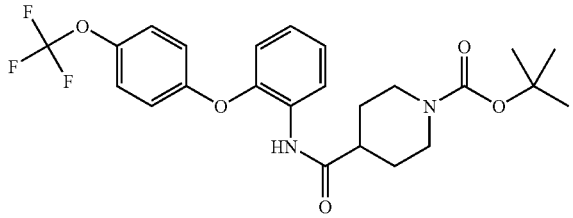

Piperidine-1,4-dicarboxylic acid mono-tert-butyl ester (HVB01062, 1.19 g, 5.2 mmol) was dissolved in anhydrous DCM (40 ml), and stirred under nitrogen. To this was added N N-4-dimethylaminopyridine (cat.), 1-(3-dimethylaminopropyl)-3-ethylcarbodiimide hydrochloride (3.0 g, 4.2 mmol) and TEA (0.84 ml). Stirred for 30 min. 2-(4-Trifluoromethoxy-phenoxy)-phenylamine (HVB01053, 1.4 g, 5.2 mmol) was added and stirred under nitrogen for 20 h. Diluted with DCM, washed with HCl (1M, 20 ml), Sodium hydrogen carbonate (sat. 20 ml), and brine (20 ml). Organic layers combined and dried over anhydrous magnesium sulphate, and evaporated in-vacuo. The crude mixture was purified using flash chromatography (DCM/hexane, 0 to 100%), to afford a yellow solid, 1.59 g, 57%. m.p. 45-48° C., Rf. 0.65 (DCM), $^1$HNMR: (CDCl$_3$, 270 MHz) δ 1.44 (9H, s, CH$_3$), 1.67 (2H, td, J=13.4, 4.4 Hz, CH$_2$), 1.80 (2H, dd, J=1.8 Hz, CH$_2$), 2.36 (1H, m, CH), 2.74 (2H, t, J=11.9 Hz, CH$_2$N), 4.12 (2H, d, J=11.6 Hz, CH$_2$N), 6.85 (1H, dd, J=6.7, 1.5 Hz, Ar H$_D$), 7.03 (2H, d, Ar H$_F$), 7.04 (1H, m, Ar H$_B$), 7.13 (1H, td, J=1.5, 6.4 Hz, ArH$_C$), 7.20 (2H, d, J=1.5, 6.4 Hz ArH$_F$), 7.64 (1H, s, NH), 8.40 (1H, d, J=8.2 Hz, Ar H$_A$.

Piperidine-4-carboxylic acid [2-(4-trifluoromethoxy-phenoxy)-phenyl]-amide HVB01069 C$_{19}$H$_{19}$F$_3$N$_2$O$_3$, MW 380.0

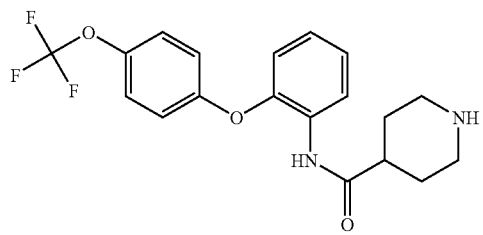

4-[2-(4-Trifluoromethoxy-phenoxy)-phenylcarbamoyl]-piperidine-1-carboxylic acid tert-butyl ester (HVB01064, 0.3 g, 0.62 mmol) was dissolved in anhydrous DCM (7 ml), cooled to 0° C. and to this was added TFA (2.8 ml), and the reaction mixture was stirred under nitrogen for 1.5 h. The reaction mixture was poured onto solid potassium carbonate (6 g), and water (25 ml) added. Extracted with DCM and the organic layers dried over anhydrous magnesium sulphate, and evaporated in-vacuo, 0.21 g, 87%. Rf: 0.35 (DCM), $^1$HNMR: (CDCl$_3$, 270 MHz) δ 1.64 (2H, m, CH$_2$), 1.79 (2H, dd, J=2.7, 12.9 Hz, CH$_2$), 2.32 (1H, m, CH), 2.61 (2H, td, J=2.7, 12.3 Hz, NCH$_2$), 2.94 (1H, s, NH), 3.10 (2H, td, J=3.3, 12.6 Hz, NCH$_2$), 6.79 (1H, dd, J=1.2, 8.1, ArH$_D$), 6.95 (2H, m, ArH$_E$), 6.95 (1H, m, ArH$_E$), 7.08 (1H, td, J=1.5, 7.8 Hz, ArH$_C$), 7.13 (2H, d, J=8.4 Hz, ArH$_F$), 7.62 (1H, s, NH), 8.34 (1H, dd, J=1.2, 8.1 Hz, ArH$_A$).

1-Acetyl-piperidine-4-carboxylic acid [2-(4-trifluoromethoxy-phenoxy)-phenyl]-amide (HVB01070, STX1624) C$_{21}$H$_{21}$F$_3$N$_2$O$_4$, MW 422.41

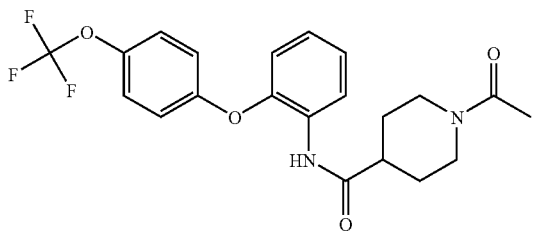

Piperidine-4-carboxylic acid [2-(4-trifluoromethoxy-phenoxy)-phenyl]-amide (HVB01069, 105 mg, 0.28 mmol) was dissolved in DCM (8 ml) and cooled to 0° C. To this was added acetyl chloride (0.04 ml, 0.56 mmol) and TEA (0.18 ml). The reaction mixture was allowed to warm to room temperature and stirred for 1 h. The reaction was quenched with sodium hydrogen carbonate (15 ml), extracted with DCM and washed with hydrochloric acid (1M) and brine. The organic layers were dried over anhydrous magnesium sulphate and evaporated in-vacuo. The crude mixture was purified using flash chromatography (0-5% methanol in ethyl acetate), to afford a white solid, 55 mg, 47%. m.p. 44-46° C., R.f. 0.45 (DCM) LCMS t$_r$=1.08 min (95% MeOH and 5% water at 1.0 ml/min), m/z M$^+$H 423.48, HPLC t$_r$=2.12 min (isocratic 90% acetonitrile and 10% water at 1.0 ml/min), 96.69%, $^1$HNMR (CDCl$_3$, 270 MHz) δ 1.62 (2H, m, CH$_2$), 1.80 (2H, m, CH$_2$), 2.02 (3H, s, CH$_3$), 2.40 (1H, m, CH), 2.60 (1H, td, J=3.0, 14.7 Hz, CH$_2$), 3.03 (1H, m, CH$_2$), 3.79 (1 h, d, J=13.5 Hz, CH$_2$), 4.52 (1H, d, J=13.2 Hz, CH$_2$), 6.79 (1H, dd, J=1.2, 8.1 Hz, ArH$_D$), 6.96 (1H, m, ArH$_B$), 6.96 (2H, m, ArH$_E$), 7.08 (1H, td, J=1.2, 7.8 Hz, ArH$_C$), 7.15 (2H, dd, J=0.6, 9.0 Hz, ArH$_F$), 7.26 (1H, s, NH), 8.32 (1H, dd, J=1.2, 8.1 Hz, ArH$_A$). Anal. Calcd for C$_{21}$H$_{21}$F$_3$N$_2$O$_4$: C, 59.71; H, 5.01; N, 6.63%. Found: C, 58.0; H, 4.93; N, 6.37%.

1-Benzoyl-piperidine-4-carboxylic acid [2-(4-trifluoromethoxy-phenoxy)-phenyl]-amide HVB01072, STX1625 C$_{26}$H$_{23}$F$_3$N$_2$O$_4$, MW 484.45

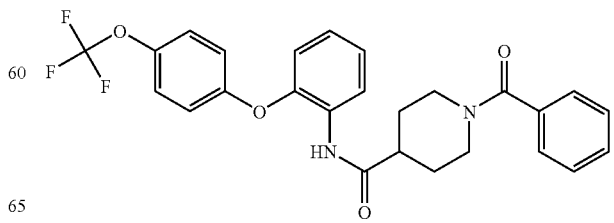

Piperidine-4-carboxylic acid [2-(4-trifluoromethoxy-phenoxy)-phenyl]-amide (HVB01069 105 mg, 0.28 mmol) was dissolved in DCM (8 ml) and cooled to 0° C. To this was added benzoyl chloride (0.064 ml, 0.56 mmol) and TEA (0.18 ml). The reaction mixture was allowed to warm to room temperature and stirred for 1 h. The reaction was quenched with sodium hydrogen carbonate (15 ml), extracted with DCM and washed with hydrochloric acid (1M) and brine. The organic layers were dried over anhydrous magnesium sulphate and evaporated in-vacuo. The crude mixture was purified using flash chromatography (0-5% methanol in DCM), to afford a white solid, 105 mg, 78%. m.p. 53-55° C., R.f. 0.45 (DCM) LCMS $t_r$=4.9 min (50% MeOH and 50% water at 0.5 ml/min), m/z M$^+$H 485.43, HPLC: 98.0%, $^1$HNMR (CDCl$_3$, 270 MHz) δ 1.74 (4H, m, 2CH$_2$), 2.45 (1H, m, CH), 2.90 (2H, s, CH$_2$), 3.77 (1H, s, CH$_2$), 4.63 (1H, s, CH$_2$), 6.80 (1H, dd, J=1.2, 8.1 Hz, ArH$_D$), 6.95 (1H, m, ArH$_B$), 6.95 (2H, m, ArH$_E$), 7.09 (1H, td, J=1.5, 7.8 Hz, ArH$_C$), 7.15 (2H, dd, J=0.6, 9.0 Hz, ArH$_F$), 7.33 (5H, m, ArH), 7.63 (1H, s, NH), 8.32 (1H, d, J=7.2 Hz, ArH$_A$). Anal. Calcd for $C_{26}H_{23}F_3N_2O_4$: C, 64.46; H, 4.79; N, 5.78%. Found: C, 63.7; H, 4.76; N, 5.57%.

Synthetic Route to STX1666-1669

Piperidine-4-carboxylic acid [2-(2,4-dichloro-phenoxy)-phenyl]-amide HVB01079 $C_{18}H_{18}Cl_2N_2O_2$, MW 365.25

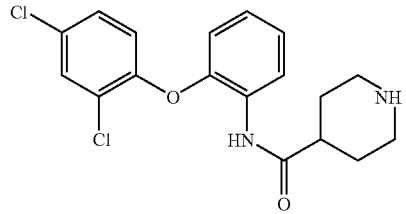

4-[2-(2,4-Dichloro-phenoxy)-phenylcarbamoyl]-piperidine-1-carboxylic acid tert-butyl ester (AMR01046, 1.0 g, 2.15 mmol) was dissolved in DCM (20 ml), and cooled to 0° C. and to this was added TFA (5 ml). This was allowed to warm to room temperature and stirred for 30 min. The reaction mixture was poured onto solid potassium carbonate (12 g), and water (50 ml) added. Extracted with DCM and the organic layers dried over anhydrous magnesium sulphate, and evaporated in-vacuo, to afford a cream oil, 0.77 g, 98%. R.f. 0.2 (EtOAc) $^1$HNMR (CDCl$_3$, 300 MHz) δ 1.72 (2H, m, CH$_2$), 1.87 (2H, m, CH$_2$), 2.39 (1H, m, CH), 2.68 (2H, td, J=2.7, 12.3 Hz, CH$_2$), 3.16 (2H, dt, J=3.6, 7.2, 12.6 Hz, CH$_2$), 6.66 (1H, dd, J=1.5, 8.1 Hz, ArH), 6.87 (1H, d, J=8.7 Hz, ArH), 6.94 (1H, td, J=1.8, 8.1 Hz, ArH), 7.07 (1H, td, J=1.2, 7.8 Hz, ArH), 7.15 (1H, dd, J=2.7, 9.0 Hz, ArH), 7.43 (1H, d, J=2.4 Hz, ArH), 8.34 (1H, dd, J=6.9 Hz, ArH).

1-Cyclohexanecarbonyl-piperidine-4-carboxylic acid [2-(2,4-dichloro-phenoxy)-phenyl]-amide HVB01081, STX 1666 $C_{25}H_{25}Cl_2N_2O_3$, MW 475.41

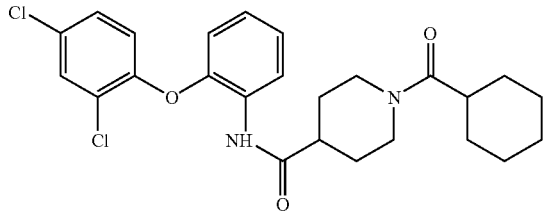

Piperidine-4-carboxylic acid [2-(2,4-dichloro-phenoxy)-phenyl]-amide (HVB01079 0.1 g, 0.27 mmol) was dissolved in DCM (5 ml) and cooled to 0° C. To this was added TEA (0.2 ml) and cyclohexane carbonyl chloride (0.072 ml, 0.54 mmol), and allowed to warm to room temperature, and stirred for 30 min. NaHCO$_3$ added, and extracted with DCM, dried over MgSO$_4$ and evaporated in-vacuo. The crude mixture was purified using flash chromatography (0-5% methanol in DCM), to afford a white solid, 120 mg, 95%. m.p. 46-48° C., Rf. 0.65 (EtOAc), LCMS $t_r$=5.42 min (50% MeOH and 50% water at 0.5 ml/min), m/z M$^+$H 475.16, HPLC $t_r$=4.241 min (isocratic 80% acetonitrile and 20% water at 1.0 ml/min), 96.57%, $^1$HNMR (CDCl$_3$, 270 MHz) δ 1.50 (14H, m, 7CH$_2$), 2.28 (1H, m, CH$_2$), 2.38 (1H, m, CH), 2.61 (1H, t, J=10.0 Hz, CH$_2$), 3.02 (1H, t, J=9.5 Hz, CH$_2$), 3.92 (1H, d, J=11.3 Hz, CH$_2$), 4.57 (1H, d, J=11.9 Hz, CH$_2$), 6.67 (1H, dd, J=7.3, 1.4 Hz, ArH$_D$), 6.89 (1H, d, J=7.8 Hz, ArH$_E$), 6.95 (1H, td, J=7.0, 1.4 Hz, ArH$_C$), 7.07 (1H, td, J=1.4, 7.6 Hz, ArH$_B$), 7.16 (1H, dd, J=2.4, 8.1 Hz, ArH$_F$), 7.43 (1H, d, J=2.2 Hz, ArH$_G$), 7.69 (1H, s, NH), 8.34 (1H, d, J=7.02 Hz, ArH$_A$). Anal. Calcd for $C_{25}H_{25}Cl_2N_2O_3$: C, 63.16; H, 5.94; N, 5.89. Found C, 64.1; H, 6.41; N, 5.32.

1-Cyclopentanecarbonyl-piperidine-4-carboxylic acid [2-(2,4-dichloro-phenoxy)-phenyl]-amide HVB01082: STX1667 $C_{24}H_{26}Cl_2N_2O_3$, MW 461.38

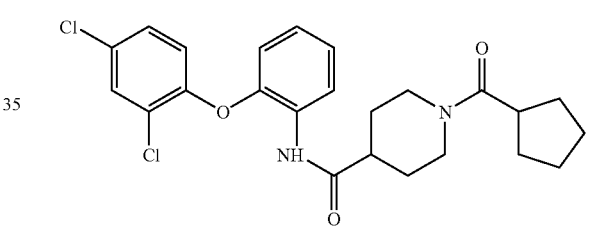

Piperidine-4-carboxylic acid [2-(2,4-dichloro-phenoxy)-phenyl]-amide (HVB01079 0.1 g, 0.27 mmol) was dissolved in DCM (5 ml) and cooled to 0° C. To this was added TEA (0.2 ml) and cyclopentane carbonyl chloride (0.066 ml, 0.54 mmol), and allowed to warm to room temperature, and stirred for 30 min. NaHCO$_3$ added, and extracted with DCM, dried over MgSO$_4$ and evaporated in-vacuo. The crude mixture was purified using flash chromatography (0-100% DCM in hexane). Recrystallised from diethyl ether/hexane to afford a white solid, 46 mg, 37%. m.p. 135-137° C., Rf. 0.67 (EtOAc), LCMS $t_r$=5.29 min (50% MeOH and 50% water at 0.5 ml/min), m/z M$^+$H 461.32, HPLC $t_r$=3.963 min (isocratic 80% acetonitrile and 20% water at 1.0 ml/min), 98.3%, $^1$HNMR (CDCl$_3$, 270 MHz) δ 1.8 (8H, m, 4CH$_2$), 1.8 (4H, m, 2CH$_2$), 2.51 (1H, m, CH), 2.68 (1H, m, CH$_2$), 2.88 (1H, m, CH), 3.05 (1H, m, CH$_2$), 4.03 (1H, d, J=13.8 Hz, CH$_2$), 4.63 (1H, d, J=13.1 Hz, CH$_2$), 6.72 (1H, dd, J=8.15, 1.46 Hz, ArH$_D$), 6.95 (1H, d, J=8.7 Hz, ArH$_E$), 7.00 (1H, td, J=7.6, 1.73 Hz, ArH$_C$), 7.13 (1H, td, J=7.91, 1.2 Hz, ArH$_B$), 7.22 (1H, dd, J=8.64, 2.48 Hz, ArH$_F$), 7.49 (1H, d, J=2.5 Hz, ArH$_G$), 7.76 (1H, s, NH), 8.4 (1H, dd, J=8.15 Hz, ArH$_A$). Anal. Calcd for $C_{24}H_{26}Cl_2N_2O_3$: C, 62.48; H, 5.68; N, 6.07. Found C, 62.5; H, 5.63; N, 5.96.

1-Isobutyryl-piperidine-4-carboxylic acid [2-(2,4-dichloro-phenoxy)-phenyl]-amide HVB01083: STX 1668 $C_{22}H_{24}Cl_2N_2O_3$, MW 435.34

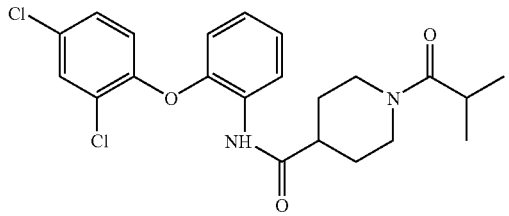

Piperidine-4-carboxylic acid [2-(2,4-dichloro-phenoxy)-phenyl]-amide (HVB01079, 0.1 g, 0.27 mmol) was dissolved in DCM (5 ml) and cooled to 0° C. To this was added TEA (0.2 ml) and isobutyryl chloride (0.057 ml, 0.54 mmol), and allowed to warm to room temperature, and stirred for 30 min. NaHCO$_3$ added, and extracted with DCM, dried over MgSO$_4$ and evaporated in-vacuo. The crude mixture was purified using flash chromatography (0-10% methanol in DCM). Recrystallised from diethyl ether/hexane to afford a white solid, 89 mg, 75%, m.p. 50-52° C., Rf. 0.65 (EtOAc), LCMS $t_r$=5.0 min (50% MeOH and 50% water at 1.0 ml/min), m/z M$^+$H 435.31, HPLC $t_r$=2.58 min (isocratic 90% acetonitrile and 10% water at 1.0 ml/min), 97.34%, $^1$HNMR (CDCl$_3$, 270 MHz) δ 1.09 (6H, m, CH$_3$), 1.66 (2H, m, CH$_2$), 1.88 (2H, m, CH$_2$), 2.46 (1H, m, CH), 2.63 (1H, m, CH$_2$), 2.74 (1H, m, CH), 3.04 (1H, t, J=11.1 Hz, CH$_2$), 3.94 (1H, d, J=12.2 Hz, CH$_2$), 4.58 (1H, d, J=111.6 Hz, CH$_2$), 6.67 (1H, td, J=6.2, 1.4 Hz, ArH$_D$), 6.89 (1H, d, J=8.1 Hz, ArH$_E$), 6.95 (1H, td, J=6.8 Hz, ArH$_D$), 7.07 (1H, td, J=7.29, 1.1 Hz, ArH$_B$), 7.16 (1H, dd, J=7.83, 2.16 Hz, ArH$_F$), 7.43 (1H, d, J=2.2 Hz, ArH$_G$), 7.71 (1H, s, NH), 8.3 (1H, dd, J=7.29, 1.1 Hz, ArH$_A$). $^{13}$CNMR (CDCl$_3$, 400 MHz) δ 19.3, 19.6 (CH$_3$), 28.6, 29.1 (CH$_2$), 30.10 (CH), 41.1 (CH$_2$), 44.30 (CH), 44.7 (CH$_2$), 116.4, 121.3, 121.42, 124.2, 124.6, 126.34, 128.40, 128.81, 130.20, 130.70, 145.11, 150.30 (ArC), 172.2, 175.30 (C=O), Anal. Calcd for $C_{22}H_{24}Cl_2N_2O_3$: C, 60.70; H, 5.56; N, 6.43. Found C, 61.0; H, 5.71; N, 6.38.

1-(3-Methyl-butyryl)-piperidine-4-carboxylic acid [2-(2,4-dichloro-phenoxy)-phenyl]-amide HVB01084, STX1669 $C_{23}H_{26}Cl_2N_2O_3$, MW 449.37

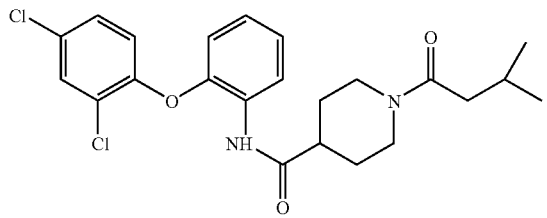

Piperidine-4-carboxylic acid [2-(2,4-dichloro-phenoxy)-phenyl]-amide (HVB01079 0.1 g, 0.27 mmol) was dissolved in DCM (5 ml) and cooled to 0° C. To this was added TEA (0.2 ml) and isovaleryl chloride (0.057 ml, 0.54 mmol), and allowed to warm to room temperature, and stirred for 30 min. NaHCO$_3$ added, and extracted with DCM, dried over MgSO$_4$ and evaporated in-vacuo. The crude mixture was purified using flash chromatography (0-10% methanol in DCM) to afford a white waxy solid, 80 mg, 65%, m.p. 60-62° C. Rf. 0.65 (EtOAc), LCMS $t_r$=5.08 min (50% MeOH and 50% water at 0.5 ml/min), m/z M$^+$H 449.35, HPLC $t_r$=2.69 min (isocratic 90% acetonitrile and 10% water at 1.0 ml/min), 94.83%, $^1$HNMR (CDCl$_3$, 270 MHz) δ 0.73 (6H, d, J=5.9 Hz, 2CH$_3$), 1.48 (2H, m, CH$_2$), 1.70 (2H, m, CH$_2$), 1.87 (1H, m, CH), 2.27 (1H, m, CH), 2.45 (1H, td, J=12.4, 2.4 Hz, CH$_2$), 2.85 (1H, td, J=12.4, 2.16 Hz, CH$_2$), 3.70 (1H, dd, J=12.2, CH$_2$), 4.40 (1H, d, J=1.9 Hz, CH$_2$), 6.49 (1H, dd, J=7.3, 1.1 Hz, ArH$_D$), 6.72 (1H, d, J=7.8 Hz, ArH$_E$), 6.77 (1H, td, J=6.8, 1.4 ArH$_C$), 6.90 (1H, td, J=7.3, 1.4 Hz, ArH$_B$), 6.99 (1H, dd, J=7.8, 2.2 Hz, ArH$_F$), 7.26 (1H, d, J=2.4 Hz, ArH$_G$), 7.53 (1H, s, NH), 8.16 (1H, d, J=7.0 Hz, ArH$_A$). $^{13}$CNMR (CDCl$_3$, 400 MHz) δ 22.70, 22.80 (CH$_3$), 25.80, 28.64, 29.03, 40.89, (CH$_2$), 42.13, 44.24 (CH), 45.14 (CH$_2$), 116.45, 121.42, 124.22, 124.56, 126.36, 128.36, 128.82, 130.16, 130.66, 145.16, 150.27 (ArC), 170.97, 172.22 (C=O), Anal. Calcd for $C_{23}H_{26}Cl_2N_2O_3$: C, 61.47; H, 5.83; N, 6.23. Found C, 61.70; H, 6.02; N, 6.33.

Synthetic Route to STX1715-1718, 1749

1-Trifluoromethoxy-4-(2-nitro-phenoxy)-benzene HVB01037 $C_{13}H_8F_3NO_4$, MW 299.21

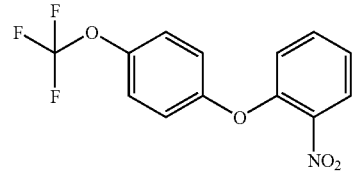

4-(trifluoromethoxy)phenol (1.36 ml, 10.6 mmol), 2-fluoro-1-nitrobenzene (0.74 ml, 7 mmol), potassium carbonate (1.46 g, 10.5 mmol) were mixed together in DMF (4 ml) and heated at reflux for 5 h. Allowed to cool, and evaporated in-vacuo. Residue partitioned between diethyl ether and sodium hydroxide (1 M). Organic layers combined and dried over anhydrous magnesium sulphate and evaporated in-vacuo, to afford a yellow oil, 2.34 g, >100%. Rf: 0.72 (DCM), $^1$HNMR (CDCl$_3$, 270 MHz) δ 7.03 (3H, m, Ar H$_D$, Ar H$_F$), 7.20 (2H, dd, J=0.9, 10.1 Hz, Ar H$_E$), 7.23 (1H, m, Ar H$_B$), 7.53 (1H, m, Ar H$_C$), 7.97 (1H, dd, J=1.5, 8.2 Hz, Ar H$_A$).

2-(4-Trifluoromethoxy-phenoxy)-phenylamine HVB01040 $C_{13}H_{10}F_3NO_2$, MW 269.23

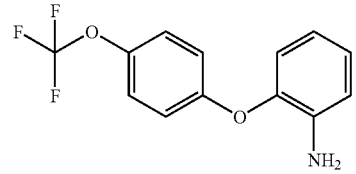

1-Trifluoromethoxy-4-(2-nitro-phenoxy)-benzene (HVB01037, 2.1 g, 7.02 mmol) was added to a solution of iron powder (2.15 g, 38.61 mmol) and ammonium chloride (0.27 g, 4.9 mmol) in ethanol (40 ml) and water (4 ml) at reflux. Stirred at reflux for 3 h. Ethanol removed in-vacuo and the residue was extracted with sodium hydrogen carbonate. Organic layers dried over anhydrous magnesium sulphate and evaporated to dryness, to afford a brown oil, 1.9 g, 100%. Rf:

0.6 (DCM) ¹HNMR (CDCl₃, 270 MHz) δ 3.81 (2H, s, NH₂), 6.76 (1H, m, ArH$_B$), 6.84 (1H, dd, J=1.2, 7.9 Hz, ArH$_A$), 6.91 (1H, dd, J=1.0, 7.9 Hz, ArH$_D$), 6.98 (2H, D, J=9.1 Hz, ArH$_F$), 7.04 (1H, m, Ar H$_C$), 7.18 (2H, d, J=8.7 Hz, Ar H$_E$).

Piperidine-1,4-dicarboxylic acid mono-tert-butyl ester HVB01031 C₁₁H₁₉NO₄ MW 229.28

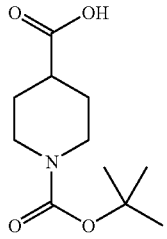

Di-t-butyl dicarbonate (3.4 g, 15.6 mmol) and sodium hydroxide (6.2 g, 154.5 mmol) were added to a solution of isonipecotic acid (2 g, 15.5 mmol) in 1,4-dioxane (50 ml) and water (50 ml). Stirred at room temperature for 21 h. Concentrated in-vacuo to approximately 15 ml, diluted with ethyl acetate and acidified to pH 3-4 using hydrochloric acid (1M). Extracted with ethyl acetate and washed with water. Organic layers dried over anhydrous magnesium sulphate and evaporated to dryness, to afford a white solid, 2.16 g, 61%. m.p. 151-153° C., Rf: 0.72 (10% MeOH in DCM), ¹H NMR (270 MHz, CDCl₃) δ 1.4 (9H, s, CH₃), 1.64 (2H, m, CH₂), 1.89 (2H, dd, J=3.0, 13.4 Hz, CH₂), 2.5 (1H, m, CH), 2.83 (2H, t, J=11.1 Hz, N—CH₂), 4.03 (2H, d, J=12.0 Hz, N—CH₂).

4-[2-(4-Trifluoromethoxy-phenoxy)-phenylcarbamoyl]-piperidine-1-carboxylic acid tert-butyl ester HVB01051, STX1749 C₂₄H₂₇F₃N₂O₅ MW 480.49

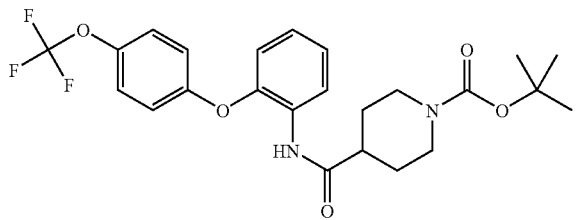

Piperidine-1,4-dicarboxylic acid mono-tert-butyl ester (HVB01045, 1.19 g, 5.2 mmol) was dissolved in anhydrous DCM (40 ml), and stirred under nitrogen. To this was added N N-4-dimethylaminopyridine (cat.), 1-(3-dimethylaminopropyl)-3-ethylcarbodiimide hydrochloride (3.0 g, 4.2 mmol) and TEA (0.84 ml). Stirred for 30 min. 2-(4-Trifluoromethoxy-phenoxy)-phenylamine (HVB01040, 1.4 g, 5.2 mmol) was added and stirred under nitrogen for 20 h. Diluted with DCM, washed with HCl (1M, 20 ml), Sodium hydrogen carbonate (sat. 20 ml), and brine (20 ml). Organic layers combined and dried over anhydrous magnesium sulphate, and evaporated in-vacuo. The crude mixture was purified using flash chromatography (DCM/hexane, 0 to 100%), to afford a yellow solid, 0.77 g, 31%. m.p. 45-48° C., R.f: 0.65 (DCM), ¹HNMR: (CDCl₃, 270 MHz) δ 1.44 (9H, s, CH₃), 1.67 (2H, td, J=13.4, 4.4 Hz, CH₂), 1.80 (2H, dd, J=1.8 Hz, CH₂), 2.36 (1H, m, CH), 2.74 (2H, t, J=11.9 Hz, CH₂N), 4.12 (2H, d, J=11.6 Hz, CH₂N), 6.85 (1H, dd, J=6.7, 1.5 Hz, Ar H$_D$), 7.03 (2H, d, Ar H$_F$), 7.04 (1H, m, Ar H$_B$), 7.13 (1H, td, J=1.5, 6.4 Hz, ArH$_C$), 7.20 (2H, d, J=1.5, 6.4 Hz, ArH$_E$), 7.64 (1H, s, NH), 8.40 (1H, d, J=8.2 Hz, Ar H$_A$).

Piperidine-4-carboxylic acid [2-(4-trifluoromethoxy-phenoxy)-phenyl]-amide HVB01069 C₁₉H₁₉F₃N₂O₃, MW 380.0

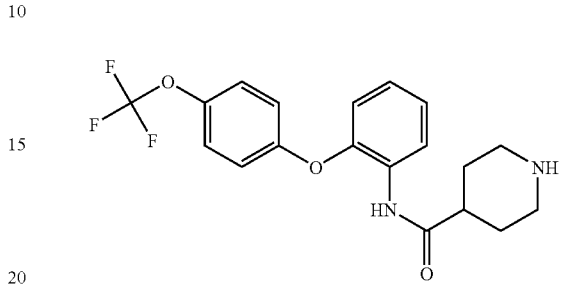

4-[2-(4-Trifluoromethoxy-phenoxy)-phenylcarbamoyl]-piperidine-1-carboxylic acid tert-butyl ester (HVB01064, 0.3 g, 0.62 mmol) was dissolved in anhydrous DCM (7 ml), cooled to 0° C. and to this was added TFA (2.8 ml), and the reaction mixture was stirred under nitrogen for 1.5 h. The reaction mixture was poured onto solid potassium carbonate (6 g), and water (25 ml) added. Extracted with DCM and the organic layers dried over anhydrous magnesium sulphate, and evaporated in-vacuo, 0.21 g, 87%. Rf: 0.35 (DCM), ¹HNMR: (CDCl₃, 270 MHz) δ 1.64 (2H, m, CH₂), 1.79 (2H, dd, J=2.7, 12.9 Hz, CH₂), 2.32 (1H, m, CH), 2.61 (2H, td, J=2.7, 12.3 Hz, NCH₂), 2.94 (1H, s, NH), 3.10 (2H, td, J=3.3, 12.6 Hz, NCH₂), 6.79 (1H, dd, J=1.2, 8.1, ArH$_D$), 6.95 (2H, m, ArH$_E$), 6.95 (1H, m, ArH$_E$), 7.08 (1H, td, J=1.5, 7.8 Hz, ArH$_C$), 7.13 (2H, d, J=8.4 Hz, ArH$_F$), 7.62 (1H, s, NH), 8.34 (1H, dd, J=1.2, 8.1 Hz, ArH$_A$).

HVB01089-HVB01092 were synthesised using parallel synthesis as described below.

1-Cyclohexanecarbonyl-piperidine-4-carboxylic acid [2-(4-trifluoromethoxy-phenoxy)-phenyl]-amide HVB01089, STX1715 C₂₆H₂₉F₃N₂O₄, MW 490.51

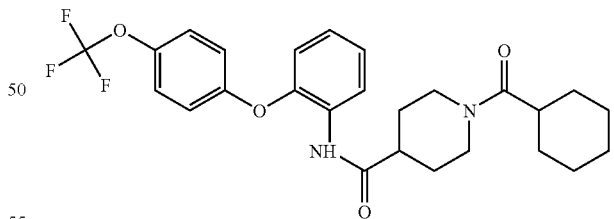

Piperidine-4-carboxylic acid[2-(4-trifluoromethoxy-phenoxy)-phenyl]-amide (HVB01087, 0.1 g, 0.26 mmol) was dissolved in DCM (5 ml), and cooled to 0° C. To this was added TEA (0.2 ml) and cyclohexane carbonyl chloride (0.072 ml, 0.52 mmol) and allowed to warm to room temperature, and stirred for 30 min. NaHCO₃ added, and extracted with DCM, dried over MgSO₄ and evaporated in-vacuo. The crude mixture was purified using flash chromatography (0-100% ethyl acetate in hexane) to afford a white waxy solid. 98 mg, 76%, m.p. 98-100° C., R.f. 0.70 (EtOAc), LCMS t$_r$=5.08 min (50% MeOH and 50% water at 0.5 ml/min), m/z M$^+$H 489.33, HPLC t$_r$=2.57 min (Isocratic 90% acetonitrile and 10% water at 1.0 ml/min), 97.93%, $^1$HNMR (CDCl$_3$, 270 MHz) δ 1.76 (12H, m, 6CH$_2$), 2.42 (2H, m, 2CH), 2.61 (1H, t, J=11.6 Hz, CH$_2$), 3.03 (1H, t, J=12.2 Hz, CH$_2$), 3.94 (1H, d, J=13.1 Hz, CH$_2$), 4.62 (1H, d, J=12.9 Hz, CH$_2$), 6.85 (1H, dd, J=1.5, 8.2 Hz, ArH$_D$), 7.00 (2H, d, J=9.2, ArH$_E$), 7.01 (1H, m, ArH$_B$), 7.14 (td, J=1.5, 7.9 Hz, ArH$_C$), 7.20 (2H, d, J=8.4 Hz, ArH$_F$), 7.68 (1H, s, NH), 8.39 (1H, d, J=8.2 Hz, ArH$_A$). $^{13}$CNMR (CDCl$_3$, 400 MHz) δ 25.81, 25.84, 28.57, 29.25, 29.52 (CH$_2$), 40.46 (CH), 40.94 (CH$_2$), 44.38 (CH), 44.63 (CH$_2$), 117.92, 119.34, 121.38, 122.92, 124.43, 124.67, 129.47, 129.47, 144.98, 145.28 (ArC), 154.79 (OCF$_3$), 172.22, 174.53 (C=O), Anal. Calcd for C$_{26}$H$_{29}$F$_3$N$_2$O$_4$: C, 63.66; H, 5.96; N, 5.71. Found C, 63.6; H, 5.86; N, 5.58.

1-Cyclopentanecarbonyl-piperidine-4-carboxylic acid [2-(4-trifluoromethoxy-phenoxy)-phenyl]-amide HVB01090, STX1716 C$_{25}$H$_{27}$F$_3$N$_2$O$_4$, MW 476.49

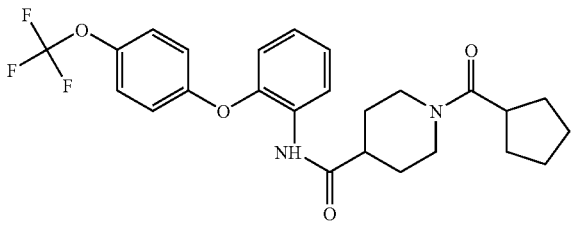

Piperidine-4-carboxylic acid[2-(4-trifluoromethoxy-phenoxy)-phenyl]-amide (HVB01087, 0.1 g, 0.26 mmol) was dissolved in DCM (5 ml), and cooled to 0° C. To this was added TEA (0.2 ml) and cyclopentane carbonyl chloride (0.066 ml, 0.52 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. 85 mg, 68% Rf. 0.68 (EtOAc), m.p. 48-50° C. LCMS t$_r$=5.00 min (50% MeOH and 50% water at 0.5 ml/min), m/z M$^+$H 477.56, HPLC t$_r$=2.50 min (Isocratic 90% acetonitrile and 10% water at 1.0 ml/min), 98.49%, $^1$HNMR (CDCl$_3$, 270 MHz) δ 1.77 (14H, m, 7CH$_2$), 2.46 (1H, m, CH), 2.64 (1H, m, CH$_2$), 2.86 (1H, m, CH), 3.05 (1H, m, CH$_2$), 4.01 (1H, d, J=13.4 Hz, CH$_2$), 4.62 (1H, d, J=13.4 Hz, CH$_2$), 6.85 (1H, dd, J=1.2, 7.9 Hz, ArH$_D$), 7.00 (2H, d, J=9.2 Hz, ArH$_E$), 7.01 (1H, m, ArH$_C$), 7.14 (1H, td, J=1.8, 7.9 Hz, ArH$_B$), 7.20 (2H, d, J=0.8, 9.1 Hz, ArH$_F$), 7.69 (1H, s, NH), 8.39 (1H, dd, J=1.5, 8.2 Hz, ArH$_A$). $^{13}$CNMR (CDCl$_3$, 400 MHz) δ 25.99, 28.56, 29.09, 30.22 (CH$_2$), 41.07 (CH), 41.16 (CH$_2$), 44.39 (CH), 44.76 (CH$_2$), 117.91, 119.41, 121.36, 122.91, 124.41, 124.42, 124.67, 129.49, 145.00, 145.27 (ArC), 154.78 (OCF$_3$), 172.24, 174.44 (C=O). Anal. Calcd for C$_{25}$H$_{27}$F$_3$N$_2$O$_4$: C, 63.02; H, 5.71; N, 5.88. Found C, 63.2; H, 5.77; N, 5.86.

1-Isobutyryl-piperidine-4-carboxylic acid [2-(4-trifluoromethoxy-phenoxy)-phenyl]-amide HVB01091, STX1717 C$_{23}$H$_{25}$F$_3$N$_2$O$_4$, MW 450.45

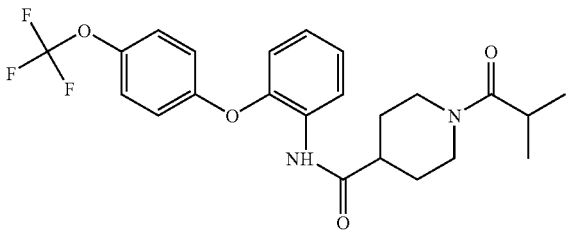

Piperidine-4-carboxylic acid [2-(4-trifluoromethoxy-phenoxy)-phenyl]-amide (HVB01087, 0.1 g, 0.26 mmol) was dissolved in DCM (5 ml), and cooled to 0° C. To this was added TEA (0.2 ml) and isobutyryl chloride (0.057 ml, 0.52 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. 89 mg, 75% m.p. 101-103° C. Rf. 0.56 (EtOAc), LCMS t$_r$=5.37 min (50% MeOH and 50% water at 0.5 ml/min), m/z M$^+$H 449.35, HPLC t$_r$=2.86 min (Isocratic 90% acetonitrile and 10% water at 1.0 ml/min), 97.9%, $^1$HNMR (CDCl$_3$, 270 MHz) δ 1.1 (6H, m, CH$_3$), 1.68 (2H, m, CH$_2$), 1.87 (2H, m, CH$_2$), 2.46 (1H, m, CH$_2$), 2.64 (1H, m, CH$_2$), 2.78 (1H, m, CH$_2$), 3.06 (1H, t, J=12.4 Hz, CH$_2$), 3.98 (1H, d, J=12.8 Hz, CH$_2$), 4.63 (1H, d, J=13.1 Hz, CH$_2$), 6.84 (1H, dd, J=1.5, 7.9 Hz, ArH$_D$), 7.01 (2H, d, J=9.1 Hz, ArH$_E$), 7.02 (1H, m, ArH$_B$), 7.14 (1H, td, J=1.5, 7.7 Hz, ArH$_C$), 7.20 (2H, d, J=8.9 Hz, ArH$_F$), 7.67 (1H, s, NH), 8.39 (1H, dd, J=1.5, 8.2 Hz, ArH$_A$). $^{13}$CNMR (CDCl$_3$, 400 MHz) δ 19.28, 19.53 (CH$_3$), 28.57, 29.15 (CH$_2$), 30.07 (CH), 41.04 (CH$_2$), 44.35 (CH), 44.66 (CH$_2$), 117.91, 119.41, 121.36, 122.91, 124.43, 124.67, 129.47, 144.99, 149.28 (Arc), 154.78 (CF$_3$), 172.20, 175.34 (C=O).

1-(3-Methyl-butyryl)-piperidine-4-carboxylic acid [2-(4-trifluoromethoxy-phenoxy)-phenyl]-amide HVB01092, STX1718 C$_{24}$H$_{27}$F$_3$N$_2$O$_4$, MW 464.48

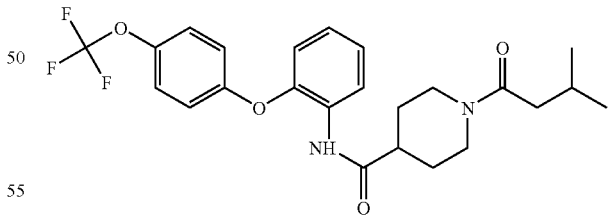

Piperidine-4-carboxylic acid [2-(4-trifluoromethoxy-phenoxy)-phenyl]-amide (HVB01087, 0.1 g, 0.26 mmol) was dissolved in DCM (5 ml), and cooled to 0° C. To this was added TEA (0.2 ml) and isovaleryl chloride (0.066 ml, 0.52 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. 82 mg, 67% Rf. 0.60 (EtOAc), m.p. 82-85° C., LCMS t$_r$=5.38 min (50% MeOH and 50% water at 0.5 ml/min), m/z M+H 463.33, HPLC $t_r$=2.42 min (Isocratic 90% acetonitrile and 10% water at 1.0 ml/min), 98.30%, $^1$HNMR (CDCl$_3$, 270 MHz) δ 0.94 (6H, m, CH$_3$), 1.67 (2H, m, CH$_2$), 1.87 (2H, m, CH$_2$), 2.09 (1H, m, CH), 2.19 (2H, m, CH$_2$), 2.46 (1H, m, CH), 2.64 (1H, m, CH$_2$), 3.05 (1H, m, CH$_2$), 3.91 (1H, d, J=14.1 Hz, CH$_2$), 4.63 (1H, d, J=13.6 Hz, CH$_2$), 6.85 (1H, dd, J=1.5, 8.2 Hz, ArH$_D$), 7.00 (2H, d, J=9.2 Hz, ArH$_E$), 7.01 (1H, m, ArH$_B$), 7.14 (1H, td, J=1.5, 7.7 Hz, ArH$_C$), 7.20 (2H, d, J=9.2 Hz, ArH$_F$), 7.67 (1H, s, NH), 8.39 (1H, dd, J=1.5, 8.2 Hz, ArH$_A$). $^{13}$CNMR (CDCl$_3$, 400 MHz) δ 22.67, 22.77 (CH$_3$), 25.77 (CH), 28.57, 29.02, 40.84, 42.01 (CH$_2$), 44.25 (CH), 45.11 (CH$_2$), 117.91, 119.41, 121.38, 122.92, 124.44, 124.67, 129.47, 145.01 (ArC), 145.30 (OCF$_3$), 154.78, 170.95 (C=O). Anal. Calcd for C$_{24}$H$_{27}$F$_3$N$_2$O$_4$: C, 62.06; H, 5.86; N, 6.03. Found C, 62.1; H, 5.96; N, 6.01.

Synthetic Route to STX1665, 1735, 36, 47, 49.

2-(4-Trifluoromethyl-phenoxy)-phenylamine.
HVB01029 C$_{13}$H$_{10}$F$_3$NO, MW 253.23

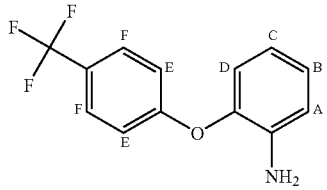

2-(4-Trifluoromethyl-phenoxy)-nitrobenzene (HVB01021, 1.24 g, 4.4 mmol) was added to a solution of iron (1.35 g, 24.2 mmol) and ammonium chloride (0.16 g, 3.08 mmol) in ethanol (23 ml), and water (2.2 ml) at reflux, and stirred at reflux for 1.5 h. Ethanol removed in-vacuo and the residue extracted with sodium sodium bicarbonateonate (20 ml) and DCM (3×20 ml). Organic layers combined and dried over anhydrous magnesium sulphate and evaporated to dryness, to afford a light yellow oil, 0.97 g, 82%. R$_f$ 0.45 (DCM, hexane, 1:1); $^1$HNMR (400 MHz, CDCl$_3$) δ 3.84 (2H, s, NH$_2$), 6.84 (1H, td, J=7.2, 1.2 Hz, Ar H$_B$), 6.91 (1H, dd, J=1.6, 8.0 Hz, Ar H$_D$), 7.01 (1H, dd, J=0.8, 7.6 Hz, Ar H$_A$), 7.10 (2H, d, J=9.2 Hz, Ar H$_F$), 7.13 (1H, td, J=4.0, 7.2 Hz, Ar H$_C$), 7.63 (2H, d, J=8.4 Hz, ArH$_E$).

Piperidine-1,4-dicarboxylic acid mono-tert-butyl ester HVB01031 C$_{11}$H$_{19}$NO$_4$ MW 229.28

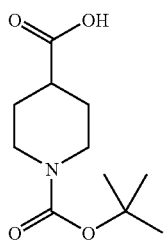

Di-t-butyl dicarbonate (3.4 g, 15.6 mmol) and sodium hydroxide (6.2 g, 154.5 mmol) were added to a solution of isonipecotic acid (2 g, 15.5 mmol) in 1,4-dioxane (50 ml) and water (50 ml). Stirred at room temperature for 21 h. Concentrated in-vacuo to approximately 15 ml, diluted with ethyl acetate and acidified to pH 3-4 using hydrochloric acid (1M). Extracted with ethyl acetate and washed with water. Organic layers dried over anhydrous magnesium sulphate and evaporated to dryness, to afford a white solid, 2.16 g, 61%. m.p. 151-153° C., Rf: 0.72 (10% MeOH in CHCl$_3$), $^1$H NMR (270 MHz, CDCl$_3$) δ 1.4 (9H, s, CH$_3$), 1.64 (2H, m, CH$_2$), 1.89 (2H, dd, J=3.0, 13.4 Hz, CH$_2$), 2.5 (1H, m, CH), 2.83 (2H, t, J=11.1 Hz, N—CH$_2$), 4.03 (2H, d, J=12.0 Hz, N—CH$_2$).

4-[2-(4-Trifluoromethyl-phenoxy)-phenylcarbamoyl]-piperidine-1-carboxylic acid tert-butyl ester.
HVB01063, STX1665 C$_{24}$H$_{27}$F$_3$N$_2$O$_4$, MW 464.49

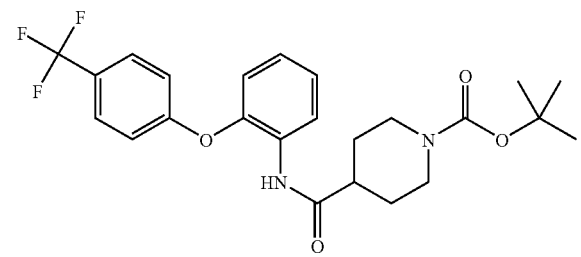

Piperidine-1,4-dicarboxylic acid mono-tert-butyl ester (HVB01053, 0.88 g, 3.85 mmol) was dissolved in anhydrous DCM (20 ml) and stirred under nitrogen. To this was added N N-4-dimethylaminopyridine (cat.), 1-(3-dimethylaminopropyl)-3-ethylcarbodiimide hydrochloride (2.2 g, 11.55 mmol) and TEA (0.62 ml). Stirred at room temperature for 30 min. To this was added 2-(4-trifluoromethyl-phenoxy)-phenylamine (HVB01061, 0.95 g, 3.8 mmol) and stirred for 3 days. The reaction mixture was diluted with DCM, washed with HCl (1M, 20 ml), Sodium hydrogen carbonate (sat. 20 ml), and brine (20 ml). Organic layers combined and dried over anhydrous magnesium sulphate, and evaporated in-vacuo to afford a white solid, 1.54 g, 88%. m.p. 48-50° C., Rf: 0.44 (DCM: Hexane, 1:1) LCMS $t_r$=4.98 min (50% MeOH and 50% water at 0.5 ml/min), m/z M+H 463.27, HPLC $t_r$=2.60 min (Isocratic 90% acetonitrile and 10% water at 1.0 ml/min), 99.22%, $^1$HNMR (CDCl$_3$, 270 MHz) δ 1.44 (9H, s, CH$_3$), 1.65 (2H, m, CH$_2$), 1.75 (2H, m, CH$_2$), 2.33 (1H, m, CH), 2.73 (2H, m, NCH$_2$), 4.13 (2H, m, NCH$_2$), 6.91 (1H, dd, J=1.5, 8.2 Hz, Ar H$_D$), 7.06 (1H, td, J=1.8, 8.2 Hz, Ar H$_B$), 7.06 (2H, d, J=8.4 Hz, Ar H$_F$), 7.18 (1H, td, J=1.8, 9.2 Hz, Ar H$_C$), 7.56 (1H, s, NH), 7.60 (2H, d, J=8.4 Hz, ArH$_E$), 8.4 (1H, dd, J=8.2 Hz, Ar H$_A$). Anal. Calcd for C$_{24}$H$_{27}$F$_3$N$_2$O$_4$: C, 62.06; H, 5.86; N, 6.03. Found C, 62.3; H, 6.39; N, 5.91.

Piperidine-4-carboxylic acid [2-(4-trifluoromethylphenoxy)-phenyl]-amide HVB01096
C$_{19}$H$_{19}$F$_3$N$_2$O$_2$, MW 364.36

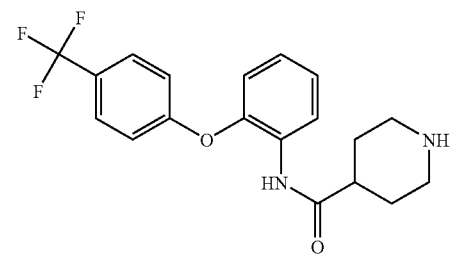

4-[2-(4-Trifluoromethyl-phenoxy)-phenylcarbamoyl]-piperidine-1-carboxylic acid tert-butyl ester (HVB01063, 1.0 g, 2.16 mmol) was dissolved in DCM (20 ml), and cooled to 0° C., and to this was added TFA (5 ml). Allowed to warm to room temperature and stirred for 1 h. The solution was poured over solid potassium carbonate (12 g), and extracted with DCM and water. Organic layers dried over MgSO$_4$ and evaporated to dryness, to afford a cream coloured solid. 0.85 g, 100%, R.f. 0.4 (5% MeOH in DCM), $^1$HNMR: (CDCl$_3$, 270 MHz) δ 1.65 (2H, m, CHCH$_2$), 1.79 (2H, m, CHCH$_2$), 2.30 (1H, m, CH), 2.64 (2H, td, J=12.4, 2.7 Hz, NCH$_2$), 3.10 (2H, m, NCH$_2$), 6.97 (1H, dd, J=6.4, 30.5 Hz, Ar H$_D$), 7.05 (2H, m, Ar H$_F$), 7.06 (1H, m, Ar H$_B$), 7.17 (1H, t, J=7.2 Hz, Ar H$_C$), 7.58, D, J=8.6 Hz, Ar H$_E$), 8.39 (1H, d, J=7.9 Hz, Ar H$_A$).

1-Cyclohexanecarbonyl-piperidine-4-carboxylic acid [2-(4-trifluoromethyl-phenoxy)-phenyl]-amide HVB01097, STX1735 C$_{26}$H$_{29}$F$_3$N$_2$O$_3$, MW 474.52

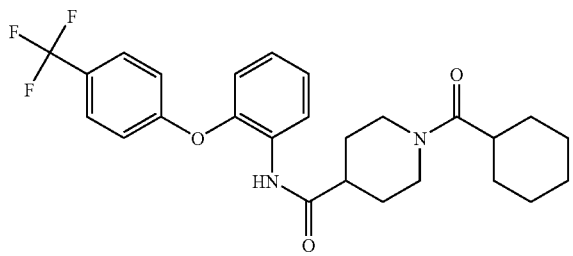

Piperidine-4-carboxylic acid [2-(4-trifluoromethyl-phenoxy)-phenyl]-amide (HVB01096, 0.1 g, 0.27 mmol) was dissolved in DCM (5 ml), and cooled to 0° C. To this was added TEA (0.2 ml) and cyclohexane carbonyl chloride (0.075 ml, 0.54 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. (128 mg, 98%) m.p. 78-80° C. Rf. 0.6 (EtOAc), LCMS t$_r$=4.69 min (50% MeOH and 50% water at 0.5 ml/min), m/z M$^+$H 475.42, HPLC t$_r$=2.58 min (Isocratic 90% acetonitrile and 10% water at 1.0 ml/min), 99.18%, $^1$HNMR (CDCl$_3$, 400 MHz) δ 1.7 (14H, m, 7CH$_2$), 2.44 (2H, m, 2CH), 2.60 (1H, t, J=11.2 Hz, CH$_2$), 3.02 (1H, t, J=12.0 Hz, CH$_2$), 3.93 (1H, d, J=13.2 Hz, CH$_2$), 4.59 (1H, d, J=13.2 Hz, CH$_2$), 6.91 (1H, dd, J=8.0, 1.2 Hz, ArH$_D$), 7.07 (2H, d, J=8.8 Hz, ArH$_E$), 7.07 (1H, m, ArH$_C$), 7.18 (1H, td, J=1.2, 8.0 Hz, ArH$_B$), 7.60 (2H, d, J=9.2 Hz, ArH$_F$), 7.62 (1H, s, NH), 8.38 (1H, dd, J=1.2, 8.0 Hz, ArH$_A$). $^{13}$CNMR (CDCl$_3$, 400 MHz) δ 25.79, 28.51, 29.00, 29.23, 29.50 (CH2), 40.42 (CH), 40.88 (CH2), 44.25 (CH), 44.57 (CH2), 117.79, 118.94, 121.75, 122.56, 124.62, 125.31, 127.37, 127.40, 127.43, 127.47, 129.86, 144.44 (ArC), 159.34 (CF3), 172.23, 174.49 (C=O).

1-Cyclopentanecarbonyl-piperidine-4-carboxylic acid [2-(4-trifluoromethyl-phenoxy)-phenyl]-amide HVB01098, STX1736 C$_{25}$H$_{27}$F$_3$N$_2$O$_3$, MW 460.49

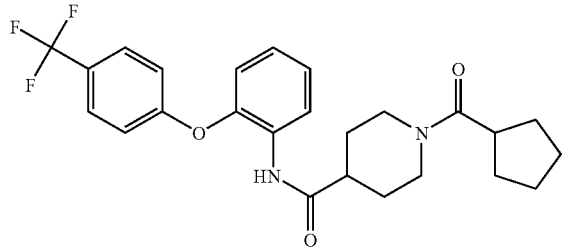

Piperidine-4-carboxylic acid [2-(4-trifluoromethyl-phenoxy)-phenyl]-amide (HVB01096, 0.1 g, 0.27 mmol) was dissolved in DCM (5 ml), and cooled to 0° C. To this was added TEA (0.2 ml) and cyclopentane carbonyl chloride (0.07 ml, 0.54 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. (105 mg, 83%), m.p. 94-97° C. Rf. 0.65 (EtOAc), LCMS t$_r$=4.86 min (50% MeOH and 50% water at 0.5 ml/min), m/z M$^+$H 461.44, HPLC t$_r$=2.43 min (Isocratic 90% acetonitrile and 10% water at 1.0 ml/min), 98.58%, $^1$HNMR (CDCl$_3$, 400 MHz) δ (1.77 (12H, m, 6CH$_2$), 2.44 (1H, m, CH), 2.63 (1H, td, J=13.6, 2.8 Hz, CH$_2$), 2.85 (1H, m, CH), 3.03 (1H, td, J=14.4, 2.4 Hz, CH$_2$), 3.98 (1H, d, J=13.2 Hz, CH$_2$), 4.59 (1H, d, J=13.2 Hz, CH$_2$), 6.91 (1H, dd, J=1.2, 7.6 Hz, ArH$_D$), 7.05 (2H, d, J=8.0 Hz, ArH), 7.08 (1H, td, J=1.6 Hz, ArH$_C$), 7.18 (1H, td, J=1.2, 8.8 Hz, ArH$_B$), 7.59 (2H, d, J=8.4 Hz, ArH), 7.64 (1H, s, NH), 8.37 (1H, dd, J=1.2, 7.2 Hz, ArH$_A$). $^{13}$CNMR (CDCl$_3$, 400 MHz) δ 25.95, 28.47, 29.03, 29.92 (CH2), 41.02 (CH), 41.09 (CH$_2$), 44.22 (CH), 44.69 (CH$_2$), 117.76, 118.94, 121.76, 124.61, 125.29, 127.33, 127.37, 127.41, 127.45, 129.85, 144.44 (ArC), 159.33 (CF$_3$), 172.26, 174.40 (C=O).

1-Isobutyryl-piperidine-4-carboxylic acid [2-(4-trifluoromethyl-phenoxy)-phenyl]-amide HVB01099, STX1747 C$_{23}$H$_{25}$F$_3$N$_2$O$_3$, MW 434.45

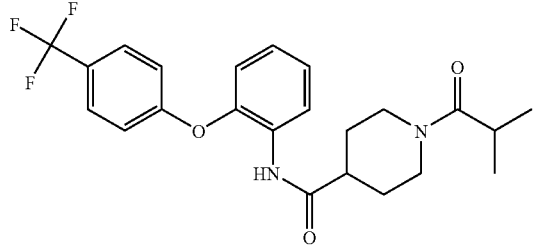

Piperidine-4-carboxylic acid [2-(4-trifluoromethyl-phenoxy)-phenyl]-amide (HVB01096, 0.1 g, 0.27 mmol) was dissolved in DCM (5 ml), and cooled to 0° C. To this was added TEA (0.2 ml) and isobutyryl carbonyl chloride (0.06 ml, 0.54 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. (98 mg, 82%), m.p. 70-72° C. Rf. 0.60 (EtOAc), LCMS $t_r$=4.28 min (50% MeOH and 50% water at 0.5 ml/min), m/z M$^+$H 435.44, HPLC $t_r$=2.23 min (Isocratic 90% acetonitrile and 10% water at 1.0 ml/min), 95.47%, 1-(3-Methyl-butyryl)-piperidine-4-carboxylic acid [2-(4-trifluoromethyl-phenoxy)-phenyl]-amide HVB01100, STX1748 C$_{24}$H$_{27}$F$_3$N$_2$O$_3$, MW 448.48

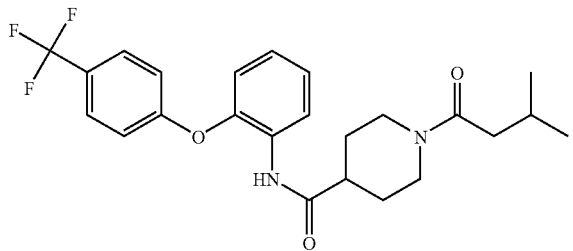

Piperidine-4-carboxylic acid [2-(4-trifluoromethyl-phenoxy)-phenyl]-amide (HVB01096, 0.1 g, 0.27 mmol) was dissolved in DCM (5 ml), and cooled to 0° C. To this was added TEA (0.2 ml) and isovaleryl carbonyl chloride (0.066 ml, 0.54 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. (78 mg, 63%) m.p. 63-64° C. Rf. 0.60 (EtOAc), LCMS $t_r$=4.66 min (50% MeOH and 50% water at 0.5 ml/min), m/z M$^+$H 449.48, HPLC $t_r$=2.35 min (Isocratic 90% acetonitrile and 10% water at 1.0 ml/min), 99.45%, $^1$HNMR (CDCl$_3$, 400 MHz) δ 0.94 (6H, d, J=6.0, 2CH$_3$), 1.64 (2H, m, CH$_2$), 1.83 (2H, m, CH$_2$), 2.07 (1H, m, CH$_2$), 2.18 (2H, m, CH$_2$), 2.44 (1H, m, CH), 2.62 (1H, t, J=13.2 Hz, CH$_2$), 3.03 (1H, t, J=14.4 Hz, CH$_2$), 3.88 (1H, d, J=7.6 Hz, CH$_2$), 4.59 (1H, d, J=13.2 Hz, CH$_2$), 6.91 (1H, d, J=7.6 Hz, ArH$_D$), 7.05 (2H, d, J=8.4 Hz, ArH$_F$), 7.05 (1H, m, ArH$_C$), 7.65 (1H, s, NH), 8.38 (1H, dd, J=0.8, 8.0 Hz, ArH$_A$). $^{13}$CNMR (CDCl$_3$, 400 MHz) δ 22.63, 22.73 (CH$_3$), 25.74 (CH), 28.48, 28.95, 40.78, 42.05 (CH$_2$), 44.08 (CH), 45.05 (CH$_2$), 117.79, 118.93, 121.75, 124.64, 125.28, 127.35 (ArCH), 127.38, 127.42, 129.81, 144.45 (ArC), 159.32 (CF$_3$), 170.93, 172.23 (C=O).

Synthetic Route to STX1779

2,4-Dichloro-1-(2-nitro-phenoxy)-benzene HVB01093 Cl$_2$H$_7$Cl$_2$NO$_3$, MW 284.09

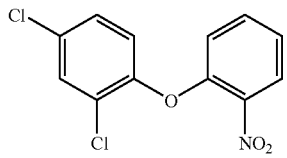

2,4-dichlorophenol (3.0 g, 18.4 mmol), 2-fluoro-1-nitrobenzene (1.28 ml, 12.1 mmol) and potassium carbonate (3.0 g, 22.1 mmol) were mixed in DMF (10 ml) and heated at reflux for 3 h. DMF removed in-vacuo. NaOH (1M) added, and extracted with diethyl ether, organic layers dried over MgSO$_4$ and evaporated to dryness, to afford a yellow solid. 3.7 g, >100%, m.p. 54-55° C., Rf. 0.80 (DCM), LCMS $t_r$=5.02 min (50% MeOH and 50% water at 0.5 ml/min), m/z M$^+$H 283.06, 285.07, HPLC $t_r$=2.39 min (Isocratic 90% acetonitrile and 10% water at 1.0 ml/min), 99.75%, $^1$HNMR (CDCl$_3$, 270 MHz) δ 6.86 (1H, dd, J=1.2, 8.4 Hz, ArH), 6.98 (1H, d, J=6.9 Hz, ArH), 7.23 (1H, m, ArH), 7.23 (1H, m, ArH), 7.50 (1H, m, ArH), 7.50 (1H, m, ArH), 7.98 (1H, dd, J=1.5, 8.2 Hz, ArH).

2-(2,4-Dichloro-phenoxy)-phenylamine HVB01094 C$_{12}$H$_9$Cl$_2$NO, MW 254.11

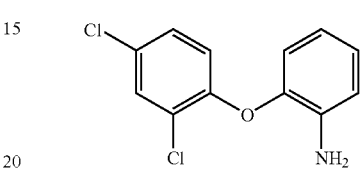

2,4-Dichloro-1-(2-nitro-phenoxy)-benzene (HVB01093, 3.7 g, 12 mmol) was added to a refluxing solution of EtOH (55 ml), water (5.5 ml), iron powder (3.7 g, 66 mmol) and ammonium chloride (0.45 g, 8.4 mmol), and stirred at reflux for 4 h. The resulting solution was filtered and evaporated in-vacuo. NaHCO$_3$ was added and extracted with DCM, organic layers dried over MgSO$_4$ and evaporated to dryness. 2.98 g, 96%, Rf. 0.60 (DCM), LCMS $t_r$=4.63 min (50% MeOH and 50% water at 0.5 ml/min), m/z M$^+$H 254.27, 256.29, HPLC $t_r$=2.51 min (Isocratic 90% acetonitrile and 10% water at 1.0 ml/min), 96%, $^1$HNMR (CDCl$_3$, 270 MHz) δ 3.82 (1H, s, NH), 6.71 (1H, td, J=1.5, 7.6 Hz, ArH), 6.79 (1H, d, J=8.7 Hz, ArH), 6.81 (2H, m, ArH), 7.00 (1H, m, ArH), 7.12 (1H, dd, J=2.5, 8.7 Hz, ArH), 7.44 (1H, d, J=2.5 Hz, ArH), 1-(Furan-2-carbonyl)-piperidin-4-one HVB01101 C$_{10}$H$_{11}$NO$_3$, MW 193.07

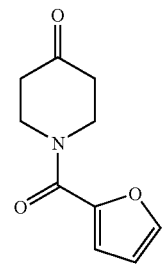

4-piperidone hydrochloride monohydate (0.23 g, 1.48 mmol) was dissolved in DCM (5 ml), and to this was added MP-Carbonate resin (0.58 g). This was stirred at room temperature for 2 h. Separately, 2-furoic acid (0.2 g, 1.78 mmol), N N-4-dimethylaminopyridine (cat.), 1-(3-dimethylaminopropyl)-3-ethylcarbodiimide hydrochloride (0.85 g, 4.44 mmol) and TEA (0.15 ml) were dissolved in DCM (5 ml) and stirred at room temperature for 2 h. The 2 reaction mixtures were then combined and stirred at room temperature for 18 h. The resulting solution was then filtered and washed with HCl (1M), NaHCO$_3$ then brine. The organic layers were combined and dried over MgSO$_4$ and evaporated to dryness, to yield a yellow oil. 250 mg, (86%), LCMS $t_r$=1.99 min (50% MeOH and 50% water at 0.5 ml/min), m/z M$^+$H 194.16, HPLC $t_r$=1.85 min (Isocratic 90% acetonitrile and 10% water at 1.0 ml/min), 97.09%, $^1$HNMR (CDCl$_3$, 270 MHz) δ 2.53 (4H, t, J=6.5 Hz, CH$_2$), 4.02 (4H, m, CH$_2$), 9.49 (1H, q, J=1.7 Hz, ArH), 7.07 (1H, dd, J=0.7, 3.5 Hz, ArH), 7.48 (1H, q, J=1.0 Hz, ArH).

{4-[2-(2,4-Dichloro-phenoxy)-phenylamino]-piperidin-1-yl}-furan-2-yl-methanone HVB01112, STX1779 C$_{22}$H$_{20}$Cl$_2$N$_2$O$_3$, MW 431.31

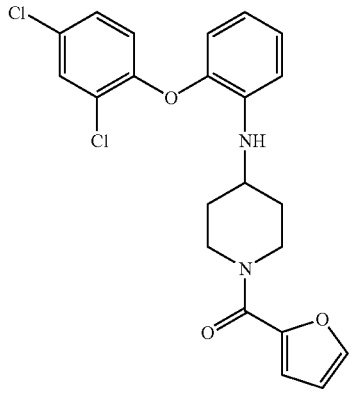

2-(2,4-Dichloro-phenoxy)-phenylamine (HVB01094, 0.1 g, 0.39 mmol), 1-(Furan-2-carbonyl)-piperidin-4-one (HVB01101, 0.091 g, 0.47 mmol), and sodium acetoxyborohydride (0.116 g, 0.55 mmol) were dissolved in DCE, to this was added acetic acid (0.1 ml), and the reaction was stirred at room temperature for 4 d. Sodium bicarbonate was added, and extracted with ethyl acetate, the organic layers were dried over MgSO4, and evaporated to dryness. The crude mixture was purified using flash chromatography (0-100% ethyl acetate in hexane), to afford the desired product as a yellow oil. 25 mg, (15%), R.f. 0.7 (5% Methanol-DCM), LCMS t$_r$=5.66 min (50% MeOH and 50% water at 0.5 ml/min), m/z M$^+$H 431.41, HPLC t$_r$=2.99 min (Isocratic 90% acetonitrile and 10% water at 1.0 ml/min), 98.92%, $^1$HNMR (CDCl$_3$, 400 MHz) δ 1.40 (2H, m, CH$_2$), 2.13 (2H, dd, J=3.6, 12.8 Hz, CH$_2$), 3.21 (2H, s, CH$_2$) 3.61 (1H, m, CH$_2$), 4.11 (1H, s, NH), 4.38 (2H, d, J=12.8 Hz, CH$_2$), 6.46 (1H, dd, J=1.6, 3.6 Hz, ArH), 6.64 (1H, td, J=1.6, 7.6 Hz, ArH), 6.74 (1H, dd, J=1.6, 8.0 Hz, ArH$_D$), 6.78 (1H, dd, J=1.2, 8.4 Hz, ArH), 6.81 (1H, d, J=8.8 Hz, ArH$_G$), 6.96 (1H, d, J=3.2 Hz, ArH), 7.05 (1H, td, J=1.2, 8.0 Hz, ArH$_B$), 7.13 (1H, dd, J=2.4, 8.8 Hz, ArH$_F$), 7.44 (1H, d, J=2.4 Hz, ArH$_E$), 7.46 (1H, d, J=2.0 Hz, ArH). $^{13}$C NMR (CDCl3, 400 MHz) δ 49.69 (CH), 112.21, 112.29, 116.15, 116.99, 118.63, 119.48, 125.31, 127.94, 128.55, 130.30, 138.25, 142.89, 143.59, 147.89 (ArC), 151.47, 159.16 (C=O).

Synthetic Route to STX1790-1793

Piperidine-4-carboxylic acid [2-(3,5-dichloro-phenoxy)-phenyl]-amide HVB01123 C$_{18}$H$_{18}$Cl$_2$N$_2$O$_2$, MW 365.25

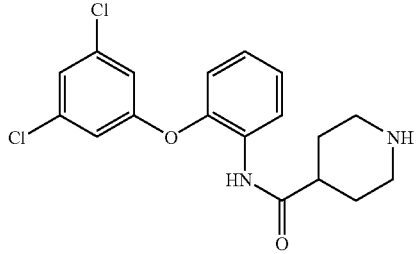

4-[2-(3,5-Dichloro-phenoxy)-phenylcarbamoyl]-piperidine-1-carboxylic acid tert-butyl ester (036 g, 0.77 mmol) was dissolved in DCM (9 ml), and to this was added TFA (4 ml). The reaction was stirred at room temperature for 2 h. This was then poured onto solid K$_2$CO$_3$, and extracted using DCM and water, to afford the desired product as a yellow solid. 0.21 g, (75%), m.p. 138-139° C., Rf. 0.3 (10% Methanol-DCM), $^1$HNMR (CDCl$_3$, 270 MHz) δ 1.65 (3H, m, CH$_2$ and NH), 1.86 (2H, m, CH$_2$), 2.36 (1H, m, CH), 2.65 (2H, td, J=2.7, 9.6, NCH$_2$), 3.16 (2H, m, NCH$_2$), 6.89 (2H, d, J=1.7, H$_E$, H$_G$), 6.90 (1H, m, H$_D$), 7.06 (1H, td, J=1.5, 7.4, H$_B$), 7.12 (1H, t, J=1.7, H$_F$), 7.18 (1H, td, J=8.2, 1.46, H$_C$), 7.55 (1H, s, NH), 8.43 (1H, dd, J=8.2, H$_A$).

1-Cyclohexanecarbonyl-piperidine-4-carboxylic acid [2-(3,5-dichloro-phenoxy)-phenyl]-amide HVB01124, STX 1790 C$_{25}$H$_{28}$Cl$_2$N$_2$O$_3$, MW 475.41

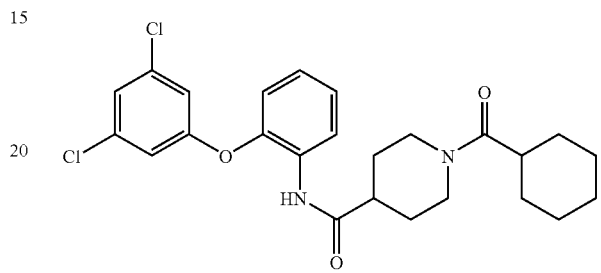

Piperidine-4-carboxylic acid [2-(3,5-dichloro-phenoxy)-phenyl]-amide (HVB01123, 0.066 g, 0.18 mmol) was dissolved in DCM (4 ml), and cooled to 0° C. To this was added TEA (0.15 ml) and cyclohexane carbonyl chloride (0.05 ml, 0.36 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. (71 mg, 83%) m.p. 64-67° C. Rf. 0.6 (EtOAc), LCMS t$_r$=2.0 min (50% to 95% MeOH in Water at 0.5 ml/min to 1.0 ml/min over 5 min), m/z M$^+$H 475.29, HPLC t$_r$=3.16 min (Isocratic 90% acetonitrile and 10% water at 1.0 ml/min), 99.46%, $^1$HNMR (CDCl$_3$, 270 MHz) δ 1.23 (4H, m, 2CH$_2$), 1.66 (10H, m, 5CH$_2$), 2.44 (2H, m, 2CH), 2.61 (1H, t, J=11.6 Hz, CH$_2$), 3.04 (1H, t, J=11.9 Hz, CH$_2$), 3.96 (1H, d, J=13.6 Hz, CH$_2$), 4.61 (1H, d, J=13.4 Hz, CH$_2$), 6.88 (2H, d, J=2.0 Hz, ArH$_E$), 6.90 (1H, dd, J=8.15, 1.2 Hz, ArH$_D$), 7.07 (1H, td, J=7.9, 1.7 Hz, ArH$_C$), 7.12 (1H, t, J=2.0 Hz, ArH$_F$), 7.18 (1H, td, J=1.2, 7.6 Hz, ArH$_B$), 7.61 (1H, s, NH), 8.39 (1H, dd, J=1.5, 8.2 Hz, ArH$_A$). $^{13}$CNMR (CDCl$_3$, 270 MHz) δ 25.95, 28.72, 29.36, 29.65 (CH$_2$), 40.56 (CH), 41.05 (CH$_2$), 44.39 (CH), 44.72 (CH$_2$), 116.90, 118.91, 121.78, 124.18, 124.75, 125.62 (ArCH), 129.90, 136.07, 144.24, 157.83 (ArC), 172.37, 174.63 (C=O)

1-Cyclopentanecarbonyl-piperidine-4-carboxylic acid [2-(3,5-dichloro-phenoxy)-phenyl]-amide HVB01125, STX 1791 C$_{24}$H$_{26}$Cl$_2$N$_2$O$_3$, MW 461.38

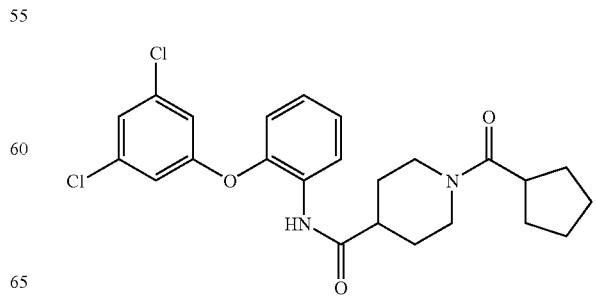

Piperidine-4-carboxylic acid [2-(3,5-dichloro-phenoxy)-phenyl]-amide (HVB01123, 0.066 g, 0.18 mmol) was dissolved in DCM (4 ml), and cooled to 0° C. To this was added TEA (0.15 ml) and cyclopentane carbonyl chloride (0.044 ml, 0.36 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. (52 mg, 63%) Rf. 0.62 (EtOAc), mp. 154-155° C. LCMS t$_r$=1.52 mm (50% to 95% MeOH in Water at 0.5 ml/min to 1.0 ml/min over 5 min), m/z M$^+$H 461.38, HPLC t$_r$=3.04 min (Isocratic 90% acetonitrile and 10% water at 1.0 ml/min), 98.99%, $^1$HNMR (CDCl$_3$, 270 MHz) δ 1.73 (12H, m, 6CH$_2$), 2.44 (1H, m, CH), 2.66 (1H, t, J=11.9 Hz, CH$_2$), 2.86 (1H, m, CH), 3.06 (1H, t, J=11.1 Hz, CH$_2$), 4.00 (1H, d, J=13.9 Hz, CH$_2$), 4.62 (1H, d, J=12.8 Hz, CH$_2$), 6.88 (3H, m, ArH$_D$+E), 7.07 (1H, td, J=7.4, 1.5 Hz, ArH$_C$), 7.13 (1H, t, J=1.7 Hz, ArH$_F$), 7.19 (1H, td, J=7.9, 1.5 Hz, ArH$_B$), 7.58 (1H, s, NH), 8.40 (1H, d, J=7.9 Hz, ArH$_A$). $^{13}$CNMR (CDCl$_3$, 270 MHz) δ 26.12, 28.70, 29.17, 30.09, 30.34 (CH$_2$), 41.19 (CH), 41.26 (CH$_2$), 44.44 (CH), 44.84 (CH$_2$), 116.84, 118.90, 121.73, 124.19, 124.73, 125.64 (ArCH), 129.91, 136.09, 144.19, 157.83 (ArC), 172.36, 174.53 (C=O).

1-Isobutyryl-piperidine-4-carboxylic acid [2-(3,5-dichloro-phenoxy)-phenyl]-amide HVB01126, STX 1792 C$_{22}$H$_{24}$Cl$_2$N$_2$O$_3$, MW 435.34

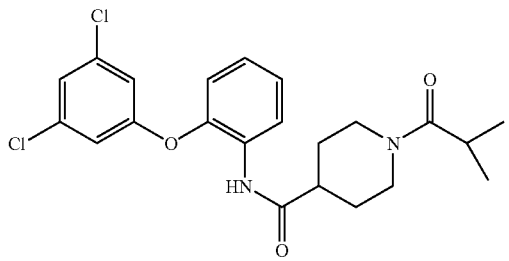

Piperidine-4-carboxylic acid [2-(3,5-dichloro-phenoxy)-phenyl]-amide (HVB01123, 0.066 g, 0.18 mmol) was dissolved in DCM (4 ml), and cooled to 0° C. To this was added TEA (0.15 ml) and isobutylryl chloride (0.038 ml, 0.36 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. (77 mg, 97%) Rf. 0.7 (EtOAc), mp. 53-55° C. LCMS t$_r$=1.87 min (50% to 95% MeOH in Water at 0.5 ml/min to 1.0 ml/min over 5 min), m/z M$^+$H 435.38, HPLC t$_r$=2.73 min (Isocratic 90% acetonitrile and 10% water at 0.8 ml/min), 97.57%, $^1$HNMR (CDCl$_3$, 270 MHz) δ 1.09 (6H, t, J=5.5 Hz, 2CH$_3$), 1.69 (2H, m, CH$_2$), 1.87 (2H, m, CH$_2$), 2.47 (1H, m, CH$_2$), 2.63 (1H, t, J=11.9 Hz, CH$_2$), 2.77 (1H, m, CH), 3.06 (1H, t, J=11.4 Hz, CH$_2$), 3.96 (1H, d, J=13.6 Hz, CH$_2$), 4.60 (1H, d, J=13.1 Hz, CH$_2$), 6.88 (3H, m, ArH0, 7.06 (1H, td, J=1.8, 8.2 Hz, ArH), 7.11 (1H, t, J=1.8 Hz, ArH), 7.18 (1H, td, J=1.6, 7.7 Hz, ArH), 7.64 (1H, s, NH), 8.37 (1H, dd, J=1.2, 8.2 Hz, ArH). $^{13}$CNMR (CDCl$_3$, 270 MHz) δ 19.41, 19.67 (CH$_3$), 28.70, 29.21 (CH$_2$), 30.19 (CH), 41.13 (CH$_2$), 44.31 (CH), 44.74 (CH$_2$), 116.82, 118.95, 121.86, 124.14, 124.78, 125.62 (ArCH), 129.91, 136.06, 144.28, 157.85 (ArC), 172.38, 175.41 (CO).

1-Isobutyryl-piperidine-4-carboxylic acid [2-(3,5-dichloro-phenoxy)-phenyl]-amide HVB01127, STX 1793 C$_{22}$H$_{24}$Cl$_2$N$_2$O$_3$, MW 435.34

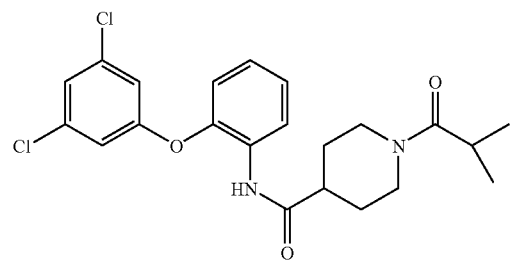

Piperidine-4-carboxylic acid [2-(3,5-dichloro-phenoxy)-phenyl]-amide (HVB01123, 0.066 g, 0.18 mmol) was dissolved in DCM (4 ml), and cooled to 0° C. To this was added TEA (0.15 ml) and isovaleryl chloride (0.044 ml, 0.36 mmol) and allowed to warm to room temperature, and stirred for 30 min. NaHCO$_3$ added, and extracted with DCM, dried over MgSO$_4$ and evaporated in-vacuo. The crude mixture was purified using flash chromatography (0-100% ethyl acetate in hexane) to afford a white waxy solid. (52 mg, 72%) Rf. 0.65 (EtOAc), mp. 119-121° C. LCMS t$_r$=1.83 min (50% to 95% MeOH in Water at 0.5 ml/min to 1.0 ml/min over 5 min), m/z M$^+$H 449.4, HPLC t$_r$=2.86 min (Isocratic 90% acetonitrile and 10% water at 0.8 ml/min), 98.90%, $^1$HNMR (CDCl$_3$, 270 MHz) δ 0.94 (6H, d, J=6.4 Hz, 2CH$_3$), 1.71 (2H, m, CH$_2$), 1.87 (2H, m, CH$_2$), 2.08 (1H, m, CH), 2.18 (2H, m, CH$_2$), 2.44 (1H, m, CH), 2.64 (1H, t, J=10.9 Hz, CH$_2$), 3.05 (1H, t, J=11.9 Hz, CH$_2$), 3.92 (1H, d, J=13.6 Hz, CH$_2$), 4.61 (1H, d, J=13.4 Hz, CH$_2$), 6.87 (2H, d, J=1.7 Hz, ArH), 6.90 (1H, m, ArH), 7.06 (1H, td, J=7.9 Hz, ArH), 7.12 (1H, t, J=1.7 Hz, ArH), 7.18 (1H, td, J=1.5 Hz, ArH), 7.61 (1H, s, NH), 8.39 (1H, dd, J=1.2, 8.2 Hz, ArH). $^{13}$CNMR (CDCl$_3$, 270 MHz) δ 22.80, 22.92 (CH3), 25.89 (CH), 28.72, 29.09, 40.95, 42.21 (CH2), 44.26 (CH), 45.19 (CH2), 116.85, 118.91, 121.78, 124.18, 124.76, 125.63 (ArCH), 129.89, 136.07, 144.24, 157.83 (ArC), 171.04, 172.34 (C=O).

Synthetic Route to STX1849-51

1-(Thiophene-2-carbonyl)-piperidin-4-one HVB01116 C$_{10}$H$_{11}$NO$_2$S, MW 209.26

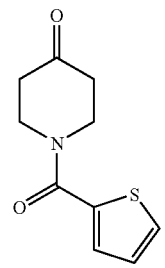

4-piperidone hydrochloride monohydrate (0.32 g, 2.1 mmol) was dissolved in DCM (7 ml), and to this was added MP-Carbonate resin (0.8 g). This was stirred at room temperature for 2 h. Separately, 2-thiophenecarboxylic acid (0.32 g, 2.52 mmol), N,N-4-dimethylaminopyridine (cat.), 1-(3-dimethylaminopropyl)-3-ethylcarbodiimide hydrochloride (1.2 g, 6.3 mmol) and TEA (0.25 ml) were dissolved in DCM (7 ml) and stirred at room temperature for 2 h. The 2 reaction mixtures were then combined and stirred at room temperature for 18 h. The resulting solution was then filtered and washed with HCl (1M), sodium bicarbonate then brine. The organic layers were combined and dried over MgSO$_4$ and evaporated to dryness. The crude mixture was purified using flash chromatography (0-100% ethyl acetate in hexane), to yield a white solid. 220 mg, (56%), mp. 81-83° C., LCMS $t_r$=2.29 min (50% MeOH and 50% water at 0.5 ml/min), m/z M$^+$H 210.11, HPLC $t_r$=1.89 min (Isocratic 90% acetonitrile and 10% water at 1.0 ml/min), 100%, $^1$HNMR (CDCl$_3$, 270 MHz) δ 2.47 (4H, t, J=6.2 Hz, CH$_2$), 3.94 (4H, t, J=6.4 Hz, CH$_2$), 7.00 (1H, dd, J=3.5, 4.9 Hz, ArH), 7.31 (1H, dd, J=1.2, 3.7 Hz, ArH), 7.43 (1H, dd, J=1.2, 4.9 Hz, ArH).

{4-[2-(2,4-Dichloro-phenoxy)-phenylamino]-piperidin-1-yl}-thiophen-2-yl-methanone HVB01130, STX1849 C$_{22}$H$_{20}$Cl$_2$N$_2$O$_2$S, MW 447.38

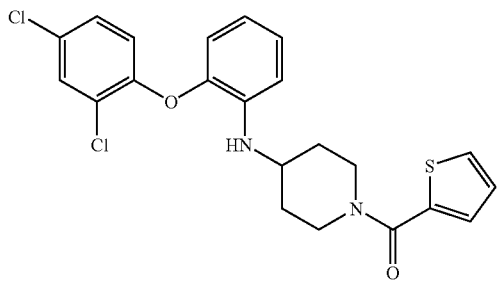

2-(2,4-Dichloro-phenoxy)-phenylamine (185 mg, 0.72 mmol), 1-(Thiophene-2-carbonyl)-piperidin-4-one (150 mg, 0.72 mmol), sodium acetoxyborohydride (230 mg, 1.08 mmol) and acetic acid (0.21 mmol, 3.6 mmol) was dissolved in DCE (5 ml) and stirred at r.t. for 7 days. NaHCO$_3$ added, and extracted with EtOAc. The organic layers were combined and dried over MgSO$_4$ and evaporated in-vacuo. The crude mixture was purified using flash chromatography (0-100% ethyl acetate in hexane) to afford a brown oil. (162 mg, 50%) m.p. 128-129° C. LCMS $t_r$=5.72 min (50% to 95% MeOH in Water at 0.5 ml/min to 1.0 ml/min over 5 min), m/z M$^+$H 447.34, HPLC $t_r$=4.03 min (Isocratic 90% acetonitrile and 10% water at 0.8 ml/min), 100%, $^1$HNMR (CDCl$_3$, 400 MHz) δ 1.47 (2H, m, CH$_2$), 2.11 (2H, dd, J=13.2, 3.2 Hz, CH$_2$), 3.22 (2H, t, J=11.6 Hz, CH$_2$), 3.61 (1H, s, CH), 4.12 (1H, s, NH), 4.29 (2H, s, CH$_2$), 6.64 (1H, td, J=1.6, 7.2 Hz, ArH), 6.74 (1H, dd, J=1.6, 7.6 Hz, ArH), 6.77 (1H, dd, J=1.6, 8.0 Hz, ArH), 6.81 (1H, d, J=8.4 Hz, ArH), 7.02 (1H, dd, J=3.6, 5.2 Hz, ArH), 7.04 (1H, td, J=7.6, 1.6 Hz, ArH), 7.13 (1H, dd, J=2.0, 8.4 Hz, ArH), 7.26 (1H, dd, J=1.2, 3.6 Hz, ArH), 7.42 (1H, dd, J=1.2, 5.2 Hz, ArH), 7.44 (1H, d, J=2.4 Hz, ArH). $^{13}$CNMR (CDCl$_3$, 400 MHz) δ 29.59, 32.38 (CH2), 49.57 (CH), 112.23, 116.98, 118.54, 119.48, 125.25 126.58, 127.89, 128.42, 128.49, 128.54, 130.23 (ArCH), 137.00, 138.14, 142.84, 151.40 (ArC), 163.47 (C=O).

1-(2-Adamantan-1-yl-acetyl)-piperidin-4-one HVB01120, C$_{17}$H$_{25}$NO$_2$, MW 275.39

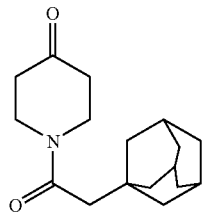

4-piperidone hydrochloride monohydrate (0.32 g, 2.1 mmol) was dissolved in DCM (7 ml), and to this was added MP-Carbonate resin (0.8 g). This was stirred at room temperature for 2 h. Separately, 1-adamantane acetic acid (0.49 g, 2.52 mmol), N N-4-dimethylaminopyridine (cat.), 1-(3-dimethylaminopropyl)-3-ethylcarbodiimide hydrochloride (1.2 g, 6.3 mmol) and TEA (0.25 ml) were dissolved in DCM (7 ml) and stirred at room temperature for 2 h. The 2 reaction mixtures were then combined and stirred at room temperature for 18 h. The resulting solution was then filtered and washed with HCl (1M), sodium bicarbonate then brine. The organic layers were combined and dried over MgSO$_4$ and evaporated to dryness. The crude mixture was purified using flash chromatography (0-100% ethyl acetate in hexane), to yield a white solid. 310 mg, (60%), mp. 114-115° C., LCMS $t_r$=4.68 min (gradient 50% to 95% MeOH in water at 0.5 ml/min), m/z M$^+$H 276.44, HPLC $t_r$=2.56 min (Isocratic 90% acetonitrile and 10% water at 1.0 ml/min), 98.92%, 2-Adamantan-1-yl-1-{4-[2-(2,4-dichloro-phenoxy)-phenylamino]-piperidin-1-yl}-ethanone HVB01132, STX1850 C$_{29}$H$_{34}$Cl$_2$N$_2$O$_2$, MW 513.50

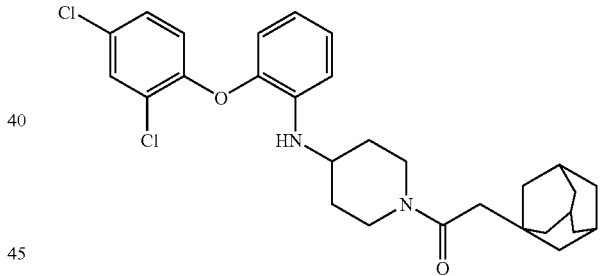

2-(2,4-Dichloro-phenoxy)-phenylamine (140 mg, 0.55 mmol), 1-(2-Adamantan-1-yl-acetyl)-piperidin-4-one (150 mg, 0.55 mmol), sodium acetoxyborohydride (175 mg, 0.83 mmol) and acetic acid (0.16 mmol, 2.75 mmol) was dissolved in DCE (5 ml) and stirred at r.t. for 7 days. NaHCO$_3$ added, and extracted with EtOAc. The organic layers were combined and dried over MgSO$_4$ and evaporated in-vacuo. The crude mixture was purified using flash chromatography (0-100% ethyl acetate in hexane) to afford a brown oil. (100 mg, 35%) LCMS $t_r$=3.57 min (50% to 95% MeOH in Water at 0.5 ml/min to 1.0 ml/min over 5 min), m/z M$^+$H 513.50, HPLC $t_r$=9.94 min (Isocratic 90% acetonitrile and 10% water at 0.8 ml/min), 98.06%, $^1$HNMR (CDCl$_3$, 400 MHz) δ 1.35 (2H, m, CH$_2$), 1.63 (12H, m, 6CH$_2$), 1.95 (3H, s, CH), 2.05 (2H, m, CH$_2$), 2.14 (2H, d, J=1.2 Hz, CH$_2$CO), 2.88 (1H, ddd, J=3.2, 11.2, 14.0 Hz, CH$_2$), 3.19 (1H, ddd, J=2.8, 11.2, 14.0 Hz, CH$_2$), 3.52 (1H, br. m, CH), 3.86 (1H, d, J=12.8 Hz, CH$_2$), 4.09 (1H, s, NH), 4.43 (1H, d, J=12.4 Hz, CH$_2$), 6.62 (1H, td, J=1.2, 8.0 Hz, ArH), 6.74 (2H, td, J=1.2, 8.4 Hz, ArH), 6.81 (1H, d, J=9.2 Hz, ArH), 7.03 (1H, td, J=1.6, 7.6 Hz, ArH), 7.12 (1H, dd, J=2.4, 8.8 Hz, ArH), 7.43 91H, d, J=2.4 Hz, ArH). $^{13}$CNMR (CDCl$_3$, 400 MHz) δ 28.60 (CH), 29.63, 32.07, 32.76 (CH$_2$), 33.56 (C), 36.68, 40.04, 42.76, 45.49 (CH$_2$), 46.03 (CH$_2$CO), 49.60 (CH$_2$), 112.23, 116.91, 118.51, 119.56, 125.25, 125.29 (ArCH), 127.91 (ArC), 128.52 (ArCH), 130.25, 138.25, 142.89, 151.45 (ArC), 169.60 (CO).

1-(Furan-3-carbonyl)-piperidin-4-one HVB01118 C$_{10}$H$_{11}$NO$_3$, MW 193.20

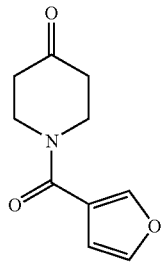

4-piperidone hydrochloride monohydrate (0.32 g, 2.1 mmol) was dissolved in DCM (7 ml), and to this was added MP-Carbonate resin (0.8 g). This was stirred at room temperature for 2 h. Separately, 3-furoic acid (0.28 g, 2.52 mmol), N N-4-dimethylaminopyridine (cat.), 1-(3-dimethylaminopropyl)-3-ethylcarbodiimide hydrochloride (1.2 g, 6.3 mmol) and TEA (0.25 ml) were dissolved in DCM (7 ml) and stirred at room temperature for 2 h. The 2 reaction mixtures were then combined and stirred at room temperature for 18 h. The resulting solution was then filtered and washed with HCl (1M), sodium bicarbonate then brine. The organic layers were combined and dried over MgSO$_4$ and evaporated to dryness. The crude mixture was purified using flash chromatography (0-100% ethyl acetate in hexane), to yield a cream oil. 225 mg, (63%), LCMS t$_r$=1.96 min (50% MeOH and 50% water at 0.5 ml/min), m/z M$^+$H 194.16, HPLC t$_r$=1.82 min (Isocratic 90% acetonitrile and 10% water at 1.0 ml/min), 100%, $^1$HNMR (CDCl$_3$, 270 MHz) δ 2.41 (4H, t, J=6.2 Hz, CH$_2$), 3.85 (4H, t, J=6.2 Hz, CH$_2$), 6.50 (1H, dd, J=1.0, 2.0 Hz, ArH), 7.37 (1H, t, J=1.7 Hz, ArH), 7.68 (1H, dd, J=1.0, 1.7 Hz, ArH).

{4-[2-(2,4-Dichloro-phenoxy)-phenylamino]-piperidin-1-yl}-furan-3-yl-methanone HVB01136, STX1851 C$_{22}$H$_{20}$Cl$_2$N$_2$O$_3$ MW 431.31

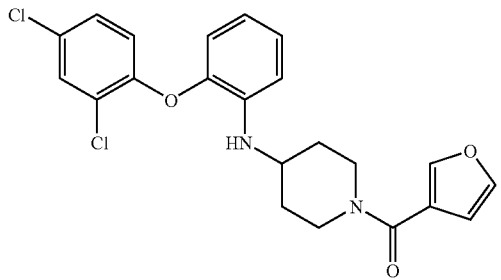

2-(2,4-Dichloro-phenoxy)-phenylamine (165 mg, 0.65 mmol), 1-(Furan-3-carbonyl)-piperidin-4-one (125 mg, 0.65 mmol), sodium acetoxyborohydride (206 mg, 0.97 mmol) and acetic acid (0.1 mmol, 3.25 mmol) was dissolved in DCE (5 ml) and stirred at r.t. for 6 days. NaHCO$_3$ added, and extracted with EtOAc. The organic layers were combined and dried over MgSO$_4$ and evaporated in-vacuo. The crude mixture was purified using flash chromatography (0-100% ethyl acetate in hexane) to afford a brown oil. (62 mg, 22%) LCMS t$_r$=6.27 min (50% to 95% MeOH in Water at 0.5 ml/min to 1.0 ml/min over 5 min), m/z M$^+$H 431.41, HPLC t$_r$=3.35 min (Isocratic 90% acetonitrile and 10% water at 0.8 ml/min), 98.82%, $^1$HNMR (CDCl$_3$, 400 MHz, 50° C.) δ 1.42 (2H, CH$_2$), 2.09 (2H, dd, J=3.6, 12.8 Hz, CH$_2$), 3.19 (2H, t, J=11.6 Hz, CH$_2$), 3.59 (1H, m, CH), 4.10 (1H, s, NH), 4.20 (1H, s, CH$_2$), 6.52 (1H, d, J=2.0 Hz, CH=CH—O—CH), 6.64 (1H, td, J=1.2, 7.2 Hz, ArH), 6.76 (2$\overline{H}$, m, ArH), 6.82 (1H, d, J=8.4 Hz, ArH), 7.04 (1H, td, J=1.6, 7.6 Hz, ArH), 7.13 (1H, dd, J=2.8, 8.8 Hz, ArH), 7.40 (1H, t, J=1.6 Hz, CH=CH—O—CH), 7.45 (1H, d, J=2.4 Hz, ArH), 7.67 (1H, t, J=0.8 $\overline{H}$z, C=CH—O). $^{13}$CNMR (CDCl$_3$, 400 MHz, 50° C.) δ 29.69, 32.$\overline{5}$6, 44.00 (CH2), 49.82 (CH), 110.02, 112.51, 117.20, 118.73, 119.56 (ArH), 121.19 (ArC), 125.37, 125.46, 127.98 (ArCH), 128.71 (ArC), 130.41, 138.38 (ArCH), 142.89, 143.14, 143.30, 151.30 (ArC), 163.76 (CO).

1-(2,4-Dichlorophenoxy)-2-nitrobenzene (AMR01025, AMR01043) C$_{12}$H$_7$Cl$_2$NO$_3$, MW 284.09

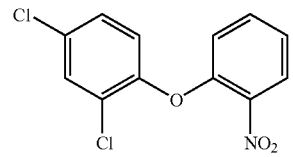

Previously described: Burnistov, S. I.; Karpishchenko, L. S. *Izvestiya Vysshikh Uchebnykh Zavedenii, Khimiya i Khimicheskaya Tekhnologiya* 1976, 19(1), 39-41. Commercially available Literature mp: 57-58° C. 69-69.6° C. AMR01025 A mixture of 2,4-dichlorophenol (2.00 g, 12.27 mmol), 1-fluoro-2-nitrobenzene (2.07 g, 14.72 mmol) and potassium carbonate (2.04 g, 14.72 mmol) in dimethylformamide (DMF, 10 mL) was stirred under reflux for 1.5 h. After removal of DMF, the residue was dissolved in DCM and washed with NaOH (5%, 3×20 mL) and brine. The organic layer was dried (MgSO$_4$), filtered and evaporated. Flash chromatography on silica gel of the crude product using DCM as eluent gave 1-(2,4-dichlorophenoxy)-2-nitrobenzene (3.4 g, 97%) as a cream oil. Rf: 0.73 (DCM) $^1$H NMR (270 MHz, CDCl$_3$) δ 6.85 (1H, dd, J=8.4, 1.2 Hz), 6.97 (1H, d, J=8.9 Hz), 7.23 (2H, m), 7.48 (1H, d, J=2.5 Hz), 7.51 (1H, m) and 7.98 (1H, dd, J=8.2, 1.7 Hz). AMR01043 Following the same procedure, from 2,4-dichlorophenol (3.00 g, 18.40 mmol), 1-fluoro-2-nitrobenzene (2.60 g, 18.40 mmol) and potassium carbonate (2.54 g, 18.40 mmol) in dimethylformamide (DMF, 15 mL), and after a reaction time of 3 h, gave AMR01043 (4.89 g, 93%) as a cream solid, mp: 51-54° C.

2-(2,4-Dichlorophenoxy)phenylamine (AMR01026)
$C_{12}H_9Cl_2NO$, MW 254.11

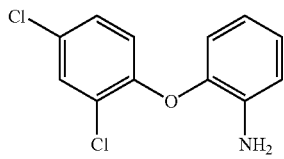

Previously described: Burnistov, S. I.; Karpishchenko, L. S. *Izvestiya Vysshikh Uchebnykh Zavedenii, Khimiya i Khimicheskaya Tekhnologiya* 1976, 19(1), 39-41. Commercially available To a refluxing mixture of iron powder (2.68 g, 48.4 mmol) and ammonium chloride (323 mg, 6.05 mmol) in ethanol (45 mL) and water (8 mL) was added 1-(2,4-dichlorophenoxy)-2-nitrobenzene (AMR01025, 2.5 g, 8.8 mmol) and the resulting mixture was stirred at reflux for 2 h. After removal of the solvent, the residue was diluted in aqueous sodium hydrogen carbonate (40 mL) and extracted with DCM (3×20 mL). The organic layer was dried ($MgSO_4$), filtered and evaporated to give 2-(2,4-dichlorophenoxy)phenylamine (2.01 g, 90%) as a colorless oil which was used in the next step without further purification. Rf: 0.56 (DCM) $^1H$ NMR (400 MHz, $CDCl_3$) δ 3.85 (2H, br s, $NH_2$), 6.75 (1H, m, ArH), 6.84 (1H, d, J=8.8 Hz, ArH), 6.84 (1H, dd, ArH), 6.87 (1H, dd, J=7.6, 1.6 Hz, ArH), 7.04 (1H, m, ArH), 7.17 (1H, dd, J=8.8, 2.4 Hz, ArH) and 7.49 (1H, d, J=2.4 Hz, ArH).

1-(4-Chlorophenoxy)-2-nitrobenzene (AMR01028)
$C_{12}H_8ClNO_3$, MW 249.65

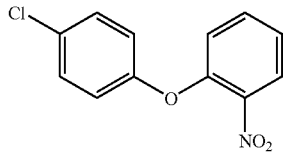

Previously described: Wardrop, A. W. H.; Gordon, L. S.; Harrison, J. M.; Inch, T. D. *J. Chem. Soc., Perkin I* 1976, 1276-1285 Commercially available Literature mp: 43-45° C.

A mixture of 4-chlorophenol (2.00 g, 15.56 mmol), 1-fluoro-2-nitrobenzene (2.20 g, 15.56 mmol) and potassium carbonate (2.15 g, 15.56 mmol) in DMF (10 mL) was stirred under reflux for 1 h. After removal of DMF, the residue was dissolved in DCM and washed with NaOH (5%, 3×20 mL) and brine. The organic layer was dried ($MgSO_4$), filtered and evaporated to give 1-(4-chlorophenoxy)-2-nitrobenzene (2.6 g, 67%) as a yellow oil which solidified upon standing at room temperature (mp 33-35° C. from EtOH) and was used in the next step without further purification. Rf: 0.77 (DCM) $^1H$ NMR (270 MHz, $CDCl_3$) δ 696 (2H, AA'BB'), 699 (1H, m), 7.22 (1H, m), 7.31 (2H, AA'BB'), 7.52 (1H, m) and 7.96 (2H, dd, J=8.2, 1.7 Hz)

2-(4-Chlorophenoxy)phenylamine (AMR01029)
$C_{12}H_{10}ClNO$, MW 219.67

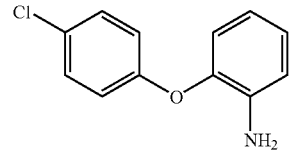

Previously described: Wardrop, A. W. H.; Gordon, L. S.; Harrison, J. M.; Inch, T. D. *J. Chem. Soc., Perkin I* 1976, 1276-1285 Commercially available To a refluxing mixture of iron powder (3.18 g, 57.28 mmol) and ammonium chloride (383 mg, 7.15 mmol) in ethanol (45 mL) and water (8 mL) was added 1-(2,4-dichlorophenoxy)-2-nitrobenzene (AMR01028, 2.2 g, 8.81 mmol) and the resulting mixture was stirred at reflux for 1 h. After removal of the solvent, the residue was diluted in aqueous sodium hydrogen carbonate (40 mL) and extracted with DCM (3×20 mL). The organic layer was dried ($MgSO_4$), filtered and evaporated to give AMR01029 (1.50 g, 78%) as a colorless oil which was used in the next step without further purification. Rf: 0.53 (DCM) $^1H$ NMR (270 MHz, $CDCl_3$) δ 3.77 (2H, br s, $NH_2$), 6.71 (1H, m), 6.83 (2H, m), 6.89 (2H, AA'BB'), 6.99 (1H, m) and 7.25 (2H, AA'BB').

4-[2-(2,4-Dichlorophenoxy)phenylamino]piperidine-1-carboxylic acid tert-butyl ester (AMR01030)
$C_{22}H_{26}Cl_2N_2O_3$, MW 437.36

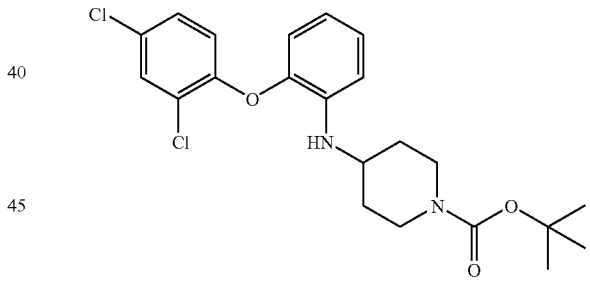

A solution of 2-(2,4-dichlorophenoxy)phenylamine (AMR01026, 1.6 g, 6.30 mmol), tert-butyl-4-oxo-1-piperidinecarboxylate (1.05 g, 5.27 mmol) and p-toluenesulfonic acid (40 mg) in toluene (40 mL) was heated at reflux under continuous separation of water for 5 h and, after addition of 2.5 g of molecular sieves (4 Amstrongs), for other additional 19 h. After cooling at room temperature, the mixture was filtered and the solvent evaporated in vacuo. The residual orange oil was dissolved in methanol (35 mL) and brought to reflux. Solid $NaBH_4$ (239 mg, 6.32 mmol) was carefully added, followed by reflux for 3 h. The mixture was concentrated in vacuo, diluted with water (50 mL) and extracted with DCM (3×30 mL). The combined organic layers were washed with water and brine, dried ($MgSO_4$), filtered and evaporated. Flash chromatography on silica gel of the crude product using DCM as eluent gave a first fraction of starting material (600 mg). Further elution gave AMR01030 (840 mg, 37%) as a white solid, mp 118-120° C. (from EtOH). Rf: 0.55 (DCM) LC/S (APCI) $t_r$=1.94 min, m/z 437.09 (M$^+$, 5), 383.04 (82), 381.02 (M$^+$-C$_4$H$_8$, 100). $^1$H NMR (270 MHz, CDCl$_3$) δ 1.35 (2H, m, CH$_2$), 1.44 (9H, s, 3CH$_3$), 2.00 (2H, m, CH$_2$), 2.93 (2H, br t, CH$_2$), 3.45 (1H, m, CH), 4.01 (3H, m, CH$_2$N and NH), 6.61 (1H, m, ArH), 6.75 (2H, m, ArH), 6.80 (1H, d, J=8.9, ArH), 7.03 (1H, m, ArH), 7.12 (1H, dd, J=8.9, 2.5 Hz, ArH), and 7.43 (1H, d, J=2.5 Hz, ArH).

4-[2-(4-Chlorophenoxy)phenylcarbamoyl]piperidine-1-carboxylic acid tert-butyl ester (AMR01031) C$_{23}$H$_{27}$ClN$_2$O$_4$, MW 430.92

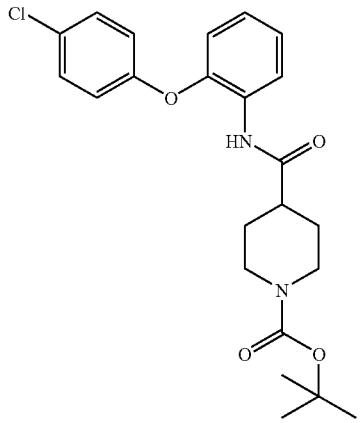

A solution of piperidine-1,4-dicarboxylic acid mono-tert-butyl ester (AMR01030, 417 mg, 1.82 mmol) in dry DCM (8 mL) was stirred under nitrogen, and 4-dimethylaminopyridine (DMPA, 40 mg, 0.327 mmol), (1-(3-dimethylaminopropyl)-3-ethylcarbodiimide hydrochloride (EDC, 1.05 g, 5.46 mmol) and triethylamine (0.25 mL) were added. The resulting mixture was stirred for 30 min under nitrogen and 2-(4-chloro-phenoxy)-phenylamine (AMR01029, 400 mg, 1.82 mmol) in dry DCM (4 mL) was added. After stirring at room temperature for 24 h, the mixture was diluted with DCM, washed with HCl 1M (3×25 mL), water, saturated NaHCO$_3$ (2×25 mL) and brine. The organic layer was dried (MgSO$_4$), filtered and evaporated. Flash chromatography on silica gel of the crude product using hexane/EtOAc 8:2 as eluent gave starting material (104 mg). Further elution using hexane/EtOAc 7:3 gave 4-[2-(4-chlorophenoxy)-phenylcarbamoyl]piperidine-1-carboxylic acid tert-butyl ester (430 mg, 55%) as a white solid, mp 97-99° C. Rf: 0.22 (hexane/EtOAc 7:3) LC/MS (APCI) $t_r$=3.83 min, m/z 431.23 (33), 429.21 (M$^-$–H, 100). $^1$H NMR (270 MHz, CDCl$_3$) δ 1.44 (9H, s, 3CH$_3$), 1.68 (2H, m, CH$_2$), 1.83 (2H, m, CH$_2$), 2.36 (1H, tt, J=11.4, 3.7 Hz), 2.75 (4H, br t, 2CH$_2$), 4.11 (4H, m, 2CH$_2$), 6.81 (1H, dd, J=8.2, 1.5 Hz, ArH), 6.93 (2H, AA'BB', ArH), 7.01 (1H, td, ArH), 7.12 (1H, td, ArH), 7.31 (2H, AA'BB', ArH), 7.68 (1H, br s, NH) and 8.40 (1H, dd, J=6.9, 1.5 Hz, ArH).

4-[2-(2,4-Dichlorophenoxy)phenylcarbamoyl]piperidine-1-carboxylic acid tert-butyl ester (AMR01032) C$_{23}$H$_{26}$Cl$_2$N$_2$O$_4$, MW 465.37

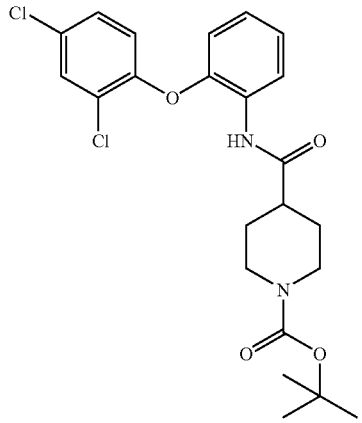

A solution of piperidine-1,4-dicarboxylic acid mono-tert-butyl ester (489 mg, 2.13 mmol) in dry DCM (10 mL) was stirred under nitrogen, and 4-dimethylaminopyridine (DMPA, 40 mg, 0.327 mmol), (1-(3-dimethylaminopropyl)-3-ethylcarbodiimide hydrochloride (EDC, 1.116 g, 5.82 mmol) and triethylamine (0.3 mL) were added. The resulting mixture was stirred for 30 min under nitrogen and 2-(2,4-dichlorophenoxy)phenylamine (AMR01026, 491 mg, 1.93 mmol) in dry DCM (5 mL) was added. After stirring at room temperature for 72 h, the mixture was diluted with DCM, washed with HCl 1M (3×25 mL), water, saturated NaHCO$_3$ (2×25 mL) and brine. The organic layer was dried (MgSO$_4$), filtered and evaporated to give 4-[2-(2,4-Dichlorophenoxy)phenylcarbamoyl]piperidine-1-carboxylic acid tert-butyl ester (754 mg, 84%) as a white solid (mp 120-121° C. from hexane), which was used in the next step without further purification. Rf: 0.31 (Hexane/EtOAc 7:3) LC/MS (APCI) $t_r$=1.39 min, m/z 464.96 (21), 462.94 (M$^-$–H, 32), 253.90 (66), 251.89 (100). $^1$H NMR (270 MHz, CDCl$_3$) δ 1.44 (9H, s, 3CH$_3$), 1.70 (2H, m, CH$_2$), 1.86 (2H, br d, CH$_2$), 2.40 (1H, tt, J=11.3, 3.7 Hz, CH), 2.77 (2H, br t, CH$_2$), 4.14 (2H, m, CH$_2$), 6.71 (1H, dd, J=8.2, 1.7 Hz, ArH), 6.94 (1H, d, J=8.9 Hz, ArH), 7.01 (1H, td, J=8.2, 1.5, ArH), 7.12 (1H, td, J=8.2, 1.5 Hz, ArH), 7.21 (1H, dd, J=8.9, 2.5 Hz, ArH), 7.48 (1H, d, J=2.5 Hz, ArH), 7.76 (1H, br s, NH) and 8.40 (1H, dd, J=7.9, 1.5 Hz, ArH).

Piperidine-4-carboxylic acid [2-(4-chlorophenoxy)phenyl]amide (AMR01033) C$_{18}$H$_{19}$ClN$_2$O$_2$, MW 330.81

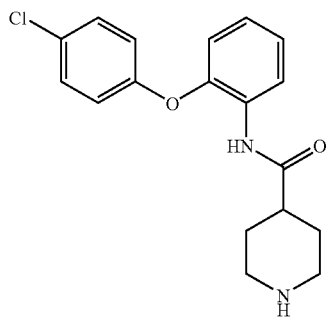

A solution of 4-[2-(4-chlorophenoxy)phenylcarbamoyl] piperidine-1-carboxylic acid tert-butyl ester (AMR01031, 410 mg, 0.95 mmol) in 4M HCl in dioxane (2 mL) was stirred at room temperature for 2 h. The resulting solution was concentrated under vacuum and the residue was dissolved in DCM, washed with 1M NaOH (1×20 mL), water and brine. The organic layer was dried (MgSO$_4$), filtered and evaporated to give piperidine-4-carboxylic acid [2-(4-chlorophenoxy)phenyl]amide (233 mg, 74%) as a white solid (mp 138-140° C. from hexane/EtOAc), which was used in the next step without further purification. Rf: 0.11 (DCM/methanol 4:1 plus 3 drops of triethylamine) $^1$H NMR (270 MHz, CDCl$_3$) δ 1.62 (2H, m, CH$_2$), 1.83 (3H, m, CH$_2$+NH), 2.35 (1H, tt, J=11.6, 3.7 Hz, CH), 2.62 (2H, br t, CH$_2$), 3.20 (2H, br d, J=12.3 Hz, CH$_2$), 6.80 (1H, td, ArH), 6.92 (2H, AA'BB', ArH), 6.98 (1H, td, ArH), 7.11 (1H, td, ArH), 7.29 (1H, AA'BB', ArH), 7.71 (1H, br s, NHCO) and 8.41 (1H, br d, J=7.9 Hz, ArH).

1-Acetylpiperidine-4-carboxylic acid [2-(4-chlorophenoxy)phenyl]amide (AMR01034, STX1617) C$_{20}$H$_{21}$ClN$_2$O$_3$, MW 372.85

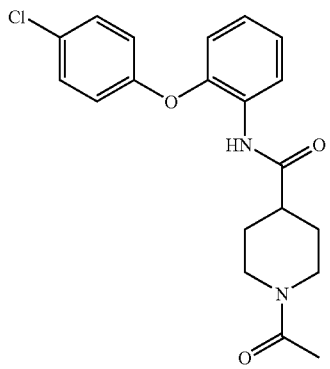

To an ice cooled solution of piperidine-4-carboxylic acid [2-(4-chlorophenoxy)phenyl]amide (AMR01033, 100 mg, 0.3 mmol) in dry DCM (6 mL) were added triethylamine (2.1 mL, 15 mmol) and acetyl chloride (0.043 mL, 0.6 mmol). The reaction mixture was stirred at room temperature until completion by TLC (1.5 h), and quenched with saturated NaHCO$_3$. The resulting solution was extracted with DCM (3×20 mL), and the combined organic layers were washed with water, 1M HCl (3×20 mL) and brine, dried (MgSO$_4$), filtered and evaporated to give 109 mg of a cream oil. Flash chromatography on silica gel of the crude product using hexane to hexane/EtOAc 1:1 gradient as eluent gave a first fraction of an unidentified compound (21 mg). Further elution with EtOAc gave 1-acetylpiperidine-4-carboxylic acid [2-(4-chlorophenoxy)phenyl]amide (37 mg, 33%) as a white solid, mp 195-196° C. Rf: 0.15 (EtOAc) LC/MS (APCI) t$_r$=1.04 min, m/z 375.31 (34), 373.36 (M$^+$+H, 100). HPLC t$_r$=2.208 min (99.70%) $^1$H NMR (270 MHz, CDCl$_3$) δ 1.69 (2H, m, CH$_2$), 1.88 (2H, m, CH$_2$), 2.08 (3H, s CH$_3$), 2.46 (1H, tt, CH), 2.66 (1H, m, 2CH$_2$), 3.09 (1H, m, ½CH$_2$), 3.86 (1H, m, ½CH$_2$), 4.55 (1H, m, ½CH$_2$), 6.82 (1H, dd, J=8.2, 1.5 Hz, ArH), 6.93 (2H, AA'BB', ArH), 7.01 (1H, td, ArH), 7.12 (1H, td, ArH), 7.30 (2H, AA'BB', ArH), 7.69 (1H, br s, NH) and 8.38 (1H, dd, J=8.2, 1.2 Hz, ArH). $^{13}$C NMR (400 MHz, CDCl$_3$), 21.53 (CH$_3$), 28.47, 28.89, 40.81 (CH$_2$), 44.15 (CH), 45.70 (CH$_2$), 117.77, 119.87, 121.31, 124.44, 124.54, 129.19, 129.45, 130.07, 154.44, 154.94, 168.95 and 172.20 (C=O).

1-Benzoylpiperidine-4-carboxylic acid [2-(4-chlorophenoxy)phenyl]amide (AMR01035, STX1615) C$_{25}$H$_{23}$ClN$_2$O$_3$, MW 434.91

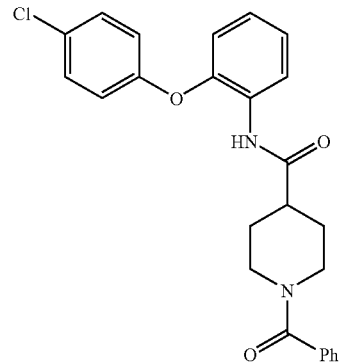

To an ice cooled solution of piperidine-4-carboxylic acid [2-(4-chlorophenoxy)phenyl]amide (AMR01033, 73 mg, 0.22 mmol) in dry DCM (6 mL) were added pyridine (0.036 mL, 0.44 mmol) and benzoyl chloride (0.038 mL, 0.33 mmol). The reaction mixture was stirred at room temperature until TLC showed consumption of starting material (1 h), and quenched with saturated NaHCO$_3$. The resulting solution was extracted with DCM (3×20 mL), and the combined organic layers were washed with water, 1M HCl (3×20 mL) and brine, dried (MgSO$_4$), filtered and evaporated. Flash chromatography on silica gel of the crude product using hexane to EtOAc gradient as eluent gave 1-benzoylpiperidine-4-carboxylic acid [2-(4-chlorophenoxy)phenyl]amide (80 mg, 83%) as a white solid, mp 158-160° C. Rf: 0.48 (EtOAc) LC/MS (APCI) t$_r$=1.05 min, m/z 437.33 (45), 435.38 (M$^+$+H, 100) HPLC t$_r$=2.551 min (98.36%) $^1$H NMR (270 MHz, CDCl$_3$) δ 1.82 (4H, m, 2CH$_2$), 2.51 (1H, tt, CH), 2.98 (2H, n, CH$_2$), 3.85 (1H, m, ½CH$_2$), 4.71 (1H, m, ½CH$_2$), 6.82 (1H, dd, J=8.2, 1.5 Hz, ArH), 6.93 (2H, AA'BB', ArH), 7.02 (1H, td, ArH), 7.13 (1H, td, ArH), 7.31 (1H, AA'BB', ArH), 7.39 (5H, s, ArH,), 7.70 (1H, br s, NH) and 8.39 (1H, dd, J=8.2, 1.5 Hz, ArH). Anal. Calcd. for C$_{25}$H$_{23}$ClN$_2$O$_3$: C, 69.04; H, 5.33; N, 6.44. Found: C, 68.9; H, 5.33; N, 6.37%.

Piperidine-4-carboxylic acid [2-(2,4-dichlorophenoxy)phenyl]amide (AMR01036, AMR01038) C$_{18}$H$_{18}$Cl$_2$N$_2$O$_2$, MW 365.25

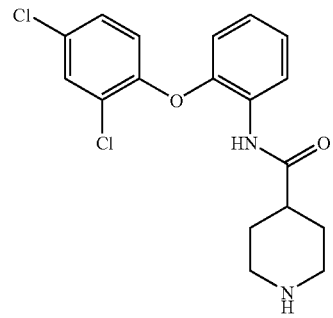

AMR01036 Trifluoroacetic acid (TFA, 1 mL) was added to a solution of 4-[2-(2,4-dichlorophenoxy)-phenylcarbamoyl]piperidine-1-carboxylic acid tert-butyl ester (AMR01.032, 100 mg, 0.215 mmol) in dry DCM (2 mL) at 0° C. After stirring at 0° C. for 30 min, the mixture was poured into solid $K_2CO_3$ (2.8 g) and water (11 mL) was added. The solution was extracted with DCM (3×20 mL) and the organic layer was dried ($MgSO_4$), filtered and evaporated to give piperidine-4-carboxylic acid [2-(2,4-dichlorophenoxy)phenyl]amide (61 mg, 90%) as an oil which was used in the next step without further purification. Rf: 0.175 (DCM/methanol 4:1 plus 3 drops of triethylamine) $^1$H NMR (270 MHz, $CDCl_3$) δ 1.66 (2H, m, $CH_2$), 1.87 (2H, m, $CH_2$), 2.24 (1H, br s, NH), 2.40 (1H, tt, CH), 2.66 (2H, td, $CH_2$), 3.15 (2H, br d, J=12.6 Hz, $CH_2$), 6.72 (1H, dd, J=8.2, 1.5 Hz, ArH), 6.93 (1H, d, J=8.6 Hz, ArH), 6.99 (1H, td, J=7.9, 1.5 Hz, ArH), 7.12 (1H, td, J=7.9, 1.2 Hz, ArH), 7.20 (1H, dd, J=8.9, 2.5 Hz, ArH), 7.47 (1H, d, J=2.5 Hz, ArH) and 8.41 (1H, dd, J=7.9, 1.2 Hz, ArH).

AMR01038 Following the same procedure, from TFA (5.0 mL), AMR01032 (500 mg, 1.079 mmol), DCM (10 mL), $K_2CO_3$ (14 g) and water (55 mL) gave piperidine-4-carboxylic acid [2-(2,4-dichlorophenoxy)phenyl]-amide (AMR01038, 380 mg, 96%) as a white solid, mp 107-113° C. LC/MS (APCI) $t_r$=2.25 min, m/z 367.32 (57), 365.30 ($M^+$+H, 100)

1-Acetylpiperidine-4-carboxylic acid [2-(2,4-dichlorophenoxy)phenyl]amide (AMR01037, STX1614) $C_{20}H_{20}Cl_2N_2O_3$, MW 407.29

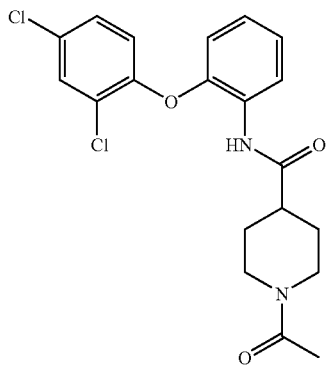

To an ice cooled solution of piperidine-4-carboxylic acid [2-(2,4-dichlorophenoxy)phenyl]-amide (AMR01036, 61 mg, 0.167 mmol) in dry DCM (6 mL) were added triethylamine (0.23 mL, 1.67 mmol) and acetyl chloride (0.024 mL, 0.334 mmol). The reaction mixture was stirred at room temperature until completion by TLC (30 min), and quenched with saturated $NaHCO_3$. The resulting solution was extracted with DCM (3×20 mL), and the combined organic layers were washed with water, 1M HCl (3×20 mL) and brine, dried ($MgSO_4$), filtered and evaporated to give 70 mg of an oil. Flash chromatography on silica gel of the crude product using hexane to EtOAc gradient as eluent gave 1-acetylpiperidine-4-carboxylic acid [2-(2,4-dichlorophenoxy)phenyl]amide (51 mg, 75%) as a white solid, mp 194-196° C. Rf: 0.15 (EtOAc) LC/MS (APCI) $t_r$=2.45 min, m/z 409.31 (55), 407.36 ($M^+$+H, 100) HPLC $t_r$=2.594 min (99.03%) $^1$H NMR (270 MHz, $CDCl_3$) δ 1.72 (2H, m, $CH_2$), 1.92 (2H, m, $CH_2$), 2.09 (3H, s $CH_3$), 2.51 (1H, tt, CH), 2.67 (1H, m, ½$CH_2$), 3.11 (1H, m, ½$CH_2$), 3.87 (1H, m, ½$CH_2$), 4.59 (1H, m, ½$CH_2$), 6.72 (1H, dd, J=8.0, 1.5 Hz, ArH), 6.94 (1H, d, J=8.9 Hz, ArH), 7.00 (1H, td, ArH), 7.12 (1H, td, ArH), 7.22 (1H, dd, J=8.7, 2.5 Hz, ArH), 7.48 (1H, d, J=2.5 Hz, ArH), 7.79 (1H, br s, NH) and 8.38 (1H, br d, J=8.2 Hz, ArH).

1-Benzoylpiperidine-4-carboxylic acid [2-(2,4-dichloro-phenoxy)phenyl]amide (AMR01039, STX1613) $C_{25}H_{22}Cl_2N_2O_3$, MW 469.36

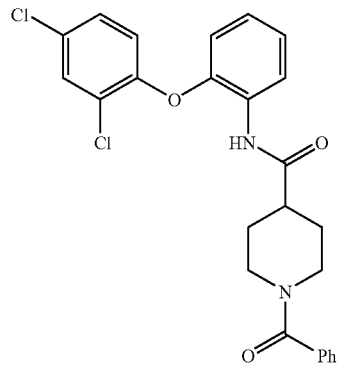

To an ice cooled solution of piperidine-4-carboxylic acid [2-(2,4-dichlorophenoxy)phenyl]-amide (AMR01038, 100 mg, 0.274 mmol) in dry DCM (10 mL) were added pyridine (0.044 mL, 0.548 mmol) and benzoyl chloride (0.047 mL, 0.411 mmol). The reaction mixture was stirred at room temperature until TLC showed consumption of starting material (1 h), and quenched with saturated $NaHCO_3$. The resulting solution was extracted with DCM (3×20 mL), and the combined organic layers were washed with water, 1M HCl (3×20 mL) and brine, dried ($MgSO_4$), filtered and evaporated. Flash chromatography on silica gel of the crude product using hexane to EtOAc gradient as eluent gave 1-benzoylpiperidine-4-carboxylic acid [2-(2,4-dichloro-phenoxy)phenyl]amide (98 mg, 76%) as a white solid, mp 176-177° C. Rf: 0.17 (hexane/EtOAc 1:1) LC/MS (APCI) $t_r$=1.10 min, m/z 471.26 (58), 469.31 ($M^+$+H, 100) HPLC $t_r$=2.88 min (99.48%) $^1$H NMR (270 MHz, $CDCl_3$) δ 1.85 (4H, m, 2$CH_2$), 2.55 (1H, tt, CH), 3.01 (2H, m, $CH_2$), 3.89 (1H, m, ½$CH_2$), 4.74 (1H, m, ½$CH_2$), 6.72 (1H, dd, J=8.2, 1.5 Hz, ArH), 6.95 (1H, d, J=8.6 Hz, ArH), 7.01 (1H, td, ArH), 7.14 (1H, td, ArH), 7.22 (1H, dd, J=8.6, 2.5 Hz, ArH), 7.39 (5H, s, ArH), 7.49 (1H, d, J=2.5 Hz, ArH), 7.78 (1H, br s, NH) and 8.38 (1H, br d, J=8.2 Hz, ArH). Anal. Calcd. for $C_{25}H_{22}Cl_2N_2O_3$: C, 63.97; H, 4.72; N, 5.97. Found: C, 64.10; H, 4.83; N, 5.88%.

[2-(2,4-Dichlorophenoxy)phenyl]piperidin-4-ylamine (AMR01040) $C_{17}H_{18}Cl_2N_2O$, MW 337.24

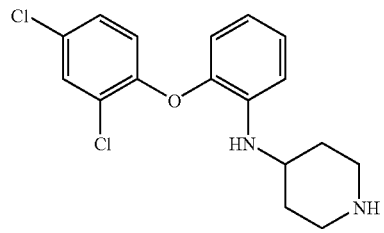

Trifluoroacetic acid (TFA, 3 mL) was added to a solution of 4-[2-(2,4-dichlorophenoxy)phenylamino]piperidine-1-carboxylic acid tert-butyl ester (AMR01030, 300 mg, 0.686 mmol) in dry DCM (6 mL) at 0° C. After stirring at 0° C. for 30 min, the mixture was poured into solid $K_2CO_3$ (8.4 g) and water (33 mL) was added. The solution was extracted with DCM (3×20 mL) and the organic layer was dried ($MgSO_4$), filtered and evaporated to give [2-(2,4-dichlorophenoxy)phenyl]piperidin-4-ylamine (225 mg, 97%) as an oil which was used in the next step without further purification. Rf: 0.13 (DCM/methanol 4:1 plus 3 drops of triethylamine) $^1$H NMR (270 MHz, $CDCl_3$) δ 1.27 (2H, m, $CH_2$), 1.84 (1H, br s, NH), 2.02 (2H, d, J=12.9 Hz, $CH_2$), 2.72 (2H, t, J=11.9 Hz, $CH_2$), 3.06 (2H, br d, J=12.6 Hz, $CH_2$), 3.39 (1H, m, NH), 4.04 (1H, d, J=6.8 Hz, CH), 6.59 (1H, m, ArH), 6.77 (2H, m, ArH), 7.01 (1H, m, ArH), 7.10 (1H, m, ArH) and 7.42 (1H, m, ArH).

1-{4-[2-(2,4-Dichlorophenoxy)phenylamino]piperidin-1-yl}ethanone (AMR01041, STX1616) $C_{19}H_{20}Cl_2N_2O_2$, MW 379.28

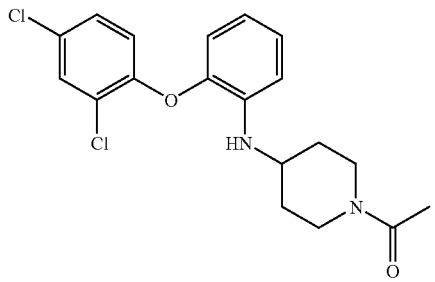

To an ice cooled solution of [2-(2,4-dichlorophenoxy)phenyl]piperidin-4-ylamine (AMR01040, 132 mg, 0.39 mmol) in dry DCM (5 mL) were added triethylamine (0.137 mL, 0.98 mmol) and acetyl chloride (0.031 mL, 0.43 mmol). The reaction mixture was stirred at room temperature until completion by TLC (1 h), and quenched with saturated $NaHCO_3$. The resulting solution was extracted with DCM (3×20 mL), and the combined organic layers were washed with water, 1M HCl (3×20 mL) and brine, dried ($MgSO_4$), filtered and evaporated. Flash chromatography on silica gel of the crude product using hexane to EtOAc gradient as eluent gave 1-{4-[2-(2,4-dichlorophenoxy)phenylamino]piperidin-1-yl}ethanone (95.3 mg, 64%) as a white solid after, mp 145-146° C. Rf: 0.22 (EtOAc) LC/MS (APCI) $t_r$=1.44 min, m/z 381.29 (63), 379.34 ($M^+$+H, 100) HPLC $t_r$=3.10 min (99.31%) $^1$H NMR (270 MHz, $CDCl_3$) δ 1.36 (2H, m, $CH_2$), 2.06 (2H, m, $CH_2$), 2.08 (3H, s, $CH_3$), 2.89 (1H, m), 3.20 (1H, m), 3.53 (1H, m), 3.74 (1H, m), 4.05 (1H, m), 4.37 (1H, m), 6.63 (1H, m, ArH), 6.74 (1H, dd, J=7.9, 1.5 Hz, ArH), 6.75 (1H, dd, J=8.2, 1.5 Hz, ArH), 6.80 (1H, d, J=8.9 Hz, ArH), 7.03 (1H, m, ArH), 7.12 (1H, dd, J=8.9, 2.5 Hz, ArH) and 7.43 (1H, d, J=2.5 Hz, ArH). Anal. Calcd. for $C_{19}H_{20}Cl_2N_2O_2$: C, 60.17; H, 5.32; N, 7.39. Found: C, 59.90; H, 5.47; N, 7.13%.

{4-[2-(2,4-Dichlorophenoxy)phenylamino]piperidin-1-yl}phenylmethanone (AMR01042, STX1623) $C_{24}H_{22}Cl_2N_2O_2$, MW 441.35

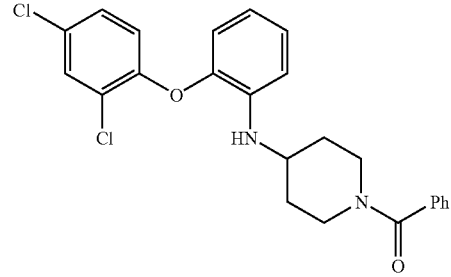

To an ice cooled solution of [2-(2,4-dichloro-henoxy)phenyl]piperidin-4-ylamine (AMR01040, 120 mg, 0.356 mmol) in dry DCM (6 mL) were added pyridine (0.057 mL, 0.71 mmol) and benzoyl chloride (0.045 mL, 0.39 mmol). The reaction mixture was stirred at room temperature until TLC showed consumption of starting material (1 h), and quenched with saturated $NaHCO_3$. The resulting solution was extracted with DCM (3×20 mL), and the combined organic layers were washed with water, 1M HCl (3×20 mL) and brine, dried ($MgSO_4$), filtered and evaporated. Flash chromatography on silica gel of the crude product using hexane to EtOAc gradient as eluent gave {4-[2-(2,4-dichlorophenoxy)phenylamino]piperidin-1-yl}phenylmethanone (122 mg, 78%) as an oil. Rf: 0.17 (hexane/EtOAc 7:3). $^1$H NMR (270 MHz, $CDCl_3$) δ 1.45 (2H, m, $CH_2$), 2.11 (2H, m, $CH_2$), 3.13 (2H, br t, $CH_2$), 3.58 (1H, tt, CH), 3.71 (1H, m, ½$CH_2$), 4.52 (1H, m, ½$CH_2$), 6.63 (1H, m, ArH), 6.75 (1H, dd, J=7.9, 1.5 Hz, ArH), 6.76 (1H, dd, J=8.2, 1.2 Hz, ArH), 6.81 (1H, d, J=8.6 Hz, ArH), 7.03 (1H, m, ArH), 7.13 (1H, dd, J=8.9, 2.5 Hz, ArH), 7.38 (5H, s, ArH) and 7.44 (1H, d, J=2.5 Hz, ArH). $^1$H NMR (300 MHz, $CDCl_3$) δ 1.37 (2H, m, $CH_2$), 2.00 (2H, m, $CH_2$), 3.08 (2H, br t, $CH_2$), 3.53 (1H, tt, CH), 3.66 (1H, m, ½$CH_2$), 4.43 (2H, m), 6.57 (1H, td, ArH), 6.68 (1H, dd, J=8.1, 1.5 Hz, ArH), 6.70 (1H, dd, J=8.1, 1.3 Hz, ArH), 6.75 (1H, d, J=8.7 Hz, ArH), 6.98 (1H, m, ArH), 7.07 (1H, dd, J=8.8, 2.5 Hz, ArH), 7.32 (5H, s, ArH) and 7.39 (1H, d, J=2.5 Hz, ArH). Further purification by flash chromatography on silica gel using DCM/MeOH 95:5 as eluent gave AMR01042 (100 mg) as a white solid, mp 55-58° C. LC/MS (APCI) $t_r$=3.82 min, m/z 443.44 (67), 441.42 ($M^+$+H, 100) HPLC $t_r$=4.78 min (98.81%)

1-Methanesulfonyl-piperidine-4-carboxylic acid [2-(2,4-dichloro-phenoxy)-phenyl]-amide (AMR01051, STX1657) $C_{19}H_{20}Cl_2N_2O_4S$, MW 443.34

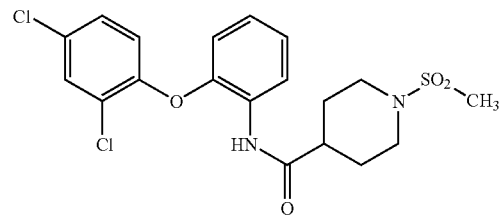

To an ice cooled solution of piperidine-4-carboxylic acid [2-(2,4-dichlorophenoxy)phenyl]-amide (AMR01038, 80 mg, 0.219 mmol) in dry DCM (6 mL) were added triethylamine (0.3 mL, 2.19 mmol) and methanesulphonyl chloride (0.034 mL, 0.438 mmol). The reaction mixture was stirred at room temperature for 24 h, and quenched with saturated NaHCO$_3$. The resulting solution was extracted with DCM (3×20 mL), and the combined organic layers were washed with water, 1M HCl (3×20 mL) and brine, dried (MgSO$_4$), filtered and evaporated. Flash chromatography on silica gel using DCM to DCM/MeOH 95:5 gradient as eluent gave 1-methanesulfonyl-piperidine-4-carboxylic acid [2-(2,4-dichloro-phenoxy)-phenyl]-amide (47.6 mg, 49%) as an oil. Rf: 0.25 (hexane/EtOAc 4:6). $^1$H NMR (300 MHz, CDCl$_3$) δ 1.88 (2H, m, CH$_2$), 2.37 (1H, m, CH), 2.72 (3H, s, CH$_3$), 2.78 (2H, m, CH$_2$), 3.71 (2H, td, J=12.5, 3.6 Hz, CH$_2$), 6.67 (1H, dd, J=8.1, 1.3 Hz, ArH), 6.89 (1H, d, J=8.8 Hz, ArH), 6.95 (1H, td, J=8.1, 1.6 Hz, ArH), 7.07 (1H, td, J=8.0, 1.3 Hz, ArH), 7.16 (1H, dd, J=8.8, 2.5 Hz, ArH), 7.43 (1H, d, J=2.5 Hz, ArH), 7.72 (1H, br s, NH) and 8.31 (1H, br d, J=8.1 Hz, ArH). Further purification by flash chromatography on silica gel using hexane/EtOAc 4:6 as eluent gave AMR01051 as a white solid, mp 150-151° C. LC/MS (APCI) t$_r$=4.63 min, m/z 443.37 (M$^+$+H, 100), 445.39 (55). HPLC t$_r$=2.52 min (100%)

1-(2,5-Dichlorobenzenesulfonyl)piperidine-4-carboxylic acid [2-(2,4-dichlorophenoxy)-phenyl]amide (AMR01053, STX1658) C$_{24}$H$_{20}$Cl$_4$N$_2$O$_4$S, MW 574.30

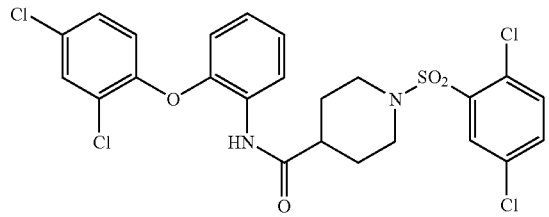

To an ice cooled solution of piperidine-4-carboxylic acid [2-(2,4-dichlorophenoxy)-phenyl]amide (AMR01038, 80 mg, 0.219 mmol) in dry DCM (6 mL) were added pyridine (0.035 mL, 0.438 mmol) and 2,5-dichlorobenzenesulphonyl chloride (59.2 mg, 0.241 mmol). The reaction mixture was stirred at room temperature for 24 h, and then at reflux for 3 h. After quenching with saturated NaHCO$_3$, the resulting solution was extracted with DCM (3×20 mL), and the combined organic layers were washed with water, 1M HCl (3×20 mL) and brine, dried (MgSO$_4$), filtered and evaporated. Flash column chromatography on silica gel using hexane/EtOAc 8:2 as eluent gave 1-(2,5-dichlorobenzenesulfonyl)piperidine-4-carboxylic acid [2-(2,4-dichlorophenoxy)-phenyl]amide (56 mg, 44%) as a white solid, mp 194-196° C. Rf: 0.81 (DCM/MeOH 9:1). $^1$H NMR (300 MHz, CDCl$_3$) δ 1.74-1.96 (4H, m, 2CH$_2$), 2.34 (1H, m, CH), 3.80 (2H, td, J=13.1, 3.4 Hz, CH$_2$), 6.65 (1H, dd, J=8.1, 1.4 Hz, ArH), 6.87 (1H, d, J=8.8 Hz, ArH), 6.94 (1H, td, J=7.7, 1.7 Hz, ArH), 7.05 (1H, td, J=8.0, 1.4 Hz, ArH), 7.15 (1H, dd, J=8.8, 2.5 Hz, ArH), 7.37 (2H, d, J=1.4 Hz, ArH), 7.41 (1H, d, J=2.5 Hz, ArH), 7.68 (1H, br s, NH), 7.97 (1H, t, J=1.4 Hz, ArH) and 8.29 (1H, dd, J=8.0, 1.0 Hz, ArH). LC/MS (APCI) t$_r$=5.62 min, m/z 577.21 (59), 575.26 (100), 573.24 (M$^+$+H, 90) HPLC t$_r$=3.363 min (97.70%)

2-(2,4-Dichlorophenoxy)benzonitrile (AMR01045, AMR01058, AMR01066) C$_{13}$H$_7$Cl$_2$NO, MW 264.11

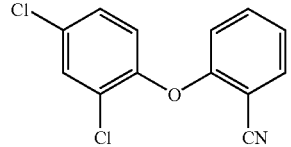

Commercially Available

AMR01045 A mixture of 2,4-dichlorophenol (2.00 g, 12.27 mmol), 2-fluorobenzonitrile (1.49 g, 12.27 mmol) and potassium carbonate (1.7 g, 12.27 mmol) in DMF (10 mL) was stirred under reflux for 1.5 h. After removal of DMF, the residue was dissolved in DCM and washed with NaOH (5%, 3×20 mL) and brine. The organic layer was dried (MgSO$_4$), filtered and evaporated and 2-(2,4-dichlorophenoxy)benzonitrile was obtained as an oil (2.73 g, 84%), which was used in the next step without further purification. Rf: 0.64 (DCM) $^1$H NMR (300 MHz, CDCl$_3$) δ 6.73 (1H, dd, J=8.4 Hz), 7.13 (1H, d, J=8.7 Hz), 7.22 (1H, td, J=8.7, 1.0 Hz), 7.35 (1H, dd, J=8.7, 2.4 Hz), 7.56 (1H, d, J=2.4 Hz) and 7.73 (1H, dd, J=7.5, 2.7 Hz).

2-(2,4-Dichlorophenoxy)benzoic acid (AMR01057, AMR01067) C$_{13}$H$_8$Cl$_2$O$_3$, MW 283.11

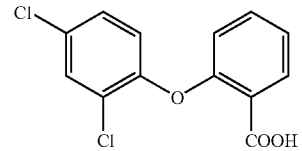

Previously described: Atkinson, D. C.; Godfrey, K. E.; Meek, B.; Saville, J. F.; Stillings, M. R. *J. Med. Chem.* 1983, 26, 1353-1360.

Commercially Available

AMR01057 A solution of 2-(2,4-dichlorophenoxy)benzonitrile (AMR01045, 1.39 g, 5.26 mmol) and KOH (1.77 g, 31.58 mmol) in EtOH (10 mL) and H$_2$O (10 mL) was heated at reflux for 20 h. After adding water (20 mL) the solution was washed with DCM (3×10 mL). The aqueous was acidified with HCl 1M and a white solid precipitated. It was filtered, washed with water and dried. Flash chromatography on silica gel using DCM to DCM/MeOH 9:1 gradient as eluent gave 2-(2,4-dichlorophenoxy)benzoic acid (1.1 g, 74%) as a white solid, mp 161-163° C. (Lit. 159-162° C.) Rf: 0.36 (DCM/MeOH 9:1). $^1$H NMR (300 MHz, CDCl$_3$) δ 6.79 (1H, dd, J=8.3, 0.8 Hz, ArH), 7.00 (1H, d, J=8.7 Hz, ArH), 7.23-7.28 (2H, m, ArH), 7.51 (1H, m, ArH), 7.52 (1H, d, J=7.5 Hz, ArH), 8.17 (1H, dd, J=7.8, 1.7 Hz, ArH), and 10.76 (1H, br s, COOH).

AMR01067 Following the same procedure, from 2-(2,4-dichlorophenoxy)benzonitrile (AMR01066, 2.1 g, 7.95 mmol), KOH (2.67 g, 47.71 mmol) in EtOH (15 mL) and H$_2$O (15 mL) gave AMR01067 (2.18 g, 97%). LC/MS (APCI) t$_r$=3.24 min, m/z 285.31 (8), 283.31 (M$^+$, 14), 267.31 (58), 265.29 (M$^+$−18, 100),

4-[2-(2,4-Dichlorophenoxy)benzoylamino]piperidine-1-carboxylic acid ethyl ester (AMR01059, AMR01061, STX1719) $C_{21}H_{22}Cl_2N_2O_4$, MW 437.32

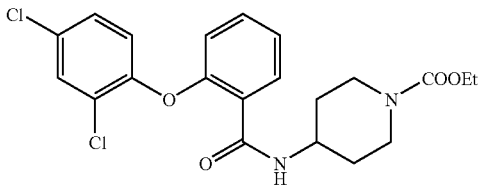

AMR01059 A solution of 2-(2,4-dichlorophenoxy)benzoic acid (AMR01057, 200 mg, 0.706 mmol) in dry DCM (10 mL) was stirred under nitrogen, and 4-dimethylaminopyridine (DMPA, 40 mg, 0.327 mmol), (1-(3-dimethylaminopropyl)-3-ethylcarbodiimide hydrochloride (EDC, 406 mg, 2.12 mmol) and triethylamine (0.15 mL) were added. The resulting mixture was stirred for 30 min under nitrogen and ethyl-4-amino-1-piperidine carboxylate (122 mg, 0.706 mmol) in dry DCM (4 mL) was added. After stirring at room temperature for 12 h, the mixture was diluted with DCM, washed with HCl 1M (3×25 mL), water, saturated $NaHCO_3$ (2×25 mL) and brine. The organic layer was dried ($MgSO_4$), filtered and evaporated. Flash chromatography on silica gel using DCM to DCM/MeOH 9:1 gradient as eluent gave 4-[2-(2,4-dichlorophenoxy)benzoylamino]piperidine-1-carboxylic acid ethyl ester (140 mg, 45%) as a white solid. Rf: 0.62 (DCM/MeOH 9:1) $^1$H NMR (300 MHz, $CDCl_3$) 11.26 (3H, t, J=7.1 Hz, $CH_3$), 1.40 (2H, m, $CH_2$), 1.97 (2H, m, $CH_2$), 3.00 (2H, m, $CH_2$), 4.03 (2H, m, $CH_2$), 4.13 (2H, q, J=7.1 Hz, $CH_3CH_2O$), 4.19 (1H, m, CH), 6.80 (1H, dd, J=8.2, 0.9 Hz, ArH), 6.90 (1H, d, J=8.8 Hz, ArH), 7.24 (1H, dd, J=8.8, 2.5 Hz, ArH), 7.27 (1H, m, ArH), 7.36 (1H, br s, NH), 7.42 (1H, m, ArH), 7.53 (1H, d, J=2.5 Hz, ArH) and 8.19 (1H, dd, J=7.8, 1.8 Hz, ArH).

AMR01061 Following the same procedure, from 2-(2,4-dichlorophenoxy)benzoic acid (AMR01057, 0.9 g, 3.18 mmol), (DMPA, 40 mg, 0.327 mmol), (1-(3-dimethylaminopropyl)-3-ethylcarbodiimide hydrochloride (EDC, 1.83 g, 9.54 mmol), triethylamine (0.5 mL) and ethyl-4-amino-1-piperidine carboxylate (548 mg, 3.18 mmol), gave AMR01061 (860 mg, 62%) as a white solid, mp 127-128° C. LC/MS (APCI) $t_r$=5.10 min, m/z 439.41 (63), 437.45 ($M^+$+H, 100). HPLC $t_r$=3.19 min (99.40%)

4-Aminopiperidine-1-carboxylic acid tert-butyl ester (AMR01068) $C_{10}H_{20}N_2O_2$, MW 200.28

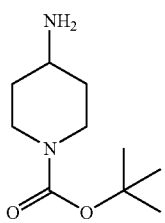

A previously described method (Miriyala, B.; Bhattacharyya, S.; Williamson, J. Tetrahedron 2004, 60, 1463-1471) has been followed.

A mixture of 1-BOC-piperidone (2 g, 10 mmol), titanium (IV) isopropoxide and ammonia in EtOH was stirred under argon in a capped flask at room temperature for 6 h. Sodium borohydride was then added and the resulting mixture was stirred at room temperature for an additional 3 h. The reaction was then quenched by pouring it into ammonium hydroxide (2M, 25 mL). The resulting inorganic precipitate was filtered off, and washed with EtOAc (2×25 mL). The organic layer was separated and the remaining aqueous layer was extracted with EtOAc (2×25 mL). The combined organic fractions were next extracted with HCl (1M, 30 mL) to separate the neutral materials. The acidic extracts were washed with EtOAc (50 mL), then treated with aqueous NaOH 2M to pH 10-12, and extracted with EtOAc (3×50 mL). The combined organic extracts were washed with brine, dried ($MgSO_4$) and concentrated in vacuo to afford 4-aminopiperidine-1-carboxylic acid tert-butyl ester as a white solid (882 mg, 44%) which was used in the next step without further purification. $^1$H NMR (300 MHz, $CDCl_3$) δ 1.12-1.27 (3H, m), 1.42 (9H, s, $3CH_3$), 1.97 (2H, m), 1.73 (2H, m), 2.76 (3H, m) and 4.01 (2H, m).

4-[2-(2,4-Dichlorophenoxy)benzoylamino]piperidine-1-carboxylic acid tert-butyl ester (AMR01070, STX1723) $C_{23}H_{26}Cl_2N_2O_4$, MW 465.37

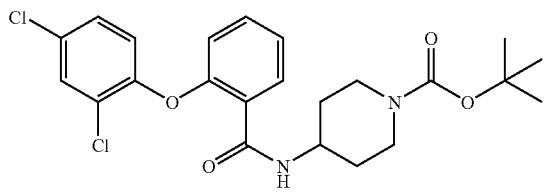

A solution of 2-(2,4-dichlorophenoxy)benzoic acid (AMR01067, 1.24 g, 4.39 mmol) in dry DCM (20 mL) was stirred under nitrogen, and 4-dimethylaminopyridine (DMPA, 40 mg, 0.327 mmol), (1-(3-dimethylaminopropyl)-3-ethylcarbodiimide hydrochloride (EDC, 2.5, 13.18 mmol) and triethylamine (0.6 mL) were added. The resulting mixture was stirred for 30 min under nitrogen and 4-aminopiperidine-1-carboxylic acid tert-butyl ester (AMR01068, 0.88 g, 4.39 mmol) in dry DCM (410 mL) was added. After stirring at room temperature for 48 h, the mixture was diluted with DCM, washed with HCl (1M, 3×25 mL), water, saturated $NaHCO_3$ (2×25 mL) and brine. The organic layer was dried ($MgSO_4$), filtered and evaporated. Flash chromatography on silica gel of the crude product using DCM/MeOH 99:1 as eluenty gave 4-[2-(2,4-dichlorophenoxy)benzoylamino]piperidine-1-carboxylic acid tert-butyl ester (953 mg, 40%) as white solid. Rf: 0.64 (DCM/MeOH 9:1) $^1$H NMR (270 MHz, $CDCl_3$) δ 1.48 (9H, s, $3CH_3$), 1.92 (2H, m, $CH_2$), 2.92 (2H, br t, $CH_2$), 3.95 (2H, br d, $CH_2$), 4.11 (1H, m, CH), 6.78 (1H, dd, J=8.2, 1.0 Hz, ArH), 6.87 (1H, d, J=8.9 Hz, ArH), 7.21 (1H, dd, J=8.6, 2.5 Hz, ArH), 7.25 (1H, m, ArH), 7.35 (1H, br s, NH), 7.40 (1H, m, ArH), 7.50 (1H, d, J=2.5 Hz, ArH) and 8.17 (1H, dd, J=7.9, 2.0 Hz, ArH). LC/MS (APCI) $t_r$=5.36 min, m/z 467.36 (18), 465.41 ($M^+$+H, 30), 411.33 (67), 409.38 ($M^+$-$C_4H_8$, 100). HPLC $t_r$=2.93 min (97.22%)

2-(4-Chlorophenoxy)benzonitrile (AMR01071) C₁₃H₇Cl₂NO, MW 229.66

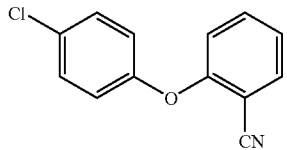

A mixture of 4-chlorophenol (2.00 g, 15.56 mmol), 2-fluorobenzonitrile (1.88 g, 15.56 mmol) and potassium carbonate (2.15 g, 15.56 mmol) in DMF (10 mL) was stirred under reflux for 4 h. After removal of DMF, the residue was dissolved in DCM and washed with NaOH (5%, 3×20 mL) and brine. The organic layer was dried (MgSO₄), filtered and evaporated to give 2-(4-chlorophenoxy)benzonitrile (3.2 g, 90%) as a white solid, mp 84-86° C., which was used in the next step without further purification. Rf: 0.62 (DCM) $^1$H NMR (270 MHz, CDCl₃) δ 6.86 (1H, dd, J=8.4, 0.8 Hz), 7.02 (2H, AA'BB'), 7.15 (1H, td, J=7.7, 1.0 Hz), 7.35 (2H, AA'BB'), 7.48 (1H, m) and 7.65 (1H, dd, J=7.7, 1.5 Hz). LC/MS (APCI) $t_r$=4.66 min, m/z 232.28 (31), 230.27 (M⁺+H, 100).

2-(4-Chlorophenoxy)benzylamine (AMR01073, AMR01076) C₁₃H₁₂ClNO, MW 233.69

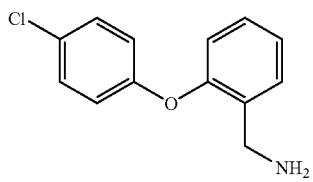

AMR01073 To an ice cooled solution of 2-(4-chlorophenoxy)benzonitrile (AMR01071, 200 mg, 8.75 mmol) in dry THF (10 mL) was added a solution of LiAlH₄ (THF 1M, 1.75 mL) under nitrogen. After stirring at room temperature for 3 h, the reaction mixture was cooled again and quenched with the minimum amount of saturated NH₄Cl solution. The insoluble material was removed by filtration, and washed with DCM. The filtrate was dried (MgSO₄) and the solvent evaporated to give 2-(4-chlorophenoxy)benzylamine (AMR01073, 203 mg, 100%) as an oil, which was used in the next step without further purification. AMR01076 Following the same procedure, from AMR01071 (1.5 g, 6.53 mmol) and LiAlH₄ solution (THF 1M, 13 mL) in dry THF (30 mL), 2-(4-chlorophenoxy)benzylamine (AMR0106, 1.38 g, 90%) was obtained as an oil. Rf: 0.35 (DCM/MeOH 9:1) $^1$H NMR (270 MHz, CDCl₃) δ 1.42 (2H, br s, NH₂), 3.84 (2H, s, CH₂), 6.84-6.90 (3H, m, ArH), 7.13 (1H, m, ArH), 7.21 (1H, dd, J=7.6, 2.0 Hz, ArH), 7.26 (2H, AA'BB', ArH) and 7.38 (1H, td, J=7.4, 1.7 Hz, ArH). LC/MS (APCI) $t_r$=1.40 min, m/z 236.38 (34), 234.36 (M⁺+H, 100), 217.29 (M+—NH₃, 35).

4-[2-(2,4-Dichlorophenoxy)-N-piperidin-4-ylbenzamide (AMR01077) C₁₈H₁₈Cl₂N₂O₂, MW 365.25

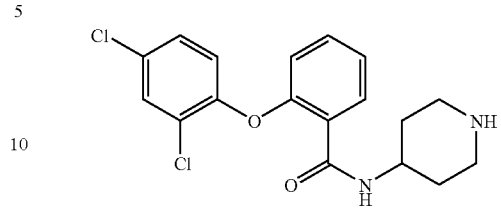

Trifluoroacetic acid (TFA, 9 mL) was added to a solution of 4-[2-(2,4-dichlorophenoxy)-benzoylamino]piperidine-1-carboxylic acid tert-butyl ester (AMR01070, 900 mg, 1.93 mmol) in dry DCM (20 mL) at 0° C. After stirring at 0° C. for 1 h, the mixture was poured into solid K₂CO₃ (2.5 g) and water (100 mL) was added. The solution was extracted with DCM (3×30 mL) and the organic layer was dried (MgSO₄), filtered and evaporated to give 4-[2-(2,4-dichlorophenoxy)-N-piperidin-4-ylbenzamide (AMR01077, 705 mg, 100%) as a white solid, which was used in the next step without further purification. Rf: 0.25 (DCM/MeOH 9:1) $^1$H NMR (270 MHz, CDCl₃) δ 1.87 (2H, m, CH₂), 2.21 (2H, d, J=11.4 Hz, CH₂), 3.01 (2H, q, J=10.9 Hz, CH₂), 3.43 (2H, d, J=13.1 Hz, CH₂), 4.22 (1H, m, CH), 6.76 (1H, dd, J=8.4, 1.0 Hz, ArH), 6.95 (1H, d, J=8.7 Hz, ArH), 7.21-7.27 (2H, m, ArH), 7.41 (1H, m, ArH), 7.51 (1H, d, J=2.5 Hz, ArH), 8.14 (1H, dd, J=7.9, 2.0 Hz, ArH), 9.25 (1H, br d, J=8.5 Hz, NH) and 9.56 (1H, br d, J=7.4 Hz, NH). $^{13}$C NMR (270 MHz, CDCl₃) δ 28.61 (CH₂), 43.11 (CH₂), 44.90 (CH), 117.10, 123.43, 124.53, 126.40, 128.58, 130.83, 130.98, 132.53, 133.24, 149.35, 154.00 (ArC) and 164.38 (C=N).

N-(1-Acetylpiperidin-4-yl)-2-(2,4-dichlorophenoxy)benzamide (AMR01078, STX1733) C₂₀H₂₀Cl₂N₂O₃, MW 407.29

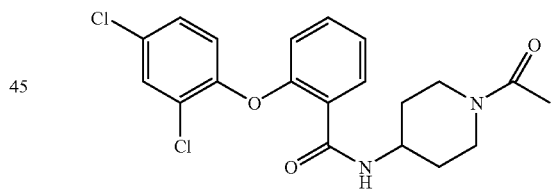

To an ice cooled solution of 4-[2-(2,4-dichlorophenoxy)-N-piperidin-4-ylbenzamide (AMR01077, 100 mg, 0.274 mmol) in dry DCM (5 mL) were added triethylamine (0.2 mL, 1.37 mmol) and acetyl chloride (0.023 mL, 0.33 mmol). The reaction mixture was stirred at room temperature until completion by TLC (1.5 h), and quenched with saturated NaHCO₃. The organic solution was evaporated to dryness and the oil obtained was purified by column chromatography using DCM/MeOH 95:5 as eluent. Further purification was carried out by treating a DCM solution of the obtained compound with trisamine scavenger (100 mg) for 2 h. The scavenger was filtered off, and the solvent evaporated to give N-(1-acetylpiperidin-4-yl)-2-(2,4-dichlorophenoxy)benzamide (84 mg, 75%) as an oil. Rf: 0.15 (EtOAc) LC/MS (APCI) $t_r$=3.78 min, m/z 409.31 (67), 407.36 (M⁺+H, 100). HPLC $t_r$=2.69 min (96.74%) $^1$H NMR (270 MHz, CDCl₃) δ 1.38 (2H, m, CH₂), 2.00 (2H, m, CH₂), 2.08 (3H, s, CH₃), 2.84

(1H, m, ½CH₂), 3.74 (1H, m, ½CH₂), 4.18 (1H, m, CH), 4.41 (1H, m, ½CH₂), 6.79 (1H, dd, J=8.2, 1.0 Hz, ArH), 6.88 (1H, d, J=8.6 Hz, ArH), 7.22 (1H, dd, J=8.9, 2.5 Hz, ArH), 7.26 (1H, m, ArH), 7.37 (1H, br s, NH), 7.41 (1H, m, ArH), 7.51 (1H, d, J=2.5 Hz, ArH) and 8.17 (1H, dd, J=7.9, 1.7 Hz, ArH).

2-(2,4-Dichlorophenoxy)-N-(1-isobutyrylpiperidin-4-yl)benzamide (AMR01079, STX1725) C₂₂H₂₄Cl₂N₂O₃, MW 435.34

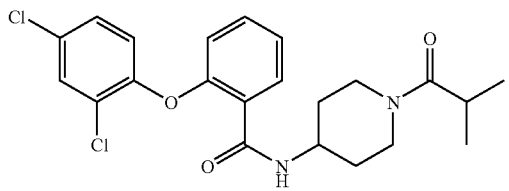

To an ice cooled solution of 4-[2-(2,4-dichlorophenoxy)-N-piperidin-4-ylbenzamide (AMR01077, 100 mg, 0.274 mmol) in dry DCM (5 mL) were added triethylamine (0.2 mL, 1.37 mmol) and isobutyryl chloride (0.035 mL, 0.33 mmol). The reaction mixture was stirred at room temperature until completion by TLC (1.5 h), and quenched with saturated NaHCO₃. The organic solution was evaporated to dryness and the oil obtained was purified by column chromatography using DCM/MeOH 95:5 as eluent. Further purification was carried out by treating a DCM solution of the obtained compound with trisamine scavenger (100 mg) for 2 h. The scavenger was filtered off, and the solvent evaporated to give 2-(2,4-dichlorophenoxy)-N-(1-isobutyrylpiperidin-4-yl)benzamide (93 mg, 77%) as a white solid. Rf: 0.15 (hexane/AcOEt 4:6), mp 51-54° C. LC/MS (APCI) t$_r$=4.66 min, m/z 437.33 (66), 435.31 (M⁺+H, 100). HPLC t$_r$=2.39 min (97.97%) ¹H NMR (270 MHz, CDCl₃) δ 1.10 (6H, d, J=6.7 Hz, 2CH₃), 1.36 (2H, m, CH₂), 2.00 (2H, m, CH₂), 2.78 (1H, hept, J=6.7 Hz, CHMe₂), 2.80 (1H, m, ½CH₂), 3.18 (1H, br t, ½CH₂), 3.83 (1H, m, ½CH₂), 4.19 (1H, m, CH), 4.44 (1H, m, ½CH₂), 6.79 (1H, d, J=8.6 Hz, ArH), 6.87 (1H, d, J=8.7 Hz, ArH), 7.19-7.28 (2H, m, ArH), 7.35 (1H, br s, NH), 7.40 (1H, m, ArH), 7.50 (1H, d, J=2.5 Hz, ArH) and 8.17 (1H, dd, J=7.7, 1.7 Hz, ArH).

2-(2,4-Dichlorophenoxy)-N-[1-(3-methylbutyryl)piperidin-4-yl]benzamide (AMR01080, STX1734) C₂₃H₂₆Cl₂N₂O₃, MW 449.37

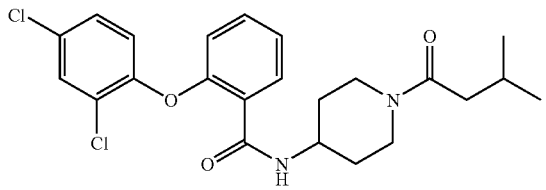

To an ice cooled solution of 4-[2-(2,4-dichlorophenoxy)-N-piperidin-4-ylbenzamide (AMR01077, 100 mg, 0.274 mmol) in dry DCM (5 mL) were added triethylamine (0.2 mL, 1.37 mmol) and isovaleryl chloride (0.04 mL, 0.33 mmol). The reaction mixture was stirred at room temperature until completion by TLC (1.5 h), and quenched with saturated NaHCO₃. The organic solution was evaporated to dryness and the oil obtained was purified by column chromatography using DCM/MeOH 95:5 as eluent. Further purification was carried out by treating a DCM solution of the obtained compound with trisamine scavenger (100 mg) for 2 h. The scavenger was filtered off, and the solvent evaporated to give 2-(2,4-dichlorophenoxy)-N-[1-(3-methylbutyryl)piperidin-4-yl]benzamide (97 mg, 79%) as a colorless oil. Rf: 0.15 (hexane/AcOEt 4:6) LC/MS (APCI) t$_r$=4.44 min, m/z 451.43 (68), 449.42 (M⁺+H, 100). HPLC t$_r$=3.17 min (98.27%) ¹H NMR (270 MHz, CDCl₃) δ 0.95 (6H, d, J=6.7 Hz, 2CH₃), 1.33 (3H, m, CH₂+½CH₂), 2.19 (2H, d, J=6.7 Hz, CH₂CO), 2.83 (1H, m, ½CH₂), 3.15 (1H, m, ½CH₂), 3.76 (1H, m, ½CH₂), 4.16 (1H, m, CH), 4.44 (1H, m, ½CH₂), 6.79 (1H, dd, J=8.2, 1.0 Hz, ArH), 6.86 (1H, d, J=8.6 Hz, ArH), 7.20 (1H, dd, J=8.7, 2.5 Hz, ArH), 7.25 (1H, m, ArH), 7.29 (1H, br s, NH), 7.41 (1H, m, ArH), 7.49 (1H, d, J=2.5 Hz, ArH) and 8.16 (1H, dd, J=7.7, 1.7 Hz, ArH).

N-(1-Cyclohexanecarbonylpiperidin-4-yl)-2-(2,4-dichlorophenoxy)benzamide (AMR01081, STX1726) C₂₅H₂₈Cl₂N₂O₃, MW 475.41

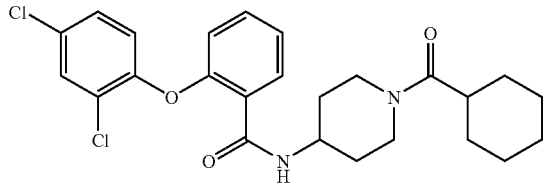

To an ice cooled solution of 4-[2-(2,4-dichlorophenoxy)-N-piperidin-4-ylbenzamide (AMR01077, 100 mg, 0.274 mmol) in dry DCM (5 mL) were added triethylamine (0.2 mL, 1.37 mmol) and cyclohexanecarbonyl chloride (0.044 mL, 0.33 mmol). The reaction mixture was stirred at room temperature until completion by TLC (1.5 h), and quenched with saturated NaHCO₃. The organic solution was evaporated to dryness and the oil obtained was purified by column chromatography using DCM/MeOH 95:5 as eluent.

Further purification was carried out by treating a DCM solution of the obtained compound with trisamine scavenger (100 mg) for 2 h. The scavenger was filtered off, and the solvent evaporated to give 2-(2,4-dichlorophenoxy)-N-[1-(3-methylbutyryl)piperidin-4-yl]benzamide (109 mg, 84%) as a white solid. Rf: 0.15 (hexane/AcOEt 4:6) LC/MS (APCI) t$_r$=4.44 min, m/z 451.43 (68), 449.42 (M⁺+H, 100). HPLC t$_r$=2.80 min (99.06%) ¹H NMR (270 MHz, CDCl₃) δ 1.24-1.52 (12H, m, 6CH₂), 2.00 (2H, m, CH₂), 2.45 (1H, m, ½CH₂), 2.81 (1H, br t, ½CH₂), 3.16 (1H, br t ½CH₂), 3.82 (1H, br d, J=13.6 Hz, ½CH₂), 4.18 (1H, m, CH), 4.43 (1H, br d, J=13.6 Hz, ½CH₂), 6.79 (1H, dd, J=8.2, 1.0 Hz, ArH), 6.87 (1H, d, J=8.6 Hz, ArH), 7.20 (1H, dd, J=8.9, 2.7 Hz, ArH), 7.26 (1H, m ArH), 7.34 (1H, br s, NH), 7.40 (1H, m, ArH), 7.50 (1H, d, J=2.5 Hz, ArH) and 8.17 (1H, dd, J=7.9, 1.7 Hz, ArH). ¹³C NMR (270 MHz, CDCl₃) δ 25.95, 29.47, 29.55, 31.72, 32.89, 40.56, 44.08 (CH₂), 47.14, 48.61 (CH), 117.77, 120.75, 124.53, 124.81, 125.93, 128.53, 130.36, 130.85, 132.60, 132.92, 149.88, 153.33 (ArC), 163.88 and 174.62 (C=O).

N-(1-Cyclopentanecarbonylpiperidin-4-yl)-2-(2,4-dichlorophenoxy)benzamide (AMR01082, STX1727) C₂₄H₂₆Cl₂N₂O₃, MW 461.38

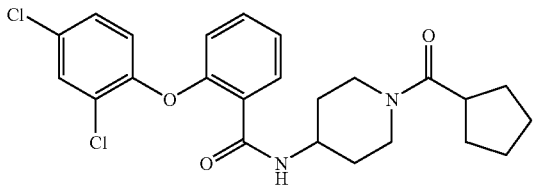

To an ice cooled solution of 4-[2-(2,4-dichlorophenoxy)-N-piperidin-4-ylbenzamide (AMR01077, 100 mg, 0.274 mmol) in dry DCM (5 mL) were added triethylamine (0.2 mL, 1.37 mmol) and cyclopentanecarbonyl chloride (0.04 mL, 0.33 mmol). The reaction mixture was stirred at room temperature until completion by TLC (1.5 h), and quenched with saturated NaHCO₃. The organic solution was evaporated to dryness and the oil obtained was purified by column chromatography using DCM/MeOH 95:5 as eluent. Further purification was carried out by treating a DCM solution of the obtained compound with trisamine scavenger (100 mg) for 2 h. The scavenger was filtered off, and the solvent evaporated to give 2-(2,4-dichlorophenoxy)-N-[1-(3-methylbutyryl)piperidin-4-yl]benzamide (99 mg, 78%) as a white solid, m.p. 57-60° C. Rf: 0.15 (hexane/AcOEt 4:6) LC/MS (APCI) $t_r$=4.94 min, m/z 463.33 (60), 461.32 (M⁺+H, 100). HPLC $t_r$=2.64 min (98.25%) ¹H NMR (270 MHz, CDCl₃) δ 1.35 (2H, m, CH₂), 1.55 (2H, m, CH₂), 1.76 (6H, m, 3CH₂), 2.00 (2H, m, CH₂), 2.87 (2H, m, CH₂), 3.17 (1H, m, ½CH₂), 3.87 (1H, br t, ½ CH₂), 4.19 (1H, m, CH), 4.43 (1H, m, ½CH₂), 6.79 (1H, d, J=8.6 Hz, ArH), 7.21 (1H, dd, J=8.9, 2.5 Hz, ArH), 7.25 (1H, m ArH), 7.35 (1H, br d, NH), 7.50 (1H, d, J=2.5 Hz, ArH) and 8.17 (1H, dd, J=7.9, 1.7 Hz, ArH). ¹³C NMR (270 MHz, CDCl₃) δ 23.81, 29.36, 32.26, 33.17 (CH₂), 39.60 (CH), 40.78 (CH₂), 43.70 (CH), 47.79 (CH₂), 118.00, 120.65, 124.43, 124.88, 126.21, 128.57, 130.85, 130.87, 132.74, 133.06, 148.97, 153.09 (ArC), 163.63 and 174.71 (C=O).

N-(1-Benzoylpiperidin-4-yl)-2-(2,4-dichlorophenoxy)benzamide (AMR01083, STX1728) C₂₅H₂₂Cl₂N₂O₃, MW 469.36

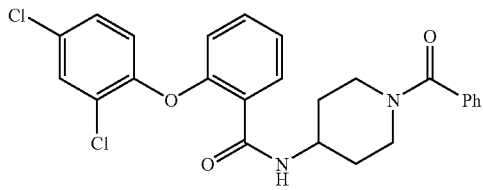

To an ice cooled solution of 4-[2-(2,4-dichloro-phenoxy)-N-piperidin-4-ylbenzamide (AMR01077, 100 mg, 0.274 mmol) in dry DCM (5 mL) were added triethylamine (0.2 mL, 1.37 mmol) and benzoyl chloride (0.038 mL, 0.33 mmol). The reaction mixture was stirred at room temperature until completion by TLC (1.5 h), and quenched with saturated NaHCO₃. The organic solution was evaporated to dryness and the oil obtained was purified by column chromatography using DCM/MeOH 95:5 as eluent. Further purification was carried out by treating a DCM solution of the obtained compound with trisamine scavenger (100 mg) for 2 h. The scavenger was filtered off, and the solvent evaporated to give N-(1-benzoylpiperidin-4-yl)-2-(2,4-dichlorophenoxy)benzamide (103 mg, 80%) as a white solid, mp 63-66° C. Rf: 0.15 (hexane/AcOEt 4:6) LC/MS (APCI) $t_r$=4.94 min, m/z 471.32 (65), 469.31 (M⁺+H, 100). HPLC $t_r$=2.35 min (98.01%) ¹H NMR (270 MHz, CDCl₃) δ 1.35 (2H, m, CH₂), 1.55 (2H, m, CH₂), 1.76 (6H, m, 3CH₂), 2.00 (2H, m, CH₂), 2.87 (2H, m, CH₂), 3.17 (1H, m, ½CH₂), 3.87 (1H, br t, ½CH₂), 4.19 (1H, m, CH), 4.43 (1H, m, ½CH₂) 6.79 (1H, d, J=8.6 Hz, ArH), 7.21 (1H, dd, J=8.9, 2.5 Hz, ArH), 7.25 (1H, m ArH), 7.35 (1H, br d, NH), 7.50 (1H, d, J=2.5 Hz, ArH) and 8.17 (1H, dd, J=7.9, 1.7 Hz, ArH). ¹³C NMR (270 MHz, CDCl₃) δ 23.81, 29.36, 32.26, 33.17 (CH₂), 39.60 (CH), 40.78 (CH₂), 43.70 (CH), 47.79 (CH₂), 118.00, 120.65, 124.43, 124.88, 126.21, 128.57, 130.85, 130.87, 132.74, 133.06, 148.97, 153.09 (ArC), 163.63 and 174.71 (C=O).

1-{4-[2-(4-Chlorophenoxy)benzylamino]piperidin-1-yl}ethanone (AMR01074, STX1724) C₂₀H₂₃ClN₂O₂, MW 358.86

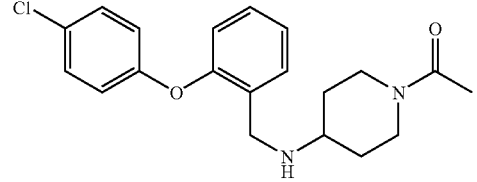

A solution of 2-(4-chlorophenoxy)benzylamine (AMR01073, 100 mg, 0.428 mmol), 1-acetylpiperidone (121 mg, 0.856 mmol) and acetic acid (0.13 mL, 2.14 mmol) in DCE (2 mL) was treated with NaBH(OAc)₃ (227 mg, 1.07 mmol) and stirred under microwave irradiation for 15 min at 100° C. The reaction mixture was diluted with DCM (10 mL) and quenched with saturated NaHCO₃ solution. The aqueous layer was washed with DCM (2×20 mL), and the combined organic layers were dried (MgSO₄), filtered and evaporated to dryness. Column chromatography on silica gel of the crude product using AcOEt to AcOEt/MeOH 9:1 gradient as eluent gave 1-{4-[2-(4-chlorophenoxy)benzylamino]piperidin-1-yl}ethanone (124 mg, 81%) as a colorless oil. Rf: 0.14 (AcOEt/MeOH 9:1) LC/MS (APCI) $t_r$=4.79 min, m/z 361.46 (35), 359.51 (M⁺+H, 100). HPLC $t_r$=3.04 min (97.37%) ¹H NMR (270 MHz, CDCl₃) δ 1.25 (2H, m, CH₂), 1.68 (br s, NH), 1.79 (2H, m, CH₂), 2.05 (3H, S, CH₃), 2.67 (2H, m, CH₂), 3.02 (1H, m, CH), 3.70 (1H, m, ½CH₂), 3.82 (2H, s, CH₂), 4.33 (1H, m, ½CH₂), 6.84 (2H, AA'BB', ArH), 6.86 (1H, m, ArH), 7.11 (1H, m, ArH), 7.21 (1H, m, ArH), 7.24 (2H, AA'BB', ArH) and 7.38 (1H, dd, J=7.2, 1.5 Hz, ArH). ¹³C NMR (270 MHz, CDCl₃) δ 21.10 (CH₃), 31.49, 32.32, 39.64, 44.47, 45.05 (CH₂), 53.21 (CH), 118.49, 119.04, 124.04, 127.51, 128.30, 129.36, 130.14, 131.02, 153.89, 155.80 (ArC), and 168.42 (C=O).

1-{4-[2-(4-Chlorophenoxy)benzylamino]piperidin-1-yl}-3-methylbutan-1-one (AMR01087, STX1755)
$C_{23}H_{29}ClN_2O_2$, MW 400.94

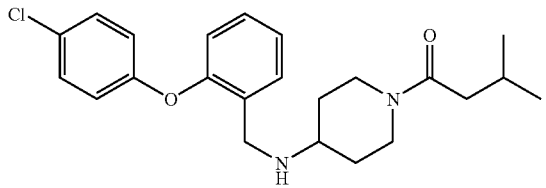

A solution of 2-(4-chlorophenoxy)benzylamine (AMR01076, 100 mg, 0.428 mmol) and 1-(3-methylbutyryl)piperidin-4-one (78.4 mg, 0.428 mmol) in DCE (5 mL) was treated with NaBH(OAc)$_3$ (127 mg, 0.60 mmol) and acetic acid (26 mg, 0.428 mmol). The mixture was stirred at room temperature under a N$_2$ atmosphere until TLC showed that the reactants were consumed (30 min). Then, it was quenched with saturated NaHCO$_3$ solution, the aqueous layer was washed with DCM (2×20 mL), and the combined organic layers were dried (MgSO$_4$), filtered and evaporated to dryness. Column chromatography on silica gel of the crude product using DCM to DCM/MeOH 95:5 gradient as eluent gave 1-{4-[2-(4-chlorophenoxy)benzylamino]piperidin-1-yl}-3-methylbutan-1-one (114 mg, 66%) as a colorless oil. Rf: 0.4 (DCM/MeOH 9:1) LC/MS (APCI) t$_r$=5.36 min, m/z 403.46 (35), 401.44 (M$^+$+H, 100). HPLC t$_r$=3.39 min (96.55%) $^1$H NMR (270 MHz, CDCl$_3$) δ 0.92 (6H, d, J=6.4 Hz, 2CH$_3$), 1.23 (2H, m, CH$_2$), 1.46 (br s, NH), 1.82 (2H, br d, J=12.9 Hz, CH$_2$), 2.05 (1H, hept, J=6.4 Hz, CHMe$_2$), 2.19 (2H, m, CH$_2$), 2.65 (2H, m, CH$_2$), 2.99 (1H, m, CHNH), 3.77 (1H, m, ½CH$_2$), 3.79 (2H, s, CH$_2$NH), 4.40 (1H, br d, J=13.3 Hz, ½CH$_2$), 6.81-6.87 (3H, m, ArH), 7.11 (1H, td, ArH), 7.19-7.25 (3H, m, ArH) and 7.38 (1H, dd, J=7.2, 1.5 Hz, ArH). $^{13}$C NMR (270 MHz, CDCl$_3$) δ 22.80 (CH$_2$), 22.90 (CH$_3$), 25.93 (CH), 32.30, 33.15, 40.23, 42.24, 44.44, 45.65 (CH$_2$), 53.87 (CH), 118.93, 119.62, 124.54, 127.94, 128.71, 129.83, 130.58, 131.79, 154.34, 156.37 (ArC), and 170.91 (C=O).

1-{4-[2-(4-Chlorophenoxy)benzylamino]piperidin-1-yl}-2-methylpropan-1-one (AMR01088, STX1756)
$C_{22}H_{27}ClN_2O_2$, MW 386.91

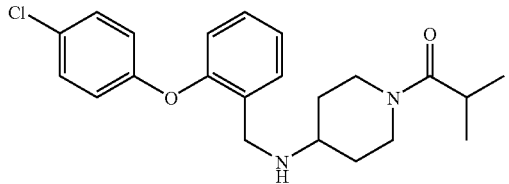

A solution of 2-(4-chlorophenoxy)benzylamine (AMR01076, 100 mg, 0.428 mmol) and 1-isobutyrylpiperidin-4-one (78.4 mg, 0.428 mmol) in DCE (5 mL) was treated with NaBH(OAc)$_3$ (127 mg, 0.60 mmol) and acetic acid (26 mg, 0.428 mmol). The mixture was stirred at room temperature under a N$_2$ atmosphere until TLC showed that the reactants were consumed (30 min). Then, it was quenched with saturated NaHCO$_3$ solution, the aqueous layer was washed with DCM (2×20 mL), and the combined organic layers were dried (MgSO$_4$), filtered and evaporated to dryness. Column chromatography on silica gel of the crude product using DCM to DCM/MeOH 95:5 gradient as eluent gave 1-{4-[2-(4-chlorophenoxy)benzylamino]piperidin-1-yl}-2-methylpropan-1-one (129 mg, 78%) as a colorless oil. Rf: 0.4 (DCM/MeOH 9:1) LC/MS (APCI) t$_r$=5.18 min, m/z 389.48 (36), 387.46 (M$^+$+H, 100). HPLC t$_r$=3.65 min 97.72%) $^1$H NMR (270 MHz, CDCl$_3$) δ 1.079 (3H, d, J=6.7 Hz, CH$_3$), δ 1.082 (3H, d, J=6.7 Hz, CH$_3$), 1.23 (2H, m, CH$_2$), 1.45 (br s, NH), 1.83 (2H, m, CH$_2$), 2.70 (2H, m, H$_2$), 2.77 (1H, hept, J=6.7 Hz, CHMe$_2$), 3.01 (1H, m, CHNH), 3.80 (2H, m, CH$_2$), 3.83 (1H, m, ½CH$_2$), 4.41 (1H, br d, J=13.4 Hz, ½CH$_2$), 6.84 (2H, AA'BB', ArH), 6.87 (1H, m, ArH), 7.12 (1H, td, ArH), 7.24 (1H, m, ArH), 7.25 (2H, AA'BB', ArH) and 7.39 (1H, dd, J=7.4, 1.7 Hz, ArH). $^{13}$C NMR (270 MHz, CDCl$_3$) δ 19.46, 19.65 (CH$_2$), 30.13 (CH), 32.39, 33.30, 40.43, 43.95, 45.67 (CH$_2$), 53.97 (CH), 118.94, 119.61, 124.54, 127.96, 128.72, 129.84, 130.58, 131.80, 154.35, 156.37 (ArC), and 175.30 (C=O).

{4-[2-(4-Chlorophenoxy)benzylamino]piperidin-1-yl}cyclopentylmethanone (AMR01089, STX1757)
$C_{24}H_{29}ClN_2O_2$, MW 412.95

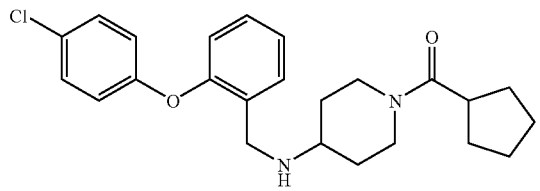

A solution of 2-(4-chlorophenoxy)benzylamine (AMR01076, 100 mg, 0.428 mmol) and 1-cyclopentanecarbonylpiperidin-4-one (83.5 mg, 0.428 mmol) in DCE (5 mL) was treated with NaBH(OAc)$_3$ (127 mg, 0.60 mmol) and acetic acid (26 mg, 0.428 mmol). The mixture was stirred at room temperature under a N$_2$ atmosphere until TLC showed that the reactants were consumed (30 min). Then it was quenched with saturated NaHCO$_3$ solution, the aqueous layer was washed with DCM (2×20 mL), and the combined organic layers were dried (MgSO$_4$), filtered and evaporated to dryness. Column chromatography on silica gel of the crude product using DCM to DCM/MeOH 95:5 gradient as eluent gave {4-[2-(4-chlorophenoxy)benzylamino]piperidin-1-yl}cyclopentylmethanone (144 mg, 81%) as a colorless oil. Rf: 0.4 (DCM/MeOH 9:1) LC/MS (APCI) t$_r$=5.42 min, m/z 415.36 (36), 413.40 (M$^+$+H, 100). HPLC t$_r$=6.82 min (98.32%) $^1$H NMR (270 MHz, CDCl$_3$) δ 1.23 (2H, m, CH$_2$), 1.52 (2H, m, CH$_2$), 1.60-1.90 (9H, m, 4CH$_2$+NH), 2.66 (2H, m, CH$_2$), 2.85 (1H, quin, J=7.9 Hz, CHCO), 3.00 (1H, m, CHNH), 3.79 (2H, m, CH$_2$), 3.85 (1H, m, ½CH$_2$), 4.40 (1H, m, ½CH$_2$), 6.83 (2H, AA'BB', ArH), 6.87 (1H, m, ArH), 7.12 (1H, td, ArH), 7.23 (1H, m, ArH), 7.24 (2H, AA'BB', ArH) and 7.38 (1H, dd, J=7.4, 1.7 Hz, ArH). $^{13}$C NMR (270 MHz, CDCl$_3$) δ 26.12, 30.09, 32.29, 32.24, 40.55 (CH$_2$), 41.19 (CH), 44.04, 45.65 (CH$_2$), 54.00 (CH), 118.93, 119.62, 124.54, 127.95, 128.70, 129.84, 130.58, 131.83, 154.34, 156.38 (ArC), and 174.37 (C=O).

{4-[2-(4-Chlorophenoxy)benzylamino]piperidin-1-yl}phenylmethanone (AMR01091, STX1758) C$_{25}$H$_{25}$ClN$_2$O$_2$, MW 420.93

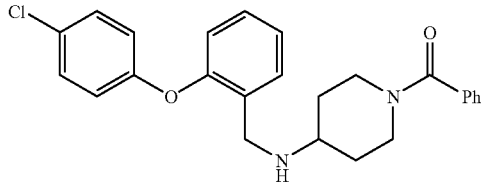

A solution of 2-(4-chlorophenoxy)benzylamine (AMR01076, 100 mg, 0.428 mmol) and N-benzoyl-4-piperidone (87 mg, 0.428 mmol) in DCE (5 mL) was treated with NaBH(OAc)$_3$ (127 mg, 0.60 mmol) and acetic acid (26 mg, 0.428 mmol). The mixture was stirred at room temperature under a N$_2$ atmosphere until TLC showed that the reactants were consumed (30 min). Then, it was quenched with saturated NaHCO$_3$ solution, the aqueous layer was washed with DCM (2×20 mL), and the combined organic layers were dried (MgSO$_4$), filtered and evaporated to dryness. Column chromatography on silica gel of the crude product using DCN to DCM/MeOH 95:5 gradient as eluent gave {4-[2-(4-chlorophenoxy)benzylamino]piperidin-1-yl}phenylmethanone (152 mg, 84%) as a colorless oil. Rf: 0.4 (DCM/MeOH 9:1) LC/MS (APCI) t$_r$=5.19 min, m/z 423.35 (36), 421.34 (M$^+$+H, 100). HPLC t$_r$=4.04 min (98.05%) $^1$H NMR (270 MHz, CDCl$_3$) δ 1.24-1.44 (3H, m, CH$_2$+NH), 1.76 (1H, m, ½CH$_2$), 1.91 (1H, m, ½CH$_2$), 2.72 (1H, hept, CHNH), 2.96 (1H, m, ½CH$_2$), 3.80 (2H, m, CH$_2$NH), 4.46 (1H, m, ½CH$_2$), 6.84 (2H, AA'BB', ArH), 6.86 (1H, m, ArH), 7.12 (1H, td, ArH), 7.23 (1H, m, ArH), 7.24 (2H, AA'BB', ArH) and 7.33-7.41 (6H, m, ArH). $^{13}$C NMR (270 MHz, CDCl$_3$) δ 32.26, 33.09, 40.78, 45.67, 46.29 (CH$_2$), 53.81 (CH), 118.95, 119.63, 124.57, 126.86, 127.97, 128.54, 128.75, 129.58, 129.85, 130.58, 131.78, 136.33, 154.35, 156.38 (ArC), and 170.00 (C=O).

Preparation of 2-(4-chlorophenoxy)phenylamine C$_{12}$H$_{10}$ClNO, MW: 219.67

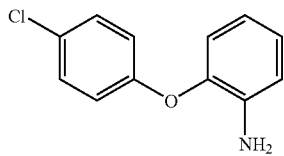

To a solution of 4-chlorophenol (1 g, 7.78 mmol) and potassium carbonate (1.29 g, 9.34 mmol) in DMF, was added 1-fluoronitrobenzene (735 mg, 5.21 mmol). The reaction mixture was heated to reflux and allowed to stir for 18 hours. The reaction mixture was allowed to cool and then diluted with 2.5M NaOH (25 ml). Extraction with ethyl acetate (3×25 ml) then proceeded and the combined organics were washed with 2.5M NaOH (2×15 ml), dried (MgSO$_4$), filtered and concentrated in vacuo. Purification by flash chromatography then followed (eluant: 1:1 DCM: hexane) and the relevant fractions evaporated in vacuo to afford a red/orange oil. This crude oil was then re-dissolved in 10:1 ethanol:water (10 ml) and added to a refluxing mixture of iron powder (1.63 g, 29.15 mmol) and ammonium chloride (198 mg, 3.71 mmol) in 10:1 ethanol:water (20 ml). The reaction mixture was allowed to stir at reflux for 1 hour before being allowed to cool. The mixture was then filtered through a pad of celite, which was then washed with copious quantities of ethyl acetate. The aqueous layer was removed by separation and the organics were dried (MgSO$_4$), filtered and concentrated in vacuo. Purification by flash chromatography then proceeded (eluant: 1:1 DCM:hexane) with the relevant fractions being evaporated in vacuo to afford the title compound as a pale yellow oil (984 mg, 85%). $^1$H NMR (CDCl$_3$, 300 MHz), δ 3.65-4.00 (2H, bs, NH$_2$), 6.70-6.77 (1H, m, ArH), 6.82-6.94 (4H, m, ArH), 6.98-7.05 (1H, m, ArH), 7.23-7.29 ppm (2, m, ArH).

Preparation of 4-[2-(4-chlorophenoxy)phenylamino]-piperidine-1-carboxylic acid tert-butyl ester STX1680 C$_{22}$H$_{27}$ClN$_2$O$_3$, MW: 402.93

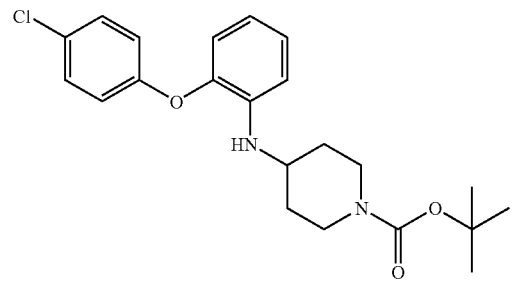

To a solution of 2-(4-chlorophenoxy)phenylamine (900 mg, 4.10 mmol), 1-BOC-4-piperidone (1.76 g, 8.82 mmol) and acetic acid (1.32 g, 22.05 mmol) in DCE (15 ml) was added sodium triacetoxyborohydride (2.34 g, 11.04 mmol). This solution was then split into 4 microwave tubes, which were individually heated at 85° C. for 15 minutes in a CEM discover microwave (fixed hold time set to on). The contents of each tube were added to a saturated aqueous sodium bicarbonate solution (25 ml) with extraction with ethyl acetate (3×25 ml) following. The combined organics were dried (MgSO$_4$), filtered and concentrated in vacuo and purification by flash chromatography proceeded (eluant: 3:1 to 1:1 hexane:DCM) to provide a white solid. Recrystallisation was then carried out, which afforded the title compound as a white crystalline solid (1.122 g, 68%). M.Pt. 112-113.4° C. $^1$H NMR (300 MHz, CDCl$_3$): δ 1.165-1.308 (2H, m, 2×CH), 1.380 (9H, s, t-Bu), 1.909-1.974 (2H, m, 2×CH), 2.822-2.897 (2H, 't', J=11.3 Hz, CH$_2$), 3.385-3.45 (1H, m, CH), 3.85-4.02 (3H, m, 2×CH, NH), 6.542-6.597 (1H, td, ArH), 6.674-6.842 (4H, m, ArH), 6.946-7.002 (1H, td, ArH), 7.157-7.209 ppm (2H, m, ArH). $^{13}$C NMR (67.93 MHz, CDCl3): δ 28.5, 32.3, 43.0, 49.8, 79.7, 112.2, 117.0, 118.7, 119.6, 125.3, 127.8, 129.7, 139.0, 143.0, 154.8, 156.2 ppm. LCMS: M$^+$H, 403.46 HPLC: 99.53% (4.9411 min, isocratic, 90% acetonitrile: 10% water, 1 ml/min). CHN: Expected, N=6.95%, C=65.58%, H=6.75% Observed, N=6.82%, C=65.5%, H=6.71%

Preparation of
4-[2-(4-chlorophenoxy)phenyl]-piperidin-4-ylamine
$C_{17}H_{19}ClN_2O$, MW: 302.82

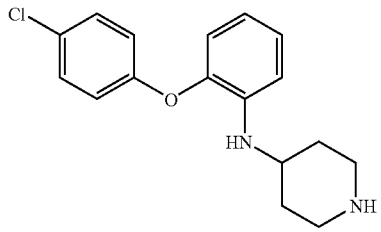

To a solution of 4-[2-(4-chlorophenoxy)phenylamino]-piperidine-1-carboxylic acid tert-butyl ester (300 mg, 0.74 mmol) in DCM (6 ml), was added trifluoroacetic acid (3 ml) at 0° C. The reaction mixture was allowed to stir at this temperature for 45 min before being poured directly onto solid potassium carbonate (9.2 g, 66.6 mmol) with dilution with water (33 ml) following. This aqueous mixture was then extracted with DCM (2×25 ml) and the combined organics dried (MgSO$_4$), filtered and concentrated in vacuo to provide the title compound as a pale yellow oil (224 mg, 99%). $^1$H NMR (400 MHz, CDCl$_3$): δ 1.3660-1.4623 (2H, m, 2×CH), 2.108-2.1509 (2H, m, 2×CH), 2.7744-2.8411 (2H, m, 2×CH), 3.1624-3.2133 (2H, dt, J=3.7, 13.1 Hz, CH$_2$), 3.4756-3.4959 (1H, m, NH), 4.0434-4.0637 (1H, bd, J=8.1 Hz, NH), 6.6649-6.6885 (1H, m, ArH), 6.7943-6.8183 (1H, dd, J=8.2, 1.4 Hz, ArH), 6.8585-6.8820 (1H, dd, J=1.5, 7.9 Hz, ArH), 6.9270-6.9665 (2H, m, ArH), 7.0714-7.1137 (1H, m, ArH), 7.2860-7.3253 ppm (2H, m, ArH).

Preparation of 1-{4-[2-(4-chlorophenoxy)phenylamino]-piperidin-1-yl}-ethanone STX1629
$C_{19}H_{21}ClN_2O_2$, MW: 344.8572

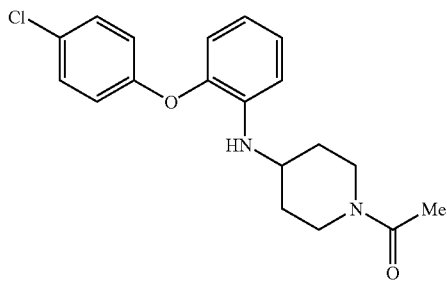

To a solution of 4-[2-(4-chlorophenoxy)phenyl]-piperidin-4-ylamine (95 mg, 0.31 mmol) in anhydrous-DCM (5 ml), was added acetyl chloride (27 mg, 0.35 mmol) followed by triethylamine (79 mg, 0.78 mmol) at 0° C. This mixture was allowed to stir at this temperature for 2 h and then quenched with a saturated aqueous solution of sodium bicarbonate (15 ml). The extraction of this mixture with DCM (2×15 ml) then proceeded and these combined organics were washed with 1M HCl (15 ml), then water (15 ml) and then dried (MgSO$_4$), filtered and concentrated in vacuo. Purification by flash chromatography (eluent: 1:1 hexane:ethyl acetate) then proceeded to afford the title compound as a transparent oil (17 mg, 16%) and an unknown product (62.4 mg). $^1$H NMR (300 MHz, CDCl$_3$): δ 1.164-1.386 (2H, m, 2×CH), 1.956-2.019 (5H, m, 2×CH, CH$_3$), 2.763-2.856 (1H, m, CH), 3.083-3.176 (1H, m, CH), 3.424-3.515 (1H, m, CH), 3.662-3.713 (1H, m, CH), 3.957-4.086 (1H, bs, NH), 4.301-4.367 (1H, m, CH), 6.555-6.611 (1H, td, ArH), 6.665-6.840 (4H, m, ArH), 6.952-7.009 (1H, td, ArH), 7.004-7.211 ppm (2H, m, ArH). $^{13}$C NMR (67.93 MHz, CDCl$_3$): δ 21.6, 32.1, 32.8, 40.4, 45.2, 49.7, 112.2, 117.2, 118.7, 119.6, 125.3, 127.9, 129.4, 129.8, 138.9, 143.1, 156.1, 169.0 ppm. LCMS: M$^+$H, 345.47 HPLC: 98.80% (3.481 min, isocratic, 80% acetonitrile: 20% water, 1 ml/min).

Preparation of 1-{4-[2-(4-chlorophenoxy)phenylamino]-piperidin-1-yl}-phenylmethanone STX1630
$C_{24}H_{23}ClN_2O_2$, MW: 406.928

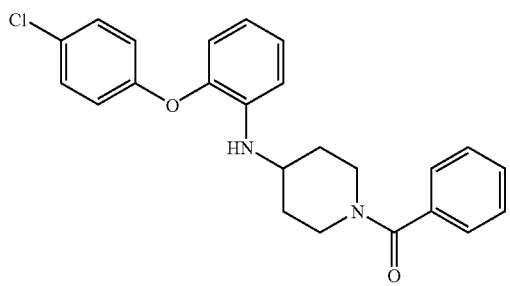

To a solution of 4-[2-(4-chlorophenoxy)phenyl]-piperidin-4-ylamine (221 mg, 0.73 mmol) in anhydrous-DCM (12 ml), was added benzoyl chloride (113 mg, 0.80 mmol) followed by triethylamine (185 mg, 1.83 mmol) at 0° C. This mixture was allowed to stir at this temperature for 90 minutes and then quenched with a saturated aqueous solution of sodium bicarbonate (15 ml). The extraction of this mixture with DCM (2×15 ml) then proceeded and these combined organics were washed with 1M HCl (15 ml), then water (15 ml) and then dried (MgSO$_4$), filtered and concentrated in vacuo. Purification by flash chromatography (eluent: 8:2 hexane:ethyl acetate) then proceeded to afford the title compound as a pale yellow solid (144 mg, 48%). $^1$H NMR (300 MHz, CDCl$_3$): δ 1.24-1.44 (2H, m, 2×CH), 1.97-2.18 (2H, m, 2×CH), 3.01-3.09 (2H, bt, J=14.8 Hz, CH$_2$), 3.47-3.56 (1H, sept, CH), 3.65-3.84 (1H, m, CH), 3.99-4.08 (1H, m, CH), 4.44-4.68 (1H, bs, NH), 6.55-6.61 (1H, td, ArH), 6.67-6.85 (4H, m, ArH), 6.94-7.02 (1H, m, ArH), 7.15-7.21 (2H, m, ArH), 7.32-7.37 ppm (5H, m, ArH). $^{13}$C NMR (67.93 MHz, CDCl$_3$): δ 32.2, 33.1, 41.1, 46.6, 49.8, 112.2, 117.3, 118.8, 119.6, 125.3, 126.9, 127.9, 128.6, 129.8, 130.0, 136.0, 138.8, 143.1, 156.1, 170.5 ppm. LCMS: M$^+$H, 407.49 HPLC: 99.74% (5.168 min, isocratic, 90% acetonitrile: 10% water, 1 ml/min).

Preparation of 1-{4-[2-(4-chlorophenoxy)phenylamino]-piperidin-1-yl}-2,2-dimethylpropan-1-one STX1631 $C_{22}H_{27}ClN_2O_2$, MW: 386.93

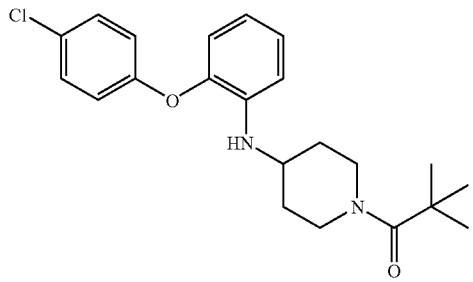

To a solution of 4-[2-(4-chlorophenoxy)phenyl]-piperidin-4-ylamine (112 mg, 0.37 mmol) in anhydrous-DCM (10 ml), was added trimethylacetyl chloride (49 mg, 0.41 mmol) followed by triethylamine (94 mg, 0.93 mmol) at 0° C. This mixture was allowed to stir at this temperature for 90 minutes and then quenched with a saturated aqueous solution of sodium bicarbonate (15 ml). The extraction of this mixture with DCM (2×15 ml) then proceeded and these combined organics were then dried (MgSO$_4$), filtered and concentrated in vacuo. Purification by flash chromatography (eluent: 8:2 hexane:ethyl acetate) then proceeded to afford the title compound as a transparent viscous oil (87.8 mg, 61%). $^1$H NMR (300 MHz, CDCl$_3$): δ 1.15-1.47 (1H, m, 2×CH, —C(CH$_3$)$_3$), 1.97-2.03 (2H, m, 2×CH), 2.93-3.01 (2H, m, 2×CH), 3.48-3.54 (1H, m, CH), 4.0 (1H, bs, NH), 4.18 (2H, 'd', J=13.5 Hz, 2×CH), 6.55-6.61 (1H, td, ArH), 6.68-6.71 (1H, dd, J=1.2, 8.0 Hz, ArH), 6.73-6.76 (1H, dd, J=1.5, 7.8 Hz, ArH), 6.79-6.85 (2H, m, ArH), 6.95-7.01 (1H, m, ArH), 7.16-7.20 ppm (2H, m, ArH). $^{13}$C NMR (67.93 MHz, CDCl$_3$): δ 28.5, 32.7, 38.8, 44.0, 49.9, 112.2, 117.1, 118.8, 119.6, 125.3, 127.9, 129.8, 138.9, 143.1, 156.1, 176.3 ppm. LCMS: M$^+$H, 387.53 HPLC: 94.02% (4.245 min, isocratic 90% acetonitrile, 10% water at 1 ml/min).

Preparation of 1-{4-[2-(4-chlorophenoxy)phenylamino]-piperidin-1-yl}-3-methylbutan-1-one STX1646 C$_{22}$H$_{27}$ClN$_2$O$_2$, MW: 386.93

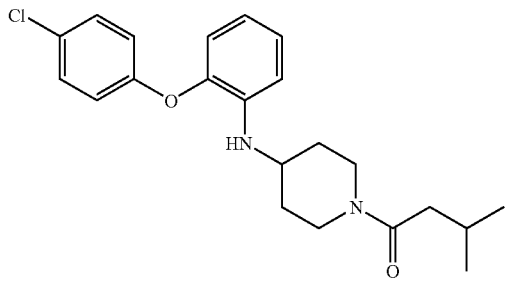

To a solution of 2-(4-chlorophenoxy)-phenylamine (WBH01038, 100 mg, 0.45 mmol) and triethylamine (66 mg, 0.65 mmol) in anhydrous-DCM (10 ml), was added isovaleryl chloride (35 mg, 0.29 mmol) at 0° C. The reaction was allowed to stir from this temperature to room temperature for 6 h before quenching with sat. aq. sodium bicarbonate solution (10 ml). This mixture was then extracted with further portions of DCM (2×10 ml) and the combined organics were dried (MgSO$_4$), filtered and concentrated in vacuo. Purification by flash chromatography then proceeded (eluent: 8:2 hexane:ethyl acetate) then proceeded and the relevant fractions were evaporated in vacuo to afford the desired product (23.2 mg, 23%). LCMS: M$^+$H, 387.53 $^1$H NMR (CDCl$_3$, 300 MHz): δ 0.89 (6H, d, J=6.6 Hz, HC(CH$_3$)$_2$), 1.16-1.33 (3H, m, 3×CH), 1.97-2.13 (2H, m, 2×CH), 2.14 (2H, d, J=7.2 Hz, CH$_2$), 2.76-2.85 (1H, m, CH), 3.06-3.15 (1H, m, CH), 3.42-3.51 (1H, m, CH), 3.73 (1H, 'd', J=12.6 Hz, CH), 4.0 (1H, bs, NH), 4.35 (1H, 'd', J=12 Hz, CH), 6.55-6.61 (1H, m, ArH), 6.68-6.71 (1H, dd, J=1.2, 8.1 Hz, ArH), 6.73-6.76 (1H, dd, J=1.5, 7.8 Hz, ArH), 6.79-6.84 (2H, m, ArH), 6.95-7.01 (1H, m, ArH), 7.16-7.21 ppm (2H, m, ArH). $^{13}$CNMR (CDCl$_3$, 67.93 MHz): δ 22.8, 22.9, 25.9, 32.3, 33.0, 40.5, 42.2, 44.6, 49.8, 112.2, 117.2, 118.8, 119.6, 125.3, 127.9, 129.8, 138.9, 143.1, 156.1, 171.0 ppm. HPLC: 96.34% (retention time 3.508 min, 90% acetonitrile 10% water, 1 ml/min)

Preparation of 1-{4-[2-(4-chlorophenoxy)phenylamino]-piperidin-1-yl}-2-phenylethanone STX1647 C$_{25}$H$_{25}$ClN$_2$O$_2$, MW: 420.94

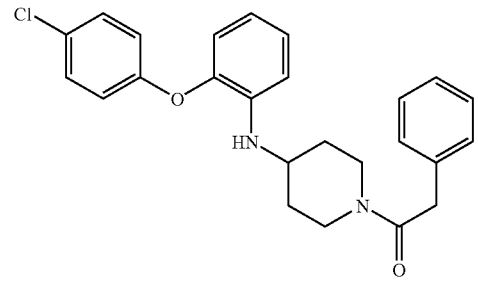

To a solution of 2-(4-chlorophenoxy)-phenylamine (WBH01038, 100 mg, 0.45 mmol) and triethylamine (66 mg, 0.65 mmol) in anhydrous-DCM (10 ml), was added phenylacetyl chloride (45 mg, 0.29 mmol) at 0° C. The reaction was allowed to stir from this temperature to room temperature for 6 h before quenching with sat. aq. sodium bicarbonate solution (10 ml). This mixture was then extracted with further portions of DCM (2×10 ml) and the combined organics were dried (MgSO$_4$), filtered and concentrated in vacuo. Purification by flash chromatography then proceeded (eluent: 8:2 hexane:ethyl acetate) then proceeded and the relevant fractions were evaporated in vacuo to afford the desired product (5.2 mg, 5%). LCMS: M$^+$H, 421.46 $^1$H NMR: see later experiment. HPLC: 96.34% (retention time 3.574 min, 90% acetonitrile 10% water, 1 ml/min).

Preparation of 1-{4-[2-(2,4-dichlorophenoxy)phenylamino]-piperidin-1-yl}-3-methylbutan-1-one STX1684 C$_{22}$H$_{26}$Cl$_2$N$_2$O$_2$, MW: 421.37

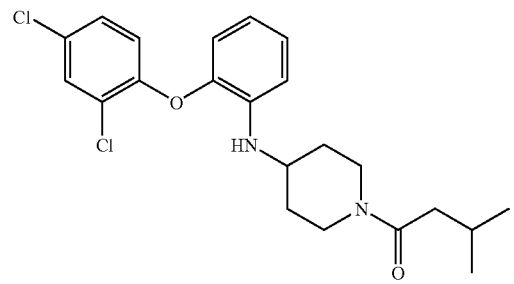

To a solution of 2-(4-chlorophenoxy)-phenylamine (WBH01043, 80 mg, 0.24 mmol) and triethylamine (60 mg, 0.59 mmol) in anhydrous-DCM (5 ml), was added isovaleryl chloride (31 mg, 0.24 mmol) at 0° C. The reaction was allowed to stir from this temperature to room temperature for 4 h before quenching with sat. aq. sodium bicarbonate solution (10 ml). This mixture was then extracted with further portions of DCM (2×10 ml) and the combined organics were dried (MgSO$_4$), filtered and concentrated in vacuo. Purification by flash chromatography then proceeded (eluent: 8:2 hexane:ethyl acetate) then proceeded and the relevant fractions were evaporated in vacuo to afford the desired product (46.4 mg, 46%). LCMS: M+H, 421.40 ¹H NMR (CDCl₃, 300 MHz): δ 0.90 (6H, d, J=6.6 Hz, HC(CH₃)₂), 1.22-1.37 (2H, m, 2×CH), 1.94-2.10 (3H, m, 3×CH), 2.15 (2H, 'd', J=6.6 Hz, CH₂), 2.78-2.92 (1H, m, CH), 3.05-3.19 (1H, m, CH), 3.42-3.53 (1H, sept, J=3.9 Hz, CH), 3.75 (1H, bd, J=13.5 Hz, CH), 4.35 (1H, bd, J=12.6 Hz, CH), 6.53-6.61 (1H, td, J=1.5, 1.2, 7.2 Hz, ArH), 6.66-6.72 (2H, m, ArH), 6.75 (1H, d, J=9.0 Hz, ArH), 6.95-7.02 (1H, td, J=1.5, 0.9, 7.8 Hz, ArH), 7.05-7.09 (1H, dd, J=2.4, 8.9 Hz, ArH), 7.38 ppm (1H, d, J=2.4 Hz, ArH). ¹³C NMR (67.93 MHz, CDCl₃): δ 22.8, 22.9, 25.9, 32.2, 33.0, 40.4, 42.2, 44.6, 49.8, 112.4, 117.1, 118.7, 119.7, 125.4, 128.1, 128.7, 129.5, 130.4, 138.4, 143.0, 151.6, 171.1 ppm HPLC: 96.77% (retention time 4.186 min, 90% acetonitrile: 10% water, 1 ml/min).

Preparation of {4-[2-(2,4-dichlorophenoxy)-phenylamino]-piperidin-1-yl}-cyclopentylmethanone STX1682 C₂₃H₂₆Cl₂N₂O₂, MW: 433.39

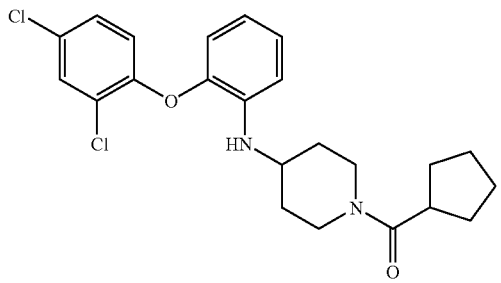

To a solution of 2-(4-chlorophenoxy)-phenylamine (WBH01043, 80 mg, 0.24 mmol) and triethylamine (60 mg, 0.59 mmol) in anhydrous-DCM (5 ml), was added cyclopentanecarbonyl chloride (35 mg, 0.26 mmol) at 0° C. The reaction was allowed to stir from this temperature to room temperature for 4 h before quenching with sat. aq. sodium bicarbonate solution (10 ml). This mixture was then extracted with further portions of DCM (2×10 ml) and the combined organics were dried (MgSO₄), filtered and concentrated in vacuo. Purification by flash chromatography then proceeded (eluent: 8:2 hexane:ethyl acetate) then proceeded and the relevant fractions were evaporated in vacuo to afford the desired product (19.6 mg, 19%). LCMS: M+H, 433.43 ¹H NMR (CDCl₃, 300 MHz): d 1.23-1.38 (2H, m, 2×CH), 1.42-1.58 (2H, m, 2×CH), 1.59-1.81 (6H, m, 6×CH), 1.93-2.08 (2H, m, 2×CH), 2.75-2.90 (2H, m, 2×CH), 3.06-3.20 (1H, m, CH), 3.43-3.54 (1H, sept, J=3.9 Hz, CH), 3.83 (1H, bd, J=14.1 Hz, CH), 3.98-4.40 (1H, m, NH), 4.35 (1H, bd, J=13.8 Hz, CH), 6.54-6.61 (1H, td, J=1.5, 1.2, 7.2 Hz, ArH), 6.66-6.72 (2H, m, ArH), 6.75 (1H, d, J=9.0 Hz, ArH), 6.95-7.02 (1H, td, J=1.5, 0.9, 7.8 Hz, ArH), 7.05-7.09 (1H, dd, J=2.4, 8.9 Hz, ArH), 7.38 ppm (1H, d, J=2.4 Hz, ArH). ¹³C NMR (67.93 MHz, CDCl₃): δ 26.1, 30.2, 30.3, 32.2, 33.0, 40.7, 41.2, 44.2, 49.9, 112.4, 117.1, 118.7, 119.7, 120.0, 125.4, 128.1, 130.2, 130.4, 138.4, 143.0, 151.6, 174.5 ppm. HPLC: 94.39% (retention time 4.646 min, 90% acetonitrile: 10% water, 1 ml/min).

Preparation of 1-{4-[2-(4-chlorophenoxy)phenylamino]-piperidin-1-yl}-ethanone STX1629 C₁₉H₂₁ClN₂O₂, MW: 344.8572

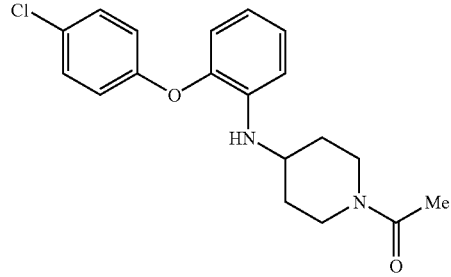

To a solution of 2-(4-chlorophenoxy)phenylamine (200 mg, 0.91 mmol), 1-acetyl-4-piperidone (277 mg, 1.96 mmol) and acetic acid (294 mg, 4.9 mmol) in DCE (3 ml) was added sodium triacetoxyborohydride (519 mg, 2.45 mmol). This solution was then heated at 100° C. for 15 minutes in a CEM discover microwave (fixed hold time set to on). The reaction mixture was then quenched with saturated aqueous sodium bicarbonate solution (10 ml) and extraction with ethyl acetate (3×10 ml) followed. The combined organics were concentrated in vacuo and purification by flash chromatography proceeded (eluant: 8:2 hexane:ethyl acetate) to provide the title compound as a transparent oil (263.5 mg, 84%). Analytical data as previously reported. HPLC: 98.13% (2.747 min; isocratic, 90% acetonitrile: 10% water at 1 ml/min).

Preparation of 1-Cyclohexanecarbonyl-4-piperidone C₁₂H₁₉NO₂, MW: 209.2879

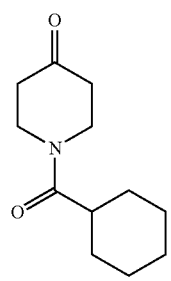

To a solution of 4-piperidonehydrochloride monohydrate (750 mg, 4.88 mmol) in DCM (25 ml), was added potassium carbonate (2.02 g, 14.65 mmol). After 5 minutes stirring, the addition of cyclohexanecarbonyl chloride (1.43 g, 9.76 mmol) proceeded at room temperature and stirring continued for a further 16 hours. The reaction was then quenched with 1M NaOH (15 ml) and then extracted with DCM (3×20 ml). The combined organics were dried (MgSO₄), filtered and concentrated in vacuo. The obtained yellow oil then underwent purification by flash chromatography (eluant; 1:1 hexane ethyl acetate) and the relevant fractions were concentrated in vacuo to provide the title compound as a transparent oil (935 mg, 92%). ¹H NMR (300 MHz, CDCl₃): δ 1.12-1.30 (3H, m, 3×CH), 1.44-1.59 (2H, m, 2×CH), 1.64-1.79 (5H, m, 5×CH), 2.39-2.53 (5H, m, 5×CH), 3.76 ppm (4H, 'bd', J=23.4 Hz, 4×CH). LCMS: M⁺H, 210.36 HPLC: 100% (2.168 min, isocratic, 90% acetonitrile, 10% water, 1 ml/min).

Preparation of 1-Cyclopentanecarbonyl-4-piperidone C₁₁H₁₇NO₂, MW: 195.2611

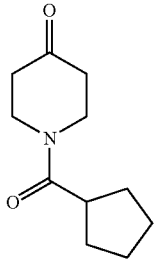

To a solution of 4-piperidonehydrochloride monohydrate (750 mg, 4.88 mmol) in DCM (25 ml), was added potassium carbonate (2.02 g, 14.65 mmol). After 5 minutes stirring, the addition of cyclopentanecarbonyl chloride (1.29 g, 9.76 mmol) proceeded at room temperature and stirring continued for a further 16 hours. The reaction was then quenched with 1M NaOH (15 ml) and then extracted with DCM (3×20 ml). The combined organics were dried (MgSO₄), filtered and concentrated in vacuo. The obtained yellow oil then underwent purification by flash chromatography (eluant; 1:1 hexane:ethyl acetate) and the relevant fractions were concentrated in vacuo to provide the title compound as a transparent oil (769 mg, 81%). ¹H NMR (300 MHz, CDCl₃): δ 1.47-1.60 (2H, m, 2×CH), 1.61-1.73 (2H, m, 2×CH), 1.74-1.85 (4H, m, 4×CH), 2.40 (4H, t, J=6.3 Hz, 4×CH), 2.85-2.96 (1H, pent, J=7.8, 8.1, 15.9 Hz, CH), 3.73-3.84 ppm (4H, m, 4×CH). LCMS: M⁺H, 196.31 HPLC: 100% (2.624 min, isocratic 90% acetonitrile, 10% water at 1 ml/min).

Preparation of 1-Phenylacetyl-4-piperidone C₁₃H₁₅NO₂, MW: 217.2673

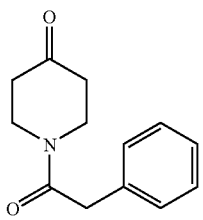

To a solution of 4-piperidonehydrochloride monohydrate (750 mg, 4.88 mmol) in DCM (25 ml), was added potassium carbonate (2.02 g, 14.65 mmol). After 5 minutes stirring, the addition of phenylacetyl chloride (1.51 g, 9.76 mmol) proceeded at room temperature and stirring continued for a further 16 hours. The reaction was then quenched with 1M NaOH (15 ml) and then extracted with DCM (3×20 ml). The combined organics were dried (MgSO₄), filtered and concentrated in vacuo. The obtained yellow oil then underwent purification by flash chromatography (eluant; 1:1 hexane:ethyl acetate) and the relevant fractions were concentrated in vacuo to provide the title compound as a transparent oil (827 mg, 78%). ¹H NMR (300 MHz, CDCl₃): δ 2.15 (2H, t, J=6.0 Hz, 2×CH), 2.43 (2H, t, J=6.0 Hz, 2×CH), 3.73 (2H, t, J=6.0 Hz, 2×CH), 3.84 (2H, s CH₂), 3.91 (2H, t, J=6 Hz, 2×CH), 7.25-7.38 ppm (5H, m, ArH). LCMS: M⁺H, 218.30 HPLC: 100% (2.002 min, isocratic 90% acetonitrile, 10% water at 1 ml/min).

Preparation of 1-(3-Methylbutyryl)-4-piperidone C₁₀H₁₇NO₂, MW: 183.2501

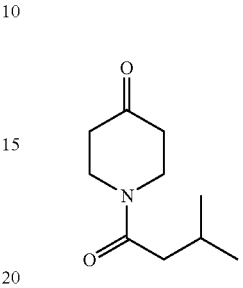

To a solution of 4-piperidonehydrochloride monohydrate (750 mg, 4.88 mmol) in DCM (25 ml), was added potassium carbonate (2.02 g, 14.65 mmol). After 5 minutes stirring, the addition of isovaleryl chloride (1.18 g, 9.76 mmol) proceeded at room temperature and stirring continued for a further 16 hours. The reaction was then quenched with 1M NaOH (15 ml) and then extracted with DCM (3×20 ml). The combined organics were dried (MgSO₄), filtered and concentrated in vacuo. The obtained yellow oil then underwent purification by flash chromatography (eluant; 1:1 hexane:ethyl acetate) and the relevant fractions were concentrated in vacuo to provide the title compound as a transparent oil (625 mg, 70%). ¹H NMR (300 MHz, CDCl₃): δ 1.0 (6H, d, J=6.6 Hz, 2×CH₃), 2.13-2.24 (1H, sept, J=6.6 Hz, CH), 2.30 (2H, 'd', J=6.6 Hz, CH₂), 2.48 (4H, t, J=6.6 Hz, 4×CH), 3.77 (2H, bt, J=6 Hz, 2×CH), 3.90 ppm (2H, bt, J=6.0 Hz, 2×CH). LCMS: M⁺H, 184.27 HPLC: 100% (2.011 min, isocratic 90% acetonitrile, 10% water at 1 ml/min).

Preparation of 1-Isobutyryl-4-piperidone C₉H₁₅NO₂, MW: 169.2233

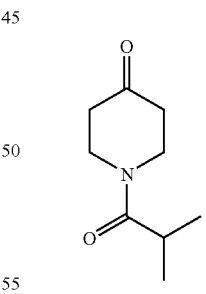

To a solution of 4-piperidonehydrochloride monohydrate (750 mg, 4.88 mmol) in DCM (25 ml), was added potassium carbonate (2.02 g, 14.65 mmol). After 5 minutes stirring, the addition of isobutyryl chloride (1.04 g, 9.76 mmol) proceeded at room temperature and stirring continued for a further 16 hours. The reaction was then quenched with 1M NaOH (15 ml) and then extracted with DCM (3×20 ml). The combined organics were dried (MgSO₄), filtered and concentrated in vacuo. The obtained yellow oil then underwent purification by flash chromatography (eluant; 1:1 hexane:ethyl acetate) and the relevant fractions were concentrated in vacuo to provide the title compound as a transparent oil (677 mg, 82%). ¹H NMR (300 MHz, CDCl₃): δ 1.12 (6H, d, J=5.1 Hz, 2×CH₃), 2.42 (4H, t, J=4.5 Hz, 4×CH), 2.77-2.85 (1H, sept, J=5.1 Hz, CH), 3.75-3.83 ppm (4H, bd, J=23.7 Hz, 4×CH). LCMS: M⁺H, 170.22 HPLC: 100% (1.960 min, isocratic 90% acetonitrile, 10% water at 1 ml/min).

Preparation of 1-{4-[N-(2-(4-chlorophenocy)phenyl)-N-methylamino]-piperidin-1-yl}-ethanone STX1861 C₂₀H₂₃ClN₂O₂, MW: 358.87

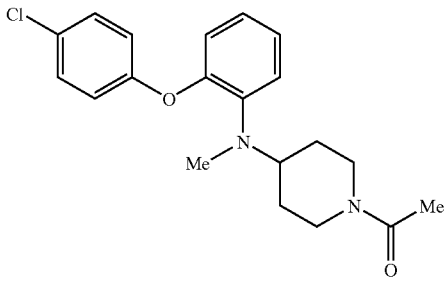

To a solution of 1-{4-[2-(4-chlorophenoxy)phenylamino]-piperidin-1-yl}-ethanone (WBH01048, 100 mg, 0.29 mmol) and formaldehyde (10 mg, 37% wt. soln. in water, 0.32 mmol) in water (1 ml), was added formic acid (15 mg, 0.32 mmol) and the reaction mixture heated in a CEM discover microwave at 150° C. for 5 min. The reaction was quenched with 1M NaOH (5 ml) and then extracted with ethyl acetate (2×5 ml). The combined organics were concentrated in vacuo with flash chromatography (eluent: hexane to 30:70 hexane:ethyl acetate) following. The relevant fractions were evaporated in vacuo to provide the desired product (61.9 mg, 59%).

¹H NMR (300 MHz, CDCl₃): δ 1.42-1.57 (4H, m, 4×CH), 2.03 (3H, s, COCH₃), 2.32-2.48 (1H, m, CH), 2.61 (3H, s, NCH₃), 2.85-2.91 (1H, m, CH), 3.41-3.47 (1H, m, CH), 3.73-3.79 (1H, m, CH), 4.57-4.62 (1H, m, CH), 6.76-6.81 (2H, m, ArH), 6.93-6.96 (2H, m, ArH), 7.02-7.13 (2H, m, ArH), 7.17-7.24 ppm (2H, m, ArH). LCMS: M⁺H, 359.45 HPLC: 90.91% (2.924 min, isocratic 90% acetonitrile, 10% water at 1 ml/min).

Preparation of {4-[2-(4-chlorophenoxy)phenylamino]-piperidin-1-yl}-cyclopentylmethanone STX1685 C₂₃H₂₇ClN₂O₂, MW: 398.94

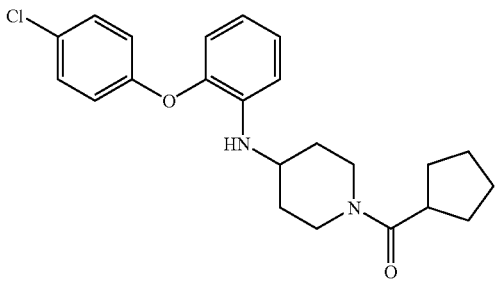

To a solution of 2-(4-chlorophenoxy)phenylamine (100 mg, 0.45 mmol), 1-cyclopentylcarbonyl-4-piperidone (144 mg, 0.735 mmol) and acetic acid (147 mg, 2.45 mmol) in DCE (1.5 ml) was added sodium triacetoxyborohydride (260 mg, 1.23 mmol). This solution was then heated at 100° C. for 15 minutes in a CEM discover microwave (fixed hold time set to on). The reaction mixture was then quenched with saturated aqueous sodium bicarbonate solution (5 ml) and extraction with ethyl acetate (3×5 ml) followed. The combined organics were concentrated in vacuo and purification by flash chromatography proceeded (eluant: 8:2 hexane:ethyl acetate) to provide the title compound as a transparent oil (82 mg, 43%). ¹H NMR (300 MHz, CDCl₃): δ 1.16-1.36 (2H, m, 2×CH), 1.47-1.56 (2H, m, 2×CH), 1.59-1.78 (6H, m, 6×CH), 1.93-2.08 (2H, m, 2×CH), 2.76-2.87 (2H, m, 2×CH), 3.07-3.18 (1H, m, CH), 3.43-3.52 (1H, sept, J=3.9 Hz, CH), 3.78-3.89 (1H, bd, J=13.8 Hz, CH), 3.97-4.10 (1H, m, CH), 4.31-4.42 (1H, bd, J=13.5 Hz, NH), 6.55-6.62 (1H, td, J=1.5, 1.2, 1.2, 7.7 Hz, ArH), 6.68-6.71 (1H, dd, J=1.5, 8.1 Hz, ArH), 6.73-6.77 (1H, dd, J=1.5, 8.1 Hz, ArH), 6.79-6.84 (2H, m, ArH), 6.95-7.01 (1H, td, J=1.5, 0.6, 1.5, 7.7 Hz, ArH), 7.16-7.22 ppm (2H, m, ArH). ¹³C NMR (67.93 MHz, CDCl₃): δ 19.5, 19.6, 30.2, 32.2, 33.2, 40.6, 44.1, 49.9, 112.2, 117.2, 118.8, 119.6, 125.3, 127.9, 129.8, 138.9, 143.1, 156.1, 175.4 ppm LCMS: M⁺H, 421.46 HPLC: 98.41% (3.124 min, isocratic 90% acetonitrile, 10% water at 1 ml/min).

Preparation of 1-{4-[2-(4-chlorophenoxy)phenylamino]-piperidin-1-yl}-2-phenylethanone STX1647 C₂₅H₂₅ClN₂O₂, MW: 420.9379

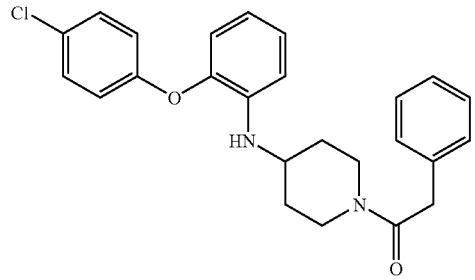

To a solution of 2-(4-chlorophenoxy)phenylamine (100 mg, 0.45 mmol), 1-phenylacetyl-4-piperidone (144 mg, 0.735 mmol) and acetic acid (147 mg, 2.45 mmol) in DCE (1.5 ml) was added sodium triacetoxyborohydride (260 mg, 1.23 mmol). This solution was then heated at 100° C. for 15 minutes in a CEM discover microwave (fixed hold time set to on). The reaction mixture was then quenched with saturated aqueous sodium bicarbonate solution (5 ml) and extraction with ethyl acetate (3×5 ml) followed. The combined organics were concentrated in vacuo and purification by flash chromatography proceeded (eluant: 8:2 hexane:ethyl acetate) to provide the title compound as a transparent oil (69 mg, 36%). ¹H NMR (270 MHz, CDCl₃): δ 1.03-1.09 (1H, m, CH), 1.22-1.31 (1H, m, CH), 1.87-1.91 (1H, m, CH), 1.99-2.04 (1H, m, CH), 2.80-2.91 (1H, m, CH), 3.11-3.18 (1H, m, CH), 3.43-3.52 (1H, m, CH), 3.68-3.76 (3H, m, CH₂+CH), 3.95 (1H, s, NH), 4.39-4.45 (1H, m, CH), 6.55-6.62 (1H, td, J=1.2, 1.5, 7.4 Hz, ArH), 6.68-6.71 (1H, dd, J=1.5, 8.2 Hz, ArH), 6.73-6.77 (1H, dd, J=1.5, 8.1 Hz, ArH), 6.79-6.84 (2H, m, ArH), 6.95-7.01 (1H, td, J=1.5, 0.7, 7.8 Hz, ArH), 7.16-7.32 ppm (7H, m, ArH). ¹³C NMR (67.93 MHz, CDCl₃): δ 32.0, 32.5, 40.7, 41.3, 44.9, 49.6, 112.2, 117.2, 118.8, 119.6, 125.3, 126.9, 127.9, 128.6, 128.9, 129.8, 135.1, 138.8, 143.0, 156.1, 169.4 ppm. LCMS: M+H, 399.49 HPLC: 99.17% (2.675 min, isocratic 90% acetonitrile, 10% water at 1 ml/min).

Preparation of 1-{4-[2-(4-chlorophenoxy)phenylamino]-piperidin-1-yl}-2-methylpropan-1-one STX1701 $C_{21}H_{25}ClN_2O_2$, MW: 372.8939

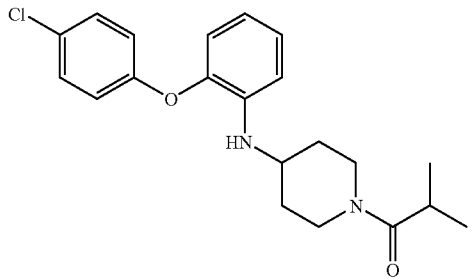

To a solution of 2-(4-chlorophenoxy)phenylamine (100 mg, 0.45 mmol), 1-isobutyryl-4-piperidone (144 mg, 0.735 mmol) and acetic acid (147 mg, 2.45 mmol) in DCE (1.5 ml) was added sodium triacetoxyborohydride (260 mg, 1.23 mmol). This solution was then heated at 100° C. for 15 minutes in a CEM discover microwave (fixed hold time set to on). The reaction mixture was then quenched with saturated aqueous sodium bicarbonate solution (5 ml) and extraction with ethyl acetate (3×5 ml) followed. The combined organics were concentrated in vacuo and purification by flash chromatography proceeded (eluant: 8:2 hexane:ethyl acetate) to provide the title compound as a transparent oil (44 mg, 26%). $^1$H NMR (270 MHz, CDCl$_3$): δ 1.10 (6H, d, J=6.7 Hz, CH(CH$_3$)$_2$), 1.25-1.35 (2H, m, 2×CH), 2.03-2.27 (2H, m, 2×CH), 2.76-2.85 (2H, m, 2×CH), 3.18 (1H, t, J=11.4 Hz, CH), 3.48-3.60 (1H, m, CH), 3.83-3.88 (1H, bd, J=13.9 Hz, CH), 3.97-4.12 (1H, m, NH), 4.41-4.46 (1H, bd, J=13.9 Hz, CH), 6.61-6.67 (1H, td, J=1.2, 0.7, 7.7 Hz, ArH), 6.74-6.77 (1H, dd, J=1.2, 8.2 Hz, ArH), 6.79-6.82 (1H, dd, J=1.5, 7.9 Hz, ArH), 6.85-6.90 (2H, m, ArH), 7.01-7.07 (1H, td, J=1.2, 0.8, 7.2 Hz, ArH), 7.20-7.25 ppm (2H, m, ArH). LCMS: M+H, 373.49 HPLC: 93.75% (2.692 min, isocratic 90% acetonitrile, 10% water at 1 ml/min).

Preparation of Cyclohexyl-{4-[2-(2,4-dichlorophenoxy)phenylamino]-piperidin-1-yl}-methanone STX1681 $C_{24}H_{28}Cl_2N_2O_2$, MW: 447.4085

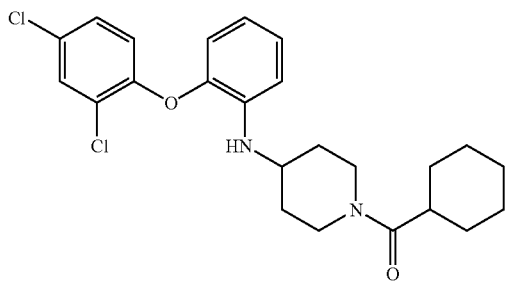

To a solution of 2-(2,4-dichlorophenoxy)phenylamine (100 mg, 0.39 mmol), 1-cyclohexanecarbonyl-4-piperidone (131 mg, 0.627 mmol) and acetic acid (126 mg, 2.09 mmol) in DCE (1.5 ml) was added sodium triacetoxyborohydride (222 mg, 1.05 mmol). This solution was then heated at 100° C. for 25 minutes in a CEM discover microwave (fixed hold time set to on). The reaction mixture was then quenched with saturated aqueous sodium bicarbonate solution (5 ml) and extraction with ethyl acetate (3×5 ml) followed. The combined organics were concentrated in vacuo and purification by flash chromatography proceeded (eluant: 8:2 hexane:ethyl acetate) to provide the title compound as a transparent oil (39 mg, 22%). $^1$H NMR (270 MHz, CDCl$_3$): δ 1.10-1.90 (12H, m, 12×CH), 1.95-2.15 (2H, m, 2×CH), 2.38-2.42 (1H, m, CH), 2.79-2.93 (1H, m, CH), 3.08-3.22 (1H, m, CH), 3.45-3.61 (1H, m, CH), 3.85 (1H, bd, J=14.1 Hz, CH), 4.06-4.12 (1H, m, CH), 4.41 (1H, bd, J=14.3 Hz, NH), 6.59-6.66 (1H, td, J=1.5, 1.2, 8.0 Hz, ArH), 6.72-6.82 (3H, m, ArH), 7.01-7.07 (1H, m, ArH), 7.10-7.15 (1H, dd, J=2.5, 8.7 Hz, ArH), 7.43 ppm (1H, d, J=2.5 Hz, ArH). $^{13}$C NMR (67.93 MHz, CDCl$_3$): δ 26.0, 29.4, 29.6, 32.2, 33.2, 40.5, 40.6, 44.1, 49.9, 112.4, 117.1, 118.7, 119.6, 125.4, 128.1, 128.7, 130.4, 130.5, 138.4, 143.0, 151.6, 174.6 ppm. LCMS: M+H, 447.4 HPLC: 96.47% (3.555 min, isocratic 90% acetonitrile, 10% water at 1 ml/min).

Preparation of 1-{4-[2-(2,4-Dichlorophenoxy)phenylamino]-piperidin-1-yl}-2-methylpropan-1-one STX1683 $C_{21}H_{24}Cl_2N_2O_2$, MW: 407.3439

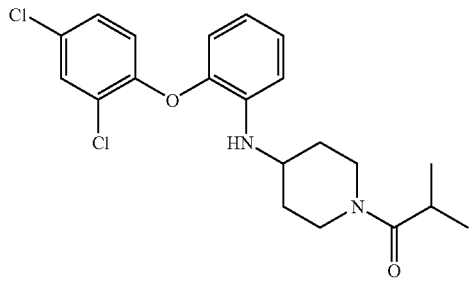

To a solution of 2-(4-chlorophenoxy)phenylamine (100 mg, 0.394 mmol), 1-isobutyryl-4-piperidone (106 mg, 0.627 mmol) and acetic acid (126 mg, 2.09 mmol) in DCE (1.5 ml) was added sodium triacetoxyborohydride (222 mg, 1.05 mmol). This solution was then heated at 100° C. for 25 minutes in a CEM discover microwave (fixed hold time set to on). The reaction mixture was then quenched with saturated aqueous sodium bicarbonate solution (5 ml) and extraction with ethyl acetate (3×5 ml) followed. The combined organics were concentrated in vacuo and purification by flash chromatography proceeded (eluant: 8:2 hexane:ethyl acetate) to provide the title compound as a transparent oil (64 mg, 40%). $^1$H NMR (270 MHz, CDCl$_3$): δ 1.10 (6H, d, J=6.7 Hz, CH(CH$_3$)$_2$), 1.22-1.43 (2H, m, 2×CH), 2.03-2.12 (2H, m, 2×CH), 2.74-2.92 (2H, m, 2×CH), 3.15-3.23 (1H, m, CH), 3.45-3.56 (1H, m, CH), 3.85 (1H, bd, J=13.8 Hz, CH), 4.09-4.14 (1H, m, CH), 4.42 (1H, bd, J=13.8 Hz, NH), 6.60-6.66 (1H, td, J=1.5, 1.5, 7.9 Hz, ArH), 6.72-6.83 (3H, m, ArH), 7.01-7.77 (1H, m, ArH), 7.10-7.15 (1H, dd, J=2.5, 8.9 Hz, ArH), 7.43 ppm (1H, d, J=2.5 Hz, ArH). $^{13}$C NMR (67.93 MHz, CDCl3): δ 19.5, 19.6, 30.2, 32.2, 33.1, 40.6, 44.1. 49.9, 112.4, 117.1, 118.7, 119.9, 125.4, 125.5, 128.1, 128.7, 130.4, 138.4, 143.0, 151.6, 175.4 ppm LCMS: M+H, 407.42 HPLC: 98.74% (2.918 min, isocratic 90% acetonitrile, 10% water at 1 ml/min).

Preparation of {4-[2-(4-chlorophenoxy)phenylamino]-piperidin-1-yl}-cyclohexylmethanone STX1702 C$_{24}$H$_{29}$ClN$_2$O$_2$, MW: 396.9785

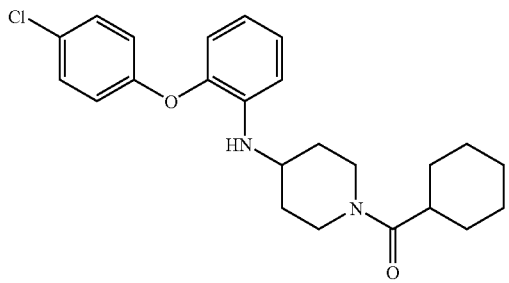

To a solution of 2-(4-chlorophenoxy)phenylamine (100 mg, 0.49 mmol), 1-cyclohexanecarbonyl-4-piperidone (154 mg, 0.735 mmol) and acetic acid (147 mg, 2.45 mmol) in DCE (1.5 ml) was added sodium triacetoxyborohydride (260 mg, 1.23 mmol). This solution was then heated at 100° C. for 15 minutes in a CEM discover microwave (fixed hold time set to on). Further 1-cyclohexanecarbonyl-4-piperidone (50 mg, 0.24 mmol) was added and this reaction mixture was again heated at 100° C. for 10 minutes in the CEM discover microwave (fixed hold time set to on). The reaction mixture was then quenched with saturated aqueous sodium bicarbonate solution (5 ml) and extraction with ethyl acetate (3×5 ml) followed. The combined organics were dried (MgSO$_4$), filtered and concentrated in vacuo and purification by flash chromatography proceeded (eluant: 8:2 hexane:ethyl acetate) to provide the title compound as a transparent oil (58 mg, 30%). $^1$H NMR (270 MHz, CDCl$_3$): δ 1.12-1.89 (12H, m, 12×CH), 2.03-2.16 (2H, m, 2×CH), 2.40-2.46 (1H, m, CH), 2.83 (2H, 't', J=11.1 Hz, CH$_2$), 3.15 (1H, 't', J=12.4 Hz, CH), 3.49-3.54 (1H, m, CH), 3.83 (1H, bd, J=13.9 Hz, CH), 4.0 (1H, s, CH), 4.42 (1H, d, J=14.1 Hz, NH), 6.60-6.66 (1H, td, J=1.2, 1.5, 7.8 Hz, ArH), 6.73-6.77 (1H, dd, J=1.2, 8.2 Hz, ArH), 6.78-6.82 (1H, dd, J=1.2, 7.9 Hz, ArH), 6.84-6.91 (2H, m, ArH), 7.00-7.06 (1H, td, J=1.5, 0.8, 7.5 Hz, ArH), 7.19-7.26 ppm (2H, m, ArH). $^{13}$C NMR (67.93 MHz, CDCl$_3$): δ 26.0, 29.4, 29.6, 32.2, 33.3, 40.5, 44.1, 49.9, 112.2, 117.2, 118.8, 119.6, 125.3, 127.9, 129.8, 138.9, 143.0, 156.1, 174.6 ppm LCMS: M$^+$H, 413.47 HPLC: 100% (retention time 3.210 min, isocratic 90% acetonitrile: 10% water, 1 ml/min).

Preparation of diethyl-5-oxazepane-1,4-dicarboxylate. C$_{12}$H$_{19}$NO$_5$, MW: 257.29

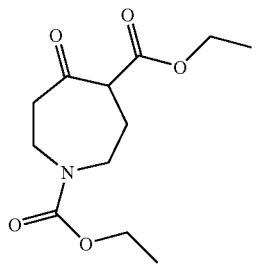

To a solution of 1-carbethoxypiperidin-4-one (250 mg, 1.46 mmol) in anhydrous-ether (14 ml), was simultaneously (and very slowly) added BF$_3$.OEt$_2$ (207 mg, 1.46 mmol) and ethyldiazoacetate (217 mg, 1.90 mmol) at −70° C. (dry-ice, IPA bath). The reaction mixture was allowed to stir from −70° C.-RT for 4 h and a further 1 h at RT. The reaction mixture was then washed with 30% potassium carbonate solution and the organics were dried (potassium carbonate), filtered and concentrated in vacuo to provide a crude orange oil (446 mg), which was used directly in the next reaction.

Preparation of ethyl-4-oxazepane-1-carboxylate. C$_9$H$_{15}$NO$_3$, MW: 185.22

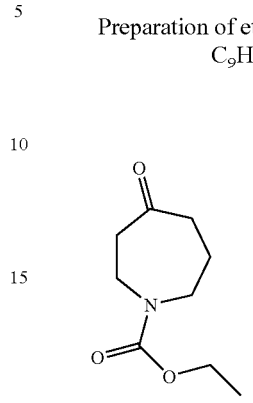

A solution of crude diethyl-5-oxazepane-1,4-dicarboxylate (WBH01062, 446 mg) in 4M HCl (10 ml) was stirred at reflux for 3 h. The reaction mixture was allowed to cool and then neutralised to pH 8 with sat. aq. sodium bicarbonate soln. This mixture was then extracted with ethyl acetate (3×15 ml), and the combined organics were dried (MgSO$_4$), filtered and concentrated in vacuo. The crude yellow/orange oil was then purified by flash chromatography (eluent: hexane to 1:1 hexane:ethyl acetate). The relevant fractions were evaporated in vacuo to provide the desired product as a pale yellow oil (205.8 mg, 76% over 2 steps). $^1$H NMR (270 MHz, CDCl$_3$): δ 1.22 (3H, t, J=6.9 Hz, CH$_3$), 1.68-1.75 (2H, m, CH$_2$), 2.53-2.70 (4H, m, 2×CH$_2$), 3.50-3.70 (4H, m, 2×CH$_2$), 4.10 ppm (2H, q, J=6.9 Hz, CH$_2$).

Preparation of 1-tert-butyl-4-ethyl-5-oxazepane-1,4-dicarboxylate. C$_{14}$H$_{23}$NO$_5$, MW: 285.34

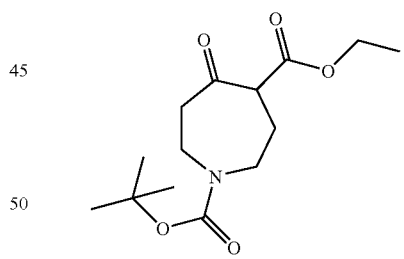

To a solution of 1-BOC-piperidin-4-one (250 mg, 1.25 mmol) in anhydrous-ether (10 ml), was simultaneously (and very slowly) added BF$_3$.OEt$_2$ (178 mg, 1.25 mmol) and ethyldiazoacetate (185 mg, 1.63 mmol) at −70° C. (dry-ice, IPA bath). The reaction mixture was allowed to stir from −70° C.-RT for 4 h and a further 1 h at RT. The reaction mixture was then washed with 30% potassium carbonate solution and the organics were dried (potassium carbonate), filtered and concentrated in vacuo to provide a crude orange oil. Purification by flash chromatography was then carried out (eluent; hexane to 1:1 hexane:ethyl acetate) and the relevant fractions were evaporated in vacuo to provide the desired product as a yellow oil (255.7 mg, 71%).

Preparation of 1-acetylazepan-4-one C₈H₁₃NO₂, MW: 155.20

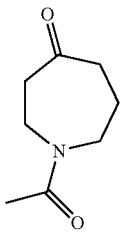

A solution of 1-tert-butyl-4-ethyl-5-oxazepane-1,4-dicarboxylate (376 mg, 1.32 mmol) in 4M HCl (25 ml) and heated to reflux for 4 h. The reaction mixture was cooled and concentrated in vacuo. The obtained crude oil was re-dissolved in DCM (25 ml) and to this solution was added potassium carbonate (546 mg, 3.95 mmol), followed by acetyl chloride (207 mg, 2.64 mmol). The reaction mixture was then allowed to stir at room temperature for 16 h. The reaction was then quenched with 2.5 M NaOH (25 ml), followed by extraction with ethyl acetate (2×30 ml). The combined organics were dried (MgSO₄), filtered and concentrated in vacuo. Purification by flash chromatography then proceeded (eluant; hexane to ethyl acetate) to afford the desired product as a transparent oil (159.4 mg, 78%). ¹H NMR (270 MHz, CDCl₃): δ 1.80-1.83 (2H, m, CH₂), 2.09 (3H, s, CH₃), 2.64-2.68 (4H, m, 2×CH₂), 3.57-3.73 ppm (4H, m, 2×CH₂).

Preparation of 4-[2-(4-chlorophenoxy)-phenylamino]-azepane-1-carboxylic acid ethylester STX 1703 C₂₁H₂₅ClN₂O₃, MW: 388.90

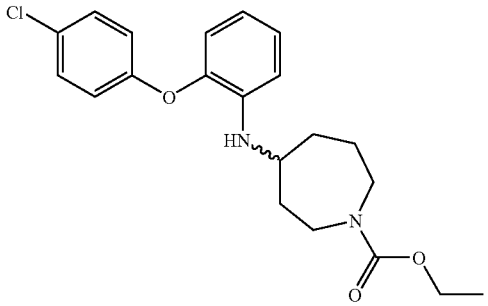

To a solution of 2-(4-chlorophenoxy)phenylamine (121 mg, 0.55 mmol), ethyl-4-oxazepane-1-carboxylate (205 mg, 1.1 mmol) and acetic acid (165 mg, 2.75 mmol) in DCE (1.8 ml) was added sodium triacetoxyborohydride (291 mg, 1.38 mmol). This solution was then heated at 100° C. for 25 minutes in a CEM discover microwave (fixed hold time set to on). The reaction mixture was then quenched with saturated aqueous sodium bicarbonate solution (5 ml) and extraction with ethyl acetate (3×5 ml) followed. The combined organics were concentrated in vacuo and purification by flash chromatography proceeded (eluant: 8:2 hexane:ethyl acetate) to provide the title compound as a transparent oil (60.7 mg, 28%). ¹H NMR (270 MHz, CDCl₃): δ 1.24 (3H, t, J=6.9 Hz, CH₃), 1.43-2.10 (6H, m, 6×CH), 3.41-3.54 (5H, m, 5×CH), 3.98-4.28 (3H, m, NH, CH₂), 6.59-6.67 (2H, m, Ar—H), 6.78-6.82 (1H, dd, J=1.5, 7.9 Hz, Ar—H), 6.86-6.89 (2H, m, Ar—H), 7.00-7.08 (1H, m, Ar—H), 7.21-7.24 ppm (2H, m, Ar—H). ¹³C NMR (67.93 MHz, CDCl₃): δ 14.7, 14.9, 15.6, 21.4, 24.6, 24.9, 25.0, 33.1, 34.2, 34.8, 35.1, 42.9, 43.1, 46.2, 46.4, 52.6, 52.8, 61.1, 61.3, 112.1, 118.6, 118.7, 120.0, 124.5, 129.7, 130.1, 137.8, 139.1, 142.9, 143.6, 145.3, 155.1, 156.2, 156.4, 168.4, 170.4 ppm LCMS: M⁺H, 389.42 HPLC: 97.79% (3.062 min, isocratic 90% acetonitrile, 10% water at 1 ml/min).

Preparation of 1-(4-(2-(4-chlorophenoxy)phenylamino)azepan-1-yl)ethanone STX1762 C₂₀H₂₃ClN₂O₂, MW: 358.86

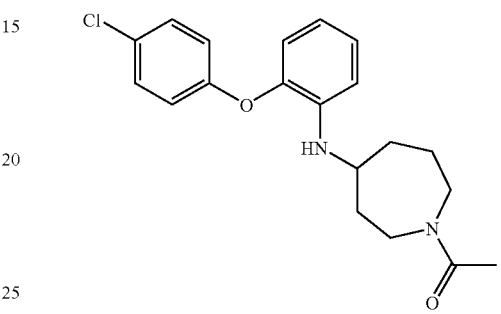

To a solution of 2-(4-chlorophenoxy)phenylamine (113 mg, 0.51 mmol), 1-acetylazepan-4-one (159 mg, 1.02 mmol) and acetic acid (153 mg, 2.55 mmol) in DCE (4 ml), was added sodium triacetoxyborohydride (270 mg, 1.28 mmol). The reaction mixture was allowed to stir at room temperature for 10 days. On return, the reaction was quenched with saturated aqueous sodium sodium bicarbonateonate (15 ml) and extracted with ethyl acetate (2×15 ml). The combined organics were dried (MgSO₄), filtered and concentrated in vacuo. Purification by flash chromatography then proceeded (eluent; 9:1 hexane:ethyl acetate to ethyl acetate) to afford the title compound as a pale yellow oil (67.1 mg, 37%). ¹H NMR (270 MHz, CDCl₃): δ 1.49-2.27 (9H, m, 3×CH₂, CH₃), 3.30-3.72 (5H, m, 5×CH), 4.10 (1H, br s, NH), 6.59-6.67 (2H, m, Ar—H), 6.78-6.89 (3H, m, Ar—H), 7.00-7.08 (1H, m, Ar—H), 7.21-7.24 ppm (2H, m, Ar—H). ¹³C NMR (67.93 MHz, CDCl₃): δ 21.9, 24.2, 25.3, 32.8, 33.0, 34.2, 35.2, 42.0, 45.0, 45.1, 48.3, 51.0, 52.0, 112.2, 118.6, 118.7, 125.4, 129.7, 129.8, 139.0, 142.8, 156.1, 156.2, 170.5 ppm. LCMS: M⁺H, 359.45 HPLC: 95.92% (2.677 min, isocratic 90% acetonitrile, 10% water at 1 ml/min).

Preparation of 1-(4-(2-(2,4-dichlorophenoxy)phenylamino)azepan-1-yl)ethanone STX1763 C₂₀H₂₂Cl₂N₂O₂, MW: 393.31

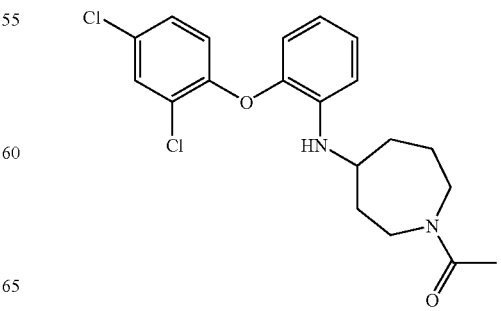

To a solution of 2-(2,4-dichlorophenoxy)phenylamine (130 mg, 0.51 mmol), 1-acetylazepan-4-one (159 mg, 1.02 mmol) and acetic acid (153 mg, 2.55 mmol) in DCE (4 ml), was added sodium triacetoxyborohydride (270 mg, 1.28 mmol). The reaction mixture was allowed to stir at room temperature for 10 days. On return, the reaction was quenched with saturated aqueous sodium sodium bicarbonateonate (15 ml) and extracted with ethyl acetate (2×15 ml). The combined organics were dried (MgSO$_4$), filtered and concentrated in vacuo. Purification by flash chromatography then proceeded (eluent; 9:1 hexane:ethyl acetate to ethyl acetate) to afford the title compound as a pale yellow oil (79.9 mg, 40%). $^1$H NMR (270 MHz, CDCl$_3$): δ 1.42-2.27 (9H, m, 3×CH$_2$, CH$_3$), 3.30-3.72 (5H, m, 5×CH), 4.10 (1H, br s, NH), 6.57-6.70 (2H, m, Ar—H), 6.72-6.85 (2H, m, Ar—H), 7.00-7.17 (2H, m, Ar—H), 7.43 ppm (1H, t, J=2.5 Hz, Ar—H). $^{13}$C NMR (67.93 MHz, CDCl3): δ 21.9, 24.2, 25.3, 32.8, 33.0, 34.2, 35.2, 42.0, 45.0, 45.1, 48.3, 51.0, 52.0, 112.2, 116.7, 116.9, 118.75, 118.85, 119.4, 125.50, 125.54, 128.0, 130.4, 139.0, 142.8, 156.1, 170.5 ppm. LCMS: M$^+$H, 393.45 HPLC: 96.22% (2.965 min, isocratic 90% acetonitrile, 10% water at 1 ml/min).

Preparation of ethyl 3-(2-(4-chlorophenoxy)phenylamino)-8-azabicyclo[3.2.1]octane-8-carboxylate STX1764 C$_{22}$H$_{25}$ClN$_2$O$_3$, MW: 400.9

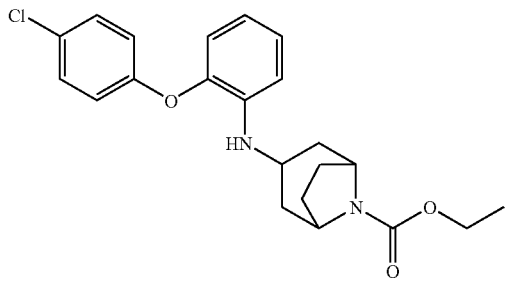

To a solution of 2-(4-chlorophenoxy)phenylamine (113 mg, 0.51 mmol), N-(ethoxycarbonyl)-tropinone (201 mg, 1.02 mmol) and acetic acid (153 mg, 2.55 mmol) in DCE (4 ml), was added sodium triacetoxyborohydride (270 mg, 1.28 mmol). The reaction mixture was allowed to stir at room temperature for 10 days. On return, the reaction was quenched with saturated aqueous sodium sodium bicarbonateonate (15 ml) and extracted with ethyl acetate (2×15 ml). The combined organics were dried (MgSO$_4$), filtered and concentrated in vacuo. Purification by flash chromatography then proceeded (eluent; 9:1 hexane:ethyl acetate to ethyl acetate) to afford the title compound as a pale yellow oil (43 mg, 21%). $^1$H NMR (270 MHz, CDCl$_3$): δ 1.24 (3H, t, J=7.2 Hz, CH$_3$), 1.65-1.90 (6H, m, 2×CH$_2$, 2×CH), 2.03-2.21 (2H, m, 2×CH), 3.67-3.72 (1H, m, CH), 4.05-4.30 (3H, m, CH$_2$, NH), 4.39 (1H, d, J=5.7 Hz, CH), 6.57-6.67 (2H, m, Ar—H), 6.85-6.89 (3H, m, Ar—H), 7.02-7.09 (1H, td, J=1.5, 1.0, 7.7 Hz, Ar—H), 7.21-7.27 ppm (2H, m, Ar—H). $^{13}$C NMR (67.93 MHz, CDCl$_3$): δ 14.9, 27.0, 27.5, 35.0, 35.6, 44.7, 52.6, 61.0, 111.3, 116.8, 118.1, 120.1, 125.7, 127.7, 129.7, 139.3, 142.3, 153.8, 156.5, ppm. LCMS: M$^+$H, 401.51 HPLC: 97.42% (4.106 min, isocratic 90% acetonitrile, 10% water at 1 ml/min).

Preparation of ethyl 3-(2-(2,4-dichlorophenoxy)phenylamino)-8-azabicyclo[3.2.1]octane-8-carboxylate STX1765 C$_{22}$H$_{24}$Cl$_2$N$_2$O$_3$, MW: 435.34

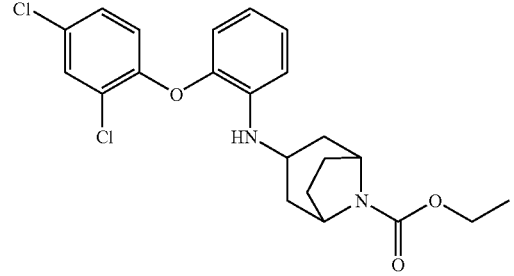

To a solution of 2-(4-chlorophenoxy)phenylamine (130 mg, 0.51 mmol), N-(ethoxycarbonyl)-tropinone (201 mg, 1.02 mmol) and acetic acid (153 mg, 2.55 mmol) in DCE (4 ml), was added sodium triacetoxyborohydride (270 mg, 1.28 mmol). The reaction mixture was allowed to stir at room temperature for 10 days. On return, the reaction was quenched with saturated aqueous sodium sodium bicarbonateonate (15 ml) and extracted with ethyl acetate (2×15 ml). The combined organics were dried (MgSO$_4$), filtered and concentrated in vacuo. Purification by flash chromatography then proceeded (eluent; 9:1 hexane:ethyl acetate to ethyl acetate) to afford the title compound as a pale yellow oil (49.7 mg, 22%). $^1$H NMR (270 MHz, CDCl$_3$): δ 1.24 (3H, t, J=7.2 Hz, CH$_3$), 1.63-1.86 (6H, m, 2×CH$_2$, 2×CH), 2.03-2.18 (2H, m, 2×CH), 3.69-3.72 (1H, m, CH), 4.05-4.30 (3H, m, CH$_2$, NH), 4.39 (1H, d, J=4.5 Hz, CH), 6.57-6.68 (2H, m, Ar—H), 6.77 (1H, d, J=8.9 Hz, Ar—H), 6.82-6.86 (1H, dd, J=1.5, 7.9 Hz, Ar—H), 7.04-7.07 (1H, d, J=1.5, 7.5 Hz, Ar—H), 7.09-7.13 (1H, dd, J=2.2, 8.8 Hz, Ar—H), 7.44-7.45 ppm (1H, d, J=2.5 Hz, Ar—H). $^{13}$C NMR (67.93 MHz, CDCl$_3$): δ 14.9, 28.0, 28.3, 35.0, 35.6, 44.5, 52.4, 61.0, 111.5, 116.8, 118.1, 120.1, 125.9, 128.0, 130.3, 132.0, 138.9, 142.0, 152.0, 153.9 ppm. LCMS: M$^+$H, 435.44 HPLC: 95.62% (5.044 min, isocratic 90% acetonitrile, 10% water at 1 ml/min).

Preparation of 1-{4-[2-(4-chlorophenoxy)benzylaminon]azepan-1-yl}ethanone WBH01098 C$_{21}$H$_{25}$ClN$_2$O$_2$, MW: 372.89

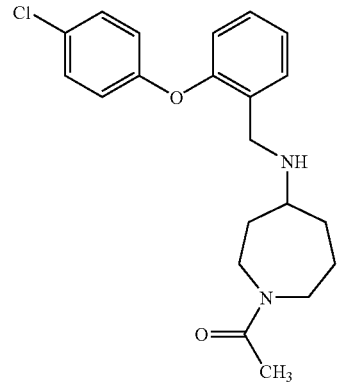

To a solution of [2-(4-chlorophenoxy)phenyl]methanamine (62 mg, 0.27 mmol), 1-acetylazepan-4-one (45 mg, 0.27 mmol) and acetic acid (16 mg, 0.27 mmol) in DCE (4 ml), was added sodium triacetoxyborohydride (78 mg, 0.37 mmol). This mixture was then allowed to stir at room temperature for 16 h. As TLC analysis indicated that [2-(4-chlorophenoxy)phenyl]methanamine still remained, the mixture was heated at 100° C. for 10 mins in a CEM discoverer microwave instrument. The reaction was quenched with a saturated aqueous solution of sodium bicarbonate (5 ml) and then extracted with ethyl acetate (2×5 ml). The combined organics were dried (MgSO$_4$), filtered and concentrated in vacuo. Purification by flash chromatography (eluant; hexane to ethyl acetate) then afforded the desired product as a pale yellow oil (57.5 mg, 57%). $^1$H NMR (270 MHz, CDCl$_3$): δ 1.35-2.03 (6H, m, 6×CH), 2.05 (3H, s, CH$_3$), 2.61-2.63 (1H, m, CH), 3.11-3.65 (5H, m, 4×CH, NH), 3.74-3.75 (2H, m, CH$_2$), 6.79-6.90 (3H, m, Ar—H), 7.09-7.15 (1H, m, Ar—H), 7.21-7.26 (3H, m, Ar—H), 7.32-7.38 ppm (1H, m, Ar—H). LCMS: M$^+$H, 373.42 HPLC: 71.34% (4.273 mins, isocratic 90% acetonitrile, 10% water at 1 ml/min).

Preparation of 1-{3-[2-(4-chlorophenoxy)benzylamino]-8-azabicyclo[3.2.1]octane-8-carboxylate STX2278 C$_{23}$H$_{27}$ClN$_2$O$_3$, MW: 414.93

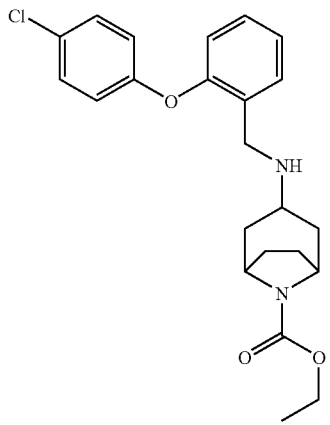

To a solution of [2-(4-chlorophenoxy)phenyl]methanamine (62 mg, 0.27 mmol), N-ethoxycarbonyl)tropinone (53 mg, 0.27 mmol) and acetic acid (16 mg, 0.27 mmol) in DCE (4 ml), was added sodium triacetoxyborohydride (78 mg, 0.37 mmol). This mixture was then allowed to stir at room temperature for 16 h. As TLC analysis indicated that [2-(4-chlorophenoxy)phenyl]methanamine still remained, the mixture was heated at 100° C. for 10 mins in a CEM discoverer microwave instrument. The reaction was quenched with a saturated aqueous solution of sodium bicarbonate (5 ml) and then extracted with ethyl acetate (2×5 ml). The combined organics were dried (MgSO$_4$), filtered and concentrated in vacuo. Purification by flash chromatography (eluant; hexane to ethyl acetate) then afforded the desired product as a pale yellow oil (34.3 mg, 31%). LCMS: M$^+$H, 415.48 HPLC: 64% (3.205 mins, isocratic 90% acetonitrile, 10% water at 1 ml/min).

Preparation of tert-butyl-1-[2-(4-chlorophenoxy) phenylcarbomoyl]-2-(1H-indol-3-yl)ethylcarbamate STX1857 C$_{21}$H$_{28}$ClN$_3$O$_4$, MW: 505.99

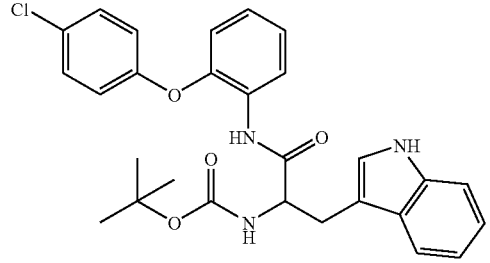

To a pre-stirred solution of N-(α)-BOC-L-tryptophan (152 mg, 0.50 mmol), EDC (265 mg, 1.38 mmol), triethylamine (70 mg, 0.69 mmol) and DMAP (6 mg, 0.046 mmol) in anhydrous DCM (25 ml), was added 2-(4-chlorophenoxy)phenylamine (100 mg, 0.46 mmol). This mixture was then allowed to stir at room temperature for 4 days. The reaction mixture was washed with 2.5M NaOH (20 ml), 2M HCl (20 ml) and the organics were then dried (MgSO$_4$), filtered and concentrated in vacuo. Purification by flash chromatography (eluant; DCM to 9:1 DCM:MeOH) then proceeded to afford the desired product as an off-white solid (109 mg, 47%). $^1$H NMR (270 MHz, CDCl$_3$): δ 1.35 (9H, br s, (CH$_3$)$_3$), 3.22-3.45 (2H, m, CH$_2$), 4.59 (1H, br s, CH), 5.14 (1H, br s, NH), 6.67-6.90 (2H, m, Ar—H), 7.00-7.25 (9H, m, Ar—H), 7.64 (1H, d, J=7.9 Hz, Ar—H), 7.95 (1H, s, NH), 8.11 (1H, s, NH), 8.42-8.45 ppm (1H, d, J=7.7 Hz, Ar—H). LCMS: M$^+$H, 506.33 HPLC: 99.73% (3.848 mins, isocratic 90% acetonitrile, 10% water at 1 ml/min).

Preparation of N-[2-(4-chlorophenoxy)phenyl]-3-acetamido-3-phenylpropanamide STX1858 C$_{23}$H$_{21}$ClN$_2$O$_3$, MW: 408.88

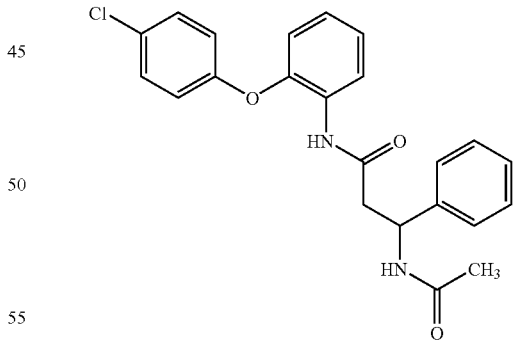

To a pre-stirred solution of N-acetyl-3-phenyl-β-alanine (104 mg, 0.50 mmol), EDC (265 mg, 1.38 mmol), triethylamine (70 mg, 0.69 mmol) and DMAP (6 mg, 0.046 mmol) in anhydrous DCM (25 ml), was added 2-(4-chlorophenoxy)phenylamine (100 mg, 0.46 mmol). This mixture was then allowed to stir at room temperature for 14 h. The reaction mixture was washed with 2.5M NaOH (20 ml), 2M HCl (20 ml) and the organics were then dried (MgSO$_4$), filtered and concentrated in vacuo. Purification by flash chromatography (eluant; DCM to 9:1 DCM:MeOH) then proceeded to afford the desired product as an off-white solid (58.9 mg, 31%). $^1$H NMR (270 MHz, CDCl$_3$): δ 2.03 (3H, s, CH$_3$), 2.83-2.99 (2H, m, CH$_2$), 5.30-5.40 (1H, m, CH), 6.73-6.77 (1H, dd, J=1.5, 8.2 Hz, Ar—H), 6.83-6.86 (2H, m, Ar—H), 6.95-7.03 (1H, td, J=1.7, 7.9 Hz, Ar—H), 7.05-7.11 (1H, td, J=1.7, 7.9 Hz, Ar—H), 7.19-7.30 (7H, m, Ar—H), 7.60 (1H, br s, Ar—H), 8.22-8.25 ppm (1H, dd, J=1.5, 8.0 Hz, Ar—H). LCMS: M$^+$H, 409.44 HPLC: 98.66% (2.268 mins, isocratic 90% acetonitrile, 10% water at 1 ml/min).

Preparation of N-[2-(4-chlorophenoxy)phenyl]-3-acetamidopropanamide STX1859 C$_{17}$H$_{17}$ClN$_2$O$_3$, MW: 333.38

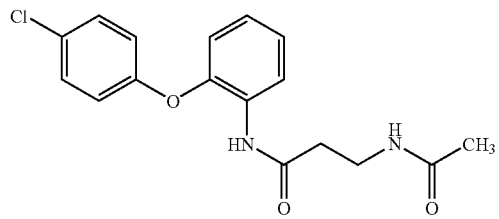

To a pre-stirred solution of Ac-β-Ala-OH (66 mg, 0.50 mmol), EDC (265 mg, 1.38 mmol), triethylamine (70 mg, 0.69 mmol) and DMAP (6 mg, 0.046 mmol) in anhydrous DCM (25 ml), was added 2-(4-chlorophenoxy)phenylamine (100 mg, 0.46 mmol). This mixture was then allowed to stir at room temperature for 3 days. The reaction mixture was washed with 2.5M NaOH (20 ml), 2M HCl (20 ml) and the organics were then dried (MgSO$_4$), filtered and concentrated in vacuo. Purification by flash chromatography (eluant; DCM to 9:1 DCM:MeOH) then proceeded to afford the desired product as an off-white solid (127.8 mg, 83%). $^1$H NMR (270 MHz, CDCl$_3$): δ 1.93 (3H, s, CH$_3$), 2.60 (2H, t, J=5.7 Hz, CH$_3$), 3.56 (2H, q, J=5.9, 11.6 Hz, CH$_2$), 6.26 (1H, br s, NH), 6.79-7.12 (5H, m, Ar—H), 7.24-7.33 (2H, m, Ar—H), 7.72 (1H, br s, Ar—H), 8.33-8.37 ppm (1H, dd, J=1.5, 7.9 Hz, Ar—H). LCMS: M$^+$H, 331.36 HPLC: 98.66% (2.268 mins, isocratic 90% acetonitrile, 10% water at 1 ml/min).

Preparation of 2-(4-chlorophenoxy)-4-methylbenzenamine WBH01108-WBH01110 C$_{13}$H$_{12}$ClNO, MW: 233.69

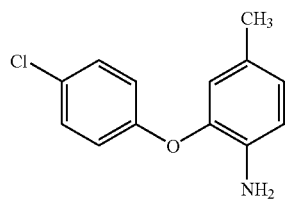

A solution of 4-chlorophenol (1 g, 7.78 mmol), 3-fluoro-4-nitrotoluene (808 mg, 5.21 mmol) and potassium carbonate (1.29 g, 9.34 mmol) in DMF (5 ml) was stirred at reflux for 6 h. The reaction mixture was allowed to cool and then re-dissolved in 2.5M NaOH (10 ml). This aqueous mixture was then extracted with ethyl acetate (3×15 ml) and the combined organics were dried (MgSO$_4$), filtered and concentrated in vacuo. An ethyl acetate solution of the crude material was filtered through a pad of silica which upon evaporation in vacuo afforded 2-(4-chlorophenoxy)-4-methyl-1-nitrobenzene as a yellow oil (1.45 g). This oil was then dissolved in 10:1 EtOH:H$_2$O (10 ml) and added to a refluxing solution of iron powder (1.20 g, 21.53 mmol) and ammonium chloride (147 mg, 2.74 mmol) in 10:1 EtOH:H$_2$O (20 ml). Stirring at this temperature continued for a further 2 h, before the reaction mixture was allowed to cool. The mixture was then filtered through a pad of celite, which was further washed with ethyl acetate (250 ml). Concentration in vacuo followed by purification by flash chromatography (eluant: 8:2 to 1:1 hexane:ethyl acetate) afforded the title compound as a pale yellow solid (868.2 mg, 70%). $^1$H NMR (270 MHz, CDCl$_3$): δ 2.20 (3H, s, CH$_3$), 3.65 (2H, br s, NH$_2$), 6.65-6.68 (1H, m, Ar—H), 6.72 (1H, d, J=10.9 Hz, Ar—H), 6.78-6.82 (1H, m, Ar—H), 6.85-6.91 (2H, m, Ar—H), 7.21-7.26 ppm (2H, m, Ar—H).

Preparation of 1-{4-[2-(4-chlorophenoxy)-4-methylphenylamino]piperidin-1-yl}ethanone STX1860 C$_{20}$H$_{23}$ClN$_2$O$_2$, MW: 358.86

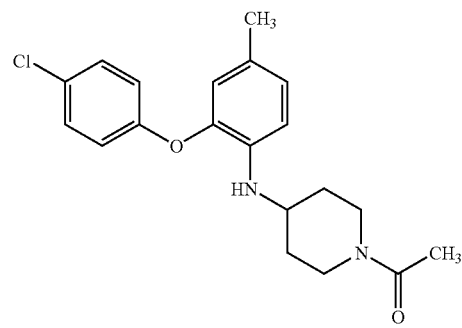

To a solution of 2-(4-chlorophenoxy)-4-methylbenzenamine (100 mg, 0.43 mmol), N-acetyl-4-piperidone (120 mg, 0.85 mmol) and acetic acid (129 mg, 2.14 mmol) in DCE (1.8 ml), was added sodium triacetoxyborohydride (227 mg, 1.07 mmol). This mixture was then heated at 100° C. for 25 min in a CEM discoverer microwave instrument. The reaction was then quenched with a saturated aqueous solution of sodium bicarbonate (5 ml) and extracted with DCM (3×5 ml). The combined organics were then dried (MgSO$_4$), filtered and concentrated in vacuo. Purification by flash chromatography (eluent: hexane to ethyl acetate) then proceeded and the relevant fractions evaporated in vacuo to provide the title compound as an off-white solid (125.2 mg, 81%). $^1$H NMR (270 MHz, CDCl$_3$): δ 1.23-1.34 (2H, m, 2×CH), 2.06 (3H, s, CH$_3$), 2.17 (3H, s, CH$_3$), 2.45-2.50 (2H, m, 2×CH), 2.82-2.84 (1H, m, CH), 3.12-3.20 (1H, m, CH), 3.47-3.59 (1H, m, CH), 3.74-3.86 (2H, m, 2×CH), 4.34-4.40 (1H, m, NH), 6.62-6.67 (2H, m, Ar—H), 6.82-6.87 (3H, m, Ar—H), 7.20-7.25 ppm (2H, m, Ar—H). LCMS: M$^+$H, 359.45 HPLC: 99.30% (3.842 mins, isocratic 90% acetonitrile, 10% water at 1 ml/min).

{4-[2-(4-Chlorophenoxy)benzylamino]piperidin-1-yl}cyclohexylmethanone (AMR01090, STX1873)
$C_{25}H_{31}ClN_2O_2$, MW 426.98

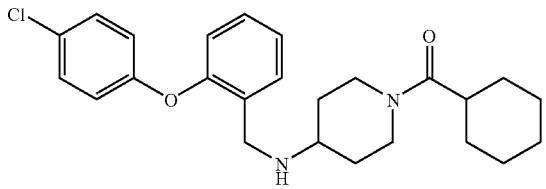

A solution of 2-(4-chlorophenoxy)benzylamine (AMR01076, 100 mg, 0.428 mmol) and 1-cyclohexanecarbonylpiperidin-4-one (89.5 mg, 0.428 mmol) in DCE (5 mL) was treated with NaBH(OAc)$_3$ (127 mg, 0.60 mmol) and acetic acid (26 mg, 0.428 mmol). The mixture was stirred at room temperature under a N$_2$ atmosphere until TLC showed that the reactants were consumed (30 min). Then, it was quenched with saturated NaHCO$_3$ solution, the aqueous layer was washed with DCM (2×20 mL), and the combined organic layers were dried (MgSO$_4$), filtered and evaporated to dryness. Column chromatography on silica gel of the crude product using DCM to DCM/MeOH 95:5 gradient as eluent gave {4-[2-(4-chlorophenoxy)benzylamino]piperidin-1-yl}cyclohexylmethanone (116 mg, 63%) as a colorless oil. Rf: 0.4 (DCM/MeOH 9:1) LC/MS (APCI) t$_r$=10.18 min, m/z 429.46 (36), 427.44 (M$^+$+H, 100). HPLC t$_r$=4.43 min (93.94%) $^1$H NMR (270 MHz, CDCl$_3$) δ 1.12-1.79 (15H, m, 7CH$_2$+NH), 2.44 (1H, m, CHCO), 2.64 (2H, m, CH$_2$), 2.99 (1H, m, CHNH), 3.80 (2H, m, CH$_2$NH), 3.82 (1H, m, ½CH$_2$), 4.39 (1H, br d, J=13.3 Hz, ½CH$_2$), 6.84 (2H, AA'BB', ArH), 6.86 (1H, m, ArH), 7.12 (1H, td, ArH), 7.22 (1H, m, ArH), 7.25 (2H, AA'BB', ArH) and 7.39 (1H, dd, J=7.3, 1.7 Hz, ArH). $^{13}$C NMR (270 MHz, CDCl$_3$) δ 25.97, 29.40, 29.59, 32.29, 33.40, 40.32 (CH$_2$), 40.54 (CH), 43.91, 45.65 (CH$_2$), 54.00 (CH), 118.94, 119.61, 124.54, 127.96, 128.70, 129.84, 130.57, 131.84, 154.35, 156.38 (ArC), and 174.48 (C=O).

2-(2,4-Dichloro-phenoxy)-N-(1-methanesulfonyl-piperidin-4-yl)-benzamide (AMR01093, STX1831)
$C_{19}H_{20}Cl_2N_2O_4S$, MW 443.34

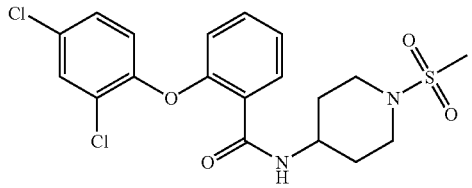

To an ice cooled solution of 4-[2-(2,4-dichlorophenoxy)-N-piperidin-4-ylbenzamide (AMR01077, 100 mg, 0.274 mmol) in dry DCM (5 mL) were added triethylamine (0.2 mL, 1.37 mmol) and methanesulphonyl chloride (0.125 mL, 1.6 mmol). The reaction mixture was stirred overnight at room temperature, and quenched with saturated NaHCO$_3$. The resulting solution was extracted with DCM (3×20 mL), and the combined organic layers were washed with water and dried (MgSO$_4$). The dessicant was filtered off and the resulting solution was treated with trisamine scavenger (100 mg) for 2 h. The scavenger was filtered off, and the solvent evaporated to dryness. Column chromatography of the crude product using DCM/MeOH 95:5 as eluent gave 2-(2,4-Dichlorophenoxy)-N-(1-methanesulfonyl-piperidin-4-yl)-benzamide (86 mg, 72%) as a white solid. LC/MS (APCI) t$_r$=4.56 min, m/z 445.32 (65), 443.31 (M$^+$+H, 100). HPLC t$_r$=3.42 min (97.52%) $^1$H NMR (270 MHz, CDCl$_3$) 1.56-1.69 (2H, m, CH$_2$), 2.06 (2H, m, CH$_2$), 2.75 (3H, s, CH$_3$), 2.86 (2H, m, CH$_2$), 3.68 (2H, m, CH$_2$), 4.09 (1H, m, CH), 6.79 (1H, dd, J=8.2, 1.0 Hz, ArH), 6.88 (1H, d, J=8.9 Hz, ArH), 7.20-7.28 (2H, m, ArH), 7.38-7.42 (2H, m, ArH+NH), 7.51 (1H, d, J=2.5 Hz, ArH) and 8.15 (1H, dd, J=7.9, 2.0 Hz, ArH). $^{13}$C NMR (270 MHz, CDCl$_3$) δ 31.47 (CH$_2$), 34.83 (CH$_3$), 44.96 (CH$_2$), 46.28 (CH), 117.76, 120.77, 124.32, 124.83, 125.88, 128.59, 130.44, 130.88, 132.56, 133.04, 149.79, 153.56 (ArC), and 163.97 (C=O).

1-{4-[2-(4-Chloro-phenylsulfanyl)-phenylamino]-piperidin-1-yl}-ethanone (AMR01098, STX1832)
$C_{19}H_{21}ClN_2OS$, MW 360.90

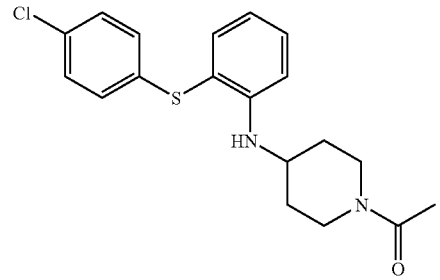

A solution of 2-aminophenyl-4-chlorophenyl sulfide (0.5 g, 2.1 mmol), 1-acetyl-4-piperidone (0.59 g, 4.2 mmol) and acetic acid (0.6 mL, 10.5 mmol) in DCE (6 mL) was treated with NaBH(OAc)$_3$ (1.11 g, 5.25 mmol). It was divided in three batches and stirred under microwave irradiation for 15 min at 100° C. The joined reaction mixture was diluted with DCM (10 mL) and quenched with saturated NaHCO$_3$ solution. The aqueous layer was washed with DCM (2×20 mL), and the combined organic layers were dried (MgSO$_4$), filtered and evaporated to dryness. Column chromatography on silica gel of the crude product using AcOEt/hexane 6:4 as eluent gave 1-{4-[2-(4-chloro-phenylsulfanyl)-phenylamino]-piperidin-1-yl}-ethanone (268 mg, 35%) as a colorless oil. Rf: 0.46 (DCM/MeOH 9:1) LC/MS (APCI) t$_r$=5.49 min, m/z 363.35 (40), 361.33 (M$^+$+H, 100). HPLC t$_r$=2.85 min (99.53%) $^1$H NMR (270 MHz, CDCl$_3$) δ 1.27 (2H, m, CH$_2$), 1.92 (2H, m, CH$_2$), 2.06 (3H, s, CH$_3$), 2.94 (1H, m, ½CH$_2$), 3.16 (1H, m, ½CH$_2$), 3.52-3.63 (2H, m), 4.20 (1H, m), 4.78 (1H, m), 6.67-6.72 (2H, m, ArH), 6.95 (2H, AA'BB', ArH), 7.15 (2H, AA'BB', ArH), 7.31 (1H, m, ArH) and 7.47 (1H, dd, J=7.9, 1.8 Hz, ArH). $^{13}$C NMR (270 MHz, CDCl$_3$) δ 21.58 (CH$_3$), 31.70, 32.36, 39.97, 44.47 (CH$_2$), 49.29 (CH), 111.23, 114.09, 117.39, 127.73, 129.16, 131.79, 138.02, 147.86 (ArC), and 168.86 (C=O).

1-{4-[2-(4-Chloro-benzenesulfinyl)-phenylamino]-piperidin-1-yl}-ethanone (AMR01103, STX1871) C₁₉H₂₁ClN₂O₂S, MW 376.90

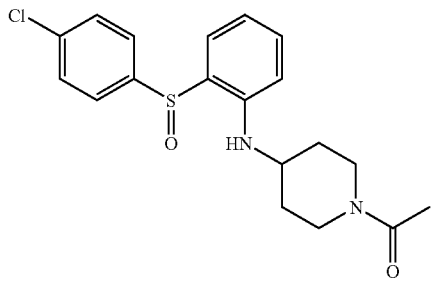

A solution of 1-{4-[2-(4-chloro-phenylsulfanyl)-phenylamino]-piperidin-1-yl}-ethanone (AMR01098, STX1832, 140 mg, 0.388 mmol) was treated with m-chloroperbenzoic acid (77%, 104.33 mg, 0.466 mmol) and stirred for 2 h, keeping the temperature between −30 and −10° C. The reaction mixture was quenched with saturated NaHCO₃ solution. The aqueous layer was washed with DCM (2×20 mL), and the combined organic layers were dried (MgSO₄), filtered and evaporated to dryness. Column chromatography on silica gel of the crude product using DCM/MeOH 95:5 as eluent gave 1-{4-[2-(4-chloro-benzenesulfinyl)-phenylamino]-piperidin-1-yl}-ethanone (119 mg, 81%) as an oil. LC/MS (APCI) $t_r$=4.53 min, m/z 379.28 (39), 377.26 (M⁺+H, 100). HPLC $t_r$=2.38 min (98.44%) ¹H NMR (270 MHz, CDCl₃) δ 1.12 (1H, m, ½CH₂), 1.45 (1H, m, ½CH₂), 1.62 (1H, m, ½CH₂), 1.95 (2H, m, CH₂), 2.04, 2.07 (3H, 2s, CH₃), 2.94-4.00 (5H, m, CH and 2CH₂), 6.20, 6.28 (1H, 2d, J=6.9 and 7.4 Hz, NH), 4.20 (1H, m), 6.60 (1H, d, J=8.4 Hz, ArH), 6.70 (1H, m, ArH) and 7.27-7.48 (6H, m, ArH). ¹³C NMR (270 MHz, CDCl₃) δ 21.58 (CH₃), 30.89, 31.17, 31.28, 31.83, 39.23, 39.46, 43.80, 44.44 (CH₂), 47.77, 48.18 (CH), 112.17, 112.44, 115.67, 115.73, 122.13, 122.58, 126.13, 126.25, 128.97, 129.04, 129.53, 129.70, 133.88, 133.93, 136.39, 136.61, 142.28, 147.47, 147.56 (ArC), and 168.96 (C=O).

2-(2-Nitro-phenylsulfanyl)-pyrimidine (AMR01102) C₁₀H₇N₃O₂S, MW 233.25

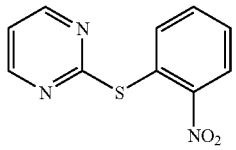

A mixture of 2 mercaptopyrimidine (2.00 g, 17.8 mmol), 1-fluoro-2-nitrobenzene (2.50 g, 17.8 mmol) and potassium carbonate (2.46 g, 17.8 mmol) in DMF (15 mL) was stirred under reflux for 2 h. After removal of DMF, the residue was dissolved in DCM and washed with NaOH (5%, 3×20 mL) and brine. The organic layer was dried (MgSO₄), filtered and evaporated to give 2-(2-nitro-phenylsulfanyl)-pyrimidine (3.45 g, 83%) as a yellow solid which was used in the next step without further purification. LC/MS (APCI) $t_r$=3.66 min, m/z 379.28 (39), 233.98 (M⁺+H, 100). HPLC $t_r$=2.22 min (99.67%) ¹H NMR (270 MHz, CDCl₃) δ 7.03 (1H, t, J=4.7 Hz, Pyrimidine-H), 7.51-7.64 (2H, m, ArH), 7.80 (1H, dd, J=7.7, 1.5 Hz, ArH), 8.03 (1H, dd, J=7.7, 2.0 Hz, ArH) and 8.48 (2H, d, J=4.7 Hz, Pyrimidine-H).

2-(Pyrimidin-2-ylsulfanyl)-phenylamine (AMR01106) C₁₀H₉N₃S, MW 203.26

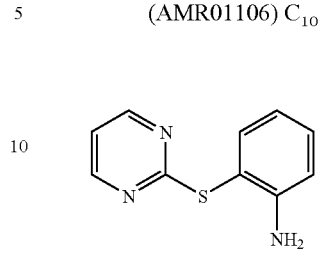

To a refluxing mixture of iron powder (2.62 g, 47.16 mmol) and ammonium chloride (315 mg, 5.89 mmol) in ethanol (45 mL) and water (8 mL) was added 1-{4-[2-(4-chloro-benzenesulfinyl)-phenylamino]-piperidin-1-yl}-ethanone (AMR01102, 2.0 g, 8.60 mmol) and the resulting mixture was stirred at reflux for 2 h. After removal of the solvent, the residue was diluted in aqueous sodium hydrogen carbonate (40 mL) and extracted with DCM (3×20 mL). The organic layer was dried (MgSO₄), filtered and evaporated. Column chromatography on silica gel of the crude product using DCM/MeOH 98:2 as eluent gave 1-{4-[2-(4-chloro-benzenesulfinyl)-phenylamino]-piperidin-1-yl}-ethanone (1.12 g, 64%) as a yellow solid. LC/MS (APCI) $t_r$=3.28 min, m/z 203.99 (M⁺+H, 100). HPLC $t_r$=2.15 min (98.18%) ¹H NMR (270 MHz, CDCl₃) δ 4.30 (2H, br s, NH₂), 6.75-6.84 (2H, m, ArH), 6.96 (1H, t, J=5.0 Hz, Pyrimidine-H), 7.27 (1H, m, ArH), 7.47 (1H, dd, J=7.7, 1.7 Hz, ArH) and 8.48 (2H, d, J=5.0 Hz, Pyrimidine-H),

1-{4-[2-(Pyrimidin-2-ylsulfanyl)-phenylamino]-piperidin-1-yl}-ethanone (AMR01108, STX1872) C₁₇H₂₀N₄OS, MW 328.43

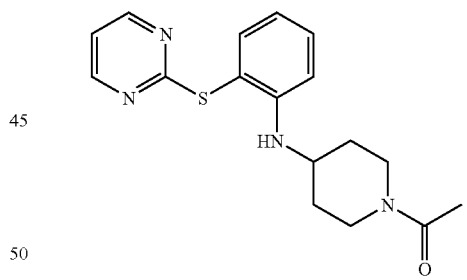

A solution of 2-(pyrimidin-2-ylsulfanyl)-phenylamine (AMR01106, 100 mg, 0.492 mmol), 1-acetylpiperidone (69.5 mg, 0.492 mmol) and acetic acid (0.15 mL, 2.46 mmol) in DCE (2 mL) was treated with NaBH(OAc)₃ (261 mg, 1.23 mmol) and stirred under microwave irradiation for 15 min at 100° C. The reaction mixture was diluted with DCM (10 mL) and quenched with saturated NaHCO₃ solution. The aqueous layer was washed with DCM (2×20 mL), and the combined organic layers were dried (MgSO₄), filtered and evaporated to dryness. Column chromatography on silica gel of the crude product using AcOEt/MeOH 98:2 as eluent gave 1-{4-[2-(pyrimidin-2-ylsulfanyl)-phenylamino]-piperidin-1-yl}-ethanone 36 mg, 22%) as a colorless oil. ¹H NMR (270 MHz, CDCl₃) δ 1.20-1.40 (2H, m, CH₂), 1.90-2.10 (2H, m, CH₂), 2.05 (3H, s, CH₃), 2.89 (1H, m, ½CH₂), 3.18 (1H, m, ½CH₂), 3.54-3.74 (2H, m, CH$_2$), 4.26 (1H, m, CH), 4.75 (1H, br s, NH), 6.69-6.75 (2H, m, ArH), 6.97 (1H, t, J=4.7 Hz, Pyrimidine-H), 7.33 (1H, m, ArH), 7.49 (1H, dd, J=7.4, 1.7 Hz, ArH) and 8.47 (2H, d, J=4.7 Hz, Pyrimidine-H), $^{13}$C NMR (270 MHz, CDCl$_3$) δ 21.57 (CH$_3$), 31.74, 32.56, 40.14, 45.00 (CH$_2$), 49.63 (CH), 111.45, 111.57, 117.35, 132.12, 138.13, 148.49, 157.88 (ArC and Pyridine-C), and 171.77 (C=O).

4-(2-Nitrophenylsulfanyl)-pyridine (AMR01105)

C$_{11}$H$_8$N$_2$O$_2$S, MW 232.26

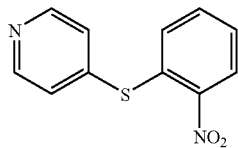

A mixture of 4-mercaptopyridine (2.00 g, 18.0 mmol), 1-fluoro-2-nitrobenzene (2.54 g, 18.0 mmol) and potassium carbonate (2.49 g, 18.0 mmol) in DMF (15 mL) was stirred under reflux for 2 h. After removal of DMF, the residue was dissolved in DCM and washed with NaOH (5%, 3×20 mL) and brine. The organic layer was dried (MgSO$_4$), filtered and evaporated. Flash Master chromatography of the crude product using DCM to DCM/MeOH 98:2 gradient as eluent gave 4-(2-nitrophenylsulfanyl)-pyridine (2.4 g, 57%) as a yellow solid, mp 119-122° C.

Rf: 0.66 (DCM/MeOH 98:2)

LC/MS (APCI) t$_r$=4.27 min, m/z 233.04 (M$^+$+H, 100).

HPLC t$_r$=2.38 min (99.71%)

$^1$H NMR (270 MHz, CDCl$_3$) δ 7.18 (1H, dd, J=7.9, 1.5 Hz, ArH), 7.33 (2H, AA'BB', Pyridine-H), 7.37-7.50 (2H, m, ArH), 8.15 (1H, dd, J=8.2, 1.7 Hz, ArH) and 8.60 (2H, AA'BB' Pyridine-H).

2-(Pyridin-4-ylsulfanyl)-phenylamine (AMR01107)

C$_{11}$H$_{10}$N$_2$S, MW 202.28

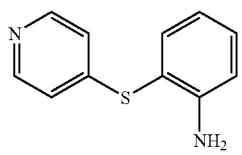

To a refluxing mixture of iron powder (3.15 g, 56.82 mmol) and ammonium chloride (380 mg, 7.1 mmol) in ethanol (45 mL) and water (8 mL) was added 4-(2-nitrophenylsulfanyl)-pyridine (AMR01105, 2.4 g, 10.33 mmol) and the resulting mixture was stirred at reflux for 2 h. After removal of the solvent, the residue was diluted in aqueous sodium hydrogen carbonate (40 mL) and extracted with DCM (3×20 mL). The organic layer was dried (MgSO$_4$), filtered and evaporated to give 2-(pyridin-4-ylsulfanyl)-phenylamine (1.7 g, 81%) as a yellow solid, mp 103-107° C., which was used in the next step without further purification.

Rf: 0.35 (DCM/MeOH 9:1)

LC/MS (APCI) t$_r$=4.28 min, m/z 202.98 (M$^+$+H, 100).

HPLC t$_r$=2.44 min (100%)

$^1$H NMR (270 MHz, CDCl$_3$) δ 4.29 (2H, brs, NH$_2$), 6.74-6.84 (2H, m, ArH), 6.88 (2H, AA'BB'z, Pyridine-H), 7.29 (1H, m, ArH), 7.41 (1H, dd, J=7.7, 1.5 Hz, ArH), 8.32 (2H, AA'BB', Pyridine-H).

4-(4-Chlorophenoxy)-3-nitropyridine (AMR01116)

C$_{11}$H$_7$ClN$_2$O$_3$, MW 250.64

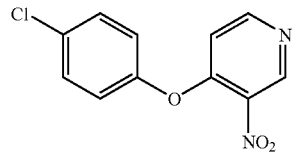

To a solution of 4-chlorophenol (1.00 g, 7.78 mmol) in DMF (5 ml) at room temperature was added potassium carbonate (2.15 g, 15.56 mmol) in DMF (10 mL) and the mixture was stirred at room temperature for 15 min. Then, 4-chloro-3-nitropyridine (1.23 g, 7.78 mmol) was added and the resulting solution was stirred at room temperature for 2 h. The mixture was poured into water and extracted with EtOAc. The organic layer was washed with water and brine, dried (MgSO$_4$), filtered and evaporated. 4-(4-Chlorophenoxy)-3-nitropyridine (1.72 g, 88%) was obtained as a yellow solid, mp 93-94° C. (from EtOH), which was used in the next step without further purification.

Rf: 0.75 (DCM/MeOH 9:1)

LC/MS (APCI) t$_r$=4.53 min, m/z 253.14 (53), 251.12 (M$^+$+H, 100).

$^1$H NMR (270 MHz, CDCl$_3$) δ 6.77 (1H, d, J=5.7 Hz, Pyridine-H), 7.10 (2H, AA'BB', ArH), 7.45 (2H, AA'BB', ArH), 8.56 (1H, d, J=5.7 Hz, Pyridine-H) and 9.13 (1H, s, Pyridine-H).

4-(4-Chlorophenoxy)-pyridin-3-ylamine (AMR01118)

C$_{11}$H$_9$ClN$_2$O, MW 220.65

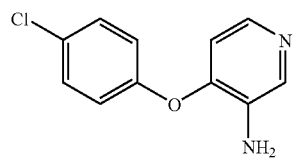

To a refluxing mixture of iron powder (1.91 g, 34.43 mmol) and ammonium chloride (230 mg, 4.30 mmol) in ethanol (45 µL) and water (8 mL) was added 4-(4-chlorophenoxy)-3-nitropyridine (AMR01116, 1.57 g, 6.26 mmol) and the resulting mixture was stirred at reflux for 1 h. After removal of the solvent, the residue was diluted in aqueous sodium hydrogen carbonate (40 mL) and extracted with DCM (3×20 mL). The organic layer was dried (MgSO$_4$), filtered and evaporated. Flashmaster chromatography of the crude product using DCM/MeOH 9:1 as eluent gave 4-(4-chlorophenoxy)-pyridin-3-ylamin (1.03 g, 75%) as a white solid, mp 104-106° C.

Rf: 0.3 (DCM/MeOH 9:1)

LC/MS (APCI) t$_r$=4.30 min, m/z 223.15 (64), 221.07 (M$^+$+H, 100).

¹H NMR (270 MHz, CDCl₃) δ 3.88 (2H, brs, NH₂), 6.54 (1H, d, J=5.4 Hz, Pyridine-H), 7.00 (2H, AA'BB', ArH), 7.34 (2H, AA'BB', ArH), 7.88 (1H. d, J=5.4 Hz, Pyridine-H) and 8.13 (1H, s, Pyridine-H).

4-(6-Methyl-pyridin-3-yloxy)-3-nitropyridine (AMR01121)

C₁₁H₉N₃O₃, MW 231.21

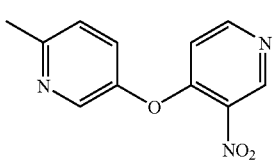

To a solution of 3-hydroxy-6-methylpyridine (1.0 g, 9.16 mmol) in DMF (5 ml) at room temperature was added potassium carbonate (2.53 g, 18.32 mmol) in DMF (10 mL) and the mixture was stirred at room temperature for 15 min. Then, 4-chloro-3-nitropyridine (1.45 g, 9.16 mmol) was added and the resulting solution was stirred at room temperature for 2 h. The mixture was poured into water and extracted with EtOAc. The organic layer was washed with water and brine, dried (MgSO₄), filtered and evaporated. 4-(6-Methylpyridin-3-yloxy)-3-nitropyridine (2.1 g, 100%) was obtained as an orange oil, which precipitated on standing, mp 87-90° C., and was used in the next step without further purification.

Rf: 0.6 (DCM/MeOH 9:1)
¹H NMR (270 MHz, CDCl₃) δ 2.60 (3H, s, CH₃), δ 74 (1H, d, J=5.7 Hz, Pyridine-H), 7.27 (1H, d, J=8.4 Hz, Pyridine-H), 7.39 (1H, dd, J=8.4, 2.7 Hz, Pyridine-H), 8.39 (1H, d, J=2.7 Hz, Pyridine-H), 8.56 (1H, d, J=5.7 Hz, Pyridine-H) and 9.13 (1H, s, Pyridine-H).

4-(6-Methylpyridin-3-yloxy)-pyridin-3-ylamine (AMR01122)

C₁₁H₁₁N₃O, MW 201.22

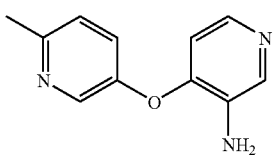

To a refluxing mixture of iron powder (2.55 g, 45.93 mmol) and ammonium chloride (307 mg, 5.74 mmol) in ethanol (45 mL) and water (8 mL) was added 4-(6-methyl-pyridin-3-yloxy)-3-nitropyridine (AMR01121, 1.93 g, 8.35 mmol) and the resulting mixture was stirred at reflux for 2 h. After removal of the solvent, the residue was diluted in aqueous sodium hydrogen carbonate (40 mL) and extracted with DCM (3×20 mL). The organic layer was dried (MgSO₄), filtered and evaporated. Flash master chromatography of the crude product using DCM to DCM/MeOH 9:1 gradient as eluent gave 4-(6-methylpyridin-3-yloxy)-pyridin-3-ylamine (1.32 g, 79%) as an orange solid, mp 74-79° C.

Rf: 0.23 (DCM/MeOH 9:1)
¹H NMR (270 MHz, CDCl₃) δ 2.55 (3H, s, CH₃), 3.94 (2H, br s, NH₂), 6.48 (1H, d, J=5.4 Hz, Pyridine-H), 7.16 (1H, d, J=8.4 Hz, Pyridine-H), 7.27 (1H, dd, J=8.4, 2.7 Hz, Pyridine-H), 7.85 (1H, d, J=5.4 Hz, Pyridine-H), 8.12 (1H, s, Pyridine-H) and 8.32 (1H, d, J=2.7 Hz, Pyridine-H).

4-[2-(Pyridin-4-ylsulfanyl)-phenylcarbamoyl]-piperidine-1-carboxylic acid tert-butyl ester (AMR01132, STX1970)

C₂₂H₂₇N₃O₃S, MW 413.53

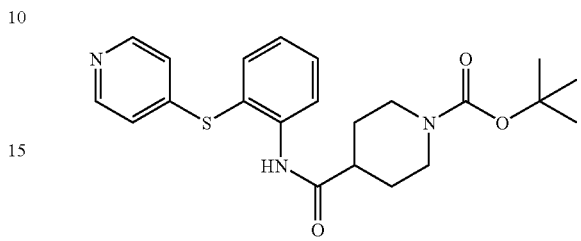

A solution of piperidine-1,4-dicarboxylic acid mono-tert-butyl ester (272 mg, 1.19 mmol) in dry dichloromethane (8 mL) was stirred under nitrogen, and 4-dimethylaminopyridine (DMPA, 40 mg, 0.327 mmol), (1-(3-dimethylaminopropyl)-3-ethylcarbodiimide hydrochloride (EDC, 570 mg, 2.97 mmol) and triethylamine (0.25 mL) were added. The resulting mixture was stirred for 30 min under nitrogen and 2-(pyridin-4-ylsulfanyl)phenylamine (AMR01107, 200 mg, 0.99 mmol) in dry dichloromethane (4 mL) was added. After stirring at room temperature for 72 h, the mixture was diluted with dichloromethane, washed saturated NaHCO₃ (2×25 mL) and brine. The organic layer was dried (MgSO₄), filtered and evaporated. Flash chromatography on silica gel of the crude product using hexane/ethyl acetate 5:5 as eluent gave AMR01132 (62 mg, 15%) as a white solid, mp 117-121° C.

Rf: 0.4 (EtOAc)
LC/MS (APCI) t_r=4.46 min, m/z 414.6 (M⁺+H, 100).
HPLC t_r=3.65 min (95.20%)
¹H NMR (270 MHz, CDCl₃) δ 1.43 (9H, s, 3 CH₃), 1.48 (2H, m, CH₂), 1.64 (2H, m, CH₂), 2.25 (1H, tt, CH), 2.68 (2H, br t, CH₂), 4.05 (2H, br d, CH₂), 6.85 (2H, AA'BB', Pyridine-H), 7.18 (1H, td, ArH), 7.50-7.60 (2H, m, ArH), 8.11 (1H, br s, NH), 8.35 (2H, AA'BB', Pyridine-H) and 8.49 (1H, dd, J=8.4, 1.2 Hz, ArH).
¹³C NMR (270 MHz, CDCl₃) δ 28.40 (CH₂), 28.50 (CH₃), 43.54 (CH₂), 44.49 (CH), 79.86 (C), 116.29, 120.19, 121.50, 125.12, 132.42, 137.27, 140.26, 147.55, 149.92 (ArC), 154.67 and 172.61 (C=O).

4-[4-(6-Methylpyridin-3-yloxy)-pyridin-3-ylcarbamoyl]-piperidine-1-carboxylic acid tert-butyl ester (AMR01135, STX1963)

C₂₂H₂₈N₄O₄, MW 412.48

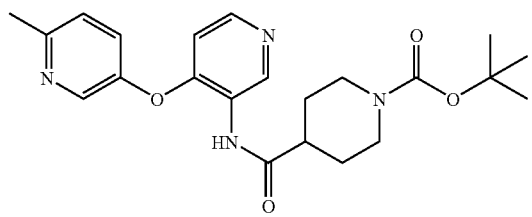

A solution of piperidine-1,4-dicarboxylic acid mono-tert-butyl ester (273 mg, 1.19 mmol) in dry dichloromethane (8 mL) was stirred under nitrogen, and 4-dimethylaminopyridine (DMPA, 40 mg, 0.327 mmol), (1-(3-dimethylaminopropyl)-3-ethylcarbodiimide hydrochloride (EDC, 570 mg, 2.97 mmol) and triethylamine (0.25 mL) were added. The resulting mixture was stirred for 30 min under nitrogen and 4-(6-methylpyridin-3-yloxy)-pyridin-3-ylamine (AMR01122, 200 mg, 0.99 mmol) in dry dichloromethane (4 mL) was added. After stirring at room temperature for 72 h, the mixture was diluted with dichloromethane, washed saturated NaHCO$_3$ (2×25 mL) and brine. The organic layer was dried (MgSO$_4$), filtered and evaporated. Flash chromatography on silica gel of the crude product using DCM/MeOH 95:5 as eluent gave AMR01135 (157 mg, 38%) as a colourless oil.

Rf: 0.6 (DCM/MeOH 9:1)

LC/MS (APCI) t$_r$=3.99 min, m/z 413.59 (M$^+$+H, 100).

HPLC t$_r$=3.63 min (96.22%).

$^1$H NMR (270 MHz, CDCl$_3$) δ 1.40 (9H, s, 3 CH$_3$), 1.66-1.82 (2H, m, CH$_2$), 1.85-1.90 (2H, m, CH$_2$), 2.50 (1H, tt, CH), 2.56 (3H, s, CH$_3$), 2.73 (2H, br t, CH$_2$), 4.11-4.15 (2H, br d, CH$_2$), 6.49 (1H, d, J=5.7 Hz, Pyridine-H), 7.21 (1H, d, J=8.4 Hz, Pyridine-H), 7.30 (1H, dd, J=8.4, 2.5 Hz, Pyridine-H), 7.92 (1H, br s, NH), 8.14 (1H, d, J=5.7 Hz, Pyridine-H), 8.29 (1H, d, J=2.5 Hz, Pyridine-H) and 9.49 (1H, s, Pyridine-H).

$^{13}$C NMR (270 MHz, CDCl$_3$) δ 23.98 (CH$_3$), 28.49 ((CH$_3$)$_3$C), 28.66, 43.06, 43.37 (CH$_2$), 44.41 (CH), 79.88 (C), 109.09, 124.41, 125.39, 128.74, 142.20, 143.40, 146.10, 148.09, 153.30, 154.71 (ArC), 156.43 and 172.85 (C=O).

4-[4-(4-Chloro-phenoxy)-pyridin-3-ylcarbamoyl]-piperidine-1-carboxylic acid tert-butyl ester (AMR01136, STX1984)

C$_{22}$H$_{26}$ClN$_3$O$_4$, MW 431.91

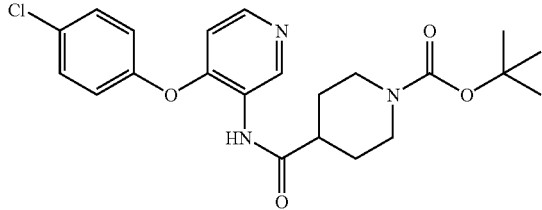

A solution of piperidine-1,4-dicarboxylic acid mono-tert-butyl ester (150 mg, 0.66 mmol) in dry dichloromethane (8 mL) was stirred under nitrogen, and 4-dimethylaminopyridine (DMPA, 40 mg, 0.327 mmol), (1-(3-dimethylaminopropyl)-3-ethylcarbodiimide hydrochloride (EDC, 316 mg, 1.65 mmol) and triethylamine (0.15 mL) were added. The resulting mixture was stirred for 30 min under nitrogen and 4-(4-chlorophenoxy)-pyridin-3-ylamine (AMR01118, 120 mg, 0.55 mmol) in dry dichloromethane (4 mL) was added. After stirring at room temperature for 72 h, the mixture was diluted with dichloromethane, washed saturated NaHCO$_3$ (2×25 mL) and brine. The organic layer was dried (MgSO$_4$), filtered and evaporated. Flash chromatography on silica gel of the crude product using EtOAc as eluent gave AMR01135 (157 mg, 38%) as a white solid, mp 134-136° C.

Rf: 0.35 (EtOAc)

LC/MS (APCI) t$_r$=4.87 min, m/z 434.56 (36), 432.54 (M$^+$+H, 100).

HPLC t$_r$=3.19 min (100%)

$^1$H NMR (270 MHz, CDCl$_3$) δ 1.44 (9H, s, 3 CH$_3$), 1.71-1.81 (2H, m, CH$_2$), 1.89-1.93 (2H, m, CH$_2$), 2.48 (1H, tt, CH), 2.77 (2H, br t, CH$_2$), 4.21 (2H, br d, CH$_2$), 6.55 (1H, d, J=5.7 Hz, Pyridine-H), 7.03 (2H, AA'BB', ArH), 7.40 (2H, AA'BB', ArH), 7.76 (1H, br s, NH), 8.18 (1H, d, J=5.7 Hz, Pyridine-H) and 9.54 (1H, s, Pyridine-H).

$^{13}$C NMR (270 MHz, CDCl$_3$) δ 28.50 (CH$_3$), 28.67, 42.96, 43.20 (CH$_2$), 44.27 (CH), 79.87 (C), 109.49, 122.16, 125.48, 130.59, 131.47, 143.21, 146.11, 152.09, 153.05 (ArC), 154.72 and 172.69 (C=O).

1-{4-[2-(4-Chlorobenzenesulfonyl)-phenylamino]-piperidin-1-yl}-ethanone (AMR01133, STX1961)

C$_{19}$H$_{21}$ClN$_2$O$_3$S, MW 392.90

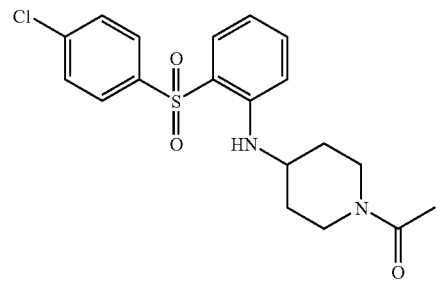

A solution of 1-{4-[2-(4-chloro-phenylsulfanyl)-phenylamino]-piperidin-1-yl}-ethanone (AMR01127, 190 mg, 0.53 mmol) was treated with m-chloroperbenzoic acid (77%, 118 mg, 0.53 mmol) and stirred keeping the temperature between −30 and −10° C. until consumption of the starting material. Then, an additional equivalent of m-chloroperbenzoic acid (118 mg, 0.53 mmol) was added and the mixture stirred for 1 h at the same temperature. The reaction mixture was quenched with saturated NaHCO$_3$ solution. The aqueous layer was washed with DCM (2×20 mL), and the combined organic layers were dried (MgSO$_4$), filtered and evaporated to dryness. Column chromatography on silica gel of the crude product using DCM/MeOH 98:2 as eluent gave 1-{4-[2-(4-chlorobenzenesulfonyl)-phenylamino]-piperidin-1-yl}-ethanone (57 mg, 27%) as an oil.

Rf: 0.64 (DCM:MeOH 9:1)

LC/MS (APCI) t$_r$=4.40 min, m/z 395.40 (40), 393.45 (M$^+$+H, 100).

HPLC t$_r$=2.81 min (99.09%)

$^1$H NMR (270 MHz, CDCl$_3$) δ 1.43 (2H, m, CH$_2$), 1.99 (2H, m, CH$_2$), 2.11 (3H, s, CH$_3$), 3.02 (1H, m, ½CH$_2$), 3.22 (1H, m, ½CH$_2$), 3.53 (1H, m, ½CH$_2$), 3.70 (1H, m, ½CH$_2$), 4.24 (1H, m, CH), 6.25 (1H, d, J=7.2 Hz, NH), 6.66 (1H, d, J=8.4 Hz, ArH), 6.75 (1H, m, ArH), 7.37 (1H, m, ArH), 7.43 (2H, AA'BB', ArH), 7.76 (2H, AA'BB', ArH) and 7.86 (1H, dd, J=7.9, 1.5 Hz, ArH), $^{13}$C NMR (400 MHz, CDCl$_3$) δ 21.46 (CH$_3$), 31.35, 32.02, 39.66, 44.49 (CH$_2$), 48.71 (CH), 112.52, 116.46, 121.05, 128.24, 129.27, 130.68, 135.58, 139.69, 140.04, 145.42 (ArC), and 168.92 (C=O).

Synthesis of STX2050, 2051 and 2531

3-(1-Benzoyl-piperidin-4-ylamino)-N-phenyl-benzamide. HVB01183, STX2050, $C_{25}H_{25}N_3O_2$, MW 399.48

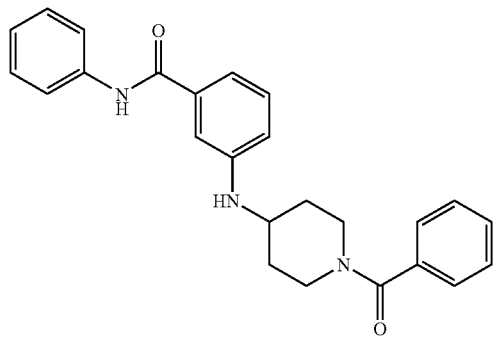

To a solution of 4-aminobenzanilide (0.1 g, 0.47 mmol) and N-benzoyl-4-piperidone (0.192 g, 0.94 mmol) in DCE (2 ml) was added acetic acid (0.24 ml) and sodium triacetoxyborohydride (0.25 g, 1.18 mmol). The resulting reaction mixture was heated in a microwave for 15 minutes at 100° C. NaHCO₃ was then added, and repeatedly extracted with EtOAc. The organic layers were combined and dried (MgSO₄), filtered and evaporated in-vacuo. The crude mixture was purified using flash chromatography (0-100% ethyl acetate in hexane) to afford the title compound as a light brown solid, 40 mg, 21%, R.f. 0.55 (EtOAc), m.p. 198-200° C., LCMS: $t_r$=4.19 min (50% to 95% MeOH in water at 0.5 ml/min to 1.0 ml/min over 5 min), m/z M⁺H 400.50, HPLC: $t_r$=4.69 min (100% MeOH at 0.4 ml/min), 99%, ¹H NMR (CDCl₃, 400 MHz,): δ 1.41-1.50 (2H, m, CH₂), 2.04-2.19 (2H, m, CH₂), 3.14 (2H, br.s, CH₂), 3.63 (1H, s, CH₂), 3.80 (1H, s, CH), 4.00-4.05 (1H, m, CH₂), 4.64 (1H, br.s, NH), 6.60-6.63 (2H, m, ArH), 7.34 (1H, t, J=8.0 Hz, ArH), 7.39-7.47 (5H, m, ArH), 7.60 (2H, d, J=7.6 Hz, ArH), 7.68 (1H, br.s, NHCO), 7.70-7.74 (2H, m, ArH).

¹³C NMR (CDCl₃, 101 MHz, ⁻10° C.): δ 31.8, 32.6, 40.1, 46.4 (CH₂), 49.6 (CH), 112.1, 119.9 (ArCH), 122.7 (ArC), 123.9, 126.7 (ArCH), 126.9 (ArC), 128.5, 128.7, 129.0, 129.8 (ArCH), 135.5, 138.2, 149.4 (ArC), 165.4, 170.4 (CO),

HRMS: Calcd for $C_{25}H_{25}N_3O_2$ (M+H)⁺ 400.2020. found (M+H)⁺ 400.2017.

3-(1-Acetyl-piperidin-4-ylamino)-N-phenyl-benzamide, HVB01186, STX2051, $C_{20}H_{23}N_3O_2$, MW 337.42

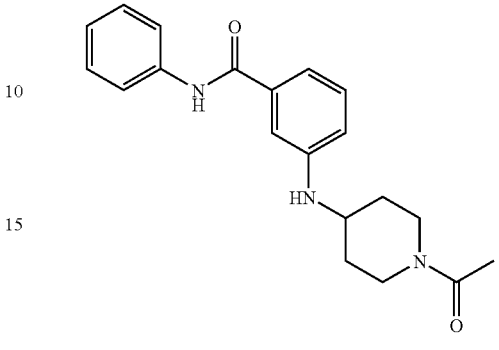

To a solution of 4-aminobenzanilide (0.1 g, 0.47 mmol) and 1-acetyl-4-piperidone (0.12 ml, 0.94 mmol) in DCE (2 ml) was added acetic acid (0.24 ml) and sodium triacetoxyborohydride (0.25 g, 1.18 mmol). The resulting reaction mixture was heated in a microwave for 20 minutes at 120° C. NaHCO₃ was then added, and repeatedly extracted with EtOAc. The organic layers were combined and dried (MgSO₄), filtered and evaporated in-vacuo. The crude mixture was purified using flash chromatography (0-10% MeOH in DCM) to afford the title compound as a light brown solid, 75 mg, 47%, R.f. 0.25 (EtOAc), m.p. 200-201° C., LCMS: $t_r$=3.58 min (50% to 95% MeOH in water at 0.5 ml/min to 1.0 ml/min over 5 min), m/z M⁺H 338.22, HPLC: $t_r$=6.72 min (70% ACN in H₂O, 0.3 ml/min), 97%, ¹H NMR (CDCl₃, 270 MHz,): δ 1.25-1.35 (2H, m, CH2), 2.09 (3H, s, CH3), 2.40-2.47 (1H, m, ½CH2), 2.77-2.86 (1H, m, ½CH2), 3.19-3.23 (1H, m, ½CH2), 3.50-3.60 (1H, m, ½CH2), 3.70-3.91 (2H, m, CH2), 4.05-4.11 (1H, m, ½CH2), 4.45 (1H, br.s, NH), 6.56-6.59 (2H, m, ArH), 7.06-7.11 (1H, m, ArH), 7.29-7.34 (2H, m, ArH), 7.59-7.63 (2H, m, ArH), 7.69-7.73 (2H, m, ArH), 7.88 (1H, br.s, NH), ¹³C NMR (CDCl₃, 68 MHz): δ 21.6 (CH3), 31.9, 32.7, 40.4, 45.1 (CH2), 49.7 (CH), 112.3, 120.2 (ArCH), 124.0 (ArC), 124.1, 129.1, 129.1 (ArCH), 138.5, 149.7 (ArC), 165.5, 169.1.

HRMS: Calcd for $C_{20}H_{23}N_3O_2$ (M+H)⁺ 338.1863. found (M+H)⁺ 338.1868.

N-(2-Nitro-phenyl)-benzamide, HVB01191

$C_{13}H_{10}N_2O_3$, MW 242.23

To a solution of 2-nitroaniline (0.2 g, 1.45 mmol), TEA (0.35 ml) and DMAP (cat.) in DCM (10 ml) at 0° C., was added benzoyl chloride (0.34 ml, 2.9 mmol), and the resulting solution stirred was allowed to warm to r.t. and stirred for 18 h, then heated at reflux for further 18 h. NaHCO₃ was then added, and repeatedly extracted with DCM, then washed with 1M HCl. The organic layers were combined and dried (MgSO₄), filtered and evaporated in-vacuo. The crude mixture was purified using flash chromatography (0-100% DCM in hexane) to afford the title compound as a yellow solid, 0.348 g, 99%, R.f. 0.63 (DCM),
m.p. 87-90° C.,
LCMS: t$_r$=7.48 min (50% to 95% MeOH in water at 0.5 ml/min to 1.0 ml/min over 5 min), m/z M⁺H 243.37,
HPLC: t$_r$=12.23 mm (70% ACN in H₂O, 0.5 ml/min), 77%,
¹H NMR (CDCl₃, 270 MHz,): δ 7.49-7.66 (3H, m, ArH and NH), 7.67-7.74 (1H, m, ArH), 7.97-8.01 (2H, m, ArH), 8.14-8.17 (1H, m, ArH), 8.28 (1H, dd, J=1.5, 8.4 Hz, ArH), 9.01 (1H, dd, J=1.2, 8.4 Hz, ArH).

N-(2-Amino-phenyl)-benzamide, HVB02001

C₁₃H₁₂N₂O, MW 212.25

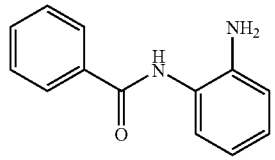

To a stirred solution of iron (0.19 g, 3.41 mmol) and ammonium chloride (0.023 g, 0.43 mmol) in EtOH (5 ml) and H₂O (0.5 ml), N-(2-nitro-phenyl)-benzamide (HVB01191, 0.15 g, 0.62 mmol) was added. This reaction mixture was stirred at reflux for 1.5 h, allowed to cool and the solvent removed in-vacuo. The residue was re-dissolved in DCM (40 ml) and washed with sat. aqueous NaHCO₃ (2×40 ml). The organic layers were dried (MgSO₄), filtered and evaporated in-vacuo to afford the desired product, to afford the desired compound as a brown solid, 0.098 g, 75%.

R.f. 0.25 (1:1, DCM:hexane),
LCMS: t$_r$=3.05 min (50% to 95% MeOH in water at 0.5 ml/min to 1.0 ml/min over 5 min), m/z M⁺H 213.26,
HPLC: t$_r$=6.56 min (100% MeOH at 0.4 ml/min), 97%,
¹H NMR (CDCl₃, 270 MHz,): δ 3.87 (2H, s, NH₂), 6.82-6.87 (2H, m, ArH), 7.07-7.13 (1H, m, ArH), 7.31-7.34 (1H, m, ArH), 7.42-7.59 (3H, m, ArH), 7.81 (1H, br.s, NH), 7.90 (2H, d, J=6.9 Hz, ArH).

2,4-Dichloro-N-(2-nitro-phenyl)-benzamide, HVB01192

C₁₃H₈Cl₂N₂O₃, MW 311.12,

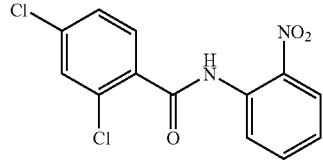

To a solution of 2-nitroaniline (0.2 g, 1.45 mmol) and K₂CO₃ (0.6 g, 4.35 mmol) in DCM (10 ml) at 0° C., was added 2,4-dichlorobenzoyl chloride (0.41 ml, 2.9 mmol), and the resulting solution stirred was allowed to warm to r.t. and stirred for 18 h. NaHCO₃ was then added, and repeatedly extracted with DCM, then washed with 1M HCl. The organic layers were combined and dried (MgSO₄), filtered and evaporated in-vacuo. The crude mixture was purified using flash chromatography (0-10% MeOH in DCM) to afford the title compound as a light brown solid, 0.335 g, 73%, R.f. 0.5 (60% DCM in hexane),
m.p. 138-140° C.,
LCMS: t$_r$=4.81 min (50% to 95% MeOH in water at 0.5 ml/min to 1.0 ml/min over 5 mm), m/z M⁺H 309.32,
HPLC: t$_r$=5.31 min (90% ACN in H₂O, 0.5 ml/min), 89%,
¹H NMR (CDCl₃, 270 MHz,): δ 7.23-7.30 (3H, m, ArH), 7.66-7.76 (2H, m, ArH), 8.26 (1H, dd, J=1.76, 8.67 Hz, ArH), 8.91 (1H, dd, J=1.24, 8.67 Hz, ArH), 10.89 (1H, br. s, NH).

N-(2-Amino-phenyl)-2,4-dichloro-benzamide, HVB02008

C₁₃H₁₀Cl₂N₂O, MW 281.14

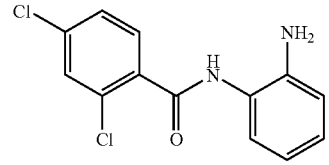

To a stirred solution of iron (0.16 g, 2.8 mmol) and ammonium chloride (0.019 g, 0.72 mmol) in EtOH (5 ml) and H₂O (0.5 ml), 2,4-dichloro-N-(2-nitro-phenyl)-benzamide (HVB01192, 0.16 g, 0.51 mmol) was added. This reaction mixture was stirred at reflux for 2 h, allowed to cool and the solvent removed in-vacuo. The residue was re-dissolved in DCM (40 ml) and washed with sat. aqueous NaHCO₃ (2×40 ml). The organic layers were dried (MgSO₄), filtered and evaporated in-vacuo to afford the desired product, to afford the desired compound as a brown oil, 0.118 g, 83%.

R.f. 0.55 (DCM),
LCMS: t$_r$=3.85 min (50% to 95% MeOH in water at 0.5 ml/min to 1.0 ml/min over 5 min), m/z M⁺H 281.35, 283.37, 285.39,
HPLC: t$_r$=3.66 min (100% MeOH at 0.4 ml/min), 98%,
¹H NMR (CDCl₃, 270 MHz,): δ 3.87 (2H, s, NH2), 6.82-6.89 (2H, m, ArH), 7.08-7.14 (1H, m, ArH), 7.35-7.40 (2H, m, ArH), 7.80 (1H, br.s, NH)

N-[2-(1-Acetyl-piperidin-4-ylamino)-phenyl]-2,4-dichloro-benzamide, HVB02009, STX2531, C₂₀H₂₁Cl₂N₃O₂, MW 406.31

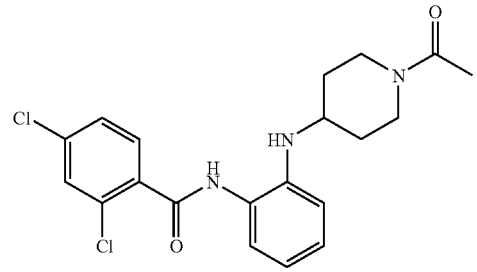

To a solution of N-(2-amino-phenyl)-2,4-dichloro-benzamide (HVB02008, 0.1 g, 0.36 mmol) and 1-acetyl-4-piperidone (0.88 ml, 0.72 mmol) in DCE (2 ml) was added acetic acid (0.19 ml) and sodium triacetoxyborohydride (0.19 g, 0.9 mmol). The resulting reaction mixture was heated in a microwave for 10 minutes at 140° C. NaHCO₃ was then added, and repeatedly extracted with EtOAc. The organic layers were combined and dried (MgSO₄), filtered and evaporated invacuo. The crude mixture was purified using flash chromatography (0-10% MeOH in DCM) to afford the title compound as a cream solid, 61 mg, 42%, R.f. 0.31 (EtOAc),
m.p. 107-109° C.,
LCMS: $t_r$=4.04 min (50% to 95% MeOH in water at 0.5 ml/min to 1.0 ml/min over 5 min), m/z M⁺H 406.42,
HPLC: $t_r$=3.8 min (90% ACN in H₂O, 0.5 ml/min), 99%.

1-(4-(2-Bromophenylamino)piperidin-1-yl)ethanone STX2060

$C_{13}H_{17}N_2O$, MW: 297.19

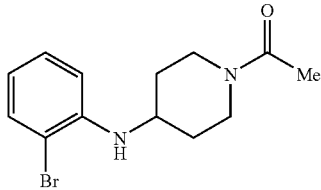

A solution of 2-bromoaniline (1.5 g, 8.72 mmol), 1-acetyl-4-piperidone (2.46 g, 17.4 mmol) and acetic acid (2.62 g, 43.6 mmol) in toluene (17.5 ml), was added to 5 MW tubes which already contained sodium triacetoxyborohydride (5×922 mg, 21.8 mmol). These tubes were then each heated in a CEM discover microwave instrument at 120° C. for 15 mins. The contents of each tube were combined and the mixture was quenched with a saturated aqueous solution of sodium bicarbonate (50 ml) and extracted with ethyl acetate (3×50 ml). The combined organics were dried (MgSO₄), filtered and concentrated in vacuo. Purification by flash chromatography (eluent; hexane to ethyl acetate) afforded the desired product as a low melting pale yellow solid (2.6 g, 100%).

¹H NMR (270 MHz, CDCl₃): δ 1.42-1.46 (2H, m, 2×CH), 1.98-2.25 (5H, s, 2×CH, CH₃), 2.88-2.93 (1H, m, CH), 3.16-3.25 (1H, m, CH), 3.45-3.60 (1H, m, CH), 3.74-3.80 (1H, m, CH), 4.22 (1H, brs, NH), 4.36-4.41 (1H, m, CH), 6.52-6.59 (1H, m, Ar—H), 6.63-6.67 (1H, dd, J=1.2, 8.4 Hz, Ar—H), 7.12-7.18 (1H, m, Ar—H), 7.40-7.43 ppm (1H, dd, J=1.5, 7.9 Hz, Ar—H).

¹³C NMR (CDCl₃, 67.93 MHz): δ 21.5, 30.3, 31.2, 32.0, 32.6, 38.8, 40.3, 43.6, 45.1, 50.1, 69.4, 110.4, 112.1, 118.6, 128.5, 133.5, 143.7, 168.9 ppm including rotomer/alernative conformation.

HPLC: 4.7 min, 95.75% purity (isocratic, 90% acetonitrile: 10% water at 0.5 ml/min).

LCMS: 4.48 min, (95% MeOH: 5% water), M⁺H, 297.10.
General Procedure for the Preparation of Biphenyl Compounds A solution of sodium carbonate (106 mg, 1 mmol) and Pd(OAc)₂ (1 mg, 0.005 mmol) in a mixture of PEG2000: water (1.75 g: 1.5 g) was heated to 50° C. To this solution was added 1-(4-(2-bromophenylamino)piperidin-1-yl)ethanone (149 mg, WBH01157, 0.5 mmol) and boronic acid (0.75 mmol) and the mixture was allowed to stir at 50° C. for 16 h. The mixture was allowed to cool and then extracted with ether (3×15 ml). These combined organics were concentrated in vacuo and subsequently purified by flash chromatography (eluent; hexane:ethyl acetate). The relevant fractions were evaporated in vacuo to afford the title compound.

1-[4-(Biphenyl-2-ylamino)piperidin-1-yl]ethanone STX2038

$C_{19}H_{22}N_2O$, MW: 294.3

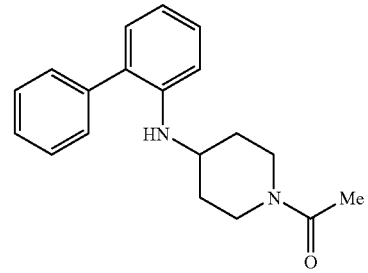

Transparent oil (94.6 mg, 64%).
¹H NMR (CDCl₃, 270 MHz): δ 1.22-1.31 (2H, m, 2×CH), 1.82-2.15 (5H, m, 2×CH, CH₃), 2.83-2.93 (1H, m, CH), 3.10-3.22 (1H, m, CH), 3.46-3.55 (1H, m, CH), 3.65-3.77 (1H, m, CH), 3.84 (1H, br s, NH), 4.25-4.36 (1H, m, CH), 6.73 (1H, d, J=8.2 Hz, Ar—H), 6.77-6.80 (1H, dd, J=1.0, 7.4 Hz, Ar—H), 7.07-7.10 (1H, dd, J=1.7, 7.4 Hz, Ar—H), 7.18-7.25 (1H, m, Ar—H), 7.34-7.44 ppm (5H, m, Ar—H).

¹³C NMR (CDCl₃, 67.93 MHz): δ 21.6, 32.0, 32.7, 40.3, 45.1, 49.8, 111.2, 117.3, 127.5, 128.0, 128.2, 128.8, 129.1, 129.4, 139.3, 143.5, 169.0 ppm LCMS: M⁺H, 295.34
HPLC: 93.1% (4.92 min, isocratic 90% acetonitrile, 10% water at 0.5 ml/min).

1-{4-(4'-Methylbiphenyl-2-ylamino)piperidin-1-yl}ethanone STX2039

$C_{20}H_{24}N_2O$, MW: 308.42

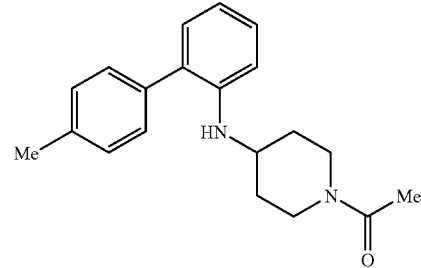

Transparent oil; 108.6 mg, 70%
¹H NMR (CDCl₃, 270 MHz): δ 1.23-1.28 (2H, m, 2×CH), 1.95-2.11 (5H, m, 2×CH, CH₃), 2.39 (3H, s, CH₃), 2.83-2.93 (1H, m, CH), 3.10-3.25 (1H, m, CH), 3.48-3.59 (1H, m, CH), 3.65-3.73 (1H, m, CH), 3.89 (1H, br s, NH), 4.26-4.32 (1H, m, CH), 6.71 (1H, d, J=7.9 Hz, Ar—H), 6.76-6.79 (1H, dd, J=1.2, 7.4 Hz, Ar—H), 7.07-7.10 (1H, dd, J=1.7, 7.4 Hz, Ar—H), 7.18-7.29 ppm (5H, m, Ar—H).

¹³C NMR (CDCl₃, 67.93 MHz): δ 21.3, 21.6, 32.0, 32.7, 40.3, 45.1, 49.8, 111.2, 117.3, 128.0, 128.6, 129.2, 129.8, 130.7, 136.3, 137.2, 143.6, 169.0 ppm LCMS: M⁺H, 309.38
HPLC: 96.93% (5.45 min, isocratic 90% acetonitrile, 10% water at 0.5 ml/min).

1-{4-(4'-Fluorobiphenyl-2-ylamino)piperidin-1-yl}ethanone STX2040

$C_{19}H_{21}FN_2O$, MW: 312.38

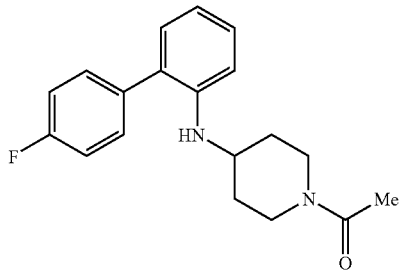

Transparent oil; 108.6 mg, 70%

$^1$H NMR (CDCl$_3$, 270 MHz): δ 1.21-1.31 (2H, m, 2×CH), 1.92-2.12 (5H, m, 2×CH, CH$_3$), 2.80-2.91 (1H, m, CH), 3.10-3.22 (1H, m, CH), 3.46-3.57 (1H, m, CH), 3.67-3.72 (2H, m, NH, CH), 4.28-4.34 (1H, m, CH), 6.70-6.75 (2H, m, 2×Ar—H), 7.11-7.33 ppm (6H, m, 6×Ar—H).

$^{13}$C NMR (CDCl$_3$, 67.93 MHz): δ 21.6, 32.0, 32.8, 40.3, 45.1, 49.9, 111.3, 115.9, 116.2, 117.4, 127.1, 129.0, 130.7, 131.0, 131.1, 135.1, 143.5, 160.3, 164.0, 169.0 ppm (including minor impurities/rotamers)

LCMS: M$^+$H, 313.22

HPLC: 95% (4.345 min, isocratic 90% acetonitrile, 10% water at 0.5 ml/min).

1-{4-[2-(6-Methoxynaphthalen-2-yl)phenylamino]piperidin-1-yl}ethanone STX2042

$C_{24}H_{26}N_2O_2$, MW: 374.48

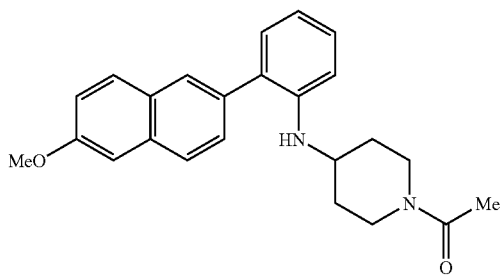

Transparent oil; 59.3 mg, 32%

$^1$H NMR (CDCl$_3$, 270 MHz): δ 1.22-1.30 (2H, m, 2×CH), 1.91-2.16 (5H, m, 2×CH, CH$_3$), 2.81-2.95 (1H, m, CH), 3.10-3.22 (1H, m, CH), 3.46-3.60 (1H, m, CH), 3.61-3.73 (1H, m, CH), 3.94 (4H, br s, OCH$_3$, NH), 4.25-4.31 (1H, m, CH), 6.78 (2H, 'q', J=8.2, 16.6 Hz, 2×Ar—H), 7.13-7.31 (4H, m, 4×Ar—H), 7.44-7.48 (1H, dd, J=1.7, 8.4 Hz, Ar—H), 7.72-7.81 ppm (3H, m, 3×Ar—H).

$^{13}$C NMR (CDCl$_3$, 67.93 MHz): δ 21.6, 32.0, 32.7, 40.3, 45.1, 49.9, 55.5, 105.7, 111.2, 111.9, 117.3, 118.1, 119.4, 127.5, 128.0, 128.8, 129.6, 130.9, 143.7, 158.0, 169.0 ppm (including minor impurities/rotamer)

LCMS: M$^+$H, 375.31

HPLC: 97.62% (16.34 min, isocratic 70% acetonitrile, 30% water at 0.35 ml/min).

1-[4-(2-Naphthalen-1-ylphenylamino)piperidin-1-yl]ethanone STX2043

$C_{23}H_{24}N_2O$, MW: 344.45

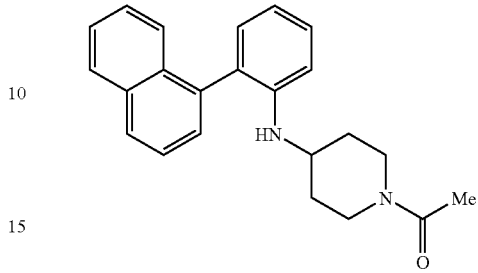

In order to push the reaction to completion, an extra portion of Pd(OAc)$_2$ was added to the reaction mixture after 16 h. This mixture was then left for a further 6 h before working up.

Transparent oil; 40.2 mg, 23%

$^1$H NMR (CDCl$_3$, 270 MHz): δ 1.22-1.29 (2H, m, 2×CH), 1.96-2.11 (5H, m, 2×CH, CH$_3$), 2.88-2.93 (1H, m, CH), 3.10-3.23 (1H, m, CH), 3.49-3.62 (1H, m, CH), 3.65-3.77 (1H, m, CH), 3.88 (1H, br s, NH), 4.25-4.36 (1H, m, CH), 6.76 (1H, d, J=8.2 Hz, Ar—H), 6.81-6.84 (1H, dd, J=1.0, 7.4 Hz, Ar—H), 7.17-7.21 (1H, dd, J=1.7, 7.7 Hz, Ar—H), 7.25-7.27 (1H, m, Ar—H), 7.49-7.54 (3H, m, 3×Ar—H), 7.83-7.92 ppm (4H, m, 4×Ar—H).

$^{13}$C NMR (CDCl$_3$, 67.93 MHz): δ 21.6, 32.0, 32.8, 40.3, 45.1, 49.9, 111.2, 117.5, 126.3-130.9 (9 Ar—CH signals), 132.4, 134.9, 136.7, 143.7, 169.0 ppm.

LCMS: M$^+$H, 345.34

HPLC: 98.24% (6.74 min, isocratic 90% acetonitrile, 10% water at 0.5 ml/min).

1-[4-(4'-Chlorobiphenyl-2-ylamino)piperidin-1-yl]ethanone STX2044

$C_{19}H_{21}ClN_2O$, MW: 328.84

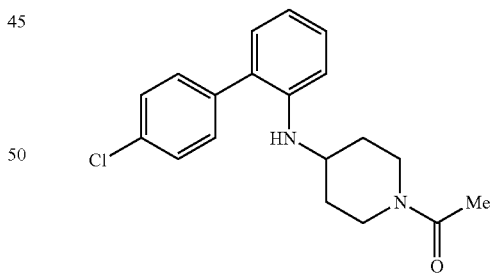

In order to push the reaction to completion, an extra portion of Pd(OAc)$_2$ was added to the reaction mixture after 16 h. This mixture was then left for a further 2 h before working up.

Transparent oil; 108.6 mg, 66%

$^1$H NMR (CDCl$_3$, 270 MHz): δ 1.23-1.31 (2H, m, 2×CH), 1.88-2.10 (5H, m, 2×CH, CH$_3$), 2.78-2.92 (1H, m, CH), 3.10-3.22 (1H, m, CH), 3.43-3.55 (1H, m, CH), 3.68-3.77 (2H, m, NH, CH), 4.29-4.35 (1H, m, CH), 6.73 (1H, d, J=8.2 Hz, Ar—H), 6.77-6.80 (1H, dd, J=1.0, 7.4 Hz, Ar—H), 7.01-7.05 (1H, dd, J=1.5, 7.4 Hz, Ar—H), 7.22-7.46 ppm (5H, m, 5×Ar—H).

$^{13}$C NMR (CDCl$_3$, 67.93 MHz): δ 21.6, 32.0, 32.8, 40.3, 45.1, 49.9, 111.3, 117.5, 126.8, 129.1, 129.3, 130.6, 130.8, 133.4, 137.8, 143.4, 169.0 ppm

LCMS: M$^+$H, 329.22

HPLC: 99% (15.04 min, isocratic 70% acetonitrile, 30% water at 0.35 ml/min).

1-[4-(4'-Methoxybiphenyl-2-ylamino)piperidin-1-yl]ethanone STX2045

C$_{20}$H$_{24}$N$_2$O$_2$, MW: 324.42

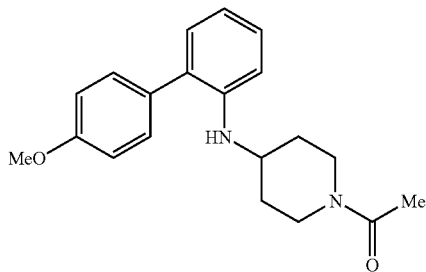

In order to push the reaction to completion, an extra portion of Pd(OAc)$_2$ was added to the reaction mixture after 16 h. This mixture was then left for a further 2 h before working up.

Transparent oil; 103.5 mg, 67%

$^1$H NMR (CDCl$_3$, 270 MHz): δ 1.21-1.31 (2H, m, 2×CH), 1.82-2.21 (5H, m, 2×CH, CH$_3$), 2.83-3.10 (1H, m, CH), 3.17-3.30 (1H, m, CH), 3.45-4.00 (6H, m, 2×CH, NH, OCH$_3$), 4.30-4.50 (1H, m, CH), 6.55-6.92 (2H, m, 2×Ar—H), 6.95-7.48 ppm (6H, m, 6×Ar—H).

$^{13}$C NMR (CDCl$_3$, 67.93 MHz): δ 21.6, 32.0, 32.7, 40.3, 45.1, 49.8, 55.4, 111.1, 111.9, 114.5, 117.3, 118.1, 128.0, 128.5, 130.5, 130.7, 131.4, 132.5, 143.7, 158.9, 169.0 ppm

LCMS: M$^+$H, 325.32

HPLC: 91% (4.68 min, isocratic 70% acetonitrile, 30% water at 0.3 ml/min).

1-[4-(3'-Chlorobiphenyl-2-ylamino)piperidin-1-yl]ethanone STX2046

C$_{19}$H$_{21}$ClN$_2$O, MW: 328.84

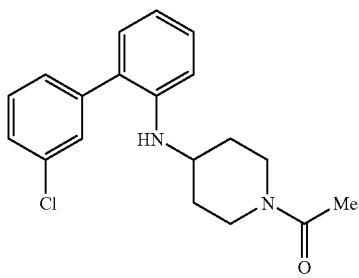

In order to push the reaction to completion, an extra portion of Pd(OAc)$_2$ was added to the reaction mixture after 16 h. This mixture was then left for a further 2 h before working up.

Transparent oil; 121.3 mg, 74%

$^1$H NMR (CDCl$_3$, 270 MHz): δ 1.21-1.34 (2H, m, 2×CH), 1.82-2.26 (5H, m, 2×CH, CH$_3$), 2.81-2.91 (1H, m, CH), 3.18-3.23 (1H, m, CH), 3.48-3.55 (1H, m, CH), 3.70 (2H, 'd', J=13.9 Hz, NH, CH), 4.32 (1H, 'd', J=13.6 Hz, CH), 6.71 (1H, d, J=7.9 Hz, Ar—H), 6.75-6.78 (1H, dd, J=1.0, 7.4 Hz, Ar—H), 7.03-7.06 (1H, dd, J=1.5, 7.4 Hz, Ar—H), 7.22-7.38 ppm (5H, m, 5×Ar—H).

$^{13}$C NMR (CDCl$_3$, 67.93 MHz): δ 21.6, 32.0, 32.8, 40.3, 45.1, 49.9, 111.4, 117.4, 126.6, 127.4, 127.6, 129.3, 129.6, 130.3, 130.6, 134.9, 141.2, 143.4, 169.0 ppm

LCMS: M$^+$H, 329.22

HPLC: 99.65% (14.87 min, isocratic 70% acetonitrile, 30% water at 0.35 ml/min).

1-[4-(3'-Hydroxybiphenyl-2-ylamino)piperidin-1-yl]ethanone STX2059

C$_{19}$H$_{22}$N$_2$O$_2$, MW: 310.39

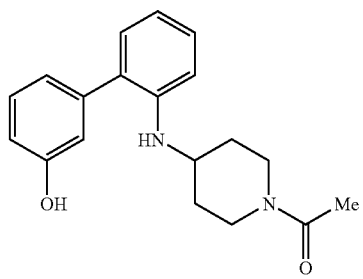

Transparent oil; 93.7 mg, 60%

$^1$H NMR (CDCl$_3$, 270 MHz): δ 1.24-1.36 (2H, m, 2×CH), 1.93-2.12 (5H, m, 2×CH, CH$_3$), 2.87-3.00 (1H, m, CH), 3.12-3.24 (1H, m, CH), 3.46-3.72 (2H, m, 2×CH), 3.85-3.96 (1H, m, NH), 4.18-4.29 (1H, m, CH), 6.54-6.60 (1H, m, Ar—OH), 6.69 (1H, d, J=8.4 Hz, Ar—H), 6.74-6.85 (1H, m, Ar—H), 6.87-6.92 (2H, m, 2×Ar—H), 7.07-7.10 (1H, dd, J=1.5, 7.4 Hz, Ar—H), 7.17-7.32 ppm (3H, m, 3×Ar—H).

LCMS: M$^+$H, 311.52

HPLC: 95.76% (7.32 min, isocratic 70% acetonitrile, 30% water at 0.3 ml/min).

Alternative General Procedure for the Preparation of Biaryl Compounds

To a solution of 1-(4-(2-bromophenylamino)piperidin-1-yl)ethanone (97 mg, WBH01149/157, 0.33 mmol), boronic acid (0.49 mmol) and sodium carbonate (70 mg, 0.66 mmol) in a mixture of 1:1 toluene:water (4 ml) was added Pd(PPh$_3$)$_4$ (19 mg, 0.017 mmol). This mixture was then heated in a CEM discover microwave instrument at 150° C. for 10 min. Analysis by TLC indicated that the reaction hadn't reached completion, therefore, further Pd(PPh$_3$)$_4$ (19 mg, 0.017 mmol) was added. This mixture was again heated in the CEM MW at 150° C. for 5 min. The organics were added directly onto a flash chromatography column and purification then proceeded (eluant; Hex:EtOAc 1:1). The relevant fractions were evaporated in vacuo to afford the desired product as a transparent oil. As a further and necessary purification step, ethereal HCl (0.23 ml, 2M in ether, 0.45 mmol) was slowly added to a stirred solution of the product in ether. This provided a white precipitate, which was then centrifuged for 10 min. The mother liquor was decanted and the obtained white solid was washed with cold ether (3×2 ml). The white solid was dried under nitrogen to afford the title compound as the desired product.

1-{4-(5'-Chloro-2'-methoxybiphenyl-2-ylamino)
piperidin-1-yl}ethanone hydrochloride STX2041

$C_{20}H_{24}Cl_2N_2O_2$, MW: 395.32

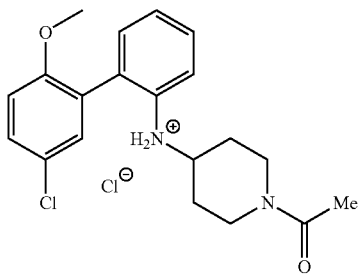

68.2 mg, 52%

Very broad due to HCl salt, however, $^1$H NMR (CDCl$_3$, 270 MHz): δ 1.58-1.96 (3H, m, 3×CH), 2.02 (3H, s, CH$_3$), 2.10-2.49 (1H, m, CH), 2.71-2.93 (1H, m, CH), 3.12-3.30 (1H, m, CH), 3.72-3.87 (1H, m, CH), 3.95 (3H, s, OMe), 4.51-4.68 (1H, m, CH), 7.02-7.11 (1H, m, Ar—H), 7.30-7.72 (6H, m, 6×Ar—H), 8.08-8.22 ppm (1H, m, NH).

LCMS: M$^+$H, 313.6

HPLC: 91.16% (3.73 mins, isocratic 90% acetonitrile, 10% water at 0.8 ml/min).

1-{4-(3'-Acetylbiphenyl-2-ylamino)piperidin-1-
yl}ethanone hydrochloride STX2047

$C_{21}H_{25}ClN_2O_2$, MW: 372.89

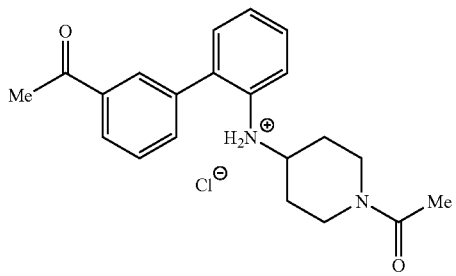

36.7 mg, 32%

$^1$H NMR (CDCl$_3$, 270 MHz): δ 1.42-1.60 (2H, m, 2×CH), 1.75-2.03 (5H, m, 2×CH, CH$_3$), 2.67 (1H, s, CH$_3$), 2.85-2.90 (1H, m, CH), 3.11-3.22 (1H, m, 2×CH), 3.47 (1H, br s, CH), 3.69 (1H, d, J=13.9 Hz, CH), 4.42 (1H, d. J=12.4 Hz, CH), 7.01-7.80 (5H, m, ArH), 7.99-8.05 ppm (2H, m, ArH).

LCMS: M$^+$H, 337.66

HPLC: 93.22% (6.404 mins, isocratic 70% acetonitrile, 30% water at 0.5 ml/min).

1-[4-(2'-Phenoxybiphenyl-2-ylamino)piperidin-1-yl]
ethanone hydrochloride STX2048

$C_{25}H_{26}N_2O_2$, MW: 386.49

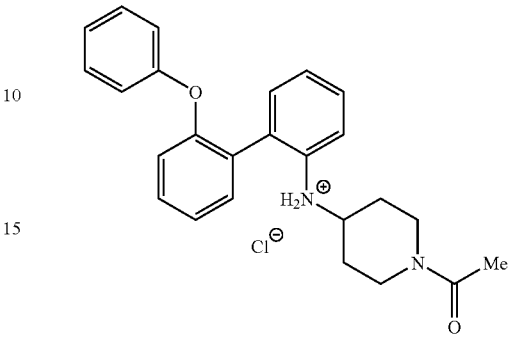

To a solution of 1-(4-(2-bromophenylamino)piperidin-1-yl)ethanone (97 mg, WBH01149, 0.33 mmol), 2-phenoxyphenyl boronic acid (105 mg, 0.49 mmol) and sodium carbonate (70 mg, 0.66 mmol) in a mixture of 1:1 toluene:water (4 ml) was added Pd(PPh$_3$)$_4$ (19 mg, 0.017 mmol). This mixture was then heated in a CEM discover microwave instrument at 150° C. for 10 min. Analysis by TLC indicated that the reaction hadn't reached completion, therefore, further Pd(PPh$_3$)$_4$ (19 mg, 0.017 mmol) was added. This mixture was again heated in the CEM MW at 150° C. for 5 min. This mixture was then diluted with water (10 ml) and extracted with EtOAc (3×10 ml). The combined organics were dried (MgSO$_4$), filtered and concentrated in vacuo. Purification by flash chromatography then proceeded (eluant; Hex:EtOAc 1:1) and the relevant fractions were evaporated in vacuo to afford the desired product as a transparent oil (41.4 mg, 33%). As a further and necessary purification step, ethereal HCl (0.23 ml, 2M in ether, 0.45 mmol) was slowly added to a stirred solution of the product in ether. This provided a white precipitate, which was then centrifuged for 10 min. The mother liquor was decanted and the obtained white solid was washed with cold ether (3×2 ml). The white solid was dried under nitrogen to afford the title compound as the desired product (11.8 mg, 9%).

LCMS: M$^+$H, 387.65 (1.38 min, 95% MeOH and 5% Water at 1.0 ml/min).

HPLC: 84.14% purity (4.92 min, isocratic 70% MeOH, 30% water at 0.5 ml/min).

1-{4-[2-(Thiophen-3-yl)phenylamino]piperidin-1-
yl}ethanone WBH01166A $C_{17}H_{21}ClN_2OS$, MW: 336.88

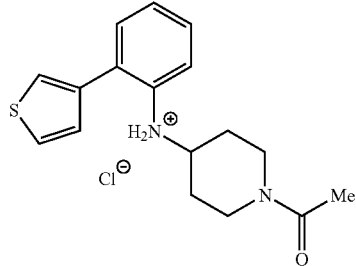

To a solution of 1-(4-(2-bromophenylamino)piperidin-1-yl)ethanone (97 mg, WBH01157, 0.33 mmol), boronic acid (0.49 mmol) and sodium carbonate (70 mg, 0.66 mmol) in a mixture of 1:1 toluene:water (4 ml) was added Pd(PPh$_3$)$_4$ (19 mg, 0.017 mmol). This mixture was then heated in a CEM discover microwave instrument at 150° C. for 10 min. Analysis by TLC indicated that the reaction hadn't reached completion, therefore, further Pd(PPh$_3$)$_4$ (19 mg, 0.017 mmol) was added. This mixture was again heated in the CEM MW at 150° C. for 5 min. The organics were added directly onto a flash chromatography column and purification then proceeded (eluant; Hex:EtOAc 1:1). The relevant fractions were evaporated in vacuo to afford the desired product as a transparent oil. As a further and necessary purification step, ethereal HCl (0.23 ml, 2M in ether, 0.45 mmol) was slowly added to a stirred solution of the product in ether. This provided a white precipitate, which was then centrifuged for 10 min. The mother liquor was decanted and the obtained white solid was washed with cold ether (3×2 ml). The white solid was dried under nitrogen to afford the title compound as the desired product. 54.9 mg, 49%

LCMS: M$^+$H, 301.26

HPLC: 74% (10.17 mins, isocratic 70% acetonitrile, 30% water at 0.35 ml/min).

Synthetic Route to STX2279

1-Acetyl-N-(2-bromophenyl)piperidine-4-carboxylate
WBH01129

C$_{14}$H$_{17}$BrN$_2$O$_2$, MW: 325.2

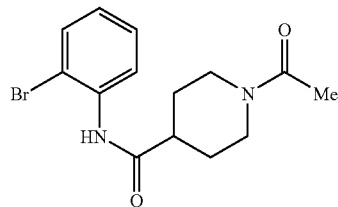

A solution of 2-bromoaniline (552 mg, 3.21 mmol), 1-acetylpiperidine-4-carboxylic acid (604 mg, WBH01127, 3.53 mmol), EDC (1.85 g, 9.63 mmol), triethylamine (1.62 g, 16.05 mmol) and DMAP (39 mg, 0.32 mmol) in DCM (100 ml) was stirred at room temperature for 24 h. HOBT (cat.) was then added and the mixture was stirred for a further 4 days. The reaction mixture was then washed with 2.5M NaOH (15 ml), then 2M HCl (15 ml) and the organics were dried (MgSO$_4$), filtered and concentrated in vacuo. Purification by flash chromatography then proceeded (eluent; hexane to ethyl acetate) to afford the desired product (110 mg, 11%).

$^1$H NMR (270 MHz, CDCl$_3$): δ 1.50-2.15 (6H, m, 3×CH, CH$_3$), 2.48-2.81 (2H, m 2×CH), 3.09-3.19 (1H, m, CH), 3.90 (1H, d, J=13.4 Hz, CH), 4.10 (1H, q, J=7.2, 14.3 Hz, CH), 4.62 (1H, d, J=13.1 Hz, CH), 4.22 (1H, brs, NH), 6.97 (1H, t, J=7.7 Hz, Ar—H), 7.51 (1H, d, J=8.2 Hz, Ar—H), 7.72 (1H, brs, NH), 8.27 ppm (1H, d, J=8.2 Hz, Ar—H).

1-Acetyl-N-(2-biphenyl)piperidine-4-carboxylate
STX2279

C$_{20}$H$_{22}$N$_2$O$_2$, MW: 322.4

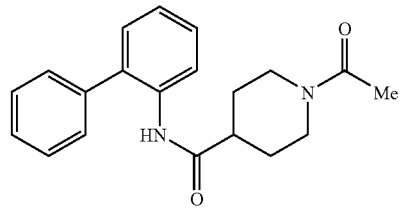

To a solution of 1-acetyl-N-(2-bromophenyl)piperidine-4-carboxylate (110 mg, WBH01129, 0.34 mmol), phenyl boronic acid (62 mg, 0.51 mmol) and sodium carbonate (72 mg, 0.68 mmol) in a 1:1 mixture of toluene and water (4 ml), was added Pd(PPh$_3$)$_4$. This mixture was then heated in a CEM discover microwave instrument at 150° C. for 10 min. This mixture was then diluted with water (10 ml) and extracted with EtOAc (2×10 ml). The combined organics were dried (MgSO$_4$), filtered and concentrated in vacuo. Purification by flash chromatography was then attempted, however, this was unsuccessful. Therefore, recrystallisation from hexane:ethyl acetate proceeded to afford the desired compound as a white solid (25 mg, 23%).

$^1$H NMR (270 MHz, CDCl$_3$): δ 1.42-1.90 (4H, m, 2×CH$_2$), 2.05 (3H, s, CH$_3$), 2.18-2.32 (1H, m, CH), 2.55-2.65 (1H, m, CH), 2.98-3.08 (1H, m, CH), 3.79 (1H, d, J=13.6 Hz, CH), 4.48 (1H, d, J=13.6 Hz, CH), 67.08-7.51 (9H, m, ArH, NH), 8.22 ppm (1H, d, J=8.2 Hz, Ar—H).

$^{13}$C NMR (CDCl$_3$, 67.93 MHz): δ 21.5, 28.3, 28.8, 40.8, 43.8, 45.8, 121.8, 124.7, 128.3, 128.6, 129.2, 129.3, 130.2, 132.5, 134.1, 138.1, 169.0, 171.8 ppm.

LCMS: M$^+$H, 323.24 (3.860 min, 50% MeOH and 50% Water at 0.5 ml/min-Gradient for 5 mins to −95% MeOH and 5% Water at 1.0 ml/min)

HPLC: 98.47% (3.8 min, isocratic 90% acetonitrile, 10% water at 0.5 ml/min).

Route to STX2049

2-(4-Chlorophenoxy)-5-fluorobenzenamine

C$_{12}$H$_9$ClFNO, MW: 237.66

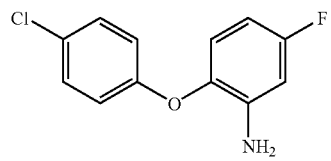

A solution of 4-chlorophenol (1 g, 7.78 mmol), 2,5-difluoronitrobenzene (829 mg, 5.21 mmol) and potassium carbonate (1.29 g, 9.34 mmol) in DMF (5 ml) was stirred at reflux for 6 h. The reaction mixture was allowed to cool and then redissolved in 2.5M NaOH (10 ml). This aqueous mixture was then extracted with ethyl acetate (3×15 ml) and the combined organics were dried (MgSO$_4$), filtered and concentrated in vacuo. An ethyl acetate solution of the crude material was filtered through a pad of silica which upon evaporation in vacuo afforded 2-(4-chlorophenoxy)-4-methyl-1-nitrobenzene as a yellow oil (1.04 g). This oil was then dissolved in 10:1 EtOH:H₂O (10 ml) and added to a refluxing solution of iron powder (1.45 g, 26.05 mmol) and ammonium chloride (195 mg, 2.74 mmol) in 10:1 EtOH:H₂O (20 ml). Stirring at this temperature continued for a further 2 h, before the reaction mixture was allowed to cool. The mixture was then filtered through a pad of celite, which was further washed with ethyl acetate (250 ml). Concentration in vacuo followed by purification by flash chromatography (eluant: 8:2 to 1:1 hexane:ethyl acetate) afforded the title compound as a pale yellow solid (1.28 g, 95%).

¹H NMR (270 MHz, CDCl₃): δ 3.85 (2H, br s, NH₂), 6.36-6.40 (1H, m, Ar—H), 6.49-6.54 (1H, dd, J=2.9, 9.9 Hz, Ar—H), 6.77-6.96 (3H, m, Ar—H), 7.21-7.29 ppm (2H, m, Ar—H).

1-{4-[2-(4-Chlorophenoxy)-5-fluorophenylamino] piperidin-1-yl}ethanone hydrochloride STX2049

$C_{19}H_{21}Cl_2FN_2O_2$, MW: 399.29

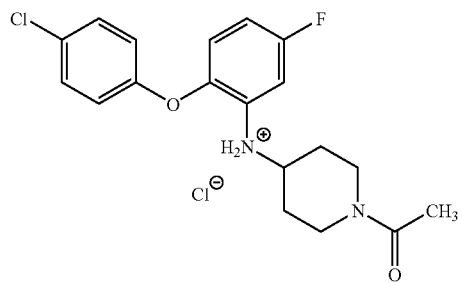

To a solution of 2-(4-chlorophenoxy)-5-fluorobenzenamine (100 mg, 0.42 mmol), N-acetyl-4-piperidone (118 mg, 0.84 mmol) and acetic acid (126 mg, 2.10 mmol) in DCE (4 ml), was added sodium triacetoxyborohydride (223 mg, 1.05 mmol). This mixture was then allowed to stir at room temperature for 16 h. The reaction was then quenched with a saturated aqueous solution of sodium bicarbonate (5 ml) and extracted with DCM (3×5 ml). The combined organics were then dried (MgSO₄), filtered and concentrated in vacuo. Purification by flash chromatography (eluent: hexane to ethyl acetate) then proceeded and the relevant fractions evaporated in vacuo to provide the desired compound as a transparent oil (51.5 mg, 34%). In order to further purify the desired compound, ethereal HCl (0.23 ml, 2 M in ether, 0.46 mmol) was slowly added to a solution of the product in ether (2 ml). Upon addition a white solid precipitated, which was then centrifuged for 10 min. The liquor was decanted and the white sediment washed with cold ether (2×2 ml). The white solid was dried under nitrogen to afford the title compound (47.5 mg, 28%).

Since the ¹H NMR broadened quite considerably for the HCl salt, the NMR data provided is for the free base:

¹H NMR (270 MHz, CDCl₃): δ 1.23-1.40 (2H, m, 2×CH), 1.98-2.10 (5H, s, 2×CH, CH₃), 2.78-2.88 (1H, m, CH), 3.14-3.22 (1H, m, CH), 3.43-3.46 (1H, m, CH), 3.72-3.84 (1H, m, CH), 4.05-4.09 (1H, m, NH), 4.37-4.43 (1H, m, CH), 6.19-6.35 (1H, m, Ar—H), 6.40-6.46 (1H, dd, J=2.9, 10.9 Hz, Ar—H), 6.73-6.78 (1H, dd, J=5.5, 8.7 Hz, Ar—H), 6.80-6.85 (2H, m, 2×Ar—H), 7.20-7.25 ppm (2H, m, Ar—H).

LCMS: M⁺H, 363.54

HPLC: 95.81% (3.84 mins, isocratic 90% acetonitrile, 10% water at 0.8 ml/min).

Route to 2-Substituted Piperidine Derivitives

Preparation of 2-Substituted N—BOC Piperidones

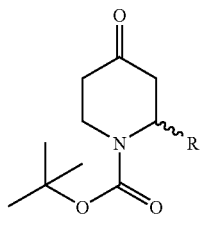

General Procedure

To a solution of 4-methoxypyridine (5 g, 45.82 mmol) in THF (90 ml) was slowly added phenyl chloroformate (7.25 g, 43.28 mmol) at −25° C. After stirring at this temperature for 1 h, the relevant Grignard reagent (48.11 mmol) was slowly added and stirring continued for a further 18 h. The reaction was quenched with water (50 ml) and extracted with diethyl ether (2×75 ml). The organics were dried (MgSO₄), filtered and concentrated in vacuo. The crude material was re-dissolved in THF (75 ml) and cooled to −40° C. To this solution was added potassium t-butoxide (20.57 g, 183.28 mmol) with stirring continuing at this temperature for 2 h. The mixture was allowed to warm to room temperature and stirred for a further 2 h before quenching with water (50 ml). Extraction with diethyl ether (3×50 ml) then proceeded and the combined organics were dried (MgSO₄), filtered and concentrated in vacuo.

The crude material was re-dissolved in AcOH (150 ml) and to this was added Zn powder (10 eq.). This mixture was stirred at room temperature for 18 h before being filtered through a pad of celite, which was washed through with ethyl acetate (250 ml). The combined organics were evaporated in vacuo with purification by flash chromatography then proceeding (eluant; 9:1 hexane:ethyl acetate).

t-Butyl-2-butyl-4-oxopiperidine-1-carboxylate $C_{14}H_{25}NO_3$, Mol. Wt.: 255.35

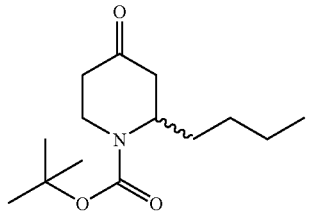

Pale yellow oil, 5.53 g, 47% (over 4 steps=83% per step).

¹H NMR: (CDCl₃, 270 MHz): δ 0.86 (3H, t, J=7.2 Hz, CH₃), 1.16-1.4 (6H, m, 3×CH₂), 1.45 (9H, s, C(CH₃)₃), 2.22-2.31 (2H, m, 2×CH), 2.39-2.52 (1H, m, CH), 2.58-2.66 (1H, m, CH), 3.07-3.18 (1H, m, CH), 4.33 (1H, br s, CH), 4.56 ppm (1H, br s, CH).

t-Butyl-2-phenyl-4-oxopiperidine-1-carboxylate

C$_{16}$H$_{21}$NO$_3$, Mol. Wt.: 275.34

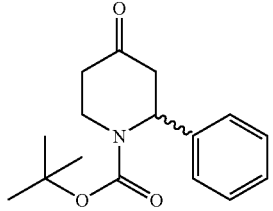

Pale yellow oil, 4.2 g, 33% (over 4 steps=76% per step).

$^1$H NMR: (CDCl$_3$, 270 MHz): δ 1.46 (9H, s, C(CH$_3$)$_3$), 2.30-2.39 (1H, m, CH), 2.46-2.58 (1H, m, CH), 2.78-3.00 (2H, m, 2×CH), 3.07-3.22 (1H, m, CH), 4.18-4.29 (1H, m, CH), 5.71 (1H, br s, CH), 7.20-7.35 ppm (5H, m, 5×ArH).

WBH02093: t-Butyl-2-methyl-4-oxopiperidine-1-carboxylate

C$_{11}$H$_{19}$NO$_3$, Mol. Wt.: 213.27

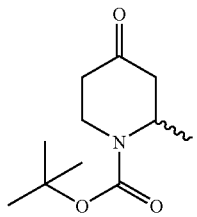

Pale yellow oil, 1.55 g, 17% (over 4 steps=64% per step).

$^1$H NMR: (CDCl$_3$, 270 MHz): Took straight through to next stage.

t-Butyl-2-i-propyl-4-oxopiperidine-1-carboxylate

C$_{13}$H$_{23}$NO$_3$, Mol. Wt.: 241.33

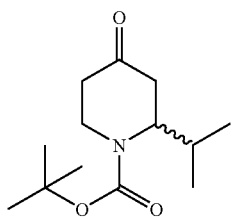

Pale yellow oil, 3.45 g, 33% (over 4 steps=76% per step).

$^1$H NMR: (CDCl$_3$, 270 MHz): Took straight through to next stage.

Preparation of 2-substituted N-acetyl piperidones

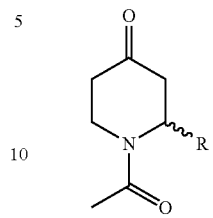

General Procedure

To a solution of the 2-substituted N—BOC piperidone in DCM (0.15 M) was added TFA (2 ml per mmol) at 0° C. This solution was allowed to stir for 1 h before being poured on to solid potassium carbonate (~25 eq.). This mixture was dissolved in water and extracted with diethyl ether (×3). The combined organics were dried (MgSO$_4$), filtered and concentrated in vacuo. The crude material was re-dissolved in DCM and cooled to 0° C. and to this was added triethylamine (3 eq.) followed by acetyl chloride (2 eq.). After stirring for 14 h, the reaction was quenched with a saturated aqueous solution of sodium bicarbonate and extracted with ethyl acetate (×3). The combined organics were dried (MgSO$_4$), filtered and concentrated in vacuo. Purification by flash chromatography (eluant; hexane:ethyl acetate) then proceeded to afford the desired product as a pale yellow oil.

N-Acetyl-2-phenyl-4-oxopiperidine-1-carboxylate

C$_{13}$H$_{15}$NO$_2$, Mol. Wt.: 217.26

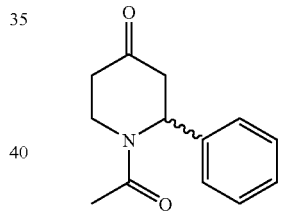

Pale yellow oil, 634 mg, 80% (over 2 steps=93% per step).

$^1$H NMR: (CDCl$_3$, 400 MHz): δ 2.18 (1.1H, s, CH$_3$), 2.25 (1.9H, s, CH$_3$), 2.38 (0.37H, s, CH), 2.42 (0.63H, s, CH), 2.47-2.55 (1H, m, CH), 2.78-2.93 (1H, m, CH), 3.00 (0.63H, s, CH), 3.04 (0.37H, s, CH), 3.26-3.33 (1H, m, CH), 3.84-3.87 (0.63H, m, CH), 4.57-4.60 (0.37H, m, CH), 5.37 (0.37H, s, CH), 6.37 (0.63H, d, J=5.6 Hz, CH), 7.21-7.39 ppm (5H, m, 5×ArH).

WBH02075: N-Acetyl-2-butyl-4-oxopiperidine-1-carboxylate

C$_{11}$H$_{19}$NO$_2$, Mol. Wt.: 197.27

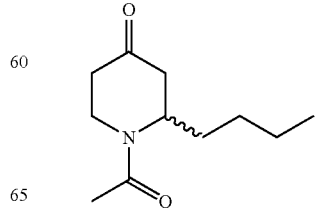

Pale yellow oil, 531 mg, 70% (over 2 steps=89% per step).
$^1$H NMR: (CDCl$_3$, 270 MHz): δ 0.86 (3H, q, J=7.2, 14.1 Hz, CH$_3$), 1.08-1.38 (4H, m, 2×CH$_2$), 1.39-1.60 (2H, m, CH$_2$), 2.18 (3H, s, CH$_3$), 2.29-2.50 (3H, m, 3×CH), 2.52-2.66 (1H, m, CH), 2.88-2.93 (0.5H, m, CH), 3.40-3.46 (0.5H, m, CH), 3.90-4.00 (0.5H, m, CH), 4.16-4.24 (0.5H, m, CH), 4.82-4.90 (0.5H, m, CH), 5.05-5.14 ppm (0.5H, m, CH).

N-Acetyl-2-methyl-4-oxopiperidine-1-carboxylate

C$_8$H$_{13}$NO$_2$, Mol. Wt.: 155.19

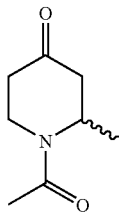

Pale yellow oil, 215 mg, 19% (over 2 steps=44% per step).
$^1$H NMR: (CDCl$_3$, 270 MHz): δ 1.11-1.28 (3H, m, CH$_3$), 2.17 (3H, s, CH$_3$), 2.22-2.56 (3H, m, 3×CH), 2.60-2.71 (1H, m, CH), 3.07-3.18 (0.5H, m, CH), 3.53-3.63 (0.5H, m, CH), 3.86-3.96 (0.5H, m, CH) 4.38-4.50 (0.5H, m, CH) 4.70-4.84 (0.5H, m, CH), 5.10-5.24 ppm (0.5H, m, CH).

N-Acetyl-2-i-propyl-4-oxopiperidine-1-carboxylate

C$_{10}$H$_{17}$NO$_2$, Mol. Wt.: 183.25

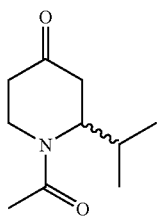

Pale yellow oil, 483 mg, 40% (over 2 steps=63% per step).
$^1$H NMR: (CDCl$_3$, 270 MHz): δ 0.75-1.10 (6H, m, CH(CH$_3$)$_2$), 1.62-1.88 (1H, m, CH), 2.18-2.20 (3H, m, CH$_3$), 2.30-2.65 (4H, m, 4×CH), 2.78-2.89 (0.5H, td, J=3.9, 4.2, 13.4 Hz, CH), 3.36-3.43 (0.5H, m, CH), 3.70-3.75 (0.5H, m, CH), 3.94-4.02 (0.5H, m, CH) 4.69-4.75 (0.5H, m, CH), 4.90-4.95 ppm (0.5H, m, CH).

General Procedure for the Microwave-Assisted Preparation of the Final Piperidine Compounds.

To a solution of 2-(4-chlorophenoxy)benzenamine (100 mg, 0.46 mmol), the relevant N-Acetyl-2-substituted-4-piperidone (0.92 mmol) and sodium triacetoxyborohydride (241 mg, 1.14 mmol) in DCE (1.5 ml) in a MW tube, was added acetic acid (83 mg, 1.38 mmol). The MW tube was sealed and heated at 140° C. for 10 mins in a CEM discover MW instrument. The reaction was quenched with a saturated aqueous solution of sodium bicarbonate (10 ml) and extracted with ethyl acetate (3×10 ml). The combined organics were dried (MgSO$_4$), filtered and concentrated in vacuo. Purification by flash chromatography (eluant: hexane:ethyl acetate) then proceeded to provide the desired compound.

1-(4-(2-(4-Chlorophenoxy)phenylamino)-2-phenylpiperidin-1-yl)ethanone STX2419

C$_{25}$H$_{25}$ClN$_2$O$_2$, Mol. Wt.: 420.93

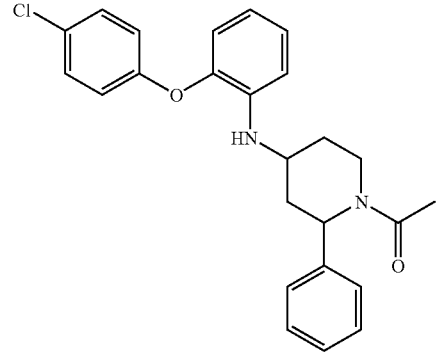

Yellow oil, 41.3 mg, 21%
$^1$H NMR: (CDCl$_3$, 270 MHz): δ 1.55-1.76 (2H, m, 2×CH), 2.10 (1.5H, s, CH$_3$), 2.23 (1.5H, s, CH$_3$), 2.69-2.82 (2H, m, CH), 3.12-3.22 (0.5H, m, CH), 3.37-3.48 (0.5H, m, CH), 3.52-3.62 (0.5H, m, CH), 3.75 (0.5H, 'd', J=14.1 Hz, CH), 3.87-4.02 (0.5H, br s, CH), 4.74 (0.5H, 'd', J=13.9 Hz, CH), 5.17-5.23 (0.5H, m, CH), 6.13-6.14 (0.5H, m, CH), 6.57-6.68 (2H, m, Ar—H), 6.79 (1H, d, J=7.9 Hz, Ar—H), 6.87 (2H, d, J=7.7 Hz, Ar—H), 7.00 (1H, 'q', J=6.7, 13.9 Hz, Ar—H), 7.19-7.46 ppm (7H, m, Ar—H).
$^{13}$C NMR (CDCl$_3$, 67.93 MHz): δ 21.6, 21.8, 32.5, 33.5, 34.5, 36.2, 37.4, 42.0, 45.8, 45.9, 50.6, 56.2, 112.2, 112.3, 117.5, 118.8, 119.6, 125.3, 125.8, 126.1, 126.5, 127.6, 128.0, 129.0, 129.4, 129.8, 138.2, 138.8, 143.1, 156.1, 167.3 ppm.
HPLC: 2.355 min, 96.2% purity, (isocratic, 90% acetonitrile: 10% water at 1.0 ml/min)
LCMS: 1.623 min, (95% MeOH: 5% water at 1.0 ml/min), ES$^-$: 419.42.

1-(4-(2-(4-Chlorophenoxy)phenylamino)-2-n-butylpiperidin-1-yl)ethanone STX2420 C$_{23}$H$_{29}$ClN$_2$O$_2$, Mol. Wt.: 400.94

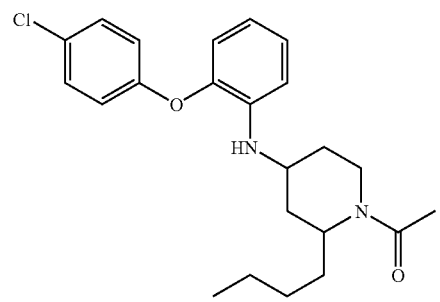

Yellow oil, 101.5 mg, 55%
$^1$H NMR: (CDCl$_3$, 270 MHz): δ 0.77-0.89 (3H, m, CH$_3$), 1.1-2.00 (10H, m, 10×CH), 2.03-2.09 (3H, m, CH$_3$), 2.57-2.74 (1H, m, CH), 3.10-3.50 (1H, m, CH), 3.70 (1H, br s, CH), 4.21 (1H, br s, NH), 4.64-4.67 (0.5H, m, CH), 4.98-5.04 (0.5H, m, CH), 6.62-6.69 (2H, m, ArH), 6.83-6.87 (3H, m, ArH), 7.03-7.07 (1H, m, ArH), 7.21-7.25 ppm (2H, m, Ar—H).

HPLC: 3.11 min, 93% purity, (isocratic, 90% acetonitrile: 10% water at 1.5 ml/min)

LCMS: 5.92 min, (95% MeOH: 5% water at 1.0 ml/min), AP⁻: 399.15.

1-(4-(2-(4-Chlorophenoxy)phenylamino)-2-iso-propylpiperidin-1-yl)ethanone

STX2523

$C_{22}H_{27}ClN_2O_2$, Mol. Wt.: 386.91

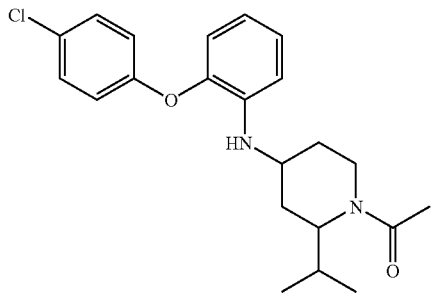

Yellow oil, 65.5 mg, 37%

$^1$H NMR: (CDCl$_3$, 270 MHz): δ 0.71 (1.4H, d, J=6.7 Hz, CH$_3$), 0.78 (1.4H, d, J=6.5 Hz, CH$_3$), 0.85 (0.2H, d, J=6.7 Hz, CH$_3$), 1.3-2.17 (8H, m, CH$_3$, CH, 2×CH$_2$), 2.53-2.69 (0.5H, m, CH), 3.08-3.51 (1.5H, m, CH), 3.58-3.74 (1H, m, CH), 4.10 (0.67H, br s, NH), 4.28 (0.33H, br s, NH), 4.37-4.55 (0.38H, m, CH), 4.68-4.71 (0.24H, m, CH), 4.97-5.04 (0.38H, m, CH), 6.62-6.69 (2H, m, ArH), 6.83-6.89 (3H, m, ArH), 7.04-7.10 (1H, td, J=1.5, 7.7 Hz, ArH), 7.20-7.25 ppm (2H, m, Ar—H).

HPLC: 2.58 min, 94% purity, (isocratic, 90% acetonitrile: 10% water at 1.5 ml/min)

LCMS: 1.34 min, (95% MeOH: 5% water at 1.0 ml/min), AP⁻: 384.98.

1-(4-(2-(4-Chlorophenoxy)phenylamino)-2-iso-propylpiperidin-1-yl)ethanone WBH02097

$C_{20}H_{23}ClN_2O_2$, Mol. Wt.: 358.86

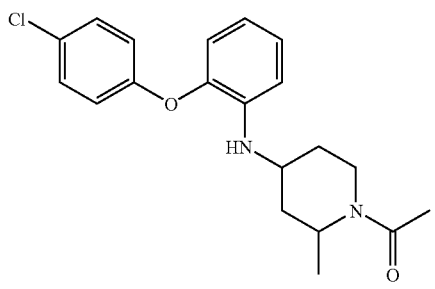

Yellow oil, 77 mg, 47%

HPLC: 2.15 min, 83% purity, (isocratic, 90% acetonitrile: 10% water at 1.5 ml/min)

LCMS: 1.23 min, (95% MeOH: 5% water at 1.0 ml/min), A⁻: 356.89.

Route to WBH02142

N-(3,3-Diethoxypropyl)acetamide WBH02111

$C_9H_{19}NO_3$, Mol. Wt.: 189.25

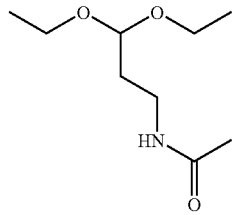

To a solution of 1-amino-3,3-diethoxypropane (5 g, 33.95 mmol) in DCM (250 ml) at 0° C., was added triethylamine (5.15 g, 50.95 mmol) followed by acetyl chloride (2.93 g, 37.35 mmol). This mixture was allowed to warm to room temperature and stirred for 14 h. The reaction was quenched with a saturated aqueous solution of sodium bicarbonate (100 ml) and extracted with DCM (3×75 ml). The combined organics were dried (MgSO$_4$), filtered and concentrated in vacuo to afford the desired product as a transparent oil (6.11 g, 95%).

$^1$H NMR (270 MHz, CDCl$_3$): δ 1.20 (6H, t, J=6.9 Hz, 2×CH$_3$), 1.79 (2H, q, J=7.4, 11.0 Hz, CH$_2$), 1.93 (3H, s, CH$_3$), 3.32 (2H, q, J=7.4, 11.0 Hz, CH$_2$), 3.42-3.53 (2H, m, CH$_2$), 3.60-3.71 (2H, m, CH$_2$), 4.54 (1H, t, J=5.2 Hz, CH), 6.15 ppm (1H, br s, NH).

N-Allyl-N-(2-formylethyl)acetamide WBH02114

$C_8H_{13}NO_2$, Mol. Wt.: 155.19

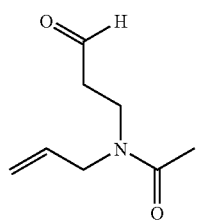

To a solution of N-(3,3-diethoxypropyl)acetamide (6.11 g, 32.28 mmol) in THF (200 ml), was slowly added n-BuLi (18.5 ml, 1.92 M in hexanes, 35.51 mmol) at −78° C. and this mixture was allowed to stir at this temperature for 1 h. Allyl bromide (19.53 g, 161.4 mmol) was then slowly added and the reaction mixture was allowed to warm to room temperature and stirred for 14 h. The reaction was quenched with water (75 ml) and extracted with diethyl ether (3×75 ml) and the combined organics were dried (MgSO$_4$), filtered and concentrated in vacuo to afford the crude acetal as a pale yellow oil (5.1615 g, 70%). This crude mixture was re-dissolved in THF (100 ml) and to this was added 2 M HCl (10 ml). This mixture was allowed to stir at room temperature for 16 h before water (25 ml) was added. Extraction with diethyl ether then proceeded and the combined organics were dried (MgSO4), filtered and concentrated in vacuo. Purification by flash chromatography followed (eluent; 20:80 hexane:ethyl acetate) to give the desired product as a transparent oil (1.6203 g, 46%).

$^1$H NMR (270 MHz, CDCl$_3$): δ 2.05 (3H, s, CH$_3$), 2.72-2.80 (2H, m, CH$_2$), 3.60 (2H, t, J=6.4 Hz, CH$_2$), 3.92 (2H, d, J=4.7 Hz, CH$_2$), 5.08-5.26 (2H, m, HC=CH$_2$), 5.68-5.85 (1H, m, HC=CH$_2$), 9.77 ppm (1H, t, J=0.5 Hz, COH).

N-(3-(2-(4-Chlorophenoxy)phenylamino)hex-5-enyl)-N-allylacetamide WBH02142

$C_{23}H_{27}ClN_2O_2$, Mol. Wt.: 398.93

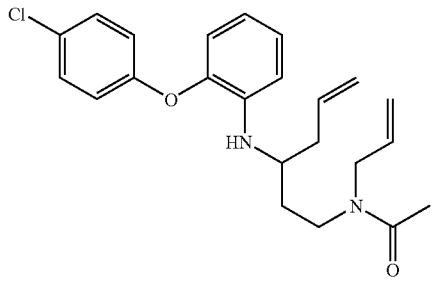

To a solution of N-allyl-N-(2-formylethyl)acetamide (455 mg, 2.93 mmol) and $MgSO_4$ (3.526 g, 29.3 mmol) in DCM (20 ml), was added 2-(4-chlorophenoxy)benzenamine (644 mg, 2.93 mmol) and this mixture was allowed to stir at room temperature for 48 h. The reaction mixture was filtered and the residue washed with further portions of DCM (30 ml). The combined organics were then concentrated in vacuo before 525 mg (1.47 mmol) was re-dissolved in THF (15 ml). To this solution was added $BF_3.OEt_2$ (209 mg, 1.47 mmol) followed by allylmagnesium bromide (4.40 ml, 1.0 M in THF, 4.40 mmol) at 0° C. This mixture was allowed to stir at this temperature for 16 h before being purified by flash chromatography (eluent; hexane:ethyl acetate). The relevant fractions were concentrated in vacuo to afford the desired product as a yellow/orange oil (46.1 mg, 8%).

LCMS: ES⁻: 397.20 (1.38 min, 95% MeOH and 5% Water at 1.0 ml/min).
Routes to WBH02154 and WBH02155

$N^1$-Methyl-$N^1$-phenylbenzene-1,2-diamine WBH02151

$C_{13}H_{14}N_2$, Mol. Wt.: 198.26

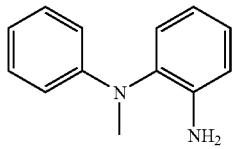

A solution of N-methylaniline (3 g, 28.0 mmol), 2-fluoronitrobenzene (2.65 g, 18.76 mmol) and potassium carbonate (4.64 g, 33.6 mmol) in DMF (20 ml) was stirred at reflux for 3.5 h. The reaction mixture was allowed to cool and then re-dissolved in 2.5M NaOH (25 ml). This aqueous mixture was then extracted with ethyl acetate (3×30 ml) and the combined organics were dried ($MgSO_4$), filtered and concentrated in vacuo. An ethyl acetate solution of the crude material was filtered through a pad of silica which upon evaporation in vacuo afforded 2-(4-chlorophenoxy)-4-methyl-1-nitrobenzene as a yellow oil (4.7 g). This oil was then dissolved in 10:1 $EtOH:H_2O$ (20 ml) and added to a refluxing solution of iron powder (6.32 g, 113.25 mmol) and ammonium chloride (771 mg, 14.41 mmol) in 10:1 $EtOH:H_2O$ (100 ml). Stirring at this temperature continued for a further 2 h, before the reaction mixture was allowed to cool. The mixture was then filtered through a pad of celite, which was further washed with ethyl acetate (250 ml). Concentration in vacuo followed by purification by flash chromatography (eluant: 8:2 to 1:1 hexane:ethyl acetate) afforded the title compound as a pale yellow oil (656 mg, 18%).

$^1$H NMR (270 MHz, $CDCl_3$): δ 2.83 (3H, s, $CH_3$), 3.70 (2H, br s, $NH_2$), 6.60-6.66 (3H, m, ArH), 6.67-6.74 (2H, m, ArH), 6.89-7.02 (1H, m, ArH), 7.16-7.25 ppm (3H, m, Ar—H).

$N^1$-Benzyl-$N^1$-methylbenzene-1,2-diamine WBH02152

$C_{14}H_{16}N_2$, Mol. Wt.: 212.29

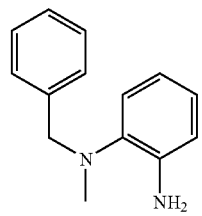

A solution of N-benzylmethylaniline (3 g, 24.76 mmol), 2-fluoronitrobenzene (2.34 g, 16.59 mmol) and potassium carbonate (4.10 g, 29.71 mmol) in DMF (20 ml) was stirred at reflux for 3.5 h. The reaction mixture was allowed to cool and then re-dissolved in 2.5M NaOH (25 ml). This aqueous mixture was then extracted with ethyl acetate (3×30 ml) and the combined organics were dried ($MgSO_4$), filtered and concentrated in vacuo. An ethyl acetate solution of the crude material was filtered through a pad of silica which upon evaporation in vacuo afforded 2-(4-chlorophenoxy)-4-methyl-1-nitrobenzene as a yellow oil (3.7 g). This oil was then dissolved in 10:1 $EtOH:H_2O$ (20 ml) and added to a refluxing solution of iron powder (4.7 g, 84.0 mmol) and ammonium chloride (572 mg, 10.69 mmol) in 10:1 $EtOH:H_2O$ (100 ml). Stirring at this temperature continued for a further 2 h, before the reaction mixture was allowed to cool. The mixture was then filtered through a pad of celite, which was further washed with ethyl acetate (250 ml). Concentration in vacuo followed by purification by flash chromatography (eluant: 8:2 to 1:1 hexane:ethyl acetate) afforded the title compound as a pale yellow oil (1.69 g, 48%).

$^1$H NMR (270 MHz, $CDCl_3$): δ 2.56 (3H, s, $CH_3$), 4.00 (2H, s, $CH_2$), 4.06 (2H, br s, $NH_2$), 6.70-6.77 (2H, m, ArH), 6.89-6.97 (1H, m, ArH), 7.01-7.04 (1H, dd, J=1.5 Hz, ArH), 7.22-7.35 ppm (5H, m, Ar—H).

General Procedure for the Microwave-Assisted Preparation of Final Amines.

To a solution of the relevant aniline (1.5 mmol), N-Acetyl-4-piperidone (424 mg, 3.0 mmol) and sodium triacetoxyborohydride (795 mg, 3.75 mmol) in DCE (3.0 ml) in a MW tube, was added acetic acid (270 mg, 4.5 mmol). The MW tube was sealed and heated at 140° C. for 10 mins in a CEM discover MW instrument. The reaction was quenched with a saturated aqueous solution of sodium bicarbonate (10 ml) and extracted with ethyl acetate (3×10 ml). The combined organics were dried ($MgSO_4$), filtered and concentrated in vacuo. Purification by flash chromatography (eluant: hexane:ethyl acetate) then proceeded to provide the desired compound.

189

1-(4-(2-(N-phenyl-N-Methylamino)phenylamino) piperidin-1-yl)ethanone WBH02154

C$_{20}$H$_{25}$N$_3$O, Mol. Wt.: 323.43

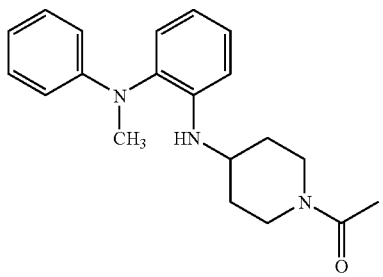

Transparent oil, (316 mg, 65%).

$^1$H NMR (270 MHz, CDCl$_3$): δ 1.61-1.67 (2H, m, 2×CH), 1.98-2.12 (5H, m, CH$_3$, 2×CH), 2.50-2.59 (1H, m, CH), 2.74 (3H, s, CH$_3$), 3.08-3.23 (2H, m, CH), 3.72-3.95 (2H, m, NH, CH), 4.73-4.80 (1H, m, CH), 6.58-6.82 (4H, m, ArH), 6.93-7.01 (1H, m, ArH), 7.20-7.31 ppm (4H, m, Ar—H).

LCMS: ES$^+$: 323.88 (1.13 min, 95% MeOH and 5% Water at 1.0 ml/min).

1-(4-(2-(N-Benzyl-N-methylamino)phenylamino) piperidin-1-yl)ethanone WBH02155 C$_{21}$H$_{27}$N$_3$O, Mol. Wt.: 337.46

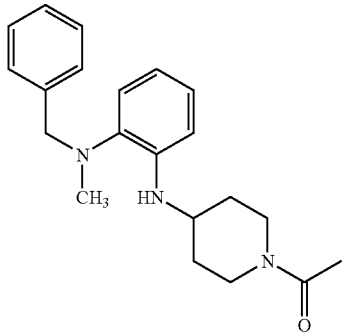

Transparent oil (378 mg, 75%).

$^1$H NMR (270 MHz, CDCl$_3$): δ 1.30-1.45 (2H, m, 2×CH), 1.98-2.15 (5H, m, CH$_3$, 2×CH), 2.54 (3H, s, CH$_3$), 2.90-3.01 (1H, m, CH), 3.16-3.27 (1H, m, CH), 3.46-3.52 (1H, m, CH), 3.67-3.78 (1H, m, CH), 3.90 (2H, s, CH$_2$), 4.29-4.38 (1H, m, CH), 4.85-4.88 (1H, m, NH), 6.62-6.65 (1H, dd, J=1.2, 7.9 Hz, ArH), 6.67-6.71 (1H, dd, J=1.5, 7.7 Hz, ArH), 6.98-7.09 (2H, m, ArH), 7.23-7.35 ppm (5H, m, Ar—H).

$^{13}$C NMR (CDCl$_3$, 67.93 MHz): 621.6, 32.2, 32.9, 40.3, 41.0, 45.1, 49.5, 60.6, 110.4, 116.7, 121.1, 125.2, 127.3, 128.5, 128.5, 138.9, 139.7, 141.9, 169.0 ppm.

LCMS: ES$^+$: 338.05 (1.37 min, 95% MeOH and 5% Water at 1.0 ml/min).

190

1-(4-(2-(N-Phenylamino)phenylamino)piperidin-1-yl)ethanone WBH02156

C$_{19}$H$_{23}$N$_3$O, Mol. Wt.: 309.41

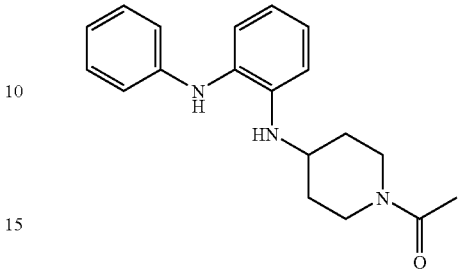

Transparent oil (344 mg, 74%).

$^1$H NMR (270 MHz, CDCl$_3$): δ 1.28-1.41 (2H, m, 2×CH), 1.98-2.12 (5H, m, CH$_3$, 2×CH), 2.82-2.92 (1H, m, CH), 3.13-3.23 (1H, m, CH), 3.47-3.56 (1H, m, CH), 3.69-3.75 (1H, m, CH), 4.06-4.12 (1H, m, NH), 4.30-4.38 (1H, m, CH), 5.04 (1H, s, NH), 6.66-6.74 (4H, m, ArH), 6.78-6.84 (1H, m, ArH), 7.06-7.22 ppm (4H, m, Ar—H).

$^{13}$C NMR (CDCl$_3$, 67.93 MHz): 621.5, 32.1, 32.8, 40.3, 45.1, 49.7, 111.6, 115.3, 117.6, 119.6, 125.7, 126.4, 128.5, 129.4, 142.5, 142.7, 168.9 ppm.

LCMS: ES$^+$: 310.02 (1.01 min, 95% MeOH and 5% Water at 1.0 ml/min).

1-(4-(2-(4-Chloro)-(N-phenylamino)phenylamino) piperidin-1-yl)ethanone

WBH02157

C$_{19}$H$_{22}$ClN$_3$O, Mol. Wt.: 343.85

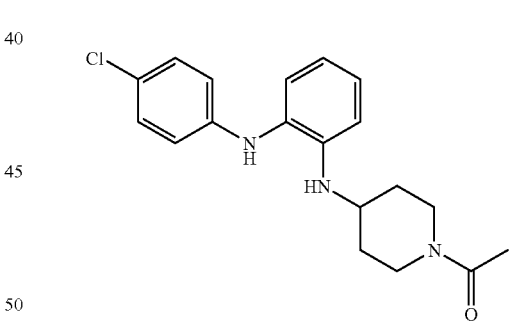

Pale yellow solid, (364 mg, 71%).

$^1$H NMR (270 MHz, CDCl$_3$): δ 1.20-1.40 (2H, m, 2×CH), 1.98-2.10 (5H, m, CH$_3$, 2×CH), 2.82-2.90 (1H, m, CH), 3.13-3.23 (1H, m, CH), 3.47-3.56 (1H, m, CH), 3.69-3.75 (1H, m, CH), 4.06-4.10 (1H, m, NH), 4.34-4.41 (1H, m, CH), 5.10 (1H, s, NH), 6.55-6.60 (2H, m, ArH), 6.65-6.69 (1H, dd, J=1.2, 7.4 Hz, ArH), 6.72 (1H, d, J=7.2 Hz, ArH), 7.05-7.14 ppm (4H, m, Ar—H).

$^{13}$C NMR (CDCl$_3$, 67.93 MHz): δ 21.5, 21.6, 30.2, 31.2, 32.1, 32.9, 38.8, 40.3, 43.6, 45.2, 49.7, 69.3, 11.7, 116.3, 117.6, 124.0, 125.9, 126.8, 127.9, 129.2, 142.7, 144.5, 169.0 ppm, signals for other rotomer also reported.

LCMS: ES$^+$: 343.97 (1.12 min, 95% MeOH and 5% Water at 1.0 ml/min).

1-(4-(2-Phenethylphenylamino)piperidin-1-yl)ethanone WBH02153

$C_{21}H_{26}N_2O$, Mol. Wt.: 322.44

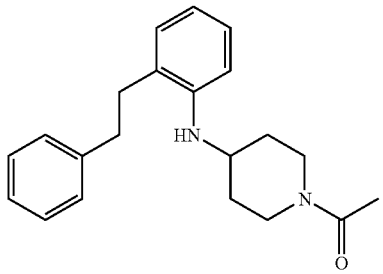

A solution of 1-(4-(2-bromophenylamino)piperidin-1-yl)ethanone (100 mg, 0.34 mmol), styrene (44 mg, 0.43 mmol), Pd(OAc)$_2$ (4 mg, 0.017 mmol) and tri-o-tolyl phosphine (21 mg, 0.07 mmol) in triethylamine (1 ml) was heated at 150° C. for 3 min in a CEM discover MW instrument. The reaction mixture was diluted with diethyl ether, filtered and concentrated in vacuo. Purification by flash chromatography then proceeded (eluent; hexane:ethyl acetate) and the relevant fractions evaporated in vacuo. This product was then re-dissolved in ethyl acetate (5 ml) and to this was added 10% Pd/C (cat.). This mixture was then stirred under a hydrogen balloon for 18 h. The reaction mixture was filtered through a pad of celite and washed with further ethyl acetate (10 ml). The organics were evaporated in vacuo to afford the desired product (14 mg, 13%).

LCMS: ES$^+$: 323.13 (1.22 min, 95% MeOH and 5% Water at 1.0 ml/min).

3-Phenylamino-propionic acid (CMS02025)
$C_9H_{11}NO_2$, Mol. Wt.: 165.19

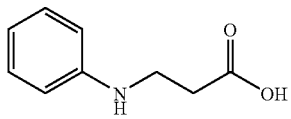

To a solution of acrylic acid (36 mL, 0.5 moles), copper(I) iodide (0.2 g) and copper(II) acetate (0.2 g) in water (28 mL) was added aniline (93 mL, 2 eq.) and the mixture was heated at reflux for 16 hours. After cooling to room temperature the reaction was quenched by the cautious addition of 30% NaOH solution (2×100 mL). The phases were separated and the organic portion extracted with 2M NaOH solution (2×100 mL). The combined aqueous fractions were washed with ethyl acetate (2×100 mL) then acidified with conc. HCl solution. This was back extracted with ethyl acetate (2×200 mL) and these combined organic portions washed with water (2×100 mL) and brine (100 mL) then dried and evaporated onto silica. Purification by column chromatography using 50% ethyl acetate/hexanes as eluent gave a crystalline solid (41 g, 50%).

M.p. 58.4-60.2° C.

$^1$H NMR (270 MHz, CDCl$_3$) δ 2.66 (2H, t, J=6.3 Hz, 2-CH$_2$), 3.45 (2H, t, J=6.3 Hz, 3-CH$_2$), 6.64 (2H, d, J=7.4 Hz, 2' and 5'-CH), 6.75 (1H, t, J=7.4 Hz, 4'-CH), 7.19 (2H, t, J=7.4 Hz, 3' and 4'-CH) and 7.71 (2H, br s, +NH$_2$);

2,3-Dihydro-1H-quinolin-4-one (CMS02026)
$C_9H_9NO$, Mol. Wt.: 147.17

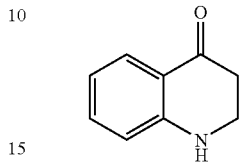

3-Phenylamino-propionic acid (40 g, 0.24 moles) and polyphosphoric acid (40 g) were heated at 100° C. for 1 hour. After cooling to 75° C., 2M NaOH solution (2×200 mL) was added with sonication of the reaction mixture at each addition to dissolve the viscous mass. The combined aqueous portions were basified to pH 12 with NaOH pellets and extracted with ethyl acetate (2×200 mL). The organics were washed with water (2×200 mL) and brine (2×200 mL) then dried, filtered and evaporated under reduced pressure to give a crude product which was purified by column chromatography using 20-50% ethyl acetate/hexanes as eluent to give the desired product (13.25 g, 37%) as a thick orange oil. Repeated chromatography failed to give a product with >95% purity, therefore Isolated as 1-Acetyl-2,3-dihydro-1H-quinolin-4-one $^1$H NMR (270 MHz, CDCl$_3$) δ 2.68 (2H, t, J=7.2 Hz, 3-CH$_2$), 3.45 (2H, t, J=7.2 Hz, 2-CH$_2$), 4.40 (1H, br s, NH); 6.65 (1H, d, J=7.2 Hz, 8-CH), 6.72 (1H, dt, J=7.2 Hz and 1.0 Hz, 6-CH), 7.28 (1H, dt, J=7.2 Hz and 1.5 Hz, 7-CH) and 7.83 (1H, dd, J=7.2 Hz and 1.5 Hz, 5-CH);

1-Acetyl-2,3-dihydro-1H-quinolin-4-one (CMS02027)
$C_{11}H_{11}NO_2$, Mol. Wt.: 189.21

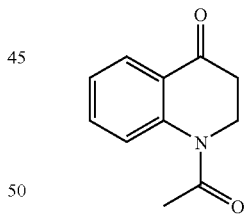

To a solution of 2,3-Dihydro-1H-quinolin-4-one (4.0 g, 27.2 mmol) in THF (100 mL) was added acetic anhydride (2.67 mL, 1.1 eq) and the mixture heated at reflux for 16 hours. After cooling to room temperature and removal of the volatile solvent the crude residue was redissolved in ethyl acetate (100 mL) then washed with 2M NaOH solution (2×100 mL), water (2×100 mL), and brine (100 mL). After drying and evaporation onto silica, purification by column chromatography using 50% ethyl acetate/hexanes as eluent gave the desired compound (3.05 g, 59%) which showed;

m.p. 88.0-91.6° C. Lit. m.p. 93° C. (J. Chem. Soc.; 1050; 1130.);

$^1$H NMR (270 MHz, CDCl$_3$) δ 2.33 (3H, s, N—Ac), 2.79 (2H, t, J=6.2 Hz, 3-CH$_2$), 4.24 (2H, t, J=6.2 Hz, 2-CH$_2$), 7.27 (1H, dt, J=8.0 and 1.8 Hz, 6 (7)-CH), 7.37-7.50 (1H, br s, 8-CH), 7.55 (1H, dt, J=8.0 and 1.8 Hz, 7 (6)-CH) and 8.00 (1H, dd, J=7.8 and 2.1 Hz, 6-CH);

$^{13}$C NMR (100 MHz, CDCl$_3$) δ 23.10 (CH$_3$), 39.50 (2×CH$_2$), 124.09 and 125.60 (both Ar—CH), 126.7 (Ar—C), 127.75 and 134.01 (both Ar—CH), 143.91 (Ar—C), 169.36 (amide C═O) and 194.00 (ketone C═O);

1-Acetyl-{4-[2-(4-Chloro-phenoxy)-phenylamino]-3,4-dihydro-2H-quinoline (CMS02020, STX2138).
C$_{23}$H$_{21}$ClN$_2$O$_2$, Mol. Wt.: 392.88

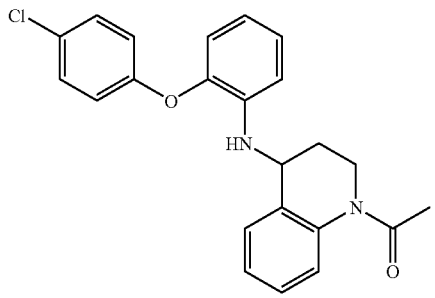

To a mixture of 1-Acetyl-2,3-dihydro-1H-quinolin-4-one (0.155 g, 0.82 mmol) and 2-(4-chlorophenoxy)-aniline (0.35 g, 1.6 mmol, 2 eq.) in toluene (10 mL) was added chlorotriisopropoxytitanium(IV) (0.4 mL, 2 eq.) and the resulting deep orange solution stirred at room temperature overnight. Saturated NaHCO$_3$ solution (10 mL) was added and the phases separated. The organic layer was separated dried over anhydrous magnesium sulphate then filtered and evaporated. The residue was re-dissolved in THF (25 mL) and cooled to 0° C. under nitrogen. A solution of succinic acid (0.189 g, 1.6 mmol) in THF (5 mL) was added followed by 1M borane tetrahydrofuran complex (1.6 mL, 2.eq.). The reaction was allowed to warm to room temperature before the addition of saturated NaHCO$_3$ solution (100 mL). The volatile solvent was removed under reduced pressure then ethyl acetate (100 mL) was added and the layers separated. The organic layer was dried, evaporated and then purified by column chromatography (flashmasterII, 50 g column) using 0-30% ethyl acetate/hexanes as eluent to give the desired product (0.246 g, 76%) as a pale yellow foam which showed;

$^1$H NMR (270 MHz, CD$_3$OD) δ 1.80-2.00 (1H, m, 3-CH), 2.24 (3H, s, CH$_3$), 2.20-2.35 (1H, m, 3-CH), 3.40-3.55 (1H, m, 2-CH), 4.05-4.25 (1H, m, 3-CH), 4.30-4.40 (1H, m, NH), 4.40-4.50 (1H, m, 4-CH), 6.69 (1H, dt, J=7.4 and 1.5 Hz), 6.77 (1H, dd, J=8.2 and 1.5 Hz), 6.83-6.94 (4H, m), 7.01-7.17 (2H, m) and 7.21-7.30 (6H, m);

$^{13}$C NMR (67.9 MHz, CDCl$_3$) δ 23.22 (CH$_3$), 31.24 (CH$_2$), 49.26 (CH), 60.39 (CH$_2$), 122.25, 117.65 and 118.69 (all Ar—CH), 118.80 (2×Ar—CH), 119.56, 124.61, 125.40, 125.54 and 127.59 (all Ar—CH), 127.90 (C), 129.79 (2×Ar—CH), 138.16, 139.11, 142.92, 156.06, and 170.08 (all C);

LRMS (AP$^+$) m/z 391.56 ((M−H)$^+$, 100%);

LC/MS (AP$^+$) t$_r$=1.41 min (>99%), m/z 391.56 (M−H)$^+$;

HPLC t$_r$=6.79 min (100%).

1-BOC-2,3-dihydro-1H-quinolin-4-one (CMS02028)
C$_{14}$H$_{17}$NO$_3$, Mol. Wt.: 247.29

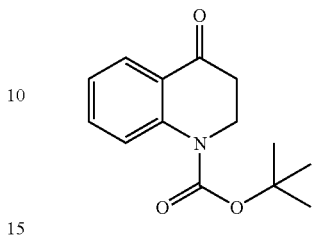

To a solution of 2,3-Dihydro-1H-quinolin-4-one (8.0 g, 54.4 mmol) in THF (200 mL) was added di-tert-butyl dicarbonate (13.0 g, 1.1 eq) and the mixture heated at reflux for 16 hours. After cooling to room temperature and removal of the volatile solvent the crude residue was redissolved in ethyl acetate (100 mL) then washed with 2M NaOH solution (2×100 mL), water (2×100 mL), and brine (100 mL). After drying and evaporation onto silica, purification by column chromatography using 50% ethyl acetate/hexanes as eluent gave the desired compound (10.42 g, 78%) which showed;
m.p. 83-84° C.

$^1$H NMR (270 MHz, CDCl$_3$) δ 1.54 (9H, s, 3×CH$_3$), 2.76 (2H, t, J=6.3 Hz, 3-CH$_2$), 4.15 (2H, t, J=6.3 Hz, 2-CH$_2$), 7.14 (1H, dt, J=8.0 and 0.6 Hz, 6-Ar—CH), 7.48 (1H, dt, J=7.6 and 1.8 Hz, 7-Ar—CH), 7.73 (1H, dd, J=8.0 and 0.6 Hz, 8-Ar—CH) and 7.97 (1H, dd, J=7.7 and 1.8 Hz, 5-Ar—CH);

$^{13}$C NMR (67.9 MHz, CDCl$_3$) δ 28.38 (3×CH$_3$), 39.10 and 44.39 (both CH$_2$), 82.49 (C), 123.80 and 123.97 (both Ar—CH), 124.92 (C), 127.41 and 134.06 (both Ar—CH), 144.22 (C) and 194.38 (C═O);

LRMS (ES$^+$) m/z 270.02 (M$^+$+Na, 90%), 247.91 (M$^+$+H, 45%), 191.85 (100%);

LC/MS (ES$^+$) t$_r$=1.02 min (>95%), m/z 170.02 (M$^+$+Na);

HPLC t$_r$=2.19 min (98.40%).

1-BOC-4-[2-(4-Chloro-phenoxy)-phenylamino]-3,4-dihydro-2H-quinoline (CMS02032, STX 2168)
C$_{26}$H$_{27}$ClN$_2$O$_3$, Mol. Wt.: 450.96

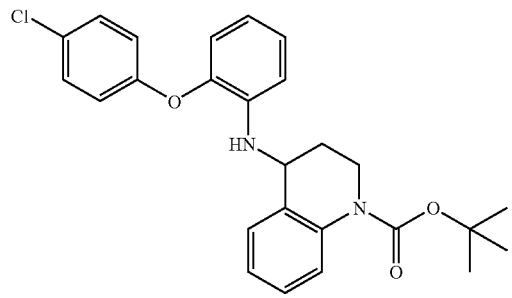

To a mixture of 1-BOC-2,3-dihydro-1H-quinolin-4-one (0.190 g, 0.77 mmol) and 2-(4-chlorophenoxy)-aniline (0.35 g, 1.6 mmol, 2.1 eq.) in toluene (10 mL) was added chlorotriisopropoxytitanium(IV) (0.4 mL, 2.1 eq.) and the resulting deep orange solution stirred at room temperature overnight. Saturated NaHCO$_3$ solution (10 mL) was added and the phases separated. The organic layer was separated dried over anhydrous magnesium sulphate then filtered and evaporated. The residue was re-dissolved in THF (25 mL) and cooled to 0° C. under nitrogen. A solution of succinic acid (0.189 g, 1.6 mmol) in THF (5 mL) was added followed by 1M borane tetrahydrofuran complex (1.6 mL, 2.1 eq.). The reaction was allowed to warm to room temperature before the addition of saturated NaHCO₃ solution (100 mL). The volatile solvent was removed under reduced pressure then ethyl acetate (100 mL) was added and the layers separated. The organic layer was dried, evaporated and then purified by column chromatography (flashmasterII, 50 g column) using 0-30% ethyl acetate/hexanes as eluent to give the desired product (0.223 g, 72%) as a colourless foam which showed;

¹H NMR (270 MHz, CDCl₃) δ 1.46 (9H, s, 3×CH₃), 1.90-2.05 (1H, m), 2.05-2.20 (1H, m), 3.44-3.55 (1H, m), 3.91-4.03 (1H, m), 4.37 (1H, br s, NH), 4.50-4.59 (1H, m), 6.65 (1H, dt, J=7.9 and 1.2 Hz), 6.80-6.90 (4H, m), 6.95-7.10 (2H, m), 7.20-7.35 (4H, m) and 7.70 (1H, d, J=7.9 Hz);

¹³C NMR (67.9 MHz, CDCl₃) δ 28.43 (CH₃), 29.94 and 41.36 (both CH₂), 49.26 (CH), 111.90 and 117.26 (both Ar—CH), 118.82 (2×Ar—CH), 119.57, 123.61, 123.89, 125.37, 127.49 and 127.92 (all Ar—CH) and 129.71 (2×Ar—CH);

1-Acetyl-1,2,3,4-tetrahydro-benzo[b]azepin-5-one (CMS02022)
C₁₂H₁₃NO₂, Mol. Wt.: 203.24

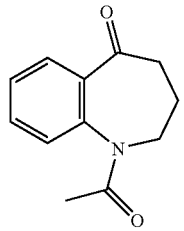

To a solution of 1,2,3,4-tetrahydro-benzo[b]azepin-5-one (0.2 g, 1.24 mmol) in THF (10 mL) was added acetic anhydride (0.12 mL, 1.1 eq) and the mixture heated at reflux for 16 hours. After cooling to room temperature and removal of the volatile solvent the crude residue was redissolved in ethyl acetate (100 mL) then washed with 2M NaOH solution (2×100 mL), water (2×100 mL), and brine (100 mL). After drying and evaporation onto silica, purification by column chromatography using 50% ethyl acetate/hexanes as eluent gave the desired compound (0.193 g, 77%) which showed;

¹H NMR (270 MHz, CDCl₃) δ 1.69-1.92 (1H, m, CH), 1.89 (3H, s, CH₃), 2.07-2.30 (1H, m, CH), 2.48-2.83 (1H, m, CH), 2.92-3.21 (1H, m, CH), 4.66-4.95 (1H, m, CH), 7.21 (1H, dd, J=7.7 and 1.0 Hz, 9-CH), 7.47 (1H, dt, J=7.7 and 1.0 Hz, 7-CH), 7.58 (1H, dt, J=7.7 and 1.7 Hz, 8-CH) and 7.86 7.58 (1H, dt, J=7.7 and 1.7 Hz, 6-CH);

¹³C NMR (67.9 MHz, CDCl₃) δ 21.17 (CH₂), 22.92 (CH₃), 39.87 and 45.41 (both CH₂), 128.20, 128.55, 129.69 and 134.07 (all Ar—CH);

LRMS (ES⁺) m/z 225.87 (M⁺+Na, 100%).

HPLC t_r=1.60 min (99.26%).

1-Acetyl-5-[2-(4-Chloro-phenoxy)-phenylamino]-2,3,4,5-tetrahydro-benzo[b]azepine (CMS02033, STX2171)

C₂₄H₂₃ClN₂O₂, Mol. Wt.: 406.90

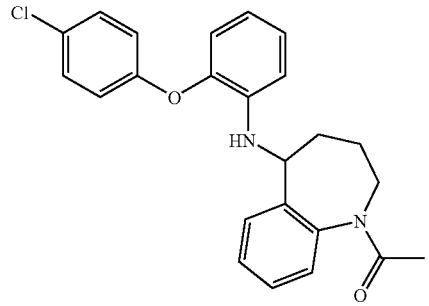

To a mixture of 1-BOC-2,3-dihydro-1H-quinolin-4-one (0.050 g, 0.25 mmol) and 2-(4-chlorophenoxy)-aniline (0.060 g, 0.27 mmol, 2.2 eq.) in toluene (5 mL) was added chlorotriisopropoxytitanium(IV) (0.3 mL, 2 eq.) and the resulting deep orange solution stirred at room temperature overnight. Saturated NaHCO₃ solution (10 mL) was added and the phases separated. The organic layer was separated dried over anhydrous magnesium sulphate then filtered and evaporated. The residue was re-dissolved in THF (25 mL) and cooled to 0° C. under nitrogen. A solution of succinic acid (0.189 g, 1.6 mmol) in THF (5 mL) was added followed by 1M borane tetrahydrofuran complex (1.6 mL, 2 eq.). The reaction was allowed to warm to room temperature before the addition of saturated NaHCO₃ solution (100 mL). The volatile solvent was removed under reduced pressure then ethyl acetate (100 mL) was added and the layers separated. The organic layer was dried, evaporated and then purified by column chromatography (flashmasterII, 50 g column) using 0-30% ethyl acetate/hexanes as eluent to give the desired product (21 mg, 21%) as a colourless foam which showed;

Rf: 0.18 (20% ethyl acetate/hexanes)

LRMS (EI⁺) m/z 429.47 (M⁺+Na, 100%);

HRMS (EI) calcd. for C₂₄H₂₃ClN₂O₂ (M⁺+H) 407.1521. found 407.1523.

3-(3-Methoxy-phenylamino)-propionic acid (CMS02059)
C₁₀H₁₃NO₃, Mol. Wt.: 195.22

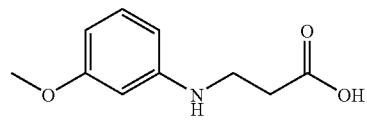

To a solution of acrylic acid (36 mL, 0.5 moles), copper(I) iodide (0.2 g) and copper(II) acetate (0.2 g) in water (28 mL) was added m-anisidine (123 mL, 2 eq.) and the mixture was heated at reflux for 16 hours. After cooling to room temperature the reaction was quenched by the cautious addition of 30% NaOH solution (2×100 mL). The phases were separated and the organic portion extracted with 2M NaOH solution (2×100 mL). The combined aqueous fractions were washed with ethyl acetate (2×100 mL) then acidified with conc. HCl solution. This was back extracted with ethyl acetate (2×200 mL) and these combined organic portions washed with water (2×100 mL) and brine (100 mL) then dried and evaporated onto silica. Purification by column chromatography using 50% ethyl acetate/hexanes as eluent gave a thick yellow oil (43.12 g, 44%) which showed.

$^1$H NMR (270 MHz, CDCl$_3$) δ 2.66 (2H, t, J=6.3 Hz, 2-CH$_2$), 3.44 (2H, t, J=6.3 Hz, 3-CH$_2$), 3.76 (3H, s, OCH$_3$), 6.18 (1H, t, J=2.2 Hz, 2'-CH), 6.25 (1H, ddd, J=0.8, 2.2 and 8.1 Hz, 6'(4')—CH), 6.30 (1H, ddd, J=0.8, 2.2 and 8.1 Hz, 4'(6')—CH), (1H, t, J=8.1 Hz, 5'-CH) and 7.64 ppm (2H, br s, N+H$_2$);

7-Methoxy-2,3-dihydro-1H-quinolin-4-one (CMS02060)
C$_{10}$H$_{11}$NO$_2$, Mol. Wt.: 170.20

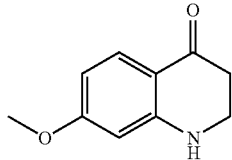

3-Phenylamino-propionic acid (20 g, 0.1 moles) and polyphosphoric acid (20 g) were heated at 100° C. for 1 hour. After cooling to 75° C., 2M NaOH solution (2×200 mL) was added with sonication of the reaction mixture at each addition to dissolve the viscous mass. The combined aqueous portions were basified to pH 12 with NaOH pellets and extracted with ethyl acetate (2×200 mL). The organics were washed with water (2×200 mL) and brine (2×200 mL) then dried, filtered and evaporated under reduced pressure to give a crude product which was purified by column chromatography using 20-50% ethyl acetate/hexanes as eluent to give the desired product (7.25 g, 40%) as a thick orange oil.

Rf: 0.29 (50% ethyl acetate/hexanes);
$^1$H NMR (270 MHz, CDCl$_3$) δ 2.64 (2H, t, J=7.2 Hz, 3-CH$_2$), 3.55 (2H, t, J=7.2 Hz, 2-CH$_2$), 3.79 (3H, s, OMe), 4.37 (1H, br s, NH), 6.07 (1H, d, 2.2 Hz, 8-CH), 6.32 (1H, dd, J=8.7 and 2.3 Hz, 6-CH) and 7.97 (1H, d, J=8.7 Hz, 5-CH);

1-Acetyl-7-Methoxy-2,3-dihydro-1H-quinolin-4-one (CMS02061)
C$_{12}$H$_{13}$NO$_3$, Mol. Wt.: 219.25

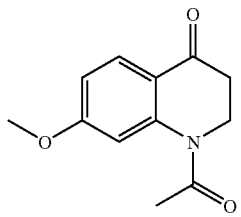

7-Methoxy-2,3-dihydro-1H-quinolin-4-one (1.0 g, 5.65 mmol) was dissolved in acetic anhydride (10 mL) and the solution heated at 100° C. for 16 hours. After cooling to room temperature the remaining acetic acid was removed by evaporation under reduced pressure and the resulting oil re-dissolved in dichloromethane (100 mL). This was washed with 2M NaOH solution (2×100 mL), water (2×100 mL) and brine (100 mL) then dried and concentrated to give a crude product which was purified by column chromatography (flashmasterII, 50 g column) using 20-50% ethyl acetate/hexanes as eluent to give the desired product (0.94 g, 76%) as a colourless oil which showed;

Rf: 0.17 (50% ethyl acetate/hexanes), cf. 0.29 (S.M.);
$^1$H NMR (270 MHz, CDCl$_3$) δ 2.35 (3H, s, NAc), 2.73 (2H, t, J=6.4 Hz, 3-CH$_2$), 3.87 (3H, s, OMe), 4.20 (2H, t, J=6.4 Hz, 2-CH$_2$), 6.78 (1H, dd, J=8.8 and 2.4 Hz, 6-CH), 6.95 (1H, br s, 8-CH) and 7.97 (1H, d, J=8.8, 5-CH);
LRMS (ES$^+$) m/z 241.87 (M$^+$+Na, 100%), 219.87 (M$^+$+H, 65%);
HPLC t$_r$=1.55 min(100%).

1-Acetyl-{4-[2-(4-Chloro-phenoxy)-phenylamino]-7-methoxy-3,4-dihydro-2H-quinoline (CMS02064, STX2425)
C$_{24}$H$_{23}$ClN$_2$O$_3$, Mol. Wt.: 422.90

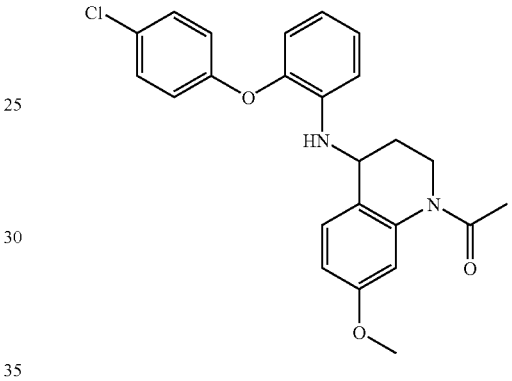

To a mixture of 1-Acetyl-7-Methoxy-2,3-dihydro-1H-quinolin-4-one (0.148 g, 0.68 mmol) and 2-(4-chlorophenoxy)-aniline (0.163 g, 1.1 mmol, 2 eq.) in toluene (10 mL) was added chlorotriisopropoxy-titanium(IV) (0.4 mL, 2.4 eq.) and the resulting deep orange solution stirred at room temperature overnight. Saturated NaHCO$_3$ solution (10 mL) was added and the phases separated. The organic layer was separated dried over anhydrous magnesium sulphate then filtered and evaporated. The residue was re-dissolved in THF (25 mL) and cooled to 0° C. under nitrogen. A solution of succinic acid (0.189 g, 1.6 mmol) in THF (5 mL) was added followed by 1M borane tetrahydrofuran complex (1.6 mL, 2.4 eq.). The reaction was allowed to warm to room temperature before the addition of saturated NaHCO$_3$ solution (100 mL). The volatile solvent was removed under reduced pressure then ethyl acetate (100 mL) was added and the layers separated. The organic layer was dried, evaporated and then purified by column chromatography (flashmasterII, 50 g column) using 0-30% ethyl acetate/hexanes as eluent to give the desired product (0.221 g, 78%) as a colourless foam which showed;

$^1$H NMR (270 MHz, CDCl$_3$) δ 1.89-2.01 (1H, m), 2.13-2.24 (1H, m), 2.21 (3H, s, NAc), 3.51-3.63 (1H, m), 3.75 (3H, s, OCH$_3$), 3.89-4.02 (1H, m), 4.50 (1H, t, J=5.8 Hz), 6.68 (1H, dd, J=7.4 and 1.5 Hz), 6.84-6.89 (4H, m), 7.06 (1H, dt, J=7.4 and 1.5 Hz), 7.14 (1H, d, J=8.7 Hz), 7.26 (2H, d, J=9.1 Hz), (9-CH not integrating due to hydrogen bonding);
LC/MS (AP$^+$) t$_r$=1.42 min (>99%), m/z 421.01 (M−H)$^+$;
LRMS (AP$^+$) m/z 421.01 ((M−H)$^+$, 100%);
HPLC t$_r$=2.95 min (97.07%).

N-(1-Acetyl-1,2,3,4-tetrahydro-quinolin-3-yl)-N-[2-(4-chloro-phenoxy)-benzyl]-acetamide (CMS02086, STX2525)
$C_{26}H_{25}ClN_2O_3$, Mol. Wt.: 448.94

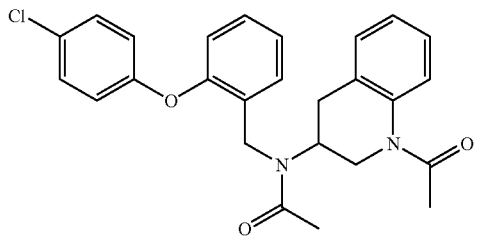

To a mixture of 2-(4-Chloro-phenoxy)-benzaldehyde (564 mg, 2.4 mmol) and 3-aminoquinoline (144 mg, 1.0 mmol in THF (50 mL) was added chlorotriisopropoxytitanium(IV) (0.6 mL, 2 eq.) and the resulting deep orange solution stirred at room temperature overnight. After cooling to 0° C., a solution of succinic acid (2.83 g, 24 mmol) in THF (5 mL) was added followed by 1M borane tetrahydrofuran complex (24 mL, 10.eq.). The reaction was allowed to warm to room temperature for 16 hours before the addition of saturated NaHCO$_3$ solution (100 mL). The volatile solvent was removed under reduced pressure then ethyl acetate (100 mL) was added and the layers separated. The organic layer was dried, evaporated and re-dissolved in acetic anhydride (10 mL). After stirring at room temperature for 4 hours, the acetic anhydride was removed by evaporation. The crude product was absorbed onto silica and then purified by column chromatography (flashmasterII, 50 g column) using 50-100% ethyl acetate/hexanes as eluent to give the desired product (0.196 g, 44%) as a pale yellow foam which showed;

$^1$H NMR (270 MHz, CDCl$_3$) δ 2.03 and 2.13 (both 3H, s, CH$_3$), 2.74-2.97 (2H, m), 3.76-3.97 (2H, m), 4.40-4.54 (2H, br s), 4.70-4.85 (1H, m), 6.75-6.89 (3H, m, 3×Ar—CH) and 7.01-7.32 (9H, m, 9×Ar—CH);
LRMS (ES$^+$) m/z 471.21 (M$^+$+Na, 100%), 449.21 (M$^+$+H, 70%).
LC/MS (ES$^+$) t$_r$=1.10 min (>99%), m/z 471.21 (M$^+$+Na, 100%), 449.21 (M$^+$+H, 70%).
HPLC t$_r$=2.22 min (98.07%).

1-BOC-3-[2-(4-Chloro-phenoxy)-benzylamino]-piperidine (CMS02070, STX2526)
$C_{23}H_{29}ClN_2O_3$, Mol. Wt.: 416.94

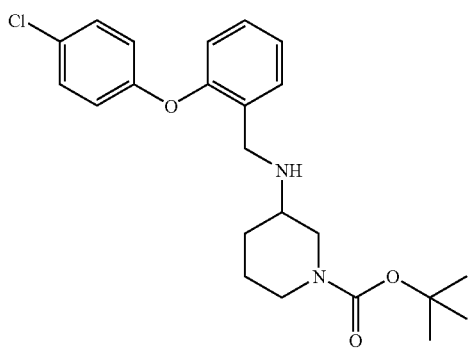

To a mixture of 2-(4-Chloro-phenoxy)-benzaldehyde (564 mg, 2.4 mmol) and 1-BOC-3-aminopiperidine (144 mg, 1.0 mmol in toluene (3 mL) was added sodium triacetoxyborohydride (265 mg, 2.5 eq.) and acetic acid (0.15 mL, 5 eq.) and the resulting mixture heated to 140° C. in a microwave (150 W) for 10 minutes. After cooling and filtration the mother liquor was evaporated onto silica and purified by column chromatography (flashmasterII, 50 g column) using 0-30% ethyl acetate/hexanes as eluent to give the desired product (0.114 g, 60%) as a colourless oil which showed;

Rf: 0.43 (50% ethyl acetate/hexanes);
$^1$H NMR (270 MHz, CDCl$_3$) δ 1.16-1.40 (2H, m), 1.42 (9H, s, 3×CH$_3$), 1.43-1.51 (1H, m), 1.57-1.70 (1H, m), 1.75-1.91 (1H, m), 2.45-2.92 (3H, m), 3.68-4.0 (4H, m), 6.82-6.88 (3H, m, 3×Ar—CH), 7.11 (1H, dt, J=7.5 and 1.0 Hz, Ar—CH), 7.21 (1H, dt, J=7.9 and 1.7 Hz, Ar—CH), 7.24 (2H, d, J=8.6 Hz, 2×Ar—CH) and 7.41 (1H, dd, J=7.4 and 1.7 Hz);
LRMS (AP$^-$) m/z 415.34 (M−H$^+$, 50%), 309.08 ((M−H$^+$)—BOC—3×H$_2$, 100%)
LC/MS (AP$^-$) t$_r$=1.45 min (>95%), m/z 415.34 (M−H$^+$, 50%), 309.08 ((M−H$^+$)—BOC—3×H$_2$, 100%);
HPLC t$_r$=4.42 min (99.44%).

[2-(4-Chloro-phenoxy)-benzyl]-piperidin-3-yl-amine (CMS02108)
$C_{18}H_{21}ClN_2O$, Mol. Wt.: 316.83

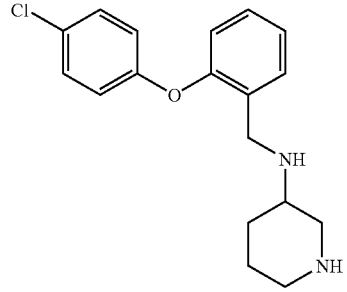

To a solution of 1-BOC-3-[2-(4-Chloro-phenoxy)-benzylamino]-piperidine (0.1 g, 0.22 mmol) in dichloromethane (10 mL) at 0° C. was added trifluoroacetic acid (1 mL) and the mixture stirred for 2 hours. The reaction was quenched by the cautious addition of NaHCO$_3$ solution (10 mL). The volatile solvent was removed under reduced pressure then ethyl acetate (100 mL) was added and the layers separated. The organic layer was dried and evaporated to give a yellow oil (69 mg, 91%) which showed;
Rf: 0.05 (60% ethyl acetate/hexanes) cf. 0.43 (S.M.);

N-(1-Acetyl-piperidin-3-yl)-N-[2-(4-chloro-phenoxy)-benzyl]-acetamide (CMS02094, STX2530)
$C_{22}H_{25}ClN_2O_3$, Mol. Wt.: 400.90

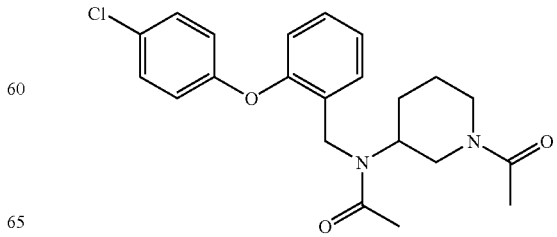

[2-(4-Chloro-phenoxy)-benzyl]-piperidin-3-yl-amine (69 mg, 0.22 mmol) was dissolved in acetic anhydride and the mixture stirred at room temperature overnight. The remaining acetic acid was removed by evaporation under reduced pressure and the resulting oil re-dissolved in dichloromethane (10 mL). This was washed with 2M NaOH solution (2×10 mL), water (2×10 mL) and brine (10 mL) then dried and concentrated to give a crude product which was purified by column chromatography (flashmasterII, 20 g column) using 10% acetone/chloroform as eluent to give the desired product (58 mg, 85%) as a colourless oil which showed;

Rf: 0.17 (ethyl acetate) cf. 0.05 (S.M.);
LRMS (ES$^+$) m/z 423.15 (M$^+$+Na, 100%), 401.17 (M$^+$+H, 20%);
LC/MS (ES) t$_r$=1.10 min (>95%), m/z 423.15 (M$^+$+Na);
HPLC t$_r$=1.93 min (98.64%).

N-(4-Chloro-phenyl)-2-nitro-benzenesulfonamide (CMS02105)
$C_{12}H_9ClN_2O_4S$, Mol. Wt.: 312.73

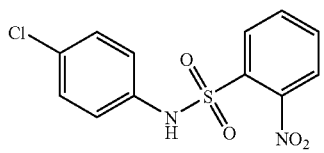

A mixture of 4-chloroaniline (5.1 g, 40 mmol), 2-nitrophenylsulfonyl chloride (8.84 g, 40 mmol) and N,N-dimethylaminopyridine (0.1 g) in pyridine (100 mL) was heated at 100° C. for 16 hours. After cooling and removal of the pyridine under reduced pressure, the residue was re-dissolved in ethyl acetate (200 mL) and washed with 2M NaOH (2×200 mL), 2M HCl (2×200 mL), water (2×200 mL) and brine (200 mL). The organic phase was dried, filtered and evaporated under reduced pressure to give a crude product as a thick oil which solidified under high vacuum. The solid was recrystallised from ethanol to give pale yellow crystals (9.44 g, 77%) which showed M.p. 121.7-124.2° C. (Lit. m.p. 123-124° C. Russ. J. Org. Chem., 41, 7, 2005, 1023.);
$^1$H NMR (270 MHz, CDCl$_3$) δ 7.13 (2H, d, J=8.4 Hz, 2×Ar—CH), 7.24 (2H, d, J=8.4 Hz, 2×Ar—CH), 7.25 (1H, br s, NH), 7.59 (1H, dt, J=7.6 and 1.2 Hz), 7.71 (1H, dt, J=7.7 and 1.5 Hz), 7.80 (1H, dd, J=7.7 and 1.5 Hz), 7.59 (1H, dd, J=7.6 and 1.2 Hz);
LRMS (ES$^-$) m/z 312.92 (M$^-$, 40%), 310.97 (M$^-$, 100%);
LC/MS (ES$^-$) t$_r$=0.81 min (>95%), m/z 310.97 (M$^-$);
HPLC t$_r$=1.57 min (100%).

2-Amino-N-(4-chloro-phenyl)-benzenesulfonamide (CMS02106)
$C_{12}H_{11}ClN_2O_2S$, Mol. Wt.: 282.75

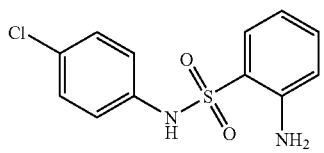

To a vigorously stirred mixture of Iron powder (5.0 g, 89 mmol) and ammonium chloride (0.65 g, 1.4 eq.), in ethanol (100 mL) and water (30 mL), at reflux, was added a solution of N-(4-Chloro-phenyl)-2-nitro-benzenesulfonamide (5.0 g, 16 mmol) and the reaction maintained at reflux for one hour. After cooling and filtration through a pad of celite, the volatile solvent was removed to give a crystalline solid which was recrystallised from ethanol to give the desired product as beige crystals (3.67 g, 81%) which showed;

Rf: 0.11 (20% ethyl acetate/hexanes);
M.p. 116.1-117.1° C.
$^1$H NMR (270 MHz, CDCl$_3$) δ 4.85 (1H, br s, NH$_2$), 6.61-6.75 (2H, m), 6.95-6.98 (3H, m, 2×CH+NH), 7.13-7.18 (2H, m), 7.25 (1H, dt, J=8.2 and 1.5 Hz) and 7.46 (1H, dd, J=8.2 and 1.5 Hz);
$^{13}$C NMR (67.9 MHz, CDCl$_3$) δ 117.90 and 118.25 (both Ar—CH), 120.69 (C) 124.25 and 129.37 (both 2×Ar—CH), 130.01 (Ar—CH), 131.59 (C), 134.79 (Ar—CH), 134.92 and 144.95 (both C);

1-Acetyl-piperidine-4-carboxylic acid [2-(4-chloro-phenylsulfamoyl)-phenyl]-amide (CMS02111)
$C_{20}H_{22}ClN_3O_4S$, Mol. Wt.: 435.92

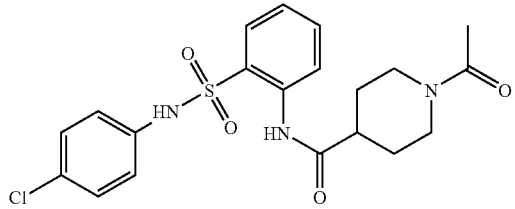

To a solution of 2-Amino-N-(4-chloro-phenyl)-benzenesulfonamide (0.282 g, 1 mmol) in toluene (4 ml) was added sodium hydride (0.04 g, 1 mmol), followed by 1-Acetyl-piperidine-4-carbonyl chloride (0.189 g, 1 mmol). The solution was heated using a CEM microwave at 140° C. for 10 min. The mixture was allowed to cool and sat. NaHCO$_3$ was added (10 ml), and extracted with EtOAc (2×20 ml). The combined organic layers were dried (MgSO$_4$), filtered and evaporated in-vacuo. The crude mixture was purified using lash chromatography (0-100% ethyl acetate/hexane) to afford the title compound as a colourless oil (153 mg, 35%) which showed;

Rf: 0.22 (60% ethyl acetate/hexanes);
$^1$H NMR (270 MHz, CDCl$_3$) δ 1.52-1.74 (2H, m), 1.83-1.97 (2H, m), 2.08 (3H, s, NAc), 2.25-2.38 (1H, m), 2.58-2.73 (1H, m), 3.03-3.17 (1H, m), 3.82-3.95 (1H, m), 4.56-4.68 (1H, m), 6.98 (2H, d, J=8.7 Hz), 7.05 (1H, br s, NH), 7.14 (1H, dt, J=7.6 and 1.2 Hz), 7.22 (1H, d, J=8.7 Hz), 7.54 (1H, dt, J=7.9 and 1.7 Hz), 7.68 (1H, dd, J=8.2 and 1.5 Hz), 8.34 (1H, d, J=8.4 Hz) and 9.14 (1H, br s, NH);

N-(4-Chloro-phenyl)-2-ethylamino-benzenesulfonamide (CMS02109)
$C_{14}H_{15}ClN_2O_2S$, Mol. Wt.: 310.80

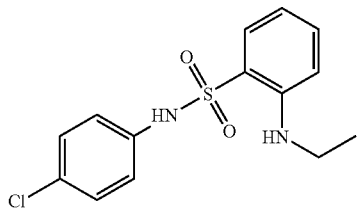

To a solution of 4-Chloro-N-(2-ethylamino-phenyl)-benzenesulfonamide (282 mg, 1 mmol) and AcOH (0.5 mL) in toluene (2 ml) was added sodium triacetoxyborohydride (0.52 g, 2.26 mmol). The solution was heated using a CEM microwave at 100° C. for 15 min. The mixture was allowed to cool and sat. NaHCO$_3$ was added (10 ml), and extracted with EtOAc (2×20 ml). The combined organic layers were dried (MgSO$_4$), filtered and evaporated in-vacuo. The crude mixture was purified using flash chromatography (0-100% EtOAc in hexane) to afford the title compound as a white solid (168 mg, 54%) which showed;

M.p. 107-109° C.
Rf: 0.38 (20% ethyl acetate/hexanes);
$^1$H NMR (270 MHz, CDCl$_3$) δ 1.27 (3H, t, J=6.7 hz, CH$_3$), 3.16 (2H, t, J=6.7 hz, CH$_2$), 5.67 (1H, br s, NH), 6.60 (1H, dt), 6.70 (1H, d), 6.91-6.95 (2H, m), 7.13-7.16 (2H, m), 7.30-7.40 (1H, m) and 2.50 (1H, dd);
$^{13}$C NMR (67.9 MHz, CDCl$_3$) δ 14.38 (CH$_3$), 38.06 (CH$_2$), 112.38 and 116.15 (both Ar—CH), 119.55 (C), 124.31 and 129.34 (both 2×Ar—CH), 130.43 (Ar—CH), 131.56 (Ar—CH) and 146.21 (C);

1-Acetyl-piperidine-4-carboxylic acid [2-(4-chloro-phenylsulfamoyl)-phenyl]-ethyl-amide (CMS02110)
$C_{22}H_{26}ClN_3O_4S$, Mol. Wt.: 463.98

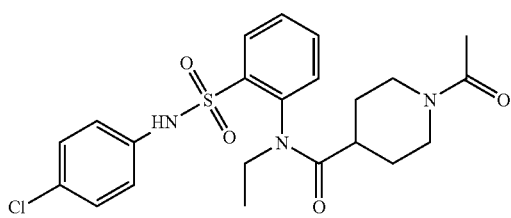

To a solution of 4-Chloro-N-(2-ethylamino-phenyl)-benzenesulfonamide (0.1 g, 0.32 mmol) in toluene (3 mL), was added sodium hydride (13 mg, 0.32 mmol) followed by 1-Acetyl-piperidine-4-carbonyl chloride (60 mg, 0.32 mmol). The solution was heated using a CEM microwave at 140° C. for 10 min. The mixture was allowed to cool and sat. NaHCO$_3$ was added (10 ml), and extracted with EtOAc (2×20 ml). The combined organic layers were dried, filtered and evaporated and the crude mixture was purified using flash chromatography (0-100% EtOAc in hexane) to afford the title compound as a colourless oil (43 mg, 29%) which showed;

R$_f$: 0.32 (ethyl acetate);
$^1$H NMR (270 MHz, CDCl$_3$) δ 1.24 (3H, t, J=6.7 Hz, CH$_2$CH$_3$), 1.47-1.71 (5H, m, 5×CH), 2.00 (3H, s, N—Ac), 2.27-2.42 (1H, m, CH), 2.73-2.88 (1H, m, CH), 3.09-3.23 (2H, m, N—CH$_2$), 3.64-3.76 (1H, m, CH), 4.35-4.48 (1H, m, CH), 6.04 (1H, br s, NH), 6.61 (2H, m, 2×Ar—CH), 7.23-7.28 (2H, m, 2×Ar—CH), 7.36-7.46 (3H, m, 3×Ar—CH) and 7.63 (1H, dd, J=8.1 and 1.5 Hz, Ar—CH);
LRMS (ES$^+$) m/z 48613 (M$^+$+Na, 100%).
LC/MS (ES$^+$) t$_r$=1.00 min (>99%), m/z 486.13 (M$^+$+Na).

Biology
Assay Protocol—17β-Hydroxysteroid Dehydrogenase Type 3 Activity in the Presence of Regulatory Agents 293-EBNA cells stably transfected with 17β-HSD Type 3 were plated at 50,000 cells/well in 24 well plates in complete growth medium. After 48 hours 2-3 nM $^3$H-Androstenedione in assay medium (500 ml MEME medium with 5 ml 100× Pen/Strep, 5 ml 100×L-Glutamine, 5 ml 100×NEAA and 5 ml 7.5% sodium bicarbonate solution) was added with or without test compound at 1.5 ml/well (triplicate), and the cells incubated at 37° C.

Two hours later 1 ml medium was removed from each well and placed in a 125×16 mm glass test tube containing 25 μl of recovery solution (5000 dpm $^{14}$C-Testosterone and 25 μg unlabelled Testosterone). Ether (4 ml) was added and the tubes vortexed at high speed for 2×30 sec. After the samples had settled into two phases they were snap-frozen in a dry ice/methanol bath. The upper organic phase was decanted into 75×12 mm tubes and evaporated to dryness under an airstream using a sample concentrator (TECHNE) at 40° C. The samples were resuspended in ether (8 drops, then a further 3), spotted onto silica 60 F254 20 cm×20 cm TLC plates, and separated using a 4:1 v/v dichloromethane:ethyl acetate mobile phase.

After drying the plates, the major spots were marked under a UV lamp, cut out, and placed in individual scintillation vials containing 0.5 ml methanol. These were then shaken lightly and allowed to stand for 15 min before adding 10 ml of EcoScint A (scintillation fluid) to each tube along with 0.5 ml assay medium, and counted in a scintillation spectrometer (Beckman) using a program for dual [$^3$H/$^{14}$C] isotopes. The number of cells/well was then counted using a Coulter counter (Beckman).

The inhibitory activity of the test compounds is then assessed by calculating the amount of product formed correcting for crossover between isotope counts, recovery, dilution and non-enzymatic degradation (fmol/hr/million cells) with and without inhibitor, (% inhibition).

Inhibition Data

The structures of representative examples of the above synthesised compounds and the data obtained are given in the table below.

Compounds were tested at 10 μM for inhibition of human 17β-HSD3 with typically ~2000,000 human 293-EBNA cells/well. Compounds showing >60% inhibition of 17θ-HSD3 when tested at 10 μM using the above protocol have been designated (a) in the table, those showing from 20 to 60% inhibition of 17β-HSD3 when tested at 10 μM using the same protocol have been designated (b) in the table, and those showing less than 20% inhibition of 17β-HSD3 when tested at 10 μM using the same protocol have been designated (c) in the table below.

| Compound No | Structure | % Inhibition of Human 17β-HSD3 in 293-EBNA cells at 10 μM |
| --- | --- | --- |
| STX1604 | 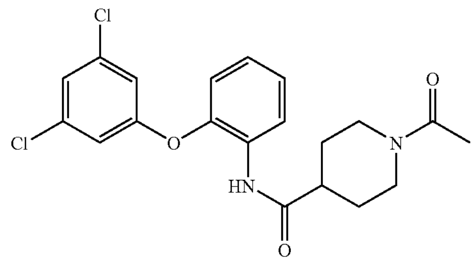 | b |
| STX1605 | 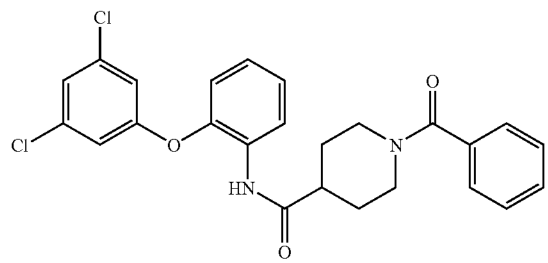 | b |
| STX1606 | 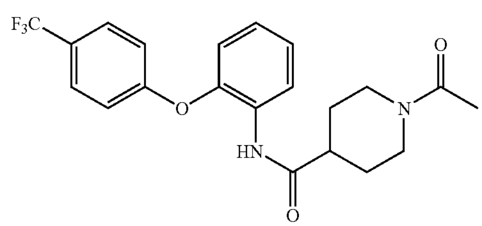 | b |
| STX1607 | 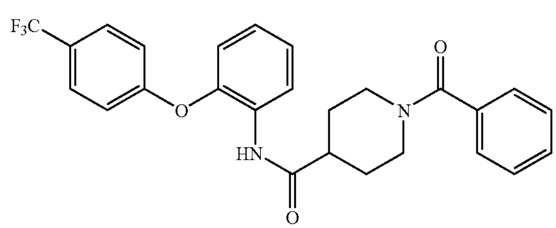 | b |
| STX1613 | 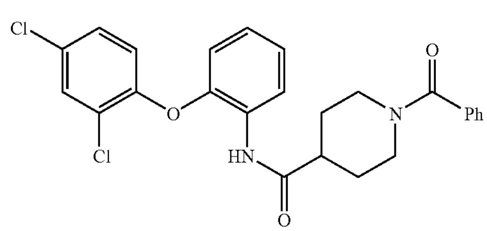 | b |
| STX1614 | 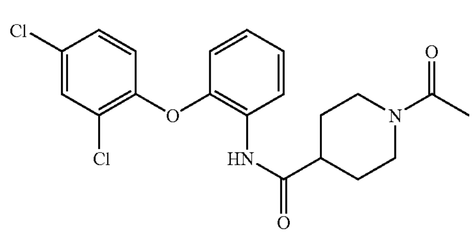 | a |

-continued

| Compound No | Structure | % Inhibition of Human 17β-HSD3 in 293-EBNA cells at 10 μM |
|---|---|---|
| STX1615 | 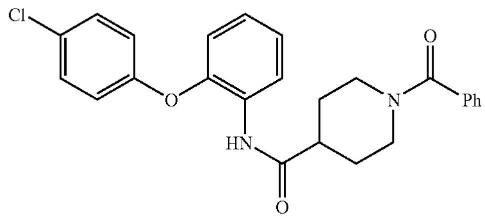 | c |
| STX1616 | 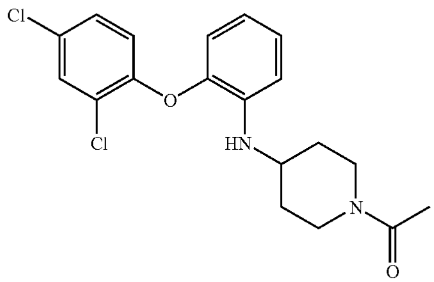 | a |
| STX1617 | 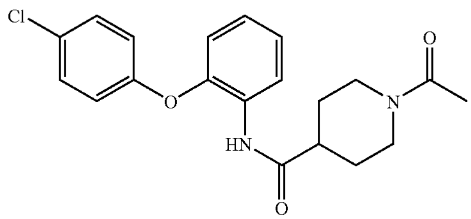 | b |
| STX1623 | 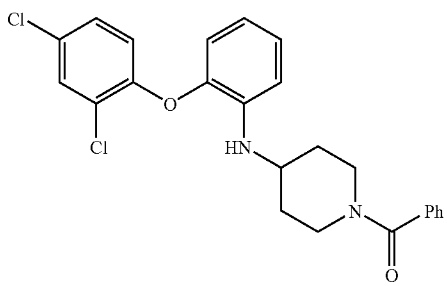 | a |
| STX1624 | 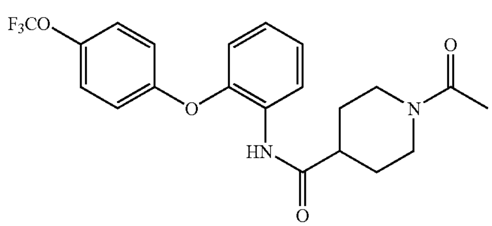 | b |
| STX1625 | 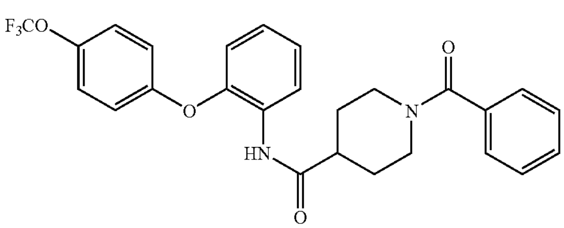 | b |

-continued

| Compound No | Structure | % Inhibition of Human 17β-HSD3 in 293-EBNA cells at 10 μM |
|---|---|---|
| STX1629 | 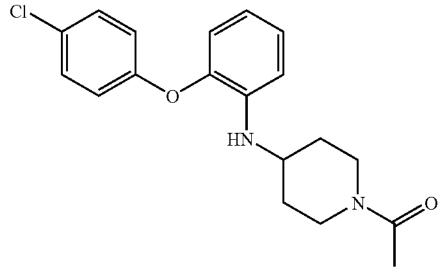 | a |
| STX1630 | 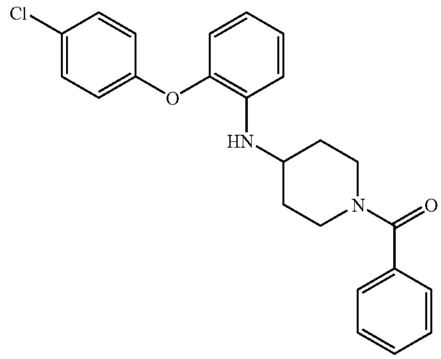 | a |
| STX1631 | 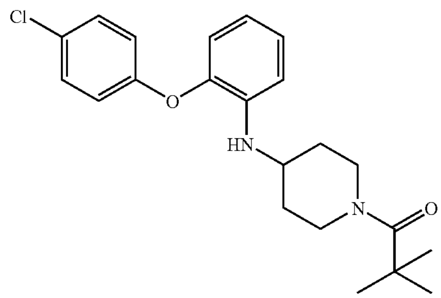 | b |
| STX1762 | 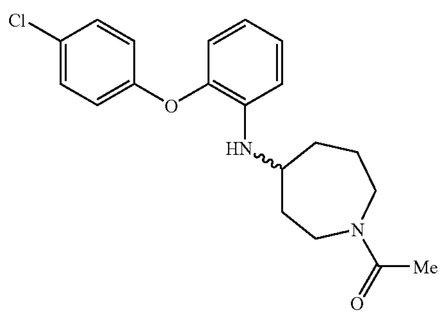 | a |
| STX1779 | 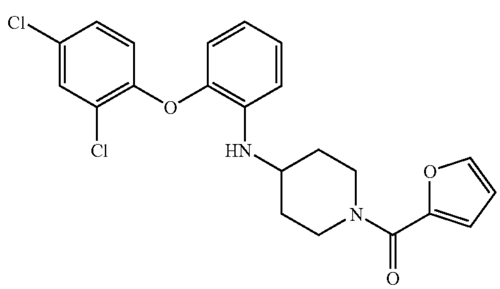 | b |

-continued

| Compound No | Structure | % Inhibition of Human 17β-HSD3 in 293-EBNA cells at 10 μM |
|---|---|---|
| STX1858 | 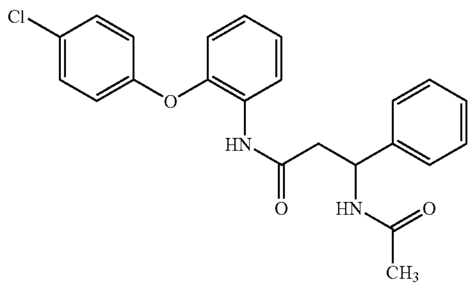 | c |
| STX1859 | 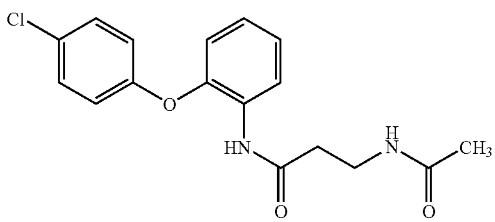 | c |
| STX2044 | 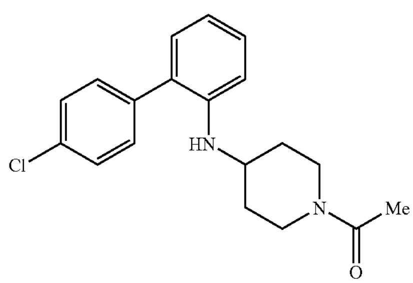 | b |
| STX2048 | 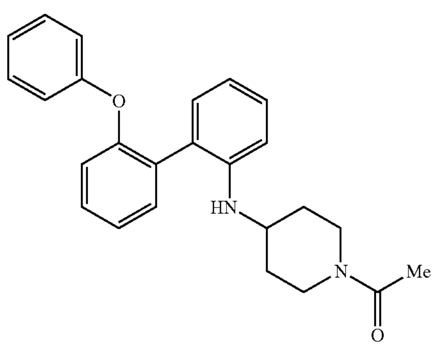 | b |
| STX2138 | 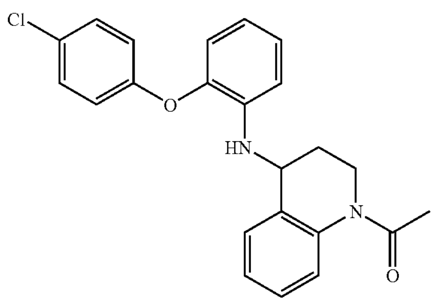 | b |

-continued

| Compound No | Structure | % Inhibition of Human 17β-HSD3 in 293-EBNA cells at 10 μM |
|---|---|---|
| STX2171 | 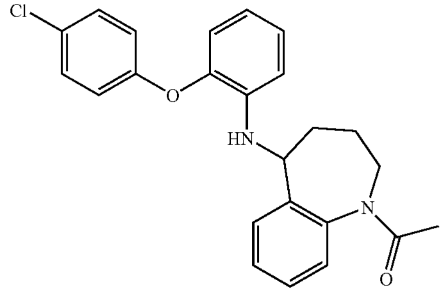 | a |
| STX2419 | 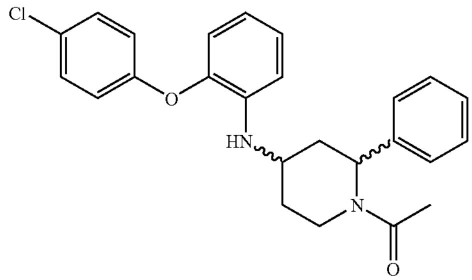 | b |
| STX2523 | 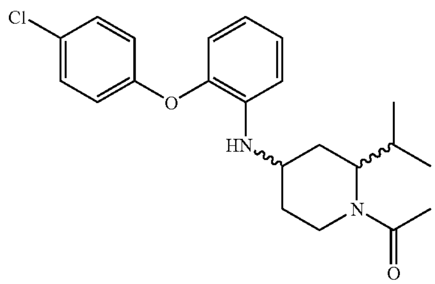 | a |
| STX2525 | 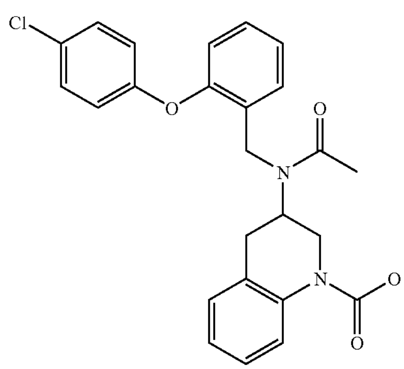 | b |

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific

The invention claimed is:
1. A compound having Formula VI

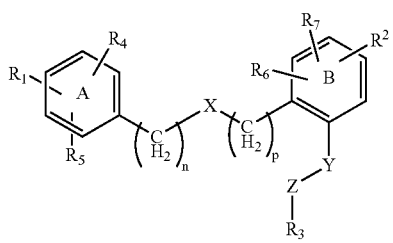

Formula VI wherein
each of $R_1$, $R_2$, $R_4$, $R_5$, $R_6$ and $R_7$ are independently selected from
(a) H,
(b) $R_{17}$, —OC$(R_{17})_3$, —OCH$(R_{17})_2$, or —OCH$_2R_{17}$, wherein $R_{17}$ is a halogen;
(c) —CN;
(d) optionally substituted alkyl,
(e) optionally substituted heteroalkyl;
(f) optionally substituted aryl;
(g) optionally substituted heteroaryl;
(h) optionally substituted arylalkyl;
(i) optionally substituted heteroarylalkyl;
(j) hydroxy;
(k) alkoxy;
(l) aryloxy;
(m) —SO$_2$-alkyl; and
(n) —N$(R_{11})$C(O)$R_{13}$,
wherein the optional substituents of (d) (e) (h) and (i) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl;
A optionally has fused thereto a further ring independently selected from five or six membered carbon rings optionally containing one or more hetero atoms selected from N, S, and O;
X is O,
wherein n and p are 0;
Y is $(R_{11})_{1-3}$ wherein each $R_{11}$ is independently selected from —NR$_{12}$, —CR$_{13}R_{14}$, —S(=O)$_2$ and —C=O, wherein $R_{12}$, $R_{13}$ and $R_{14}$ are independently selected from H and hydrocarbyl;
Z is

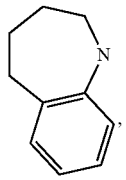

which may be optionally substituted; and
$R_3$ is selected from

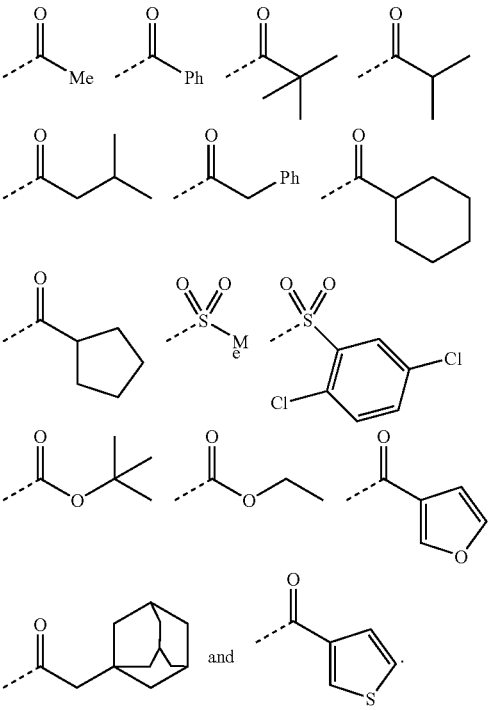

and

2. A compound according to claim 1 wherein $R_{17}$ is Cl or F.
3. A compound according to claim 1 wherein (b) is Cl, —OCF$_3$, —OCHF$_2$, —OCH$_2$F, —CF$_3$, —CHF$_2$, or —CH$_2$F.
4. A compound according to claim 1 wherein (b) is $C_1$, CF$_3$, OCF$_3$, or —OCHF$_2$.
5. A compound according to claim 1 wherein $R_1$ is selected from (b) $R_{17}$, —OC$(R_{17})_3$, —OCH$(R_{17})_2$, or —OCH$_2R_{17}$, wherein $R_{17}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —SO$_2$-alkyl; and (n) —N$(R_{11})$C(O)$R_{13}$, wherein the optional substituents of (d) (e) (f) (h) and (i) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl.
6. A compound according to claim 1 wherein $R_1$ is $C_1$, CF$_3$, OCF$_3$, or —OCHF$_2$.
7. A compound according to claim 1 wherein $R_2$ is selected from (a) H, (b) $R_{17}$, —OC$(R_{17})_3$, —OCH$(R_{17})_2$, or —OCH$_2R_{17}$, wherein $R_{17}$ is a halogen; (c) —CN; (d) optionally substituted alkyl, (e) optionally substituted heteroalkyl; and (k) alkoxy;
wherein the optional substituents of (d) and (e) are selected from the group consisting of: $C_{1-6}$ alkyl, halo, cyano, nitro, haloalkyl, hydroxy, alkoxy, carboxy, carboxyalkyl, carboxamide, mercapto, amino, alkylamino, dialkylamino, sulfonyl, sulfonamido, aryl and heteroaryl.
8. A compound according to claim 1 wherein $R_2$ is H or Me.
9. A compound according to claim 1 wherein $R_2$ is Me.
10. A compound according to claim 1 wherein $R_2$ is H.

11. A compound according to claim 1 wherein each of $R_4$, $R_5$, $R_6$ and $R_7$ is H.

12. A compound according to claim 1 wherein when A is a single ring each of $R_4$ and $R_5$ is H.

13. A compound according to claim 1 wherein each of $R_6$ and $R_7$ is H.

14. A compound according to claim 1 wherein each of $R_2$, $R_6$ and $R_7$ is H.

15. A compound according to claim 1 wherein ring A has fused thereto a further ring (ring A') and ring A together with ring A' contains more than six members.

16. A compound according to claim 1 wherein Y is $R_{11}$.

17. A compound according to claim 1 wherein Y is $(R_{11})_2$.

18. A compound according to claim 1 wherein Y is $(R_{11})_3$.

19. A compound according to claim 1 wherein $R_{12}$, $R_{13}$ and $R_{14}$ are independently selected from H and $C_{1-6}$ alkyl.

20. A compound according to claim 1 wherein Y is selected from —$NR_{12}$, —$NR_{12}$—$CR_{13}R_{14}$, —$NR_{12}C$=O, —$CR_{13}R_{14}$—$CR_{13}R_{14}$, —$CR_{13}R_{14}$—$NR_{12}$—$CR_{13}R_{14}$, and —$NR_{12}$—$S(=O)_2$.

21. A compound according to claim 1 wherein Y is selected from —$NR_{12}$, —$NR_{12}$—$CR_{13}R_{14}$, and —$NR_{12}C$=O.

22. A pharmaceutical composition comprising a compound according to claim 1 optionally admixed with a pharmaceutically acceptable carrier, diluent, excipient or adjuvant.

23. A compound according to claim 1 wherein (d) optionally substituted alkyl is —$C(R_{17})_3$, —$CH(R_{17})_2$, or —$CH_2R_{17}$, wherein $R_{17}$ is a halogen.

24. A compound according to claim 5 wherein (d) optionally substituted alkyl is —$C(R_{17})_3$, —$CH(R_{17})_2$, or —$CH_2R_{17}$, wherein $R_{17}$ is a halogen.

25. A compound according to claim 7 wherein (d) optionally substituted alkyl is —$C(R_{17})_3$, —$CH(R_{17})_2$, or —$CH_2R_{17}$, wherein $R_{17}$ is a halogen.

26. A compound according to claim 1, of the general formula

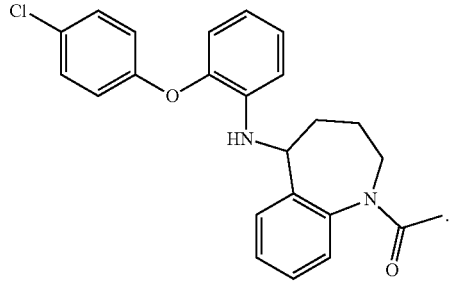

* * * * *